United States Patent
DePinho et al.

(10) Patent No.: US 9,458,510 B2
(45) Date of Patent: Oct. 4, 2016

(54) SIGNATURES AND DETERMINANTS ASSOCIATED WITH PROSTATE CANCER PROGRESSION AND METHODS OF USE THEREOF

(75) Inventors: Ronald A. DePinho, Houston, TX (US); Zhihu Ding, Brookline, MA (US); Chang-Jiun Wu, Houston, TX (US); Lynda Chin, Houston, TX (US)

(73) Assignee: MIETAMARK GENETICS, INC., Cambridge, MA (US)

( * ) Notice: Subject to any disclaimer, the term of this patent is extended or adjusted under 35 U.S.C. 154(b) by 0 days.

(21) Appl. No.: 14/127,413

(22) PCT Filed: Jun. 26, 2012

(86) PCT No.: PCT/US2012/044268
§ 371 (c)(1),
(2), (4) Date: May 22, 2014

(87) PCT Pub. No.: WO2013/003384
PCT Pub. Date: Jan. 3, 2013

(65) Prior Publication Data
US 2014/0314765 A1 Oct. 23, 2014

Related U.S. Application Data

(60) Provisional application No. 61/501,536, filed on Jun. 27, 2011, provisional application No. 61/582,787, filed on Jan. 3, 2012.

(51) Int. Cl.
*C07K 16/00* (2006.01)
*C12Q 1/68* (2006.01)
*G01N 33/50* (2006.01)
*G01N 33/574* (2006.01)
*A61N 5/10* (2006.01)

(52) U.S. Cl.
CPC .............. *C12Q 1/6886* (2013.01); *A61N 5/10* (2013.01); *G01N 33/5011* (2013.01); *G01N 33/57434* (2013.01); *C12Q 2600/106* (2013.01); *C12Q 2600/118* (2013.01); *C12Q 2600/136* (2013.01); *C12Q 2600/158* (2013.01); *G01N 2800/52* (2013.01); *G01N 2800/56* (2013.01)

(58) Field of Classification Search
None
See application file for complete search history.

(56) References Cited

U.S. PATENT DOCUMENTS

| 2005/0272052 A1 | 12/2005 | Shekar et al. |
| 2007/0248535 A1 | 10/2007 | Buttyan et al. |
| 2010/0233691 A1 | 9/2010 | Bankaitis-Davis et al. |
| 2011/0053804 A1 | 3/2011 | Massague et al. |
| 2011/0265197 A1 | 10/2011 | Depinho et al. |

FOREIGN PATENT DOCUMENTS

| WO | 2005008213 A2 | 1/2005 |
| WO | 2010009337 A2 | 1/2010 |

OTHER PUBLICATIONS

Endo et al (International Journal of Oncology, 2009, 35: 499-509).*
Horvath et al (The Prostate, 2004, 59: 234-242).*
Lin et al (Cancer Res, 2008, 68(11): 4352-4359).*
Portier, B.P., et al., "Delay to formalin fixation 'cold ischemia time': effect on ERBB2 detection by in-situ hybridization and immunohistochemistry," Modern Pathology: an Official Journal of the United States and Canadian Academy of Pathology, Inc., 26:1-9 (2013).
Pressinotti, N.C., et al., "Differential expression of apoptotic genes PDIA3 and MAP3K5 distinguishes between low- and high-risk prostate cancer," Mol Cancer, 8:130 (2009).
Punar, M., et al., "Expression of Smad4 in prostatic adenocarcinoma (PAC) whole mount sections correlates with tumor Gleason grade," Modern Pathology, 18(Suppl):159A-160A (Jan. 2005) & 94th Annual Meeting of the United States and Canadian Academy of Pathology, San Antonio, TX, USA; Feb. 26-Mar. 4, 2005.
Reese, A.C., et al., "The quantitative Gleason score improves prostate cancer risk assessment," Cancer, 118:6046-6054 (2012).
Rhodes, D.R., et al., "Multiplex biomarker approach for determining risk of prostate-specific antigen-defined recurrence of prostate cancer," J. Natl. Cancer Inst., 95:661-668 (2003).
Robertson, N.L., et al., "MRI-targeted prostate biopsy: a review of technique and results," Nat Rev Urol, 10:589-597 (2013).
Ross, A.E., et al., "Gene expression pathways of high grade localized prostate cancer," Prostate, 71:1568-1578 (2011).
Ross, H.M., et al., "Do adenocarcinomas of the prostate with Gleason score (GS) </=6 have the potential to metastasize to lymph nodes?," Am J Surg Pathol, 36:1346-1352 (2012).
Rubin, M.A., "Targeted therapy of cancer: new roles for pathologists—prostate cancer," Mod. Pathol. 21 Suppl 2, S44-S55 (2008).
Rubin, M.A., et al., "Alpha-Methylacyl coenzyme, A racemase as a tissue biomarker for prostate cancer," JAMA, 287:1662-1670 (2002).
Rubin, M.A., et al., "E-cadherin expression in prostate cancer: a broad survey using high-density tissue microarray technology," Hum. Pathol., 32:690-697 (2001).
Rudolph, K.L., et al., "Telomere dysfunction and evolution of intestinal carcinoma in mice and humans," Nat. Genet., 28:155-159 (2001).
Saal, L.H., et al., "Poor prognosis in carcinoma is associated with a gene expression signature of aberrant PTEN tumor suppressor pathway activity," Proceedings of the National Academy of Sciences fo the United States of America, 104(18):7564-7569 (May 2007).
Sandhu, G.S., et al, "Overdiagnosis of prostate cancer," J. Natl. Cancer Inst Monogr, 146-151 (2012).

(Continued)

*Primary Examiner* — Sean Aeder
(74) *Attorney, Agent, or Firm* — Lando & Anastasi, LLP

(57) ABSTRACT

The present invention provides a set of DETERMINANTS (e.g., genes and gene products) that can accurately inform about the risk of cancer progression and recurrence, as well as methods of their use.

12 Claims, 61 Drawing Sheets

(56) References Cited

OTHER PUBLICATIONS

Sattler, M., et al., "Role of the cytoskeletal protein paxillin in oncogenesis," Crit Rev Oncog, 11:63-76 (2000).
Scher, H.I., et al., "Validation and clinical utility of prostate cancer biomarkers," Nat Rev Clin Oncol, 10:225-234 (2013).
Schmitz, M., et al. "Complete loss of PTEN expression as a possibly early prognostic marker for prostate cancer metatsis," International Journal of Cancer, 120(6):1284-1292 (Mar. 2007).
Schneider, C.A., et al., "NIH Image to IMAGEJ: 25 years of image analysis," Nature Methods, 9:671-675 (2012).
Sharpless, N.E., et al., "The mighty mouse: genetically engineered mouse models in cancer drug development," Nat. Rev. Drug Discov., 5:741-754 (2006).
Sheehan, G., et al., "Smad4 protein expression correlates with grade, stage, and DNA ploidy in prostatic adenocarcinomas," Human Pathology, 36(11):1204-1209 (Nov. 2005).
Shen, M.M., et al., "Molecular genetics of prostate cancer: new prospects for old challenges," Genes Dev., 24:1967-2000 (2010).
Shikanov, S., et al., "Hazard of prostate cancer specific mortality after radical prostatectomy," J. Urol., 187:124-127 (2012).
Siegel, R., et al., "Cancer Statistics, 2014," CA Cancer J. Clin., 64:9-29 (2014).
Sommerfeld, H.J., et al., "Telomerase activity: a prevalent marker of amlignant human prostate tissue," Cancer Res., 56:218-222 (1996).
Song, M.S., "The functions and regulation of the PTEN tumour suppressor," Nat Rev Mol Cell Biol, 13:283-296 (2012).
Sowalsky, A.G., et al., "Clonal progression of prostate cancers from Gleason grade 3 to grade 4," Cancer Res., 73:1050-1055 (2013).
Stark, J.R., et al., "Gleason score and lethal prostate cancer: does 3+4=4+3?," J Clin Oncol, 27:3459-3464 (2009).
Stratton, M.R., et al., "The cancer genome," Nature, 458:719-724 (2009).
Swanson, G.P., et la., "Using molecular markers to help predict who will fail after radical prostatectomy," Prostate Cancer, 290160 (2011).
Sweet-Cordero, A., et al., "An oncogenic KRAS2 expression signature identified by cross-species gene-expression analysis," Nat. Genet., 37:48-55 (2005).
Takai, H., et al., "DNA damage foci at dysfunctional telomeres," Curr. Biol., 13:1549-1556 (2003).
Taylor, B.S., et al., "Integrative genomic profiling of human prostate cancer," Cancer Cell, 18:11-22 (2010).
Teverovskiy, M., et al., "Automated localization and quantification of protein multiplexes via multispectral fluorescence imaging," Published in: Biomedical Imaging: From Nano to Micro, pp. 300-303 (2008).
Tomlins, S.A., et al., "Integrative molecular concept modeling of prostate cancer progression," Nat. Genet., 39:41-51 (2007).
Tomlins, S.A., et al., "Recurrent fusion of TMPRSS2 and ETS transcription factor genes in prostate cancer," Science, 310:644-648 (2005).
Tomlins, S.A., et al., "The role of SPINK1 in ETS rearrangement-negative prostate cancers," Cancer Cell, 13:519-528 (2008).
Trotman, L.C., et al., "Pten Dose Dictates Cancer Progression in the Prostate," PLoS. Biol., 1:E59 (2003).
True, L., et al., "A molecular correlate to the Gleason grading system for prostate adenocarcinoma," Proc Natl Acad Sci USA, 103:10991-10996 (2006).
Truong, M., et al., "Development and multi-institutional validation of an upgrading risk tool for Gleason 6 prostate cancer," Cancer, 119:3992-4002 (2013).
Tusher, V.G., et al., "Significance analysis of microarrays applied to the ionizing radiation response," Proc. Natl. Acad. Sci. USA, 98:5116-5121 (2001).
Vanaja, D.K., et al., "Transcriptional silencing of zinc finger protein 185 identified by expression profiling is associated with prostate cancer progression," Cancer Res., 63:3877-3882 (2003).

Varambally, S., et al., "Genomic loss of microRNA-101 leads to overexpression of histone methyltransferase EZH2 in cancer," Science (2008).
Varambally, S., et al., "Integrative genomic and proteomic analysis of prostate cancer reveals signatures of metastic progression," Cancer Cell, 8:393-406 (2005).
Varambally, S., et al., "The polycomb group protein EZH2 is involved in progression of prostate cancer," Nature, 419:624-629 (2002).
Vellekoop, A., et al., "Population-based study of predictors of adverse pathology among candidates for active surveillance with Gleason 6 prostate cancer," J. Urol., 191:350-357 (2014).
Vickers, A.J., et al., "Does a delay between diagnosis and radical prostatectomy increase the risk of disease recurrence?," Cancer, 106:576-580 (2006).
Vukovic, B., et al., "Evidence of multifocality of telomere erosion in high-grade prostatic intraepithelial neoplasia (HPIN) and concurrent carcinoma," Oncogene, 22:1978-1987 (2003).
Walsh, P.C., et al., "Clinical Practice. Localized Prostate Cancer," N. Engl. J. Med., 357:2696-2705 (2007).
Wang, S., et al., "Prostate-specific deletion of the murine Pten tumor suppressor gene leads to metastatic prostate cancer," Cancer Cell, 4:209-221 (2003).
Watson, P.A., et al., "Context-dependent hormone-refractory progression revealed through characterization of a novel murine prostate cancer cell line," Cancer Res., 65:11565-11571 (2005).
Pending, U.S. Appl. No. 14/174,072, filed Feb. 6, 2014.
Pending, U.S. Appl. No. 14/213,073, filed Mar. 14, 2014.
Abate-Shen, C., et al., "Integrating differentiation and cancer: The Nkx3.1 homeobox gene in prostate organogenesis and carcinogenesis," Differentiation (2008).
Acevedo, V.D., et al., "Paths of FGFR-driven tumorigenesis," Cell Cycle, 8:580-588 (2009).
Aitchison, A.A., et al., "Promoter methylation correlates with reduced Smad4 expression in advanced prostate cancer," Prostate, 68:661-674 (2008).
Andersen, J.N., et al., "Pathway-based identification of biomarkers for targeted therapeutics: personalized oncology with P13K pathway inhibitors," Science Translational Medicine, 2:43ra55 (2010).
Ao, M., et al., "Transforming growth factor-beta promotes invasion in tumorigenic but not in nontumorigenic human prostatic epithelial cells," Cancer Res., 66:8007-8016 (2006).
Artandi, S.E, et al., "Telomere dysfunction promotes non-reciprocal translocations and epithelial cancers in mice," Nature, 406:641-645 (2000).
Baatz, et al., Comb Chem High Throughput Screen, 12(9):908-916 (2009).
Bangma, C.H., et al., "Defining and predicting indolent and low risk prostate cancer," Crit Rev Oncol Hematol, 83:235-241 (2012).
Bardeesy, N., et al., "Smad4 is dispensable for normal pancreas development yet critical in progression and tumor biology of pancreas cancer," Genes Dev., 20:3130-3146 (2006).
Barocas, D.A., et al., "What percentage of patients with newly diagnosed carcinoma of the prostate are candidates for surveillance? An analysis of the CaPSURE database," The Journal of Urology, 180:1330-1334; discussion 4-5 (2008).
Beroukhim, R., et al., "Assessing the significance of chromosomal aberrations in cancer; methodology and application to glioma," Proc. Natl. Acad. Sci. USA, 104:20007-20012 (2007).
Bierie, B., et al., "Tumour microenvironment: TGFbeta: the molecular Jekyll and Hyde of Cancer," Nat. Rev. Cancer, 6:506-520 (2006).
Birney, E., et al., "Ensembl," Nucleic Acids Res., 34:D556-D561 (2006).
Bishoff, J.T., et al., "Prognostic utility of the CCP score generated from biopsy in men treated with prostatectomy," The Journal of Urology (2014), doi: 10.1016/j.juro.2014.02.003.
Bjurlin, M.A., et al., "Standards for prostate biopsy," Curr Opin Urol, 24:155-161 (2014).
Blume-Jensen, P., et al., "Oncogenic kinase signalling," Nature, 411:355-365 (2001).

(56) References Cited

OTHER PUBLICATIONS

Boorjian, S.A., et al., "The impact of discordance between biopsy and pathological Gleason scores on survival after radical prostatectomy," J. Urol., 181:95-104; discussion 104 (2009).
Boyd, L.K., et al., "The complexity of prostate cancer: genomic alterations and heterogeneity," Nat Rev Urol, 9:652-664 (2012).
Brimo, F., et al., "Contemporary grading for prostate cancer: implications for patient care," Eur Urol, 63:892-901 (2013).
Brimo, F., et al., "Immunohistochemical pitfalls in prostate pathology," Human Pathology, 43:313-324 (2012).
Camp, R.L., "Automated subcellular localization and quantification of protein expression in tissue microarrays," Nature Medicine, 8:1323-1327 (2002).
Canton, D.A., et al., "Anchoring proteins encounter mitotic kinases," Cell cycle, Mar. 15, 2013;12(6):863-864, doi: 10.4161/cc.24192. Epub Mar. 5, 2013).
Carter, H.B., et al., "Gleason score 6 adenocarcinoma: should it be labeled as cancer?," J. Clin Oncol, 30:4294-4296 (2012).
Chaib, H., et al., "Activated in prostate cancer: a PDZ domain-containing protein highly expressed in human primary prostate tumors," Cancer Res., 61:2390-2394 (2001).
Chang, H.Y., et al., "Robustness, scalability, and integration of a wound-response gene expression signature in predicting breast cancer survival," Proc. Natl. Acad. Sci. USA, 102:3738-3743 (2005).
Chang, S., et al., "Telomerase-based crisis: functional differences between telomerase activation and ALT in tumor progression," Genes Dev., 17:88-100 (2003).
Chaplet, M., et al., "Expression of dentin sialophosphoprotein in human prostate cancer and its correlation with tumor aggressiveness," International Journal of Cancer, 118(4):850-856 (Feb. 2006).
Chen, M., et al., "Identification of PHLPP1 as a tumor suppressor reveals the role of feedback activation in PTEN-mutant prostate cancer progression," Cancer Cell, 20:173-186 (2011).
Chen, Z., et al., Crucial role of p53-dependent cellular senescence in suppression of Pten-deficient tumorigenesis, Nature, 436:725-730 (2005).
Cheng, S., et al., "Co-development of a companion diagnostic for targeted cancer therapy," N. Biotechnol., 29:682-688 (2012).
Cheville, J.C., et al., "Gene panel model predictive of outcome in men at high-risk of systemic progression and death from prostate cancer after radical retropubic prostatectomy," J. Clin. Oncol., 26:3930-3936 (2008).
Chin, K., et la., "In situ analyses of genome instability in breast cancer," Nat. Genet., 36:984-988 (2004).
Chin, L, et al., "p53 deficiency rescues the adverse effects of telomere loss and cooperates with telomere dysfunction to accelerate carcinogenesis," Cell, 97:527-538 (1999).
Cima, I., et al., "Cancer genetics-guided discovery of serum biomarker signatures for diagnosis and prognosis of prostate cancer," Proc Natl Acad Sci USA, 108:3342-3347 (2011).
Cooperberg, M., et al., "Development and validation of the biopsy-based genomic prostate score (GPS) as a predictor of high grade or extracapsular prostate cancer to improve patient selection for active surveillance," J Urol, 189(Supplement 4S):Abstract 2131 pe873 (2013).
Cooperberg, M.R., et al., "The University of California, San Francisco Cancer of the Prostate Risk Assessment score: a straightforward and reliable preoperative predictor of disease recurrence after radical prostatectomy," J. Urol., 173:1938-1942 (2005).
Cooperberg, M.R., et al., "Time trends and local variation in primary treatment of localized prostate cancer," J. Clin. Oncol., 28:1117-1123 (2010).
Cooperberg, M.R., et al., "Validation of a cell-cycle progression gene panel to improve risk stratification in a contemporary prostatectomy cohort," Journal of clinical oncology: official journal of the American Cancer Society fo Clinical Oncology, 31:1428-1434 (2013).

Corcoran, N.M., et al., "Underestimation of Gleason score at prostate biopsy reflects sampling error in lower volume tumours," BJU Int, 109:660-664 (2012).
Cuzick, J., et al., "Prognostic value of a cell cycle progression signature for prostate cancer death in a conservatively manager needle biopsy cohort," Br J Cancer, 106:1095-1099 (2012).
Cuzick, J., et al., "Prognostic value of an RNA expression signature derived from cell cycle proliferation genes in patients with prostate cancer: a retrospecitve study," The Lancet Oncology, 12:245-255 (2011).
Cuzick, J., et al., "Prognostic value of PTEN loss in men with conservatively managed localised prostate cancer," British Journal of Cancer, 108:2582-2589 (2013).
Cuzick, J., et al., "Transatlantic prostate, prognostic value of an RNA expression signature derived from cell cycle proliferation genes in patients with prostate cancer: a retrospective study," The Lancet Oncology, 12:245-255 (2011).
D'Amico, A.V., et al., "Biochemical outcome after radical prostatectomy, external beam radiation therapy, or interstitial radiation therapy for clinically localized prostate cancer," JAMA, 280:969-974 (1998).
Davies, J.D., et al., "Prostate size as a predictor of Gleason score upgrading in patients with low risk prostate cancer," J. Urol, 186:2221-2227 (2011).
De Long, E.R., et al., "Comparing the areas under two or more correlated receiver operating characteristic curves: a nonparametric approach," Biometrics, 44:837-845 (1988).
Delongchamps, N.B., et al., "Saturation biopsies on autopsied prostates for detecting and characterizing prostate cancer," BJU Int. 103:49-54 (2009).
Depinho, R.A., "The age of cancer," Nature, 408:248-254 (2000).
Dhanasekaran, S.M., et al., "Delineation of prognostic biomarkers in prostate cancer," Nature, 412:822-826 (2001).
Ding, Z., et al., "SMAD4-dependent barrier constrains prostate cancer growth and metastatic progression," Nature 470:269-273 (2011).
Kim, J.H., et al., "Integrative analysis of genomic aberrations associated with prostate cancer progression," Cancer Res., 67:8229-8239 (2007).
Kim, M., et al., "Comparative oncogenomics identifies NEDD9 as a melanoma metastasis gene," Cell, 125:1269-1281 (2006).
Koeneman, K.S., et al., "Telomerase activity, telomere length, and DNA ploidy in prostatic intraepithelial neoplasia (PIN)," J. Urol., 160:1533-1539 (1998).
Kristiansen, G., "Diagnostic and prognostic molecular biomarkers for prostate cancer," Histopathology, 60:125-141 (2012).
Kvale, R., et al., "Concordance between Gleason scores of needle biopsies and radical prostatectomy specimens: a population-based study," BJU Int, 103:1647-1654 (2009).
Kwak, E.L., "Anaplastic lymphoma kinase inhibition in non-small-cell lung cancer," The New England Journal of Medicine, 363:1693-1703 (2010).
Lapointe, J., et al., "Gene expression profiling identifies clinically relevant subtypes of prostate cancer," Proc. Natl. Acad. Sci., USA, 101:811-816 (2004).
Lapointe, J., et al., "Genomic profiling reveals alternative genetic pathways of prostate tumorigenesis," Cancer Res., 67:8504-8510 (2007).
LaTulippe, E., et al., "Comprehensive gene expression analysis of prostate cancer reveals distinct transcriptional programs associated with metastatic disease," Cancer Res., 62:4499-4506 (2002).
Lee, C., et al., "Transforming growth factor-beta in benign and malignant prostate," Prostate, 39:285-290 (1999).
Lee, H.W., et al., "Essential role of mouse telomerase in highly proliferative organs," Nature, 392:569-574 (1998).
Lenhard, B., et al., "Computational framework for transcription factor binding site analysis," Bioinformatics, 18:1135-1136 (2002).
Li, J., et al., "PTEN, a putative protein tyrosine phosphatase gene mutated in human brian, breast, and prostate cancer," Science, 275:1943-1947 (1997).

(56) References Cited

OTHER PUBLICATIONS

Li, R., et al., "High-level Cyclin D1 is Associated with High Gleason Grade and Predicts Worse Biochemical-Free Survival in Prostate Cancer", Journal of Urology, vol. 175, No. 4, Apr. 2006 p. 260.
Liehr, T., et al., "Multicolor FISH methods in current clinical diagnostics," Expert Rev Mol Diagn, 13:251-255 (2013).
Lin, Y., et al., "Telomerase activity in primary prostate cancer," J. Urol., 157:1161-1165 (1997).
Lindsey, J.K., et al., "Choosing among generalized linear models applied to medical data," Stat Med, 17:59-68 (1998).
Linkert, M., et al., "Metadata matters: access to image data in the real world," The Journal of Cell Biology, 189:777-782 (2010).
Loeb, S., et al., "Overdiagnosis and Overtreatment of Prostate Cancer," Eur. Urol. [Epub ahead of print]. 2014.
Majumder, P.K., et al., "A prostatic intraepithelial neoplasia-dependent p27 Kip1 checkpoint induces senescence and inhibits cell proliferation and cancer progression," Cancer Cell, 14:146-155 (2008).
Makarov, D.V., et al., "Biomarkers for prostate cancer," Annu Rev Med, 60:139-151 (2009).
Mansfield, J.R., et al., "Visualization of microscopy-based spectral imaging data from multi-label tissue sections," Curr Protoc Mol Biol., vol. 14 (2008).
Marino, S., et al., "Induction of medulloblastomas in p53-null mutant mice by somatic inactivation of Rb in the external granular layer cells of the cerebellum," Genes Dev., 14:994-1004 (2000).
Markert, E.K., et al., "Molecular classification of prostate cancer using curated expression signatures," Proc Natl Acad Sci USA, 108:21276-21281 (2011).
Maser, R.S., et al., "Chromosomally unstable mouse tumours have genomic alterations similar to diverse human cancers," Nature, 447:966-971 (2007).
Massague, J., et al., "Smad transcription factors," Genes Dev., 19:2783-2810 (2005).
Matys, V., et al., "TRANSFAC: transcriptional regulation, from patterns to profiles," Nucleic Acids Res., 31:374-378 (2003).
Maxwell, K.N., et al., "Cancer treatment according to BRCA1 and BRCA2 mutations," Nature Reviews Clinical Oncology, 9:520-528 (2012).
McKenney, J.K., et al., "The potential impact of reproducibility of Gleason grading in men with early stage prostate cancer managed by active surveillance: a multi-institutional study," J. Urol, 186:465-469 (2011).
McMenamin, M.E., et al., "Loss of PTEN expression in paraffin-embedded in primary prostate cancer correlates with high Gleason score and advanced stage," Cancer Research, 59:4291-4296 (1999).
Meeker, A.K., et al., "Telomere shortening is an early somatic DNA alteration in human prostate tumorigenesis," Cancer Res., 62:6405-6409 (2002).
Mills, I.G., et al., "HOXB13, RFX6 and prostate cancer risk," Nat Genet, 46:94-95 (2014).
Min, J., et al., "An oncogene-tumor suppressor cascade drives metastatic prostate cancer by coordinately activating Ras and nuclear factor-kappaB," Nat. Med., 16:286-294 (2010).
Mohler, J.L., et al., "Prostate Cancer, Version 3.2012: featured updates to the NCCN guidelines," J. Natl Compr Canc Netw, 10:1081-1087 (2012).
Moyer, V.A., "Screening for prostate cancer: U.S. Preventive Services Task Force recommendtion statement," Ann Intern Med, 157:120-134 (2012).
Mullins, J.K., et al., "The impact of anatomical radical retropubic prostatectomy on cancer control: the 30-year anniversary," J Urol, 188:2219-2224 (2012).
Nakagawa, T., et al., "A tissue biomarker panel predicting systemic progression after PSA recurrence post-definitive prostate cancer therapy," PLoS One, 3:e2318 (2008).
NCCN, Prostate cancer early detection, Version 2.2012, Available at www.NCCN.org, Accessed Feb. 14, 2014. (2012).
NCCN. NCCN clinical practice guidelines in oncology: prostate cancer. Version 3.2012. Available at: http://www.nccn.org/professionals/physician_gls/f_guidelines.asp#prostate_detection. Accessed Feb. 18, 2014.
NCCN. Prostate cancer early detection. Version 2.2012. Available at: http://www.nccn.org/professionals/physician_gls/f_guidelines.asp#prostate_detection. Accessed Feb. 18, 2014.
O'Hagan, R.C., et al., "Telomere dysfunction provokes regional amplification and deletion in cancer genomes," Cancer Cell, 2:149-155 (2002).
Ongenaert, M., et al., "PubMeth: a cancer methylation database combining text-mining and expert annotation," Nucleic Acids Res., 36:D842-D846 (2008).
Ouyang, X., et al., "Activator protein-1 transcription factors are associated with progression and recurrence of prostate cancer," Cancer Research, 68(7):2132-2144 (Apr. 2008).
Padua, D., et. al., "TGFbeta primes breast tumors for lung metastasis seeding through angiopoietin-like 4," Cell, 133:66-77 (2008).
Pardali, K., et al., "Actions of TGF-beta as tumor suppressor and pro-metastatic factor in human cancer," Biochim. Biophys. Acta, 1775:21-62 (2007).
Park, et al., "Evaluation of normalization methods for microarray date," BMC Bioinformatics, 4:33 (2003).
Pencina, M.J., et al., "Evaluating the added predictive ability of a new marker: from area under the ROC curve to reclassification and beyond," Stat Med, 27:157-172 (2008).
Pierorazio, P.M., et al., "Prognostic Gleason grade grouping: data based on the modified Gleason scoring system," BJU Int, 111:753-760 (2013).
Pinthus, J.H., et al., "Prostate cancers scored as Gleason 6 on prostate biopsy are frequently Gleason 7 tumors at radical prostatectomy: implication on outcome," J. Urol, (2006) 176:979-984: discussion 84.
Porten, S.P., et al., "Changes in prostate cancer grade on serial biopsy in men undergoing active surveillance," J. Clin Oncol., 29:2795-2800 (2011).
Welch, H.G., et al., "Prostate cancer diagnosis and treatment after the introduction of prostate-specific antigen screening: 1986-2005," J. Natl Cancer Inst, 101:1325-1329 (2009).
Wilt, T.J., et al., "Systematic Review: comparative effectiveness and harms of treatments for clinically localized prostate cancer," Ann Intern Med, 148:435-448 (2008).
Wu, X., et al., "Generation of a prostate epithelial cell-specific Cre transgenic mouse model for tissue-specific gene ablation," Mechn. Dev., 101:61-69 (2001).
Xu, J., et al., "Review of the in vivo functions of the p160 steroid receptor coactivator family," Mol. Endocrinol., 17:1681-1692 (2003).
Yan, P., et al., "An agarose matrix facilitates sectioning of tissue microarray blocks," The Journal of Histochemistry and Cytochemistry: Official Journal of the Histochemistry Society, 55:21-24 (2007).
Yang, J.Y., et al., "A new fork for clinical application: targeting forkhead transcription factors in cancer," Clinical Cancer Research: an Official Journal of the American Association for Cancer Research, 15:752-757 (2009).
Yang, Y.A., et al., "EZH2, an epigenetic driver of prostate cancer," Protein Cell, 4:331-341 (2013).
Yoshimoto, M., et al., "FISH analysis of 107 prostate cancers shows that PTEN genomic deletion is associated with poor clinical outcome," British Journal of Cancer, 97:678-685 (2007).
Yu, Y.P., et al., "Gene expression alterations in prostate cancer predicting tumor aggression and preceding development of malignancy," J. Clin. Oncol., 22:2790-2799 (2004).
Yuan, T.L., et al., "P13K pathway alterations in cancer: variations on a theme," Oncogene, 27:5497-5510 (2008).
Zavadil, J., et al. "TGF-beta and epithelial-to-mesenchymal transitions," Oncogene, 24:5764-5774 (2005).
Zender, L., et al., "Identification and validation of oncogenes in liver cancer using an integrative oncogenomic approach," Cell, 125:1253-1267 (2006).

(56) References Cited

OTHER PUBLICATIONS

Zhang, W., et al., "Telomerase activity in prostate cancer, prostatic intraepithelial neoplasia, and benign prostatic epithelium," Cancer Res. 58:619-621 (1998).
Zheng, H., et al., "p53 and Pten control neural and glicoma stem-progenitor cell renewal and differentiation," Nature, 455:1129-1133 (2008).
Hao et al., "Elevation of Expression of Smads 2, 3, and 4, Decorin and TGF-b in the Chronic Phase of Myocardial Infarct Scar Healing", J Mol Cell Cardiol 31, 667-678 (1999).
Li et al., Smad2 Overexpression Enhances Smad4 Gene Expression and Suppresses CBFA1 Gene Expression in Osteoblastic Osteosarcoma ROS17/2.8 Cells and Primary Rat Calvaria Cells, The Journal of Biological Chemistry, vol. 273, No. 47, pp. 31009-31015 (1996).
Ding, Z., et al., "SMAD4-dependent barrier constrains prostate cancer growth and metastatic progression," Nature, 470:269-273 (2011).
Ding, Z., et al., "Telomerase reactivation following telomere dysfunction yeilds murine prostate tumors with bone metastases," Cell, 148:896-907 (2012).
Donovan, M.J., et al., "Systems pathology approach for the prediction of prostate cancer progression after radical prostatectomy," Journal of Clinical Oncology: Official Journal of the American Society of Clinical Oncology, 26:3923-3929 (2008).
Eggener, S.E., et al., "Predicting 15-year prostate cancer specific mortality after radical prostatectomy," J Urol, 185:869-875 (2011).
Eichler, K., et al., "Diagnostic value of systematic biopsy methods in the investigation of prostate cancer: a systematic review," J. Urol., 175:1605-1612 (2006).
Epstein, J.I., "An update of the Gleason grading system," J. Urol, 183:433-440 (2010).
Epstein, J.I., et al., "The 2005 International Society of Urological Pathology (ISUP) Concensus Conference on Gleason Grading of Prostatic Carcinoma," Am J. Surg Pathol, 29:1228-1242 (2005).
Epstein, J.I., et al., "Upgrading and downgrading of prostate cancer from biopsy to radical prostatectomy: incidence and predictive factors using the modified Gleason grading system and factoring in tertiary grades," Eur Urol, 61:1019-1024 (2012).
Faca, V.M., et al., "A mouse to human search for plasma proteome changes associated with pancreatic tumor development," PLoS. Med., 5:e123 (2008).
Farazi, P.A., et al., "Cooperative interactions of p53 mutation, telomere dysfunction, and chronic liver damage in hepatocellular carcinoma progression," Cancer Res., 66:4766-4773 (2006).
Feldmann, G., et al., "Molecular genetics of pancreatic intraepithelial neoplasia," J. Hepatobiliary. Pancreat. Surg., 14:224-232 (2007).
Flachbartova, Z., et al., "Mortalin—a multipotent chaperone regulating cellular processes ranging from viral infection to neurodegeneration," Acta Virol, 57:3-15 (2013).
Forbes, S.A., et al., "COSMIC (the Catalogue of Somatic Mutations in Cancer): a resource to investigate acquired mutations in human cancer," Nucleic Acids Res., 38:D652-D657 (2010).
Forbes, S.A., et al., "COSMIC: mining complete cancer genomes in the Catalogue of Somatic Mutations in Cancer," Nucleic Acids Res., 39:D945-D950 (2011).
Forootan, S., et al., "Prognostic significance of osteopontin expression in human prostate cancer," International Jounal of Cancer, 118(9):2255-2261 (May 2006).
Gentleman, R.C., et al., "Bioconductor: open software development for computational biology and bioinformatics," Genome Biol., 5:R80 (2004).
Glinsky, G.V., et al., "Gene expression profiling predicts clinical outcome of prostate cancer," J. Clin. Invest., 113:913-923 (2004).
Gonzalez-Suarez, E., et al., "Telomerase-deficient mice with short telomeres are resistant to skin tumorigenesis," Nat. Genet., 26:114-117 (2000).
Goodman, M., et al., "Frequency and determinants of disagreement and error in gleason scores: a population-based study of prostate cancer," Prostate, 72:1389-1398 (2012).
Gopalan, A., et al., "TMPRSS2-ERG gene fusion is not associated with outcome in patients treated by prostatectomy," Cancer Res, 69:1400-1406 (2009).
Gorlov, I.P., et al., "Prioritizing genes associated with prostate cancer development," BMC Cancer, 10:599 (2010).
Graefen, M., et al., "Reasonable delay of surgical treatment in men with localized prostate cancer-impact on prognosis?," Eur Urol, 47:756-760 (2005).
Graff, J.R., et al., "eIF4E activation is commonly elevated in advanced human prostate cancers and significantly related to reduced patient survival," Cancer Res., 69:3866-3873 (2009).
Guo, Y., et al., "Loss of the cyclin-dependent kinase inhibitor p27(Kip1) protein in human prostate cancer correlates with tumor grade," Clin. Cancer Res., 3:2269-2274 (1997).
Hahn, W.C., et al., "Inhibition of telomerase limits the growth of human cancer cells," Nat. Med., 5:1164-1170 (1999).
Heidenreich, A., et al., "EAU guidelines on prostate cancer, part 1: screening, diagnosis, and local treatment with curative intent-update 2013," Eur Urol, 65:124-137 (2014).
Hicks, D.G., "The challenge and importance of standardizing pre-analytical variables in surgical pathology specimens for clinical care and translational research," Biotech. Histochem., 87:14-17 (2012).
Ho Sui, S.J., et al.,"oPOSSUM: identification of over-represented transcription factor binding sites in co-epxressed genes," Nucleic Acids Res., 33:3154-3164 (2005).
Holmstrom, B., et al., "Outcome of primary versus deferred radical prostatectomy in the National Prostate Cancer Register of Sweden Follow-Up Study," The Journal of Urology, 184:1322-1327 (2010).
Holzbeierlein, J., et al., "Gene expression analysis of human prostate carcinoma during hormonal therapy identifies androgen-responsive genes and mechanisms of therapy resistance," Am. J. Pathol., 164:217-227 (2004).
Holzer, T.R., et al., "Ischemic time impacts biological integrity of phospho-proteins in PI3K/Akt, Erk/MAPK, and p38 MAPK signaling networks," Anticancer Research, 31:2073-2081 (2011).
Howrey, B.T., et al., "The impact of PSA screening on prostate cancer mortality and overdiagnosis of prostate cancer in the United States," J Gerontol A Biol Sci Med Sci, 68:56-61 (2013).
Hu, G., et al., "The multifaceted role of MTDH/AEG-1 in cnacer progression," Clin Cancer Res, 15:5615-5620 (2009).
Hudson, T.J., "Genome variation and personalized cancer medicine," J. Intern. Med., 274:440-450 (2013).
Hunter, T., "Signaling—2000 and Beyond," Cell, 100:113-117 (2000).
Ijpma, A.S., et al., "Short telomeres induce a DNA damage response in *Saccharomyces cerevisiae*," Mol. Biol. Cell, 14:987-1001 (2003).
International Preliminary Report on Patentability and Written Opinion, International Application No. PCT/US2009/050885, mailed on Jan. 27, 2011.
International Preliminary Report on Patentability and Written Opinion, International Application No. PCT/US2012/044268, date of mailing Jan. 7, 2014.
International Search Report, International Application No. PCT/US12/44268, date of mailing, Dec. 7, 2012.
International Search Report, International Application No. PCT/US2009/050885, mailing date Jun. 9, 2010.
Invitation to Pay Additional Fees, International Application No. PCT/US12/44268, date of mailing, Sep. 26, 2012.
Irizarry, R.A., et al., "Summaries of Affymetrix GeneChip probe level data," Nucleic Acids Res., 31:e15 (2003).
Irshad, S., et al., "A molecular signature predictive of indolent prostate cancer," Sci Transl Med, 5:3006408 (2013).
Jaskelioff, M., et al., "Telomerase deficiency and telomere dysfunction inhibit mammary tumors induced by polyomavirus middle T oncogene.,"Oncogene, 28:4225-4236 (2009).
Jemel, A., et al., "Cancer Statistics, 2008," CA Cancer J. Clin., 58:71-96 (2008).

(56) References Cited

OTHER PUBLICATIONS

Jenkins, R.B., et al., "Detection of c-myc oncogene amplification and chromosomal anomalies in metastic prostatic carcinoma by fluorescence in situ hybridization," Cancer Res. 57:524-531 (1997).
Jonkers, J., et al., "Synergistic tumor suppressor activity of BRCA2 and p53 in a conditional mouse model for breast cancer," Nat. Genet., 29:418-425 (2001).
Kaklamani, V., "A genetic signature can predict prognosis and response to therapy in breast cancer: Oncotype DX," Expert Rev. Mol. Diagn., 6:803-809 (2006).
Kallakury, B., et al., "Telomerase activity in human benign prostate tissue and prostatic adenocarcinomas," Diagn. Mol. Pathol., 6:192-198 (1997).
Khoo, C.M., et al., "Ink4a/Arf tumor suppressor does nto modulate the degenerative conditions or tumor spectrum of the telomerase-deficient mouse," Proc. Natl. Acad. Sci. USA, 104:3931-3936 (2007).
Brooke et al., "FUS/TLS Is a Novel Mediator of Androgen-Dependent Cell-Cycle Progression and Prostate Cancer Growth", Cancer Research, vol. 71, No. 3, pp. 914-924, Dec. 17, 2010.
Giordano et al., "Organ-Specific Molecular Classification of Primary Lung, Colon, and Ovarian Adenocarcinomas Using Gene Expression Profiles", American Journal of Pathology, 159(4):1231-1238 (Oct. 2001).
International Search Report and Written Opinion from International Application No. PCT/US2014/029158 dated Feb. 13, 2015.
Vanaja et al., "PDLIM4 Repression by Hypermethylation as a Potential Biomarker for Prostate Cancer", Clinical Cancer Research, 12(4):1128-1136; Feb. 15, 2006.

* cited by examiner

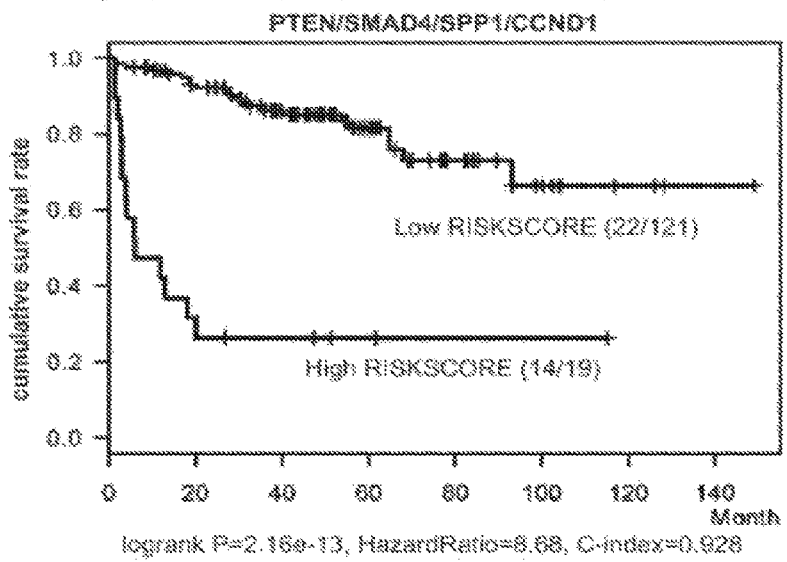

FIG 15A  The previous 4-gene signature (SMAD4/PTEN/CCND1/SPP1) can significantly dichotomize prostate cancer cases into low versus high risk groups for BCR in Taylor et al. dataset (2010):

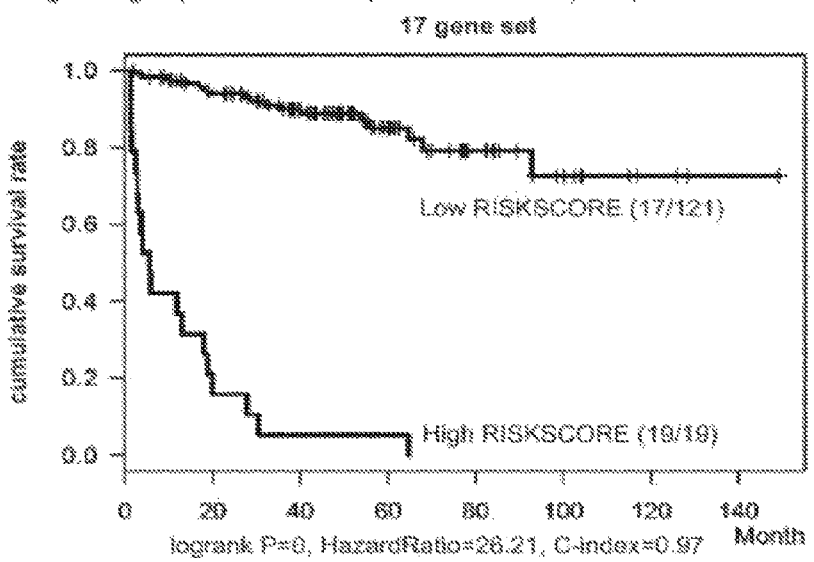

FIG 15B  The 17 gene set (DNAJC15, KIF5B, LECT1, DSG2, ACAA2, ASAP1, LMO7, SVIL, DSC2, PCDH9, SMAD7, WDR7, LAMA3, PCDH8, MKX, M6R1, POLR2K) can significantly dichotomize prostate cancer cases into low versus high risk groups for BCR in Taylor et al. dataset (2010):

C  The combined new 17 gene set can significantly enhance the sensitivity and specificity of SMAD4/PTEN/CCND1/SPP1 dichotomize prostate cancer cases into low versus high risk groups for BCR in Taylor *et al.* dataset (2010):

A   The previous 4-gene signature (SMAD4/PTEN/CCND1/SPP1) can significantly dichotomize prostate cancer cases into low versus high risk groups for BCR in Glinsky et al., (2004):

B   The 17 gene set can significantly dichotomize prostate cancer cases into low versus high risk groups for BCR in Glinsky dataset (2004):

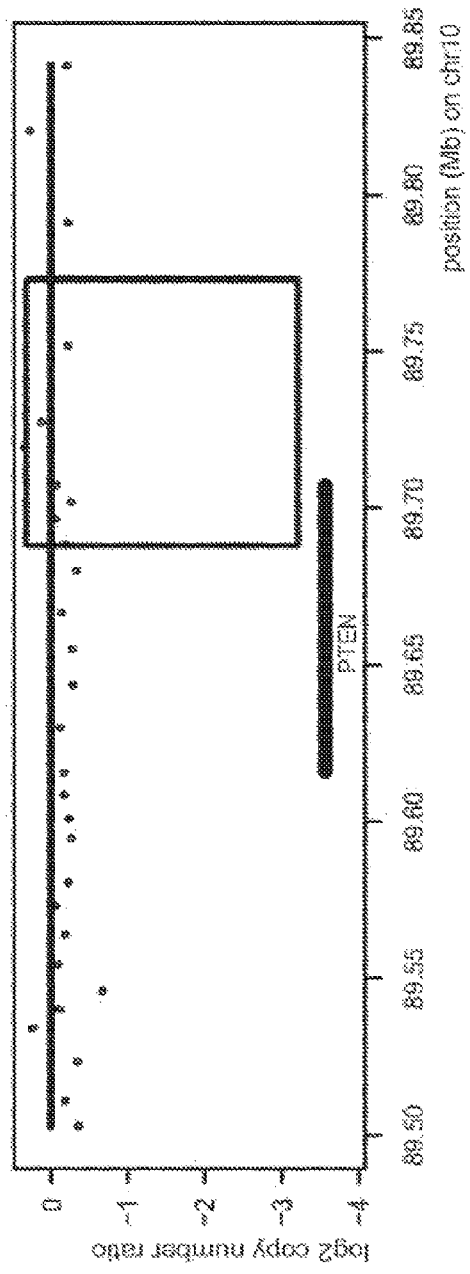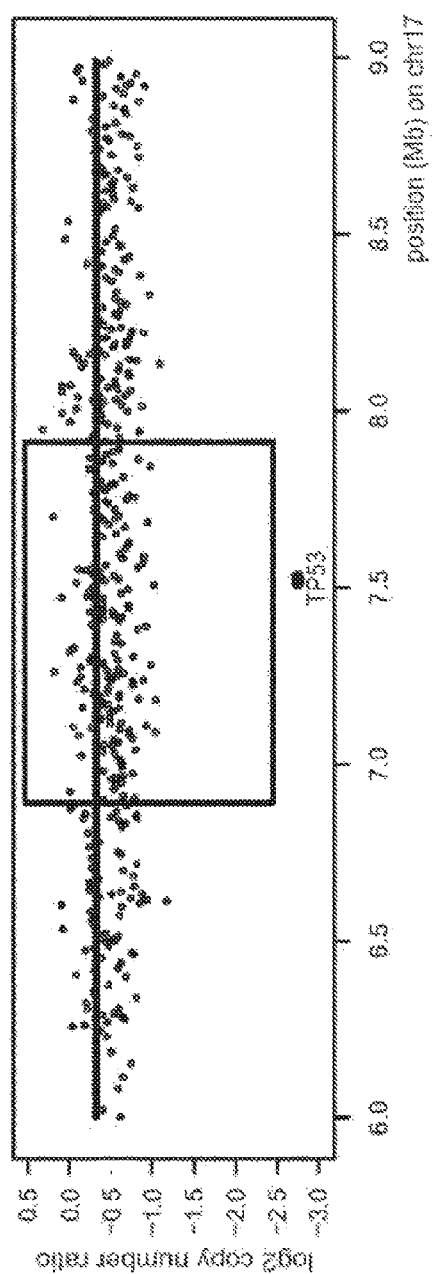
FIG. 31A
FIG. 31B

A  New gene set of ATP5A1/ATP6V1C1/CUL2/CYC1/DCC/ERCC3/MBD2/
   MTERF/PARD3/PTK2/RBL2/SMAD2/SMAD4/SMAD7:

N=79, HR=4.4, logrank test: raw.P=9.89e-05, adj.P=0.00623, C=0.806551

B  PTEN/SMAD4/SPP1/CCND1:

N=79, HR=3.7, logrank test: raw.P=0.00017, adj.P=0.0107, C=0.809322

SIGNATURES AND DETERMINANTS ASSOCIATED WITH PROSTATE CANCER PROGRESSION AND METHODS OF USE THEREOF

CROSS REFERENCES TO OTHER APPLICATIONS

This application is a national stage application under 35 U.S.C. 371 of International Application No. PCT/US2012/044268 (now pending), filed Jun. 26, 2012, which claims priority from U.S. Provisional Application 61/501,536, filed Jun. 27, 2011, and from U.S. Provisional Application 61/582,787, filed Jan. 3, 2012. The disclosures of those applications are incorporated by reference in their entirety.

GOVERNMENT INTEREST

This invention was made with government support under grant numbers U01CA141508, R01CA084628, CA084313 awarded by the National Institutes of Health and W81XWH-07-PCRP-IDA awarded by the Department of The Army. The government has certain rights in the invention.

FIELD OF THE INVENTION

The present invention relates generally to the identification of biological signatures associated with and genetic determinants effecting cancer and methods of using such biological signatures and determinant in the screening, prevention, diagnosis, therapy, monitoring, and prognosis of cancer. The invention further relates to genetically engineered mouse models of metastatic prostate cancer.

BACKGROUND OF THE INVENTION

Prostate cancer (PCA) is the most frequent male cancer and a leading cause of cancer death in US. Most elderly men harbor prostatic neoplasia with the vast majority of cases remaining localized and indolent without need for therapeutic intervention.

Current methods of stratifying tumors to predict outcome are based on clinicopathological factors including Gleason grade, PSA, and tumor stage. Although these formulae are helpful, they do not fully predict outcome and importantly are not reliably linked to the most meaningful clinical endpoints of risk of metastatic disease and PCA-specific death. This unmet medical need has fueled efforts to define the genetic and biological bases of PCA progression with the goals of identifying biomarkers capable to assigning progression risk and providing opportunities for targeted interventional therapies. Genetic studies of human PCA has identified a number of signature events including PTEN tumor suppressor inactivation and ETS family translocation and dysregulation, as well as many other important genetic and/or epigenetic alterations including Nkx3.1, c-Myc and SPINK. Global molecular analyses have also identified an array of potential recurrence/metastasis biomarkers, such as ECAD, AIPC, Pim-1 Kinase, hepsin, AMACR, and EZH2. However, the intense heterogeneity of human PCA has limited the utility of single biomarkers in the clinical setting, thus prompting more comprehensive transcriptional profiling studies to define prognostic multi-gene biomarker panels or signatures. Furthermore, the clinical utility of these predictive signatures have remained uncertain due to the inherent noise and context-specific nature of transcriptional networks and the extreme instability of cancer genomes with myriad bystander genetic and epigenetic events producing significant disease heterogeneity. These factors have conspired to impede the identification of biomarkers capable of accurately assigning risk of disease progression. Accordingly, a need exists for more accurate models of human cancer that can be used together with complex human datasets to identify robust biomarkers that can be used to predict the occurrence and the behavior of cancer, particularly at an early stage.

In this invention, we have generated new engineered mouse models of prostate cancer and identified genes and pathways associated with prostate cancer progression. This model, coupled with comparison of human data and functional validation, has led to discovery of many new therapeutic targets as well as prognostic markers with strong clinical relevance in metastatic cancer.

SUMMARY OF THE INVENTION

The present invention relates in part to the discovery that certain biological markers (referred to herein as "DETERMINANTS"), such as proteins, nucleic acids, polymorphisms, metabolites, and other analytes, as well as certain physiological conditions and states, are present or altered which endow these neoplasm with an increased risk of recurrence and progression to metastatic cancer.

The invention provides a method for predicting prognosis of a cancer patient. In this method, one obtains a tissue sample from the patient, and measures the levels of two or more DETERMINANTS selected from Table 2, 3 or 5 (see below) in the sample, wherein the measured levels are indicative of the prognosis of the cancer patient. In some embodiments, the levels of two, three, four, five, six, seven, eight, nine, ten, fourteen, fifteen, sixteen, seventeen, eighteen, nineteen, twenty, thirty, forty, fifty, or more DETERMINANTS are measured.

In some embodiments, the prognosis may be that the patient is at a low risk of having metastatic cancer or recurrence of cancer. In other embodiments, the prognosis may be that the patient is at a high risk of having metastatic cancer or recurrence of cancer. In these embodiments, the patient may have melanoma, breast cancer, prostate cancer, or colon cancer.

In some embodiments, an increased risk of cancer recurrence or developing metastatic cancer in the patient is determined by measuring a clinically significant alteration in the levels of the selected DETERMINANTS in the sample. Alternatively, an increased risk of developing metastatic prostate cancer in the patient is determined by comparing the levels of the selected DETERMINANTS to a reference value. In some embodiments, the reference value is an index.

The invention also provides a method for analyzing a tissue sample from a cancer patient. In this method, one obtains the tissue sample from the patient, measures the levels of two or more DETERMINANTS selected from Table 2, 3 or 5 in the sample.

This invention additionally provides a method for identifying a cancer patient in need of adjuvant therapy. In this method, one obtains a tissue sample from the patient, measures the levels of two or more DETERMINANTS selected from Table 2, 3 or 5 in the sample, wherein the measured levels indicate that the patient is in need of adjuvant therapy. For example, the adjuvant therapy may be selected from the group consisting of radiation therapy, chemotherapy, immunotherapy, hormone therapy, and targeted therapy. In some embodiments, the patient has been subjected to a standard of care therapy. In some embodiments, the targeted therapy targets another component of a signaling pathway in which one or more of the selected DETERMINANTS is a component. In alternative embodiments, the targeted therapy targets one or more of the selected DETERMINANTS.

This invention also provides a further method for treating a cancer patient. In this method, one measures the levels of two or more DETERMINANTS selected from Table 2, 3 or 5 in a tissue sample from the patient, and treats the patient with adjuvant therapy if the measured levels indicate that the patient is at a high risk of having metastatic cancer or recurrence of cancer. In some embodiments, the adjuvant therapy is an experimental therapy.

This invention additionally provides a method for monitoring the progression of a tumor in a patient. In this method, one obtains a tumor tissue sample from the patient; and measures the levels of two or more DETERMINANTS selected from Table 2, 3 or 5 in the sample, and wherein the measured levels are indicative of the progression of the tumor in the patient. In some embodiments, a clinically significant alteration in the measured levels between the tumor tissue sample taken form the patient at two different time points is indicative of the progression of the tumor in the patient. In some embodiments, the progression of a tumor in a patient is measured by detecting the levels of the selected DETERMINANTS in a first sample from the patient taken at a first period of time, detecting the levels of the selected DETERMINANTS in a second sample from the patient taken at a second period of time and then comparing the levels of the selected DETERMINANTS to a reference value. In some aspects, the first sample is taken from the patient prior to being treated for the tumor and the second sample is taken from the patient after being treated for the tumor.

The invention also provides a method for monitoring the effectiveness of treatment or selecting a treatment regimen for a recurrent or metastatic cancer in a patient by measuring the levels of two or more DETERMINANTS selected from Table 2, 3, or 5 in a first sample from the patient taken at a first period of time and optionally measuring the level of the selected DETERMINANTS in a second sample from the patient taken at a second period of time. The levels of the selected DETERMINANTS detected at the first period of time are compared to the levels detected at the second period of time or alternatively a reference value. The effectiveness of treatment is monitored by a change in the measured levels of the selected DETERMINANTS from the patient.

The invention also provides a kit for measuring the levels of two or more DETERMINANTS selected from Table 2, 3 or 5. The kit comprises reagents for specifically measuring the levels of the selected DETERMINANTS. In some embodiments, the reagents are nucleic acid molecules. In these embodiments, the nucleic acid molecules are PCR primers or hybridizing probes. In alternative embodiments, the reagents are antibodies or fragments thereof, oligonucleotides, or aptamers.

This invention also provides a method for treating a cancer patient in need thereof. In this method, one measures the level of a DETERMINANT selected from Table 2, 3 or 5, and administers an agent that modulates the level of the selected DETERMINANT. In some embodiments, the administered agent may be a small molecule modulator. In some embodiments, the administered agent may be a small molecule inhibitor. In some embodiments, the administered agent may be, for example, siRNA or an antibody or fragment thereof. In some embodiments, the selected DETERMINANT is AGPAT6, ATAD2, ATP6V1C1, AZIN1, COX6C, CPNE3, DPYS, EBAG9, EFR3A, EXT1, GRINA, HRSP12, KIAA0196, MAL2, MTDH, NSMCE2, NUDCD1, PDE7A, POLR2K, POP1, PTK2, SPAG1, SQLE, SRI, STK3, TAF2, TGS1, TMEM65, TMEM68, TOP1MT, UBR5, WDYHV1, WWP1, or YWHAZ. In some embodiments, the selected DETERMINANT is AGPAT6, AZIN1, CPNE3, DPYS, NSMCE2, NUDCD1, SRI, TGS1, UBR5, or WDYHV1.

This invention also provides a method of identifying a compound capable of reducing the risk of cancer recurrence or development of metastatic cancer. In this method, one provides a cell expressing a DETERMINANT selected from Table 2, 3 or 5, contacts the cell with a candidate compound, and determines whether the candidate compound alters the expression or activity of the selected DETERMINANT, whereby the alteration observed in the presence of the compound indicates that the compound is capable of reducing the risk of cancer recurrence or development of metastatic cancer.

This invention also provides a method of identifying a compound capable of treating cancer. In this method, one provides a cell expressing a DETERMINANT selected from Table 2, 3 or 5, contacts the cell with a candidate compound, and determines whether the candidate compound alters the expression or activity of the selected biomarker, whereby the alteration observed in the presence of the compound indicates that the compound is capable of treating cancer.

This invention also provides a method of identifying a compound capable of reducing the risk of cancer occurrence or development of cancer. In this method, one provides a cell expressing a DETERMINANT selected from Table 2, 3 or 5, contacts the cell with a candidate compound, and determines whether the candidate compound alters the expression or activity of the selected biomarker, whereby the alteration observed in the presence of the compound indicates that the compound is capable of reducing the risk of cancer occurrence or development of cancer.

According to the invention, a DETERMINANT that can be used in the methods or kits provided by the invention may be selected from the DETERMINANTS listed on Table 2, Table 3, or Table 5. In some embodiments, the selected DETERMINANTS may comprise one or more of MAP3K8, RAD21, and TUSC3. In some embodiments, the selected DETERMINANTS may comprise one or more of ATP5A1, ATP6V1C1, CUL2, CYC1, DCC, ERCC3, MBD2, MTERF, PARD3, PTK2, RBL2, SMAD2, SMAD4, SMAD7, DNAJC15, KIF5B, LECT1, DSG2, ACAA2, ASAP1, LMO7, SVIL, DSC2, PCDH9, WDR7, LAMA3, PCDH8, MKX, MSR1, and POLR2K. In some embodiments, the selected DETERMINANTS may comprise one or more of ATP5A1, ATP6V1C1, CUL2, CYC1, DCC, ERCC3, MBD2, MTERF, PARD3, PTK2, RBL2, SMAD2, SMAD4, and SMAD7. In some embodiments, the selected DETERMINANTS may comprise one or more of DNAJC15, KIF5B, LECT1, DSG2, ACAA2, ASAP1, LMO7, SVIL, DSC2, PCDH9, SMAD7, WDR7, LAMA3, PCDH8, MKX, MSR1, and POLR2K. In some embodiments, the selected DETERMINANTS comprise one or more of DNAJC15, KIF5B, LECT1, DSG2, ACAA2, ASAP1, and LMO7. In some embodiments, the selected DETERMINANTS comprise one or more of SVIL, DSC2, PCDH9, SMAD7, WDR7, LAMA3, PCDH8, MKX, MSR1, and POLR2K. In various embodiments, the methods or the kits provided by the invention further comprise measuring the levels of one or more of PTEN, cyclin D1, SMAD4, and SPP1. In some embodiments, the selected DETERMINANTS comprise two or more of ATP5A1, ATP6V1C1, CUL2, CYC1, DCC, ERCC3, MBD2, MTERF, PARD3, PTK2, RBL2, SMAD2, SMAD4, SMAD7, DNAJC15, KIF5B, LECT1, DSG2, ACAA2, ASAP1, LMO7, SVIL, DSC2, PCDH9, WDR7, LAMA3, PCDH8, MKX, MSR1, POLR2K, PTEN, cyclin D1 and SPP1. See, for example, Table 7 for two-DETERMINANT combination.

In another aspect of the invention, the selected DETERMINANTS are associated with DNA gain or the selected DETERMINANTS have a clinically significant increase in the measured levels. For example, the DETERMINANTS are selected from 1) the group consisting of DETERMINANTS 1-300 of Table 2; or 2) the group consisting of DETERMINANTS 8, 9, 12, 13, 18-20, 22, 23, 34, 41, 48-50, 56, 64, 65, 70, 72-79, 81, 84, 87, 88, 102, 104, 114, 124, 134, 139, 154, 169-172, 185, 186, 193, 196, 199, 203, 204, 207, 209, 212, 217, 218, 221, 245, 247, 248, 254, 257, 260, 263, 264, 268, 269, 277, 279-281, 283, 284, 286, 287, 292, 294, and 296-298 of Table 3; or 3) the group consisting of DETERMINANTS 9, 12, 18, 19, 22, 23, 41, 56, 70, 72, 75, 76, 77, 87, 102, 114, 134, 139, 171, 172, 185, 196, 199, 207, 209, 217, 221, 247, 248, 260, 263, 264, 268, 269, 279, 296, and 298 of Table 5.

In another aspect of the invention, the selected DETERMINANTS are associated with DNA loss or the selected DETERMINANTS have a clinically significant decrease in the measured levels. For example, the DETERMINANTS are selected from 1) the group consisting of DETERMINANTS 301-741 of Table 2; 2) DETERMINANTS 303, 308, 310, 312, 313, 316, 319, 322, 324, 326, 328, 329, 343, 353, 360, 368, 371, 376, 378, 384, 386, 389, 391, 392, 398, 400, 403, 404, 405, 406, 407, 412, 416, 421, 422, 424, 430, 432, 435, 437, 440, 445, 446, 451, 459, 466, 468, 469, 470, 471, 473, 477, 481, 482, 484, 485, 486, 487, 490, 492, 493, 494, 496, 498, 502, 503, 505, 506, 509, 514, 515, 520, 521, 522, 525, 526, 527, 530, 533, 534, 536, 542, 547, 552, 553, 554, 555, 563, 570, 580, 582, 584, 585, 586, 587, 589, 592, 594, 595, 599, 600, 603, 604, 612, 614, 616, 617, 622, 625, 628, 629, 632, 637, 642, 648, 651, 652, 654, 655, 656, 658, 659, 660, 661, 662, 666, 669, 670, 671, 675, 676, 680, 681, 682, 685, 687, 689, 690, 691, 692, 695, 711, 718, 719, 722, 723, 724, 725, 730, 735, and 740 of Table 3; or 3) DETERMINANTS 308, 312, 319, 322, 324, 326, 328, 329, 343, 371, 378, 386, 389, 391, 392, 400, 416, 422, 424, 440, 445, 466, 471, 481, 482, 484, 490, 492, 493, 494, 496, 498, 503, 505, 506, 514, 521, 522, 525, 526, 527, 533, 542, 554, 555, 570, 582, 584, 585, 586, 592, 594, 595, 612, 617, 628, 629, 637, 642, 648, 651, 658, 659, 660, 661, 675, 680, 681, 685, 687, 692, 718, 719, 723, 730, and 735 of Table 5.

In some embodiments, at least one of the selected DETERMINANTS is associated with REACTOME TGF-beta signaling pathway. In some embodiments, at least one of the selected DETERMINANTS is associated with BIOCARTA TGF-beta signaling pathway. In some embodiments, at least one of the selected DETERMINANTS is associated with KEGG TGF-beta signaling pathway. In some embodiments, at least one of the selected DETERMINANTS is associated with KEGG colorectal cancer pathway. In some embodiments, at least one of the selected DETERMINANTS is associated with KEGG Adherens junction pathway. In some embodiments, at least one of the selected DETERMINANTS is associated with REACTOME RNA Polymerase I/III and mitochondrial transcription pathway. In some embodiments, at least one of the selected DETERMINANTS is associated with KEGG cell cycle pathway. In some embodiments, at least one of the selected DETERMINANTS is associated with KEGG oxidative phosphorylation pathway. In some embodiments, at least one of the selected DETERMINANTS is associated with KEGG pathways in cancer.

In another aspect of the invention, at least one of the selected DETERMINANTS is associated with DNA gain and at least one of the selected DETERMINANTS is associated with DNA loss. In some embodiments, at least one of the selected DETERMINANTS has a clinically significant increase in the measured levels and at least one of the selected DETERMINANTS has a clinically significant decrease in the measured levels.

The levels of the selected DETERMINANTS may be measured electrophoretically or immunochemically. For example, the levels of the selected DETERMINANTS are detected by radioimmunoassay, immunofluorescence assay or by an enzyme-linked immunosorbent assay. Optionally, the DETERMINANTS are detected using non-invasive imaging technology.

In some embodiments, the levels of the selected DETERMINANTS are determined based on the DNA copy number alteration. In these embodiments, the DNA copy number alteration of the selected DETERMINANT indicates DNA gain or loss. In some embodiments, the RNA transcript levels of the selected DETERMINANTS are measured. In certain embodiments, the RNA transcript levels may be determined by microarray, quantitative RT-PCR, sequencing, nCounter® multiparameter quantitative detection assay (NanoString), branched DNA assay (e.g., Panomics QuantiGene® Plex technology), or quantitative nuclease protection assay (e.g., Highthroughput Genomics qNPA™). nCounter® system is developed by NanoString Technology. It is based on direct multiplexed measurement of gene expression and capable of providing high levels of precision and sensitivity (<1 copy per cell) (see 72.5.117.165/applications/technology/). In particular, the nCounter® assay uses molecular "barcodes" and single molecule imaging to detect and count hundreds of unique transcripts in a single reaction. Panomics QuantiGene® Plex technology can also be used to assess the RNA expression of DETERMINANTS in this invention. The QuantiGene® platform is based on the branched DNA technology, a sandwich nucleic acid hybridization assay that provides a unique approach for RNA detection and quantification by amplifying the reporter signal rather than the sequence (Flagella et al., *Analytical Biochemistry* (2006)). It can reliably measure quantitatively RNA expression in fresh, frozen or formalin-fixed, paraffin-embedded (FFPE) tissue homogenates (Knudsen et al., *Journal of Molecular Diagnostics* (2008)). In some embodiments, the protein levels of the selected DETERMINANTS are measured. In certain embodiments, the protein levels may be measured, for example, by antibodies, immunohistochemistry or immunofluorescence. In these embodiments, the protein levels may be measured in subcellular compartments, for example, by measuring the protein levels of DETERMINANTS in the nucleus relative to the protein levels of the DETERMINANTS in the cytoplasm. In some embodiments, the protein levels of DETERMINANTS may be measured in the nucleus and/or in the cytoplasm.

In some embodiments, the levels of the DETERMINANTS may be measured separately. Alternatively, the levels of the DETERMINANTS may be measured in a multiplex reaction.

In some embodiments, the noncancerous cells are excluded from the tissue sample. In some embodiments, the tissue sample is a solid tissue sample, a bodily fluid sample, or circulating tumor cells. In some embodiments, the bodily fluid sample may be blood, plasma, urine, saliva, lymph fluid, cerebrospinal fluid (CSF), synovial fluid, cystic fluid, ascites, pleural effusion, interstitial fluid, or ocular fluid. In some embodiments, the solid tissue sample may be a formalin-fixed paraffin embedded tissue sample, a snap-frozen tissue sample, an ethanol-fixed tissue sample, a tissue sample fixed with an organic solvent, a tissue sample fixed with plastic or epoxy, a cross-linked tissue sample, surgically removed tumor tissue, or a biopsy sample (e.g., a core biopsy, an excisional tissue biopsy, or an incisional tissue biopsy). In some embodiments, the tissue sample is a cancerous tissue sample. In some embodiments, the cancerous tissue is melanoma, prostate cancer, breast cancer, or colon cancer tissue.

In some embodiments, at least one standard parameter associated with the cancer is measured in addition to the measured levels of the selected DETERMINANTS. The at least one standard parameter may be, for example, tumor stage, tumor grade, tumor size, tumor visual characteristics, tumor location, tumor growth, lymph node status, tumor thickness (Breslow score), ulceration, age of onset, PSA level, PSA kinetics, or Gleason score.

In some embodiments, the patient may have a primary tumor, a recurrent tumor, or metastatic prostate cancer.

Also included in the invention is metastatic prostate cancer reference expression profile containing a pattern of marker levels of an effective amount of two or more markers selected from Tables 2, 3 or 5. Also included is a machine readable media containing one or more metastatic tumor reference expression profiles and optionally, additional test results and subject information. In a further aspect the invention provides a DETERMINANT panel containing one or more DETERMINANTS that are indicative of a physiological or biochemical pathway associated metastasis or the progression of a tumor.

The invention also provides a mouse wherein the genome of at least one prostate epithelial cell contains a homozygous inactivation of the endogenous PTEN gene, p53 gene, and TERT gene, and the TERT gene can be inducibly re-activated and therefore expressed, and wherein the mouse exhibits an increased susceptibility to development of metastatic prostate cancer upon expression of the TERT gene.

The invention also provides a mouse wherein the genome of at least one prostate epithelial cell contains a homozygous inactivation of the endogenous PTEN gene, p53 gene, and SMAD4 gene, and wherein the mouse exhibits an increased susceptibility to development of metastatic prostate cancer. The invention also provides cells from the mouse models and in some aspects, such cells are epithelial cancer cells.

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

Other features and advantages of the invention will be apparent from and encompassed by the following detailed description and claims.

Aggressive spread of G3/4 LSL-mTert PB-Pten/p53 prostate tumors to spinal bones at 24 weeks of age. H&E sections of the HPIN in the anterior prostate (AP) tumors at age of 9 weeks from G0 mTert PB-Pten/p53 (denoted as G0 mTert), G4 mTert-/- PBPten/p53 (denoted as G4 mTert-/-), and G4 LSL-mTert PB-Pten/p53 (denoted as G4 LSLmTert). Prostate tumor cells from the primary sites and from spinal bones of G4 LSL-Tert PB-Pten/p53 mouse at 24 weeks of age. Prostate tumor cells from spinal bones of G4 LSL-Tert PB-Pten/p53 mouse were micro-dissected, and the purified genomic DNA was used to detect the genomic status of floxed Pten by PCR.

Figure 12:
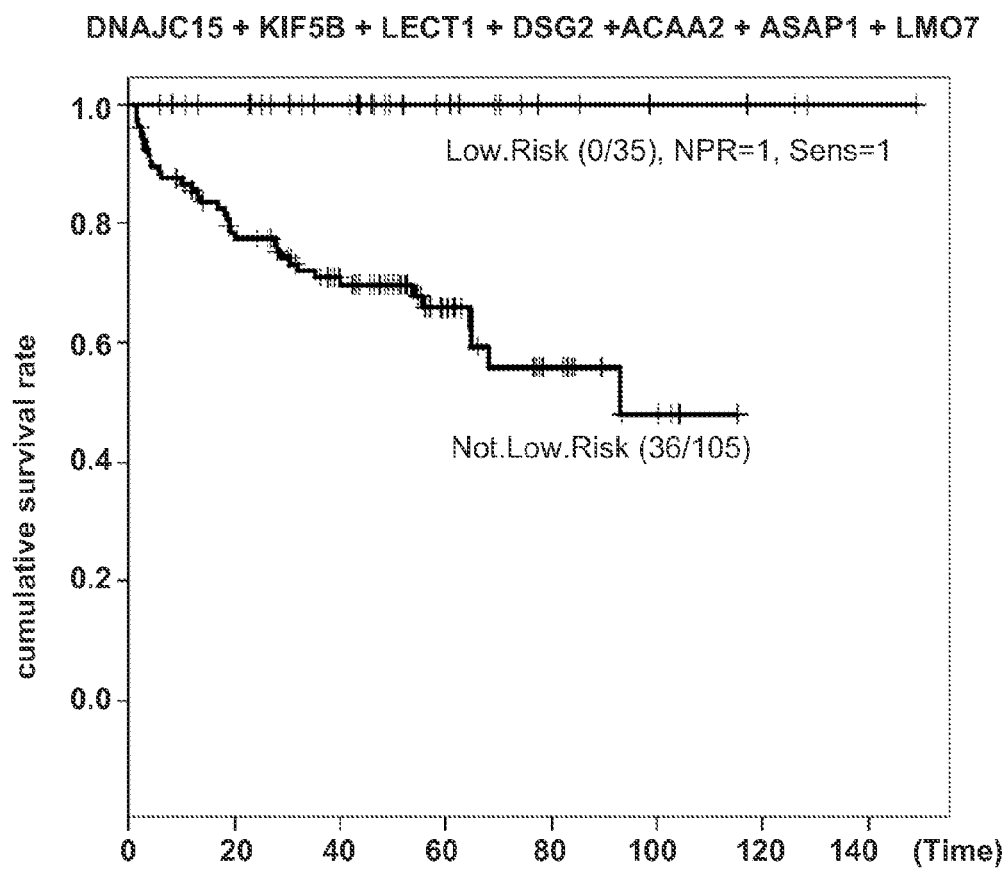

FIG. 12. A high-sensitivity model contains 7 genes of DNAJC15, KIF5B, LECT1, DSG2, ACAA2, ASAP1, LMO7 that aims to minimize false negative rates.

Figure 13:
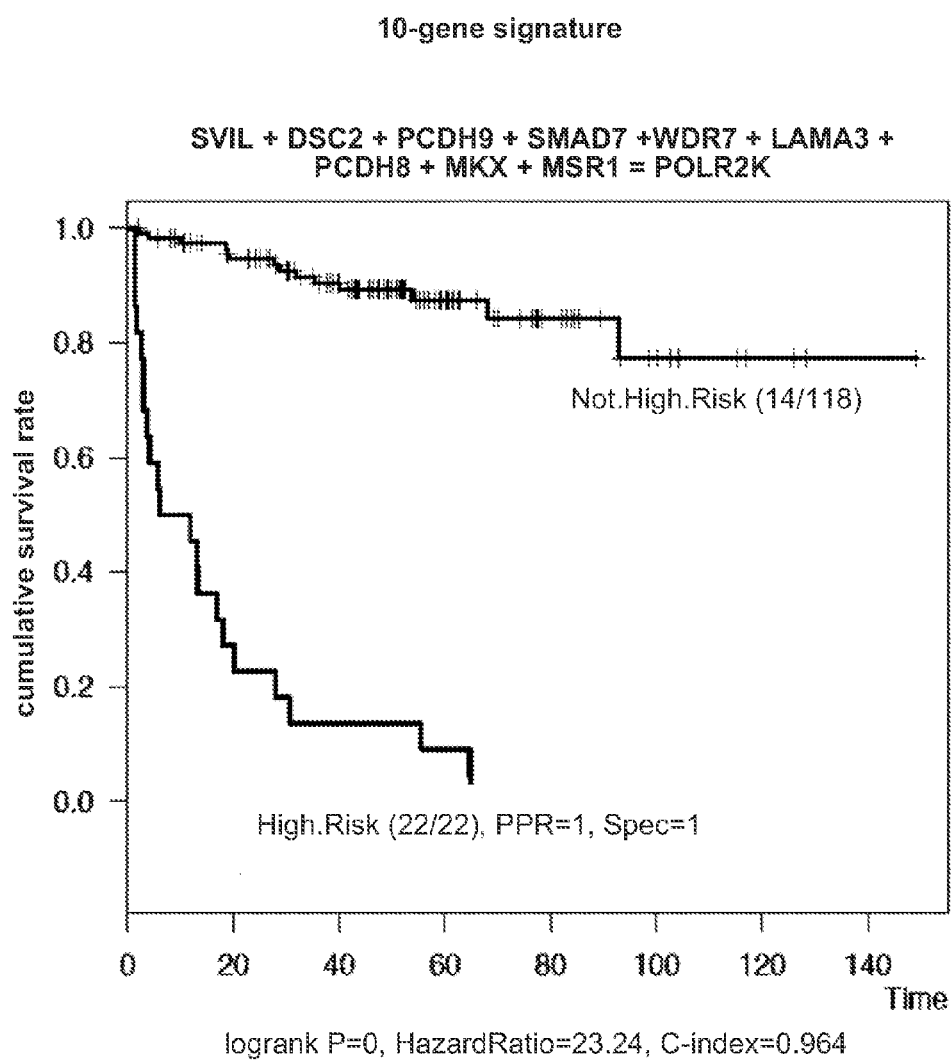

FIG. 13. A high-specificity model contains 10 genes of SVIL, DSC2, PCDH9, SMAD7, WDR7, LAMA3, PCDH8, MKX, MSR1, POLR2K that minimize false positive rates.

Figure 14:
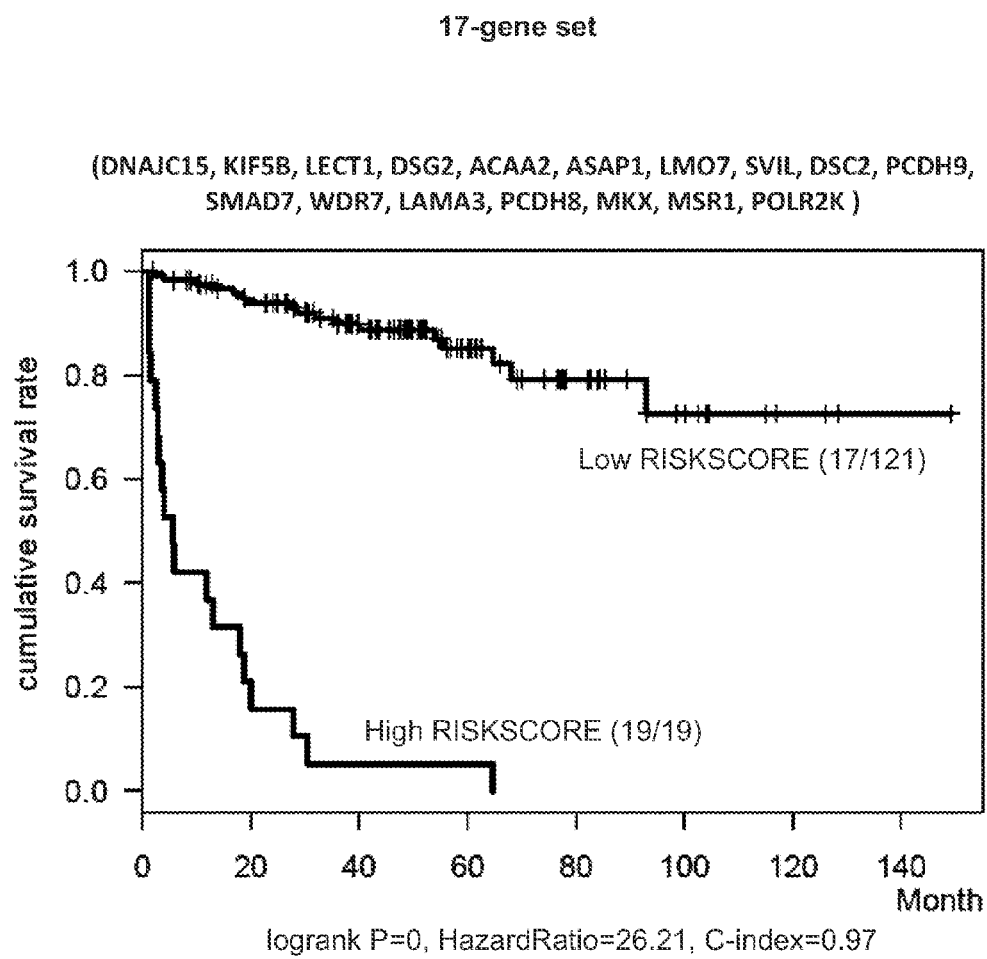

FIG. 14. The new 17 gene set from the combination of high-sensitivity model of DNAJC15, KIF5B, LECT1, DSG2, ACAA2, ASAP1, LMO7 and the high-specificity model of SVIL, DSC2, PCDH9, SMAD7, WDR7, LAMA3, PCDH8, MKX, MSR1, POLR2K can significantly dichotomize prostate cancer cases into low versus high risk groups for BCR in Taylor et al dataset (2010) (Taylor et al., *Cancer Cell* (2010).

Figure 15:
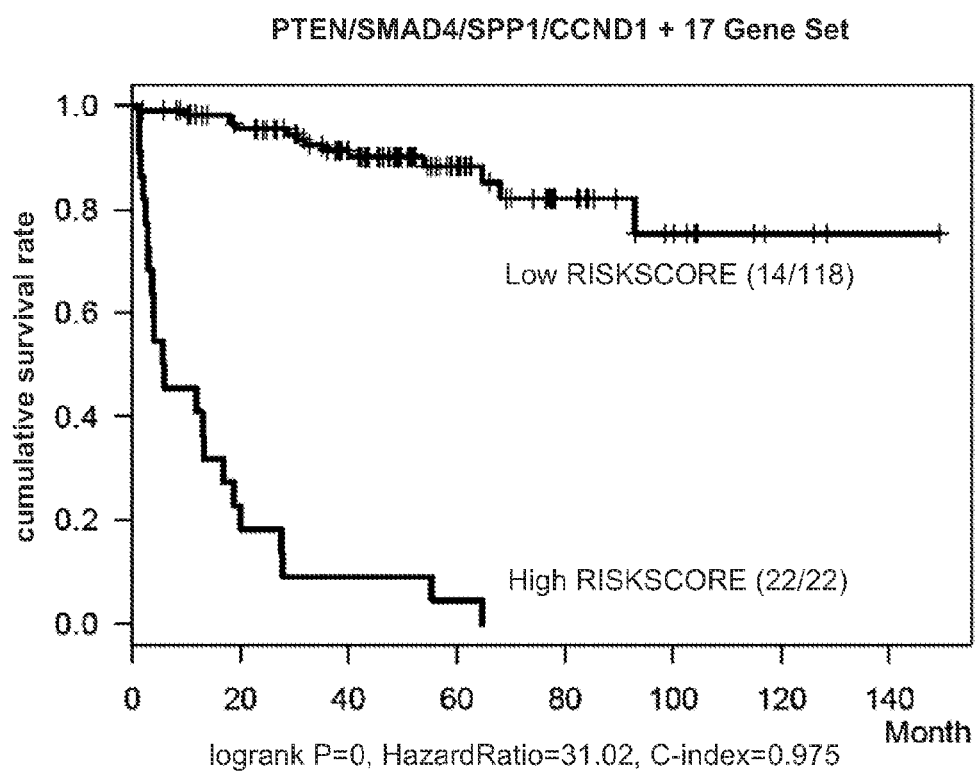

FIGS. 15A and 15B. The new 17 gene set can significantly enhance the previous 4 gene signature of PTEN/SMAD4/SPP1/CCND1 (Ding et al., *Nature* (2011)) to dichotomize prostate cancer cases into low versus high risk groups for BCR in Taylor et al dataset (2010) (Taylor et al. *Cancer Cell* (2010). (FIG. 15A) The previous 4-gene signature (SMAD4/PTEN/CCND1/SPP1) can significantly dichotomize prostate cancer cases into low versus high risk groups for BCR in Taylor et al dataset (2010). (FIG. 15B) The 17 gene set (DNAJC15, KIF5B, LECT1, DSG2, ACAA2, ASAP1, LMO7, SVIL, DSC2, PCDH9, SMAD7, WDR7, LAMA3, PCDH8, MKX, MSR1, POLR2K) can significantly dichotomize prostate cancer cases into low versus high risk groups for BCR in Taylor et al dataset (2010). (C) The combined new 17 gene set can significantly enhance the sensitivity and specificity of SMAD4/PTEN/CCND1/SPP1 dichotomize prostate cancer cases into low versus high risk groups for BCR in Taylor et al dataset (2010).

Figure 16:
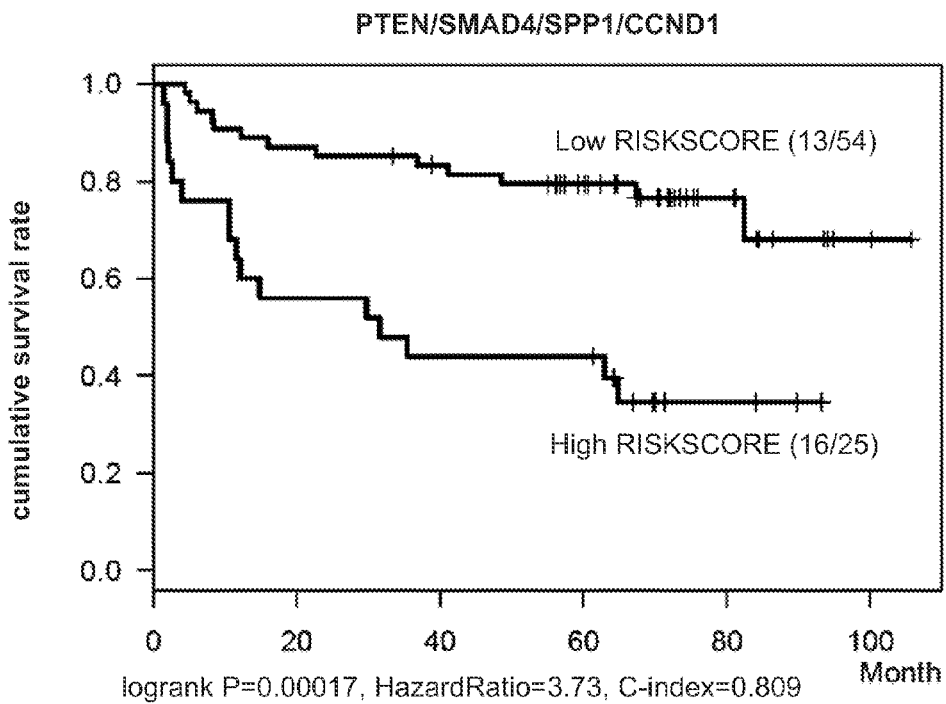
Figure 16:
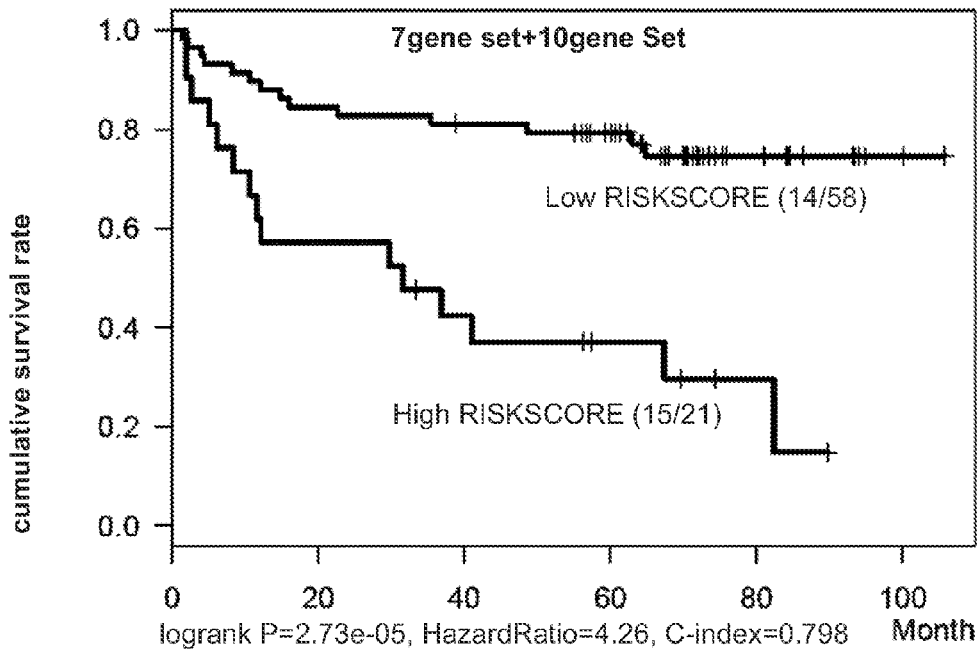
Figure 16:
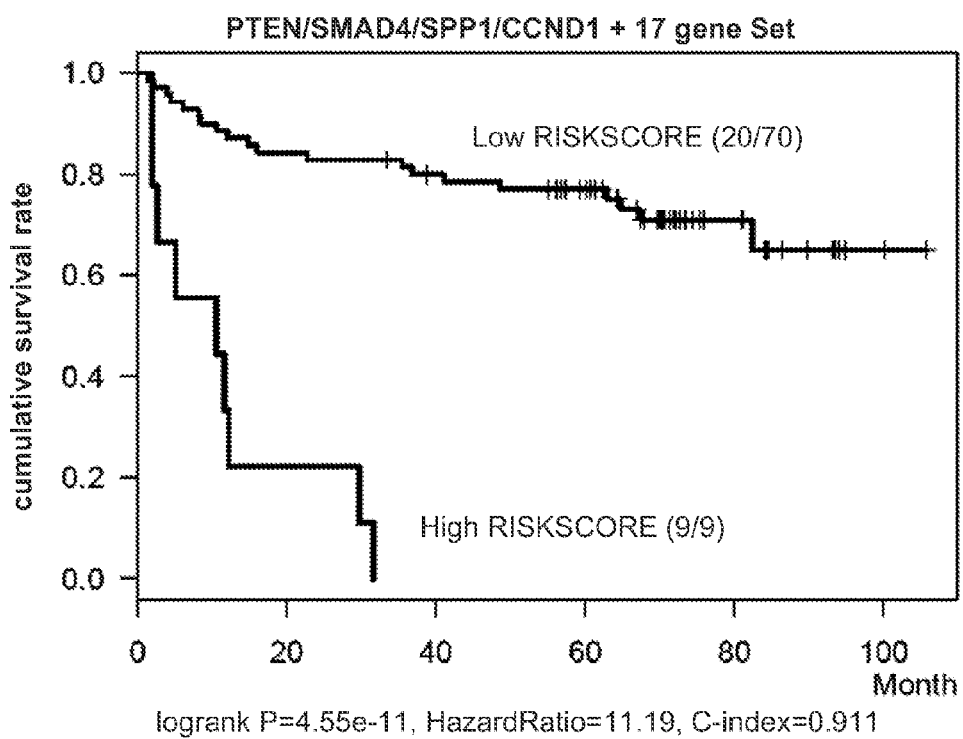

FIG. 16. The new 17 gene set can significantly enhance the previous 4 gene signature of PTEN/SMAD4/SPP1/CCND1 (Ding et al., *Nature* (2011)) to dichotomize prostate cancer cases into low versus high risk groups for BCR in Glinsky et al dataset (2004) (Glinsky et al., *J. Clin. Invest* (2004)). (A) The previous 4-gene signature (SMAD4/PTEN/CCND1/SPP1) can significantly dichotomize prostate cancer cases into low versus high risk groups for BCR in Glinsky et al dataset (2004). (B) The 17 gene set (DNAJC15, KIF5B, LECT1, DSG2, ACAA2, ASAP1, LMO7, SVIL, DSC2, PCDH9, SMAD7, WDR7, LAMA3, PCDH8, MKX, MSR1, POLR2K) can significantly dichotomize prostate cancer cases into low versus high risk groups for BCR in Glinsky et al dataset (2004). (C) The combined new 17 gene set can significantly enhance the sensitivity and specificity of SMAD4/PTEN/CCND1/SPP1 dichotomize prostate cancer cases into low versus high risk groups for BCR in Glinsky et al dataset (2004).

Figure 17:
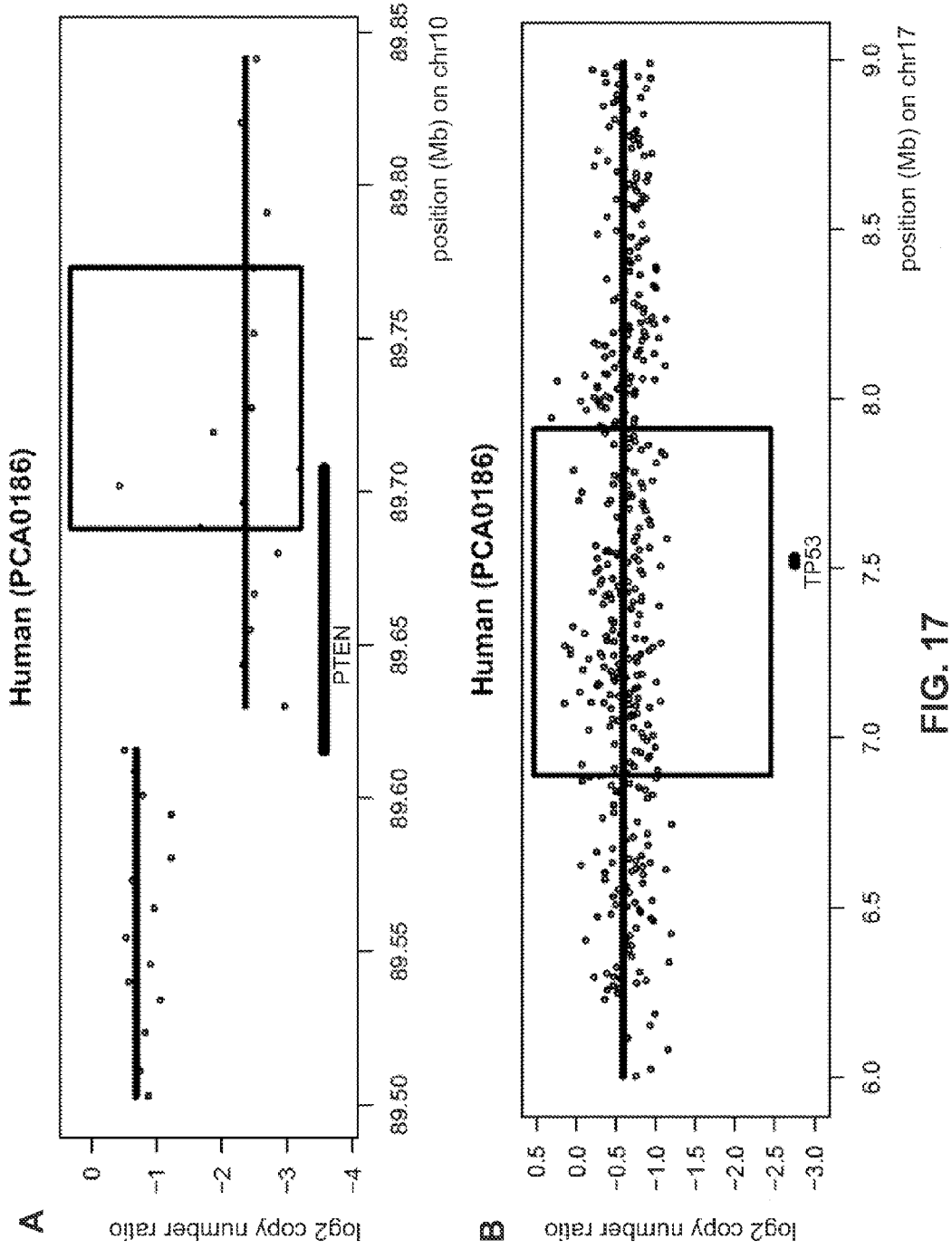
Figure 17:
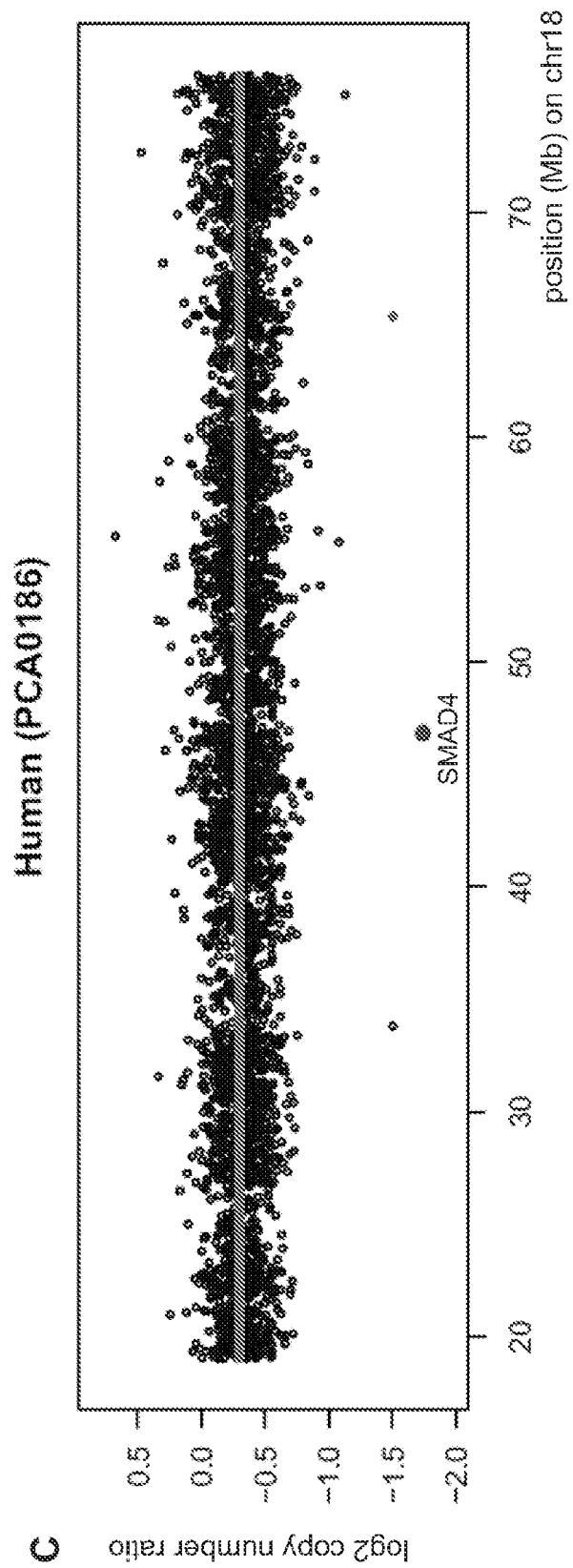

FIG. 17. Co-deletion analysis of PTEN, TP53 and SMAD4 in human prostate cancer sample PCA0186. Log$_2$ ratio of array-CGH plots showing conserved deletion of PTEN (A), TP53 (B), and SMAD4 (C). They axis shows log$_2$ of copy number ratio (normal, log$_2$=0); amplifications are above and deletions are below this axis; x axis is chromosome position, in Mbp.

Figure 18:
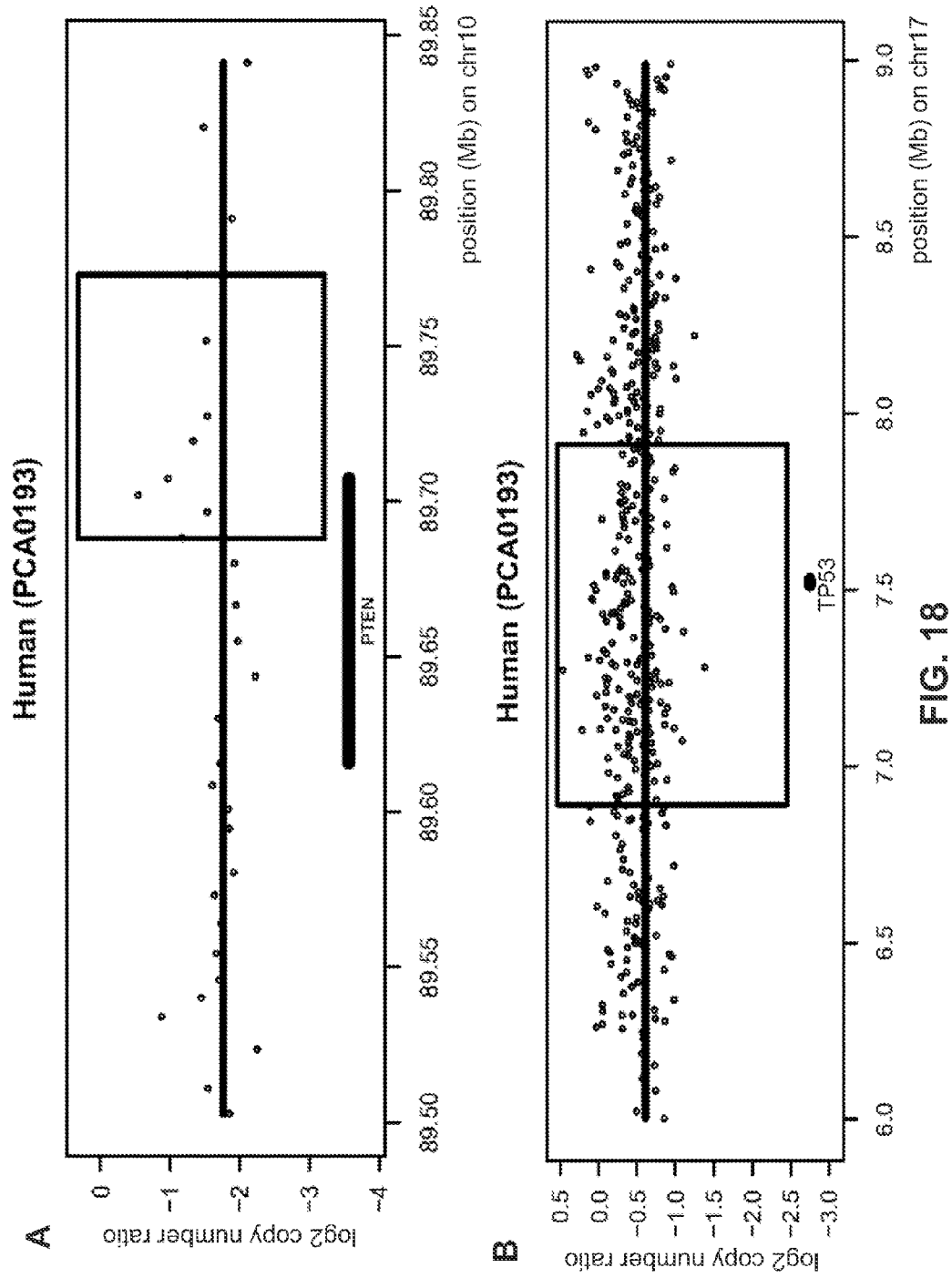
Figure 18:
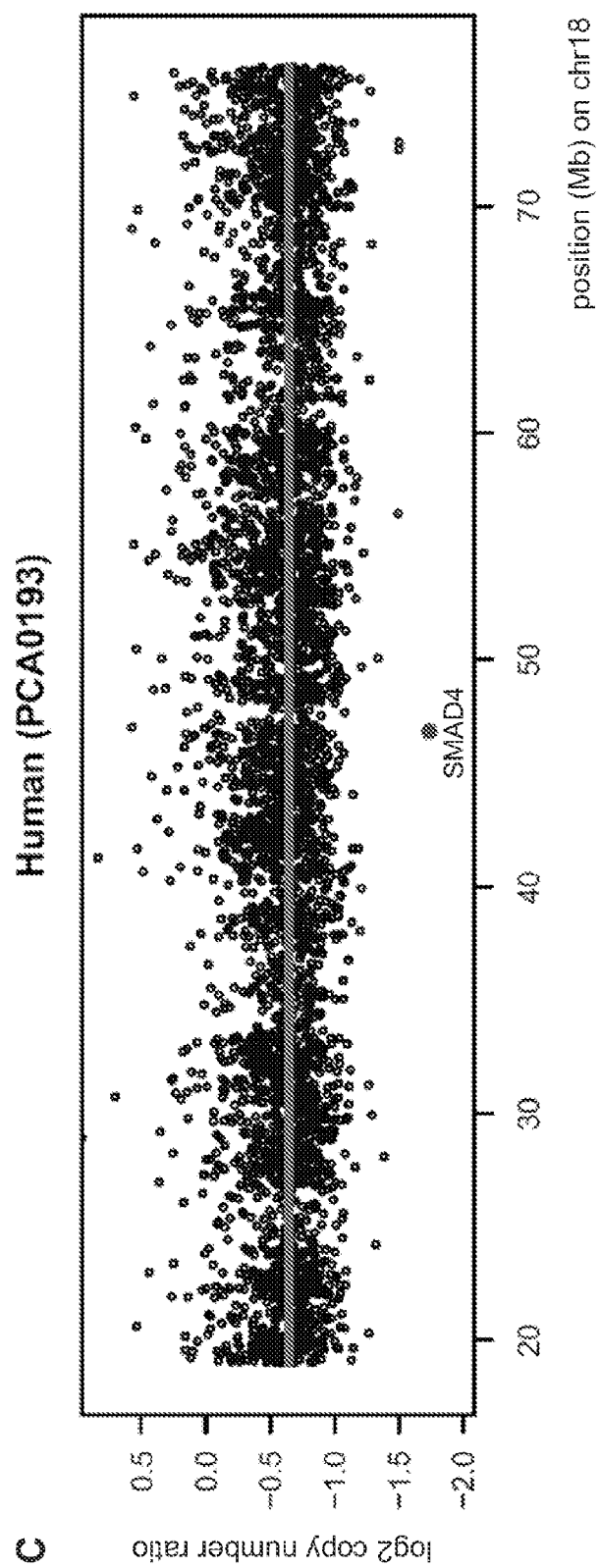

FIG. 18. Co-deletion analysis of PTEN, TP53 and SMAD4 in human prostate cancer sample PCA0193. Log$_2$ ratio of array-CGH plots showing conserved deletion of PTEN (A), TP53 (B), and SMAD4 (C). They axis shows log$_2$ of copy number ratio (normal, log$_2$=0); amplifications are above and deletions are below this axis; x axis is chromosome position, in Mbp.

Figure 19:
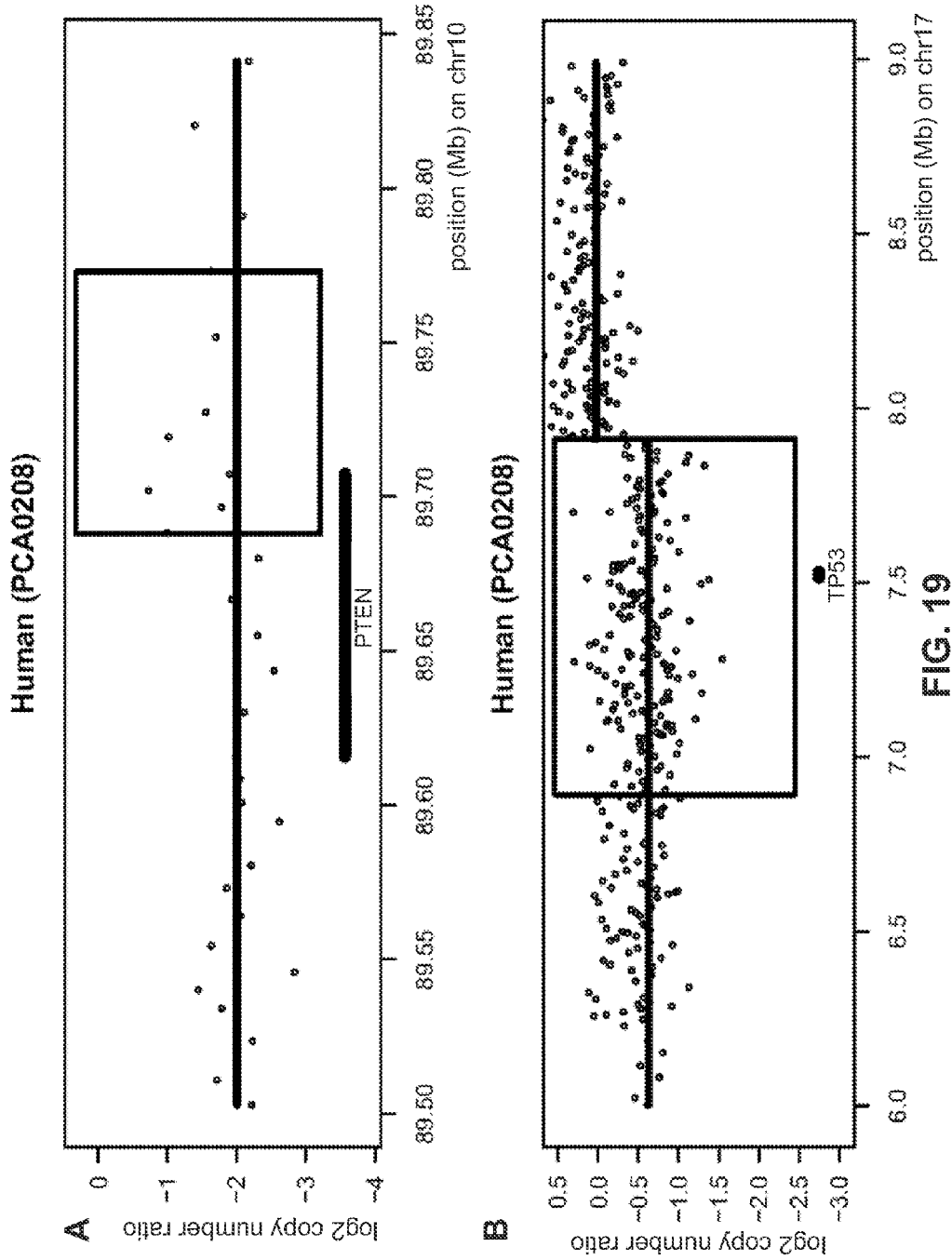
Figure 19:
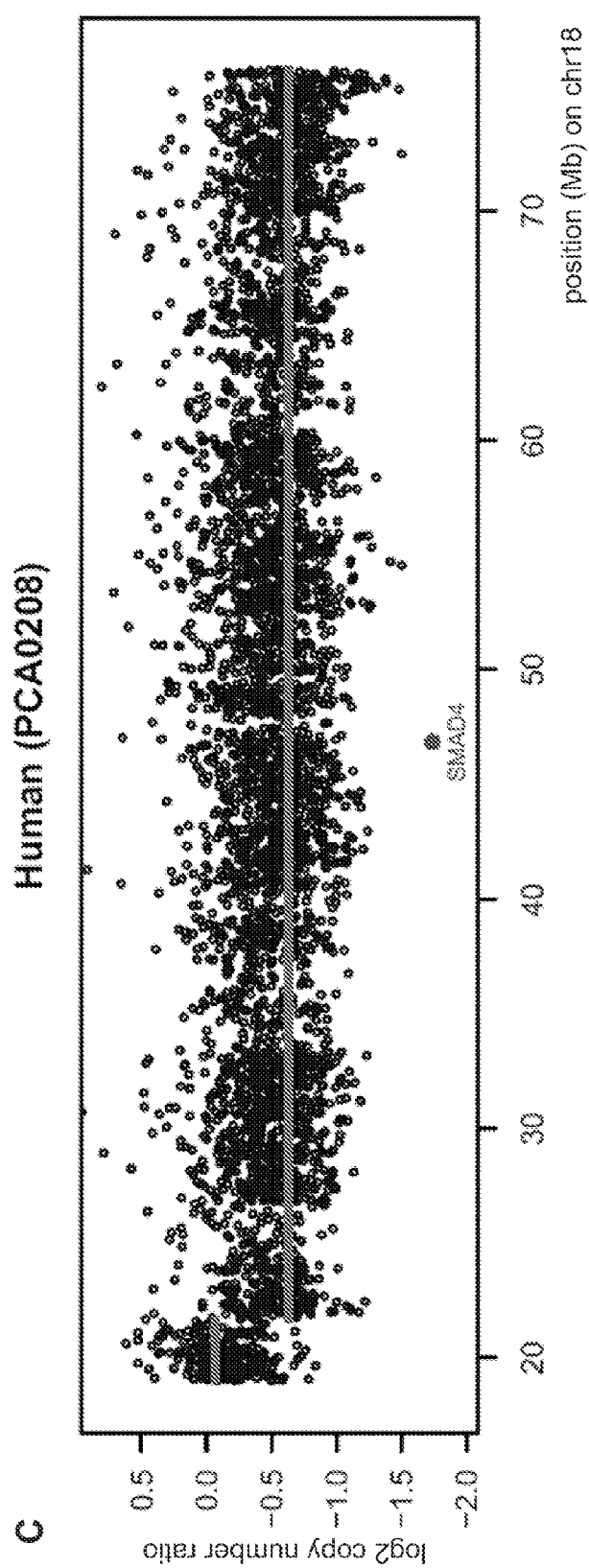

FIG. 19. Co-deletion analysis of PTEN, TP53 and SMAD4 in human prostate cancer sample PCA0208. $\log_2$ ratio of array-CGH plots showing conserved deletion of PTEN (A), TP53 (B), and SMAD4 (C). They axis shows $\log_2$ of copy number ratio (normal, $\log_2=0$); amplifications are above and deletions are below this axis; x axis is chromosome position, in Mbp.

Figure 20:
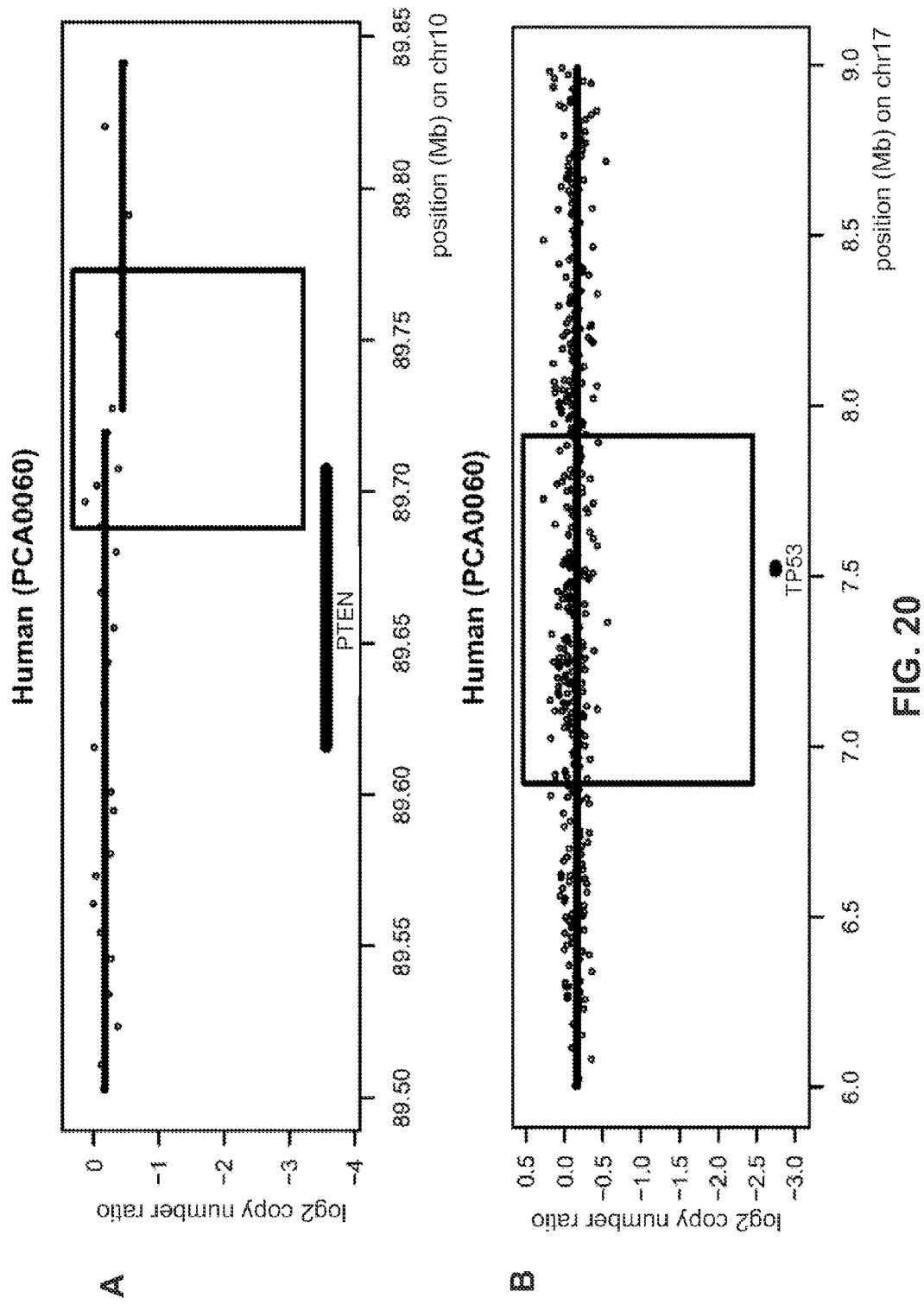
Figure 20:
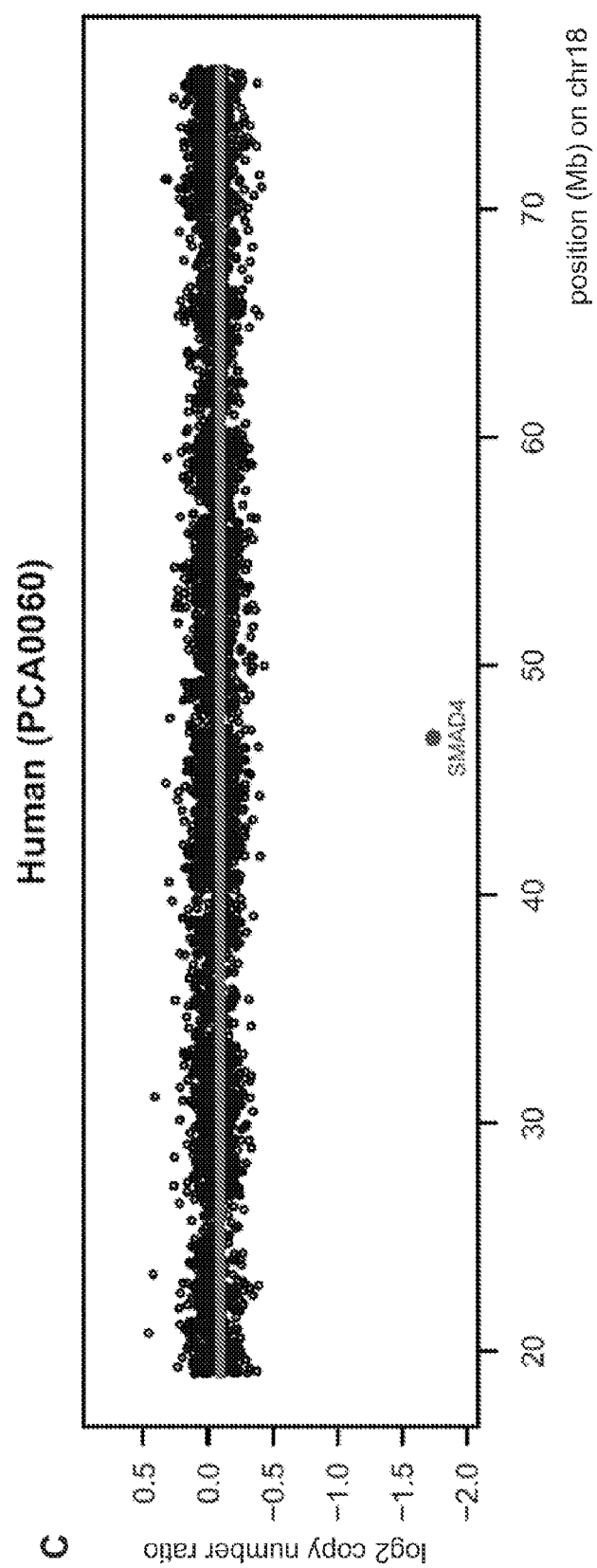

FIG. 20. Co-deletion analysis of PTEN, TP53 and SMAD4 in human prostate cancer sample PCA0060. $\log_2$ ratio of array-CGH plots showing conserved deletion of PTEN (A), TP53 (B), and SMAD4 (C). They axis shows $\log_2$ of copy number ratio (normal, $\log_2=0$); amplifications are above and deletions are below this axis; x axis is chromosome position, in Mbp.

Figure 21:
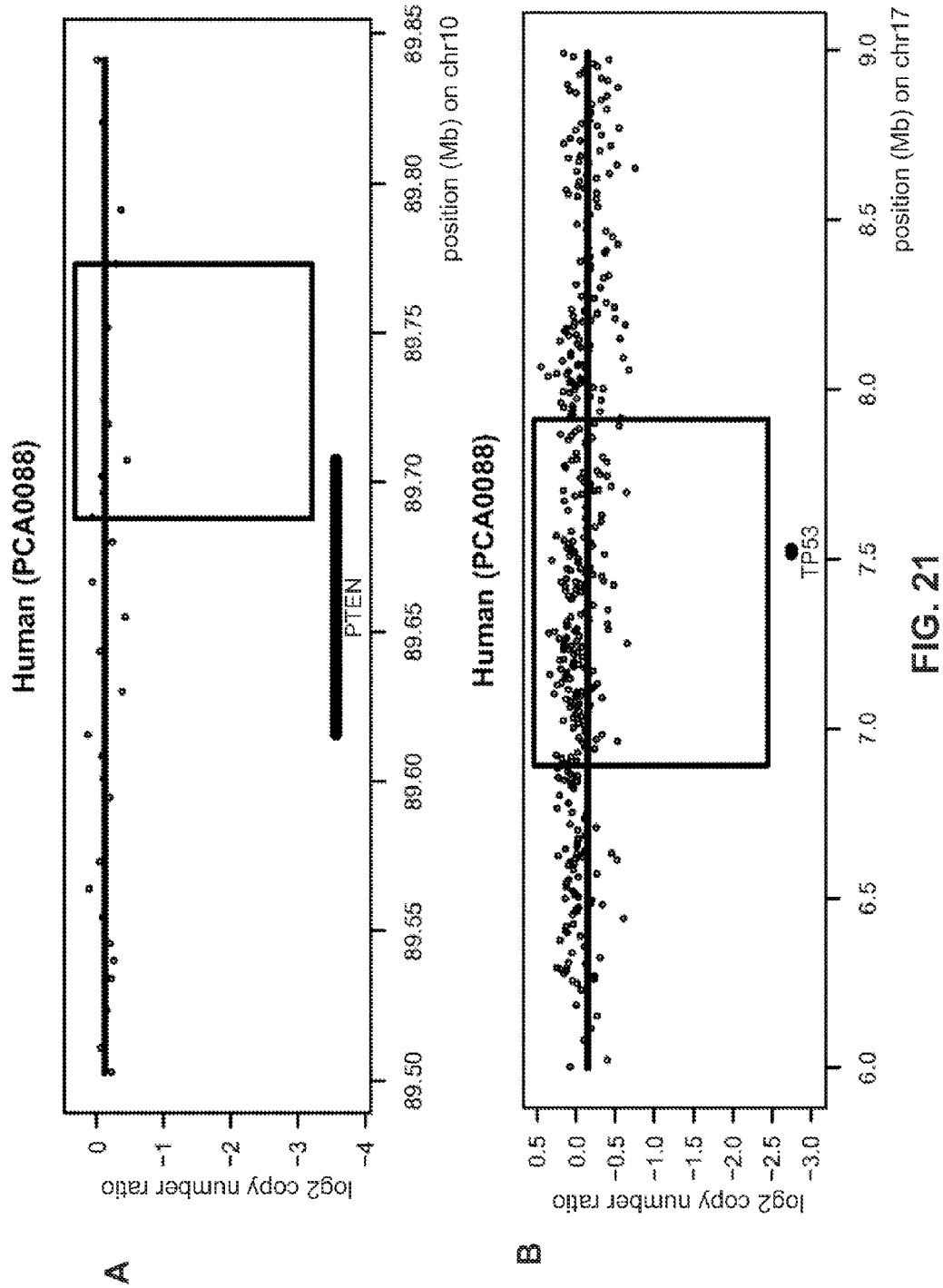
Figure 21:
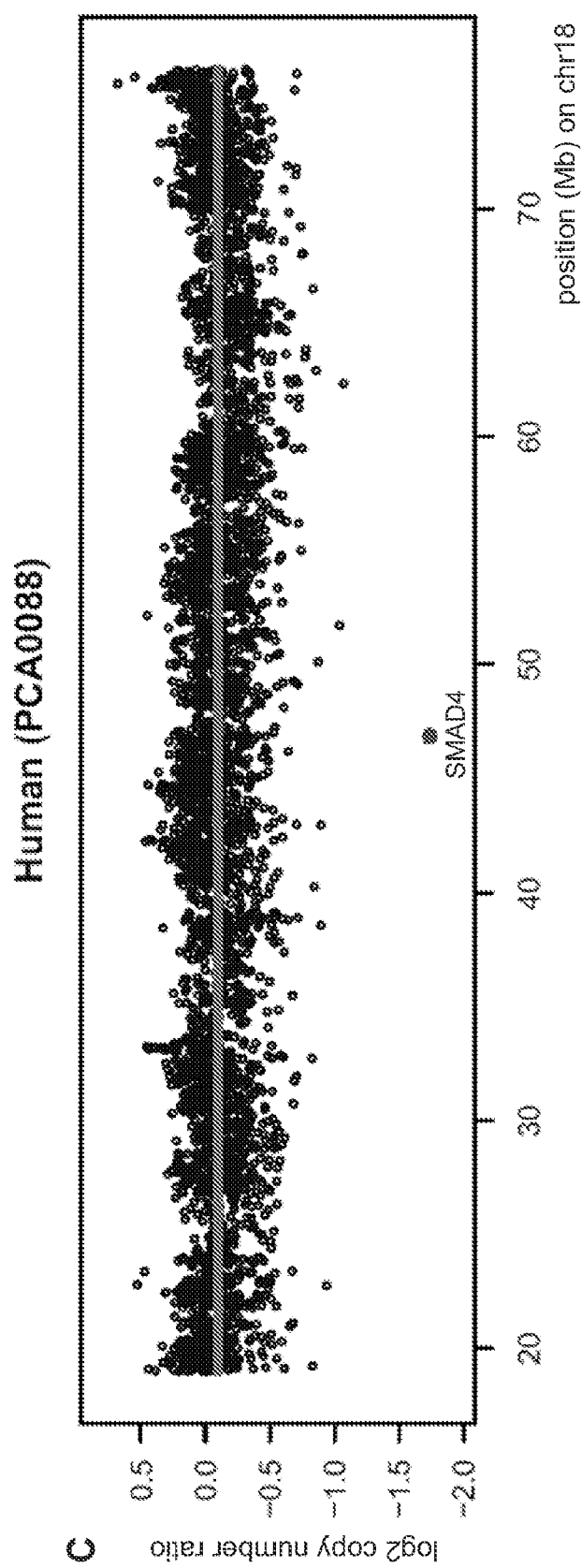

FIG. 21. Co-deletion analysis of PTEN, TP53 and SMAD4 in human prostate cancer sample PCA0088. $\log_2$ ratio of array-CGH plots showing conserved deletion of PTEN (A), TP53 (B), and SMAD4 (C). They axis shows $\log_2$ of copy number ratio (normal, $\log_2=0$); amplifications are above and deletions are below this axis; x axis is chromosome position, in Mbp.

Figure 22:
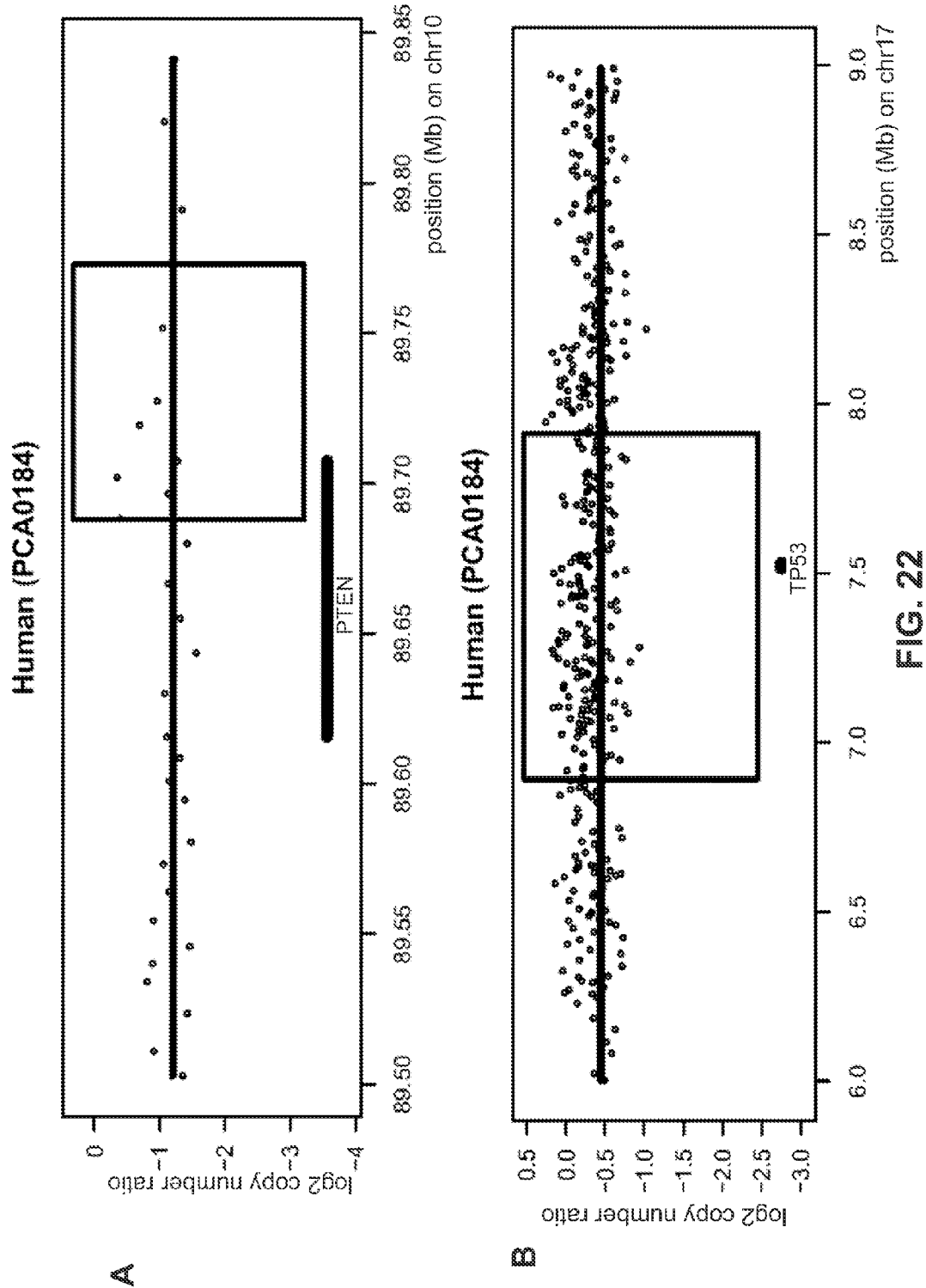
Figure 22:
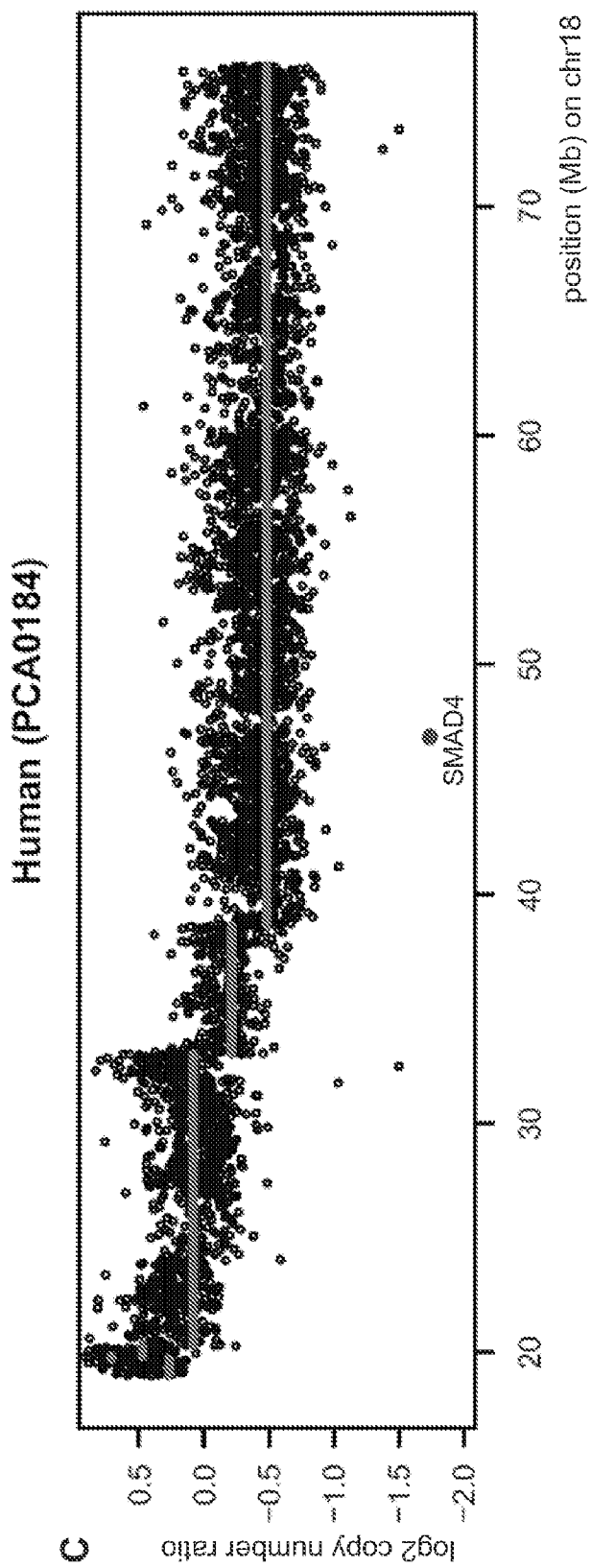

FIG. 22. Co-deletion analysis of PTEN, TP53 and SMAD4 in human prostate cancer sample PCA0184. $\log_2$ ratio of array-CGH plots showing conserved deletion of PTEN (A), TP53 (B), and SMAD4 (C). They axis shows $\log_2$ of copy number ratio (normal, $\log_2=0$); amplifications are above and deletions are below this axis; x axis is chromosome position, in Mbp.

Figure 23:
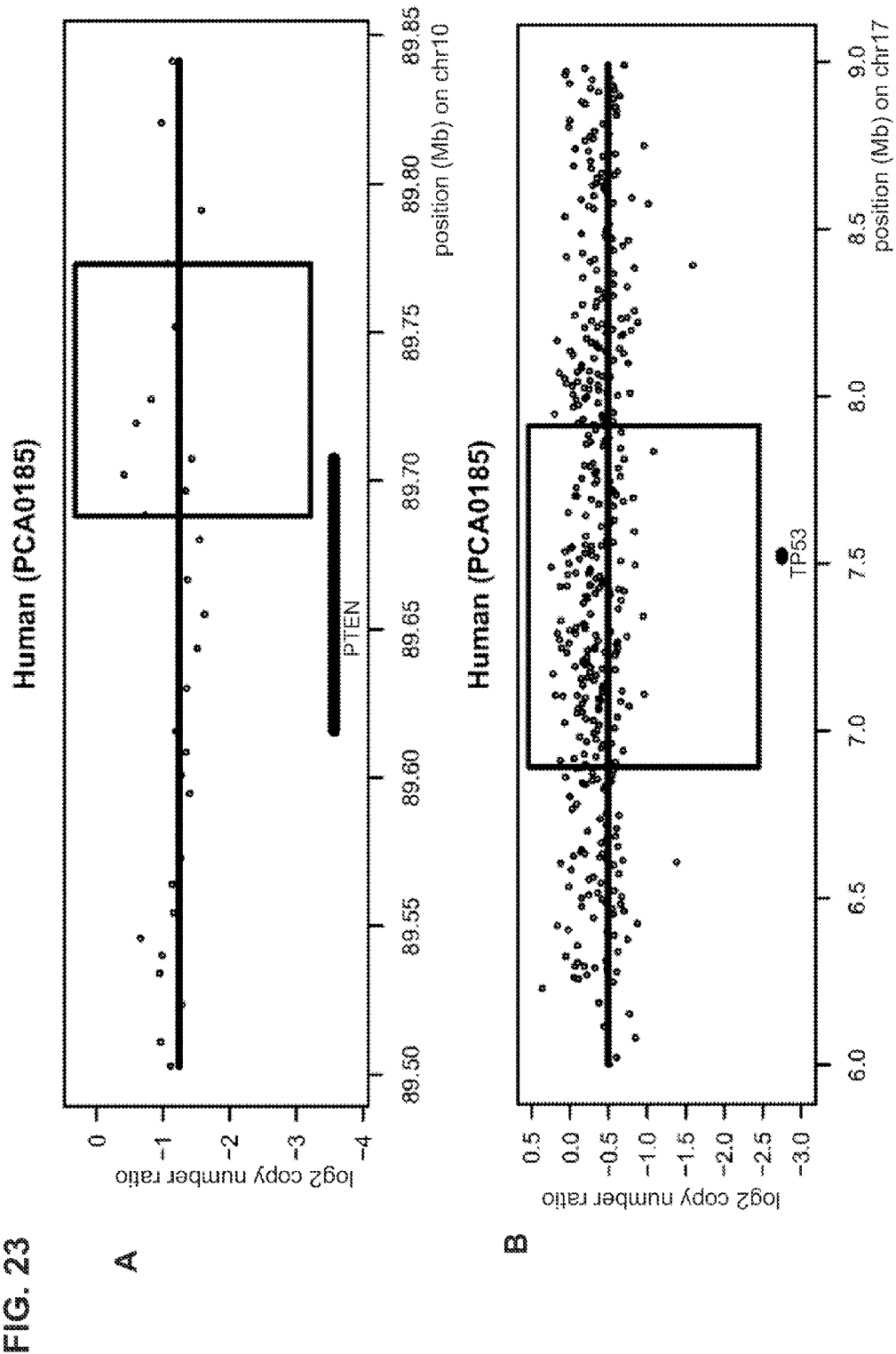
Figure 23:
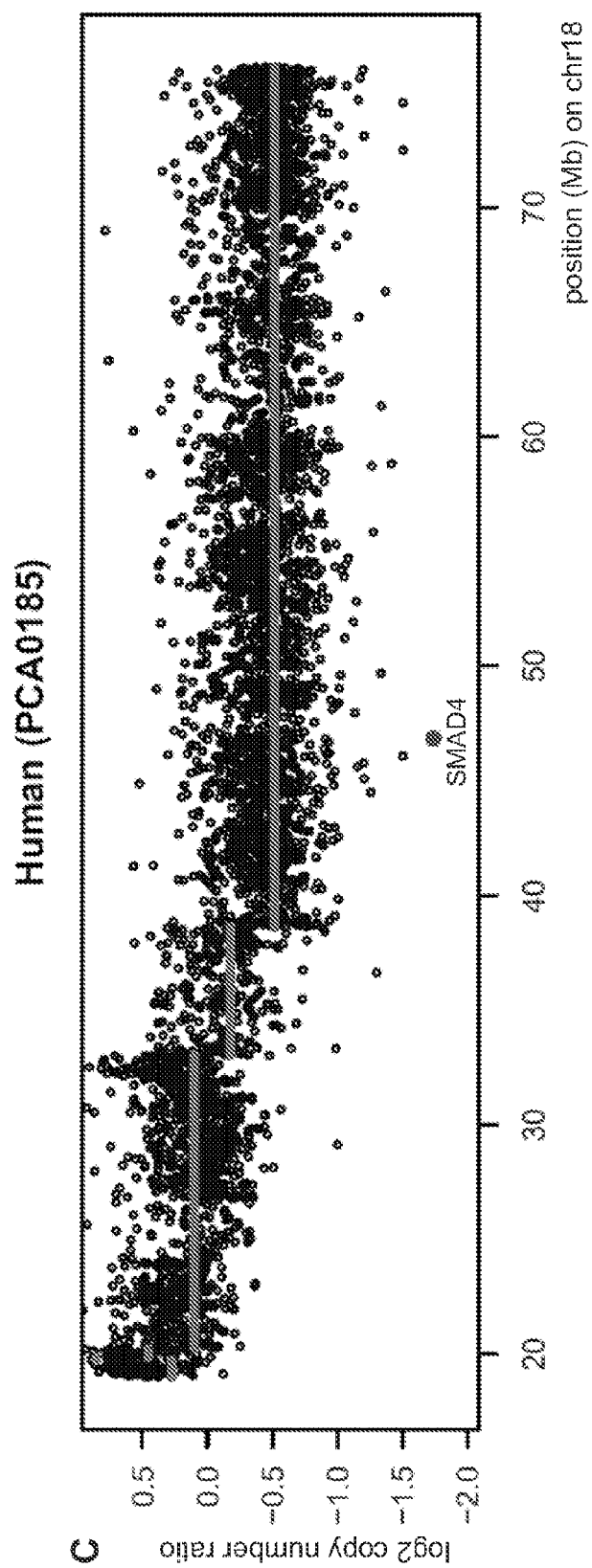

FIG. 23. Co-deletion analysis of PTEN, TP53 and SMAD4 in human prostate cancer sample PCA0185. $\log_2$ ratio of array-CGH plots showing conserved deletion of PTEN (A), TP53 (B), and SMAD4 (C). They axis shows $\log_2$ of copy number ratio (normal, $\log_2=0$); amplifications are above and deletions are below this axis; x axis is chromosome position, in Mbp.

Figure 24:
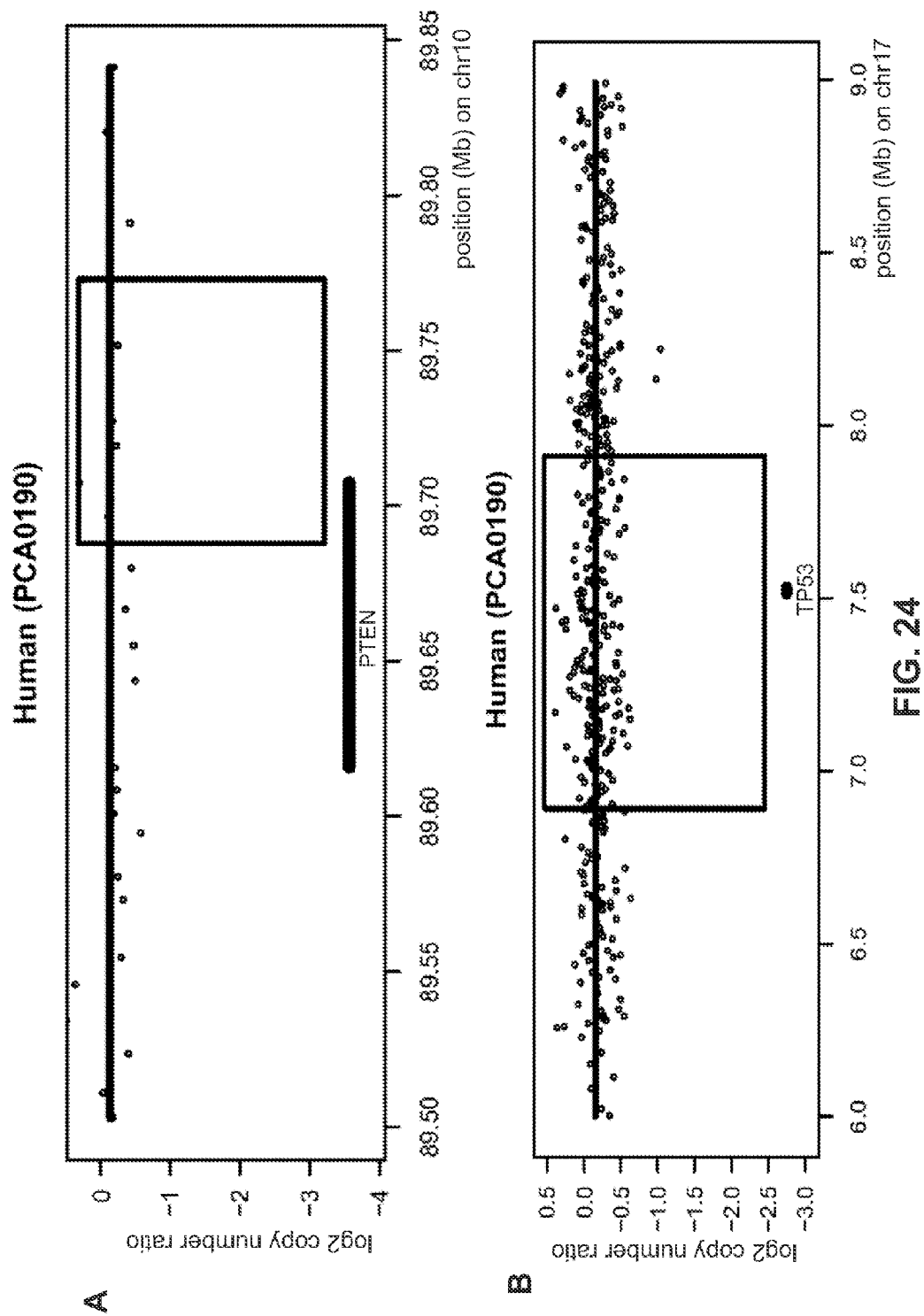
Figure 24:
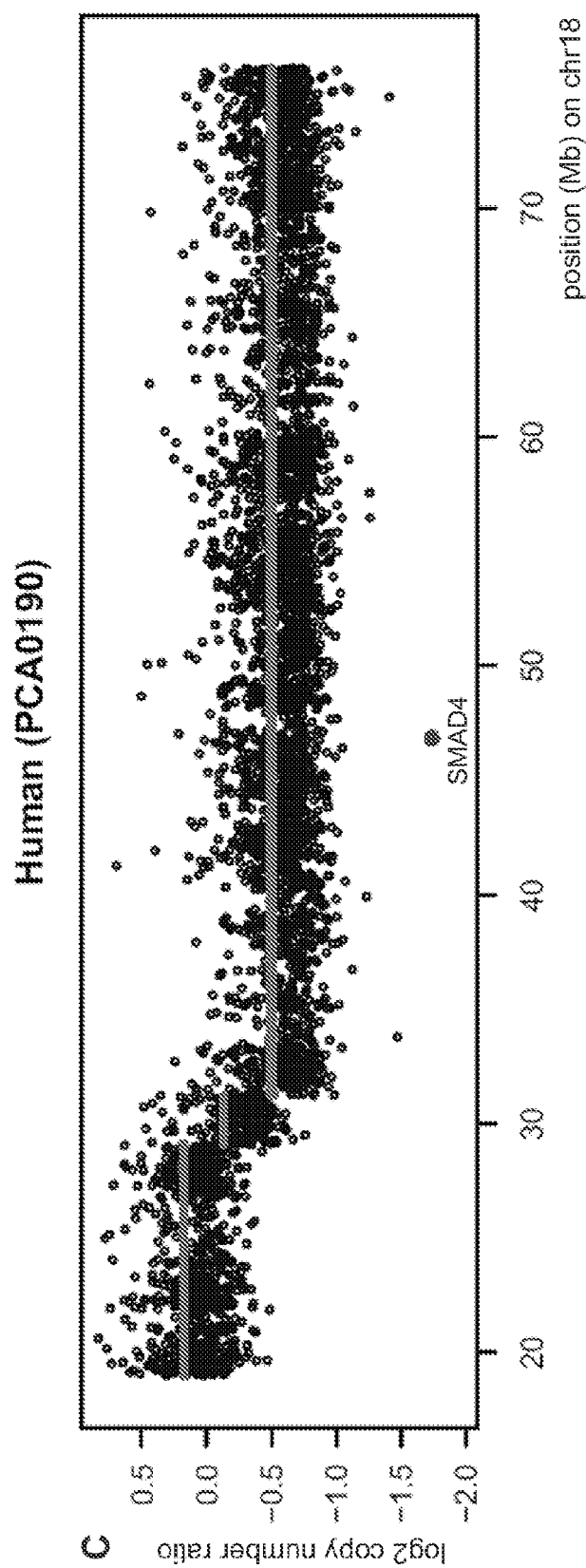

FIG. 24. Co-deletion analysis of PTEN, TP53 and SMAD4 in human prostate cancer sample PCA0190. $\log_2$ ratio of array-CGH plots showing conserved deletion of PTEN (A), TP53 (B), and SMAD4 (C). They axis shows $\log_2$ of copy number ratio (normal, $\log_2=0$); amplifications are above and deletions are below this axis; x axis is chromosome position, in Mbp.

Figure 25:
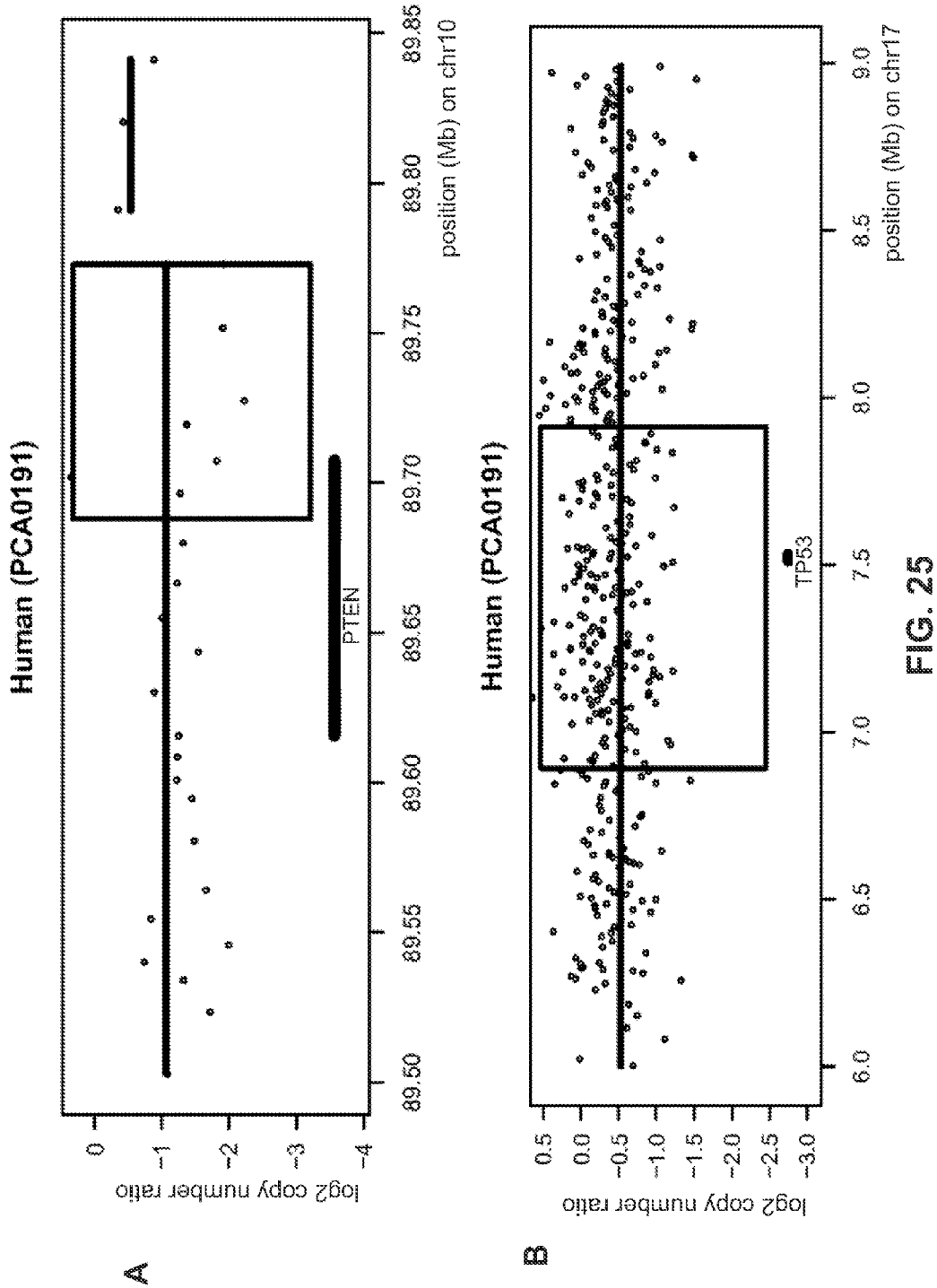
Figure 25:
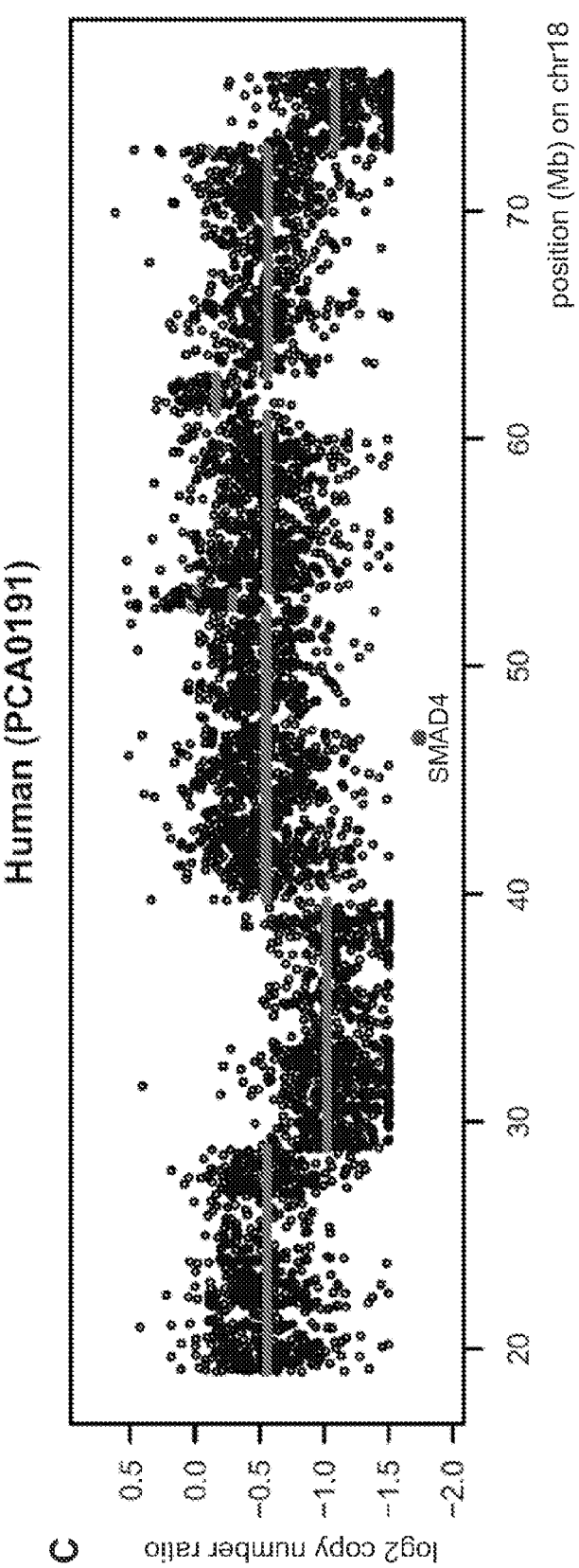

FIG. 25. Co-deletion analysis of PTEN, TP53 and SMAD4 in human prostate cancer sample PCA0191. $\log_2$ ratio of array-CGH plots showing conserved deletion of PTEN (A), TP53 (B), and SMAD4 (C). They axis shows $\log_2$ of copy number ratio (normal, $\log_2=0$); amplifications are above and deletions are below this axis; x axis is chromosome position, in Mbp.

Figure 26:
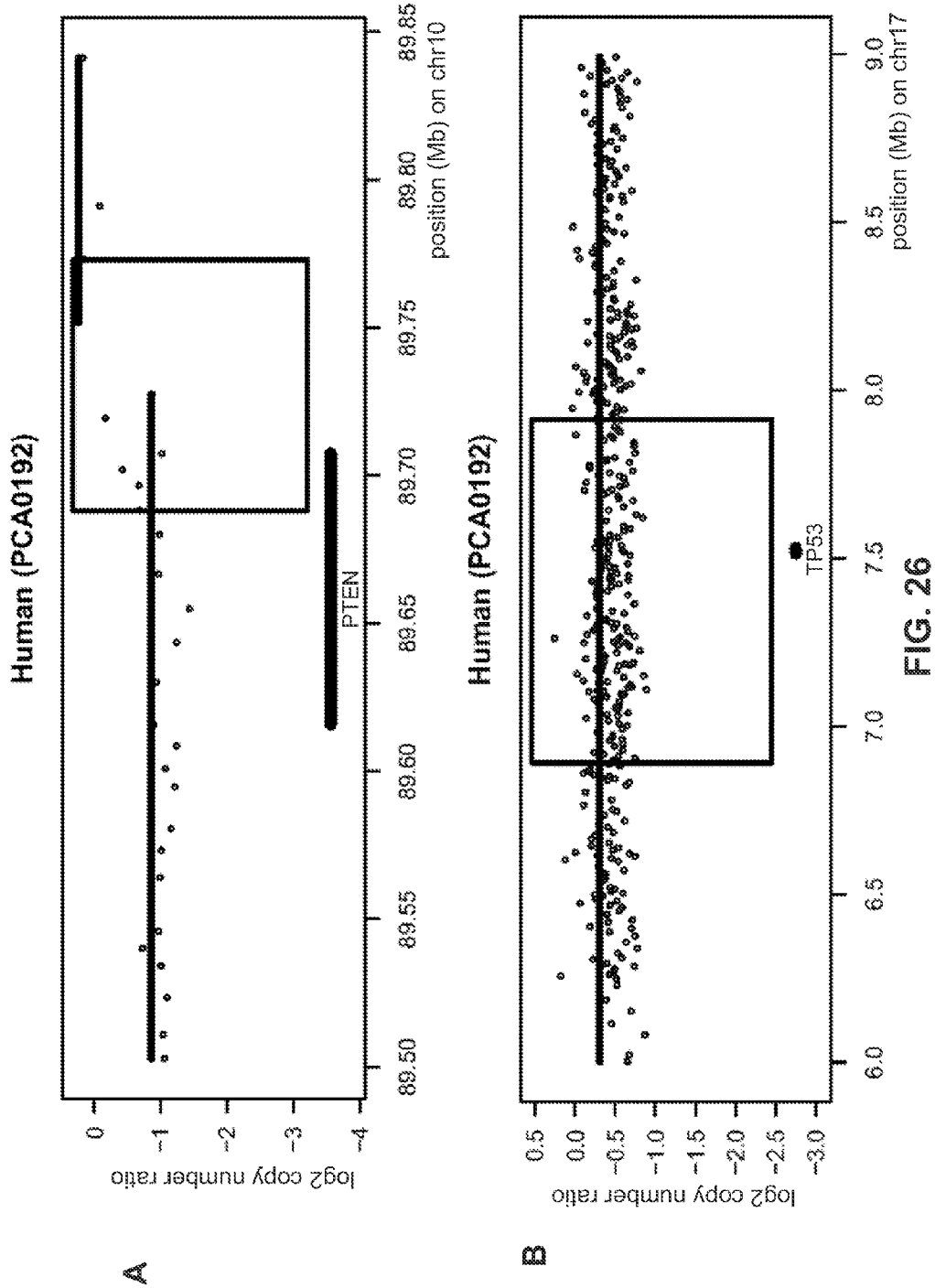
Figure 26:
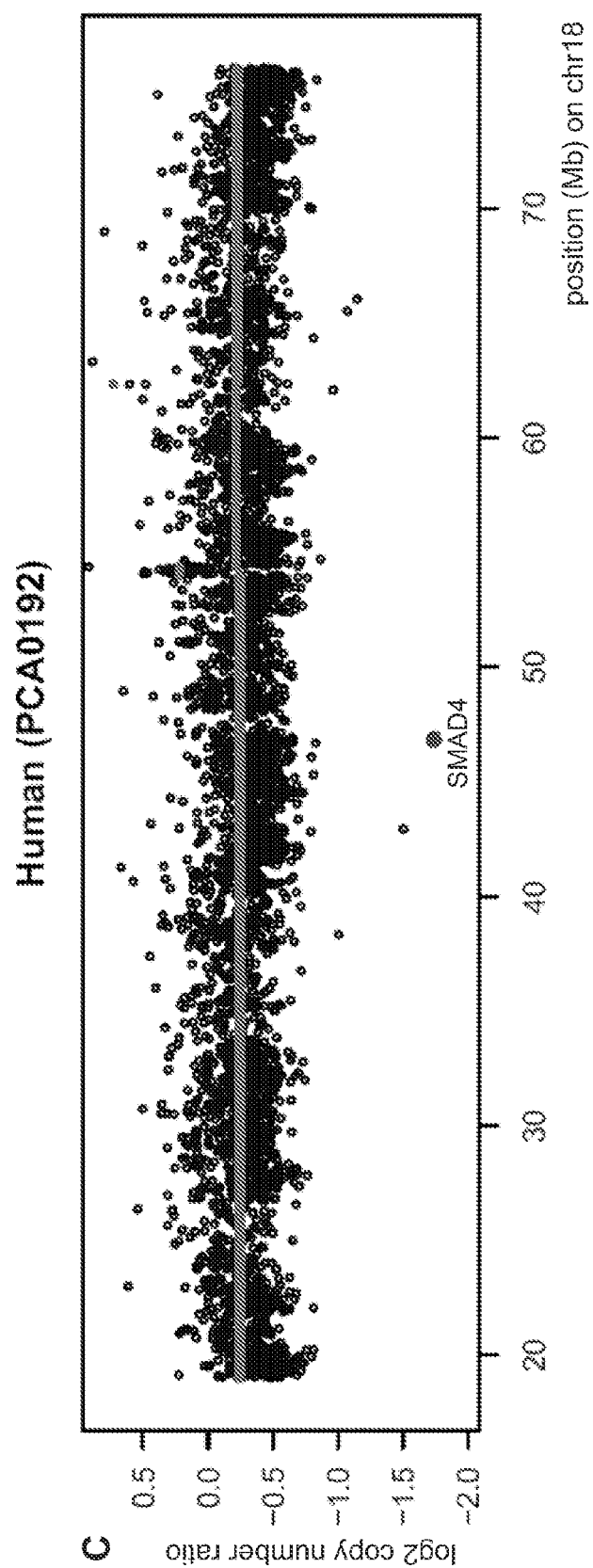

FIG. 26. Co-deletion analysis of PTEN, TP53 and SMAD4 in human prostate cancer sample PCA0192. $\log_2$ ratio of array-CGH plots showing conserved deletion of PTEN (A), TP53 (B), and SMAD4 (C). They axis shows $\log_2$ of copy number ratio (normal, $\log_2=0$); amplifications are above and deletions are below this axis; x axis is chromosome position, in Mbp.

Figure 27:
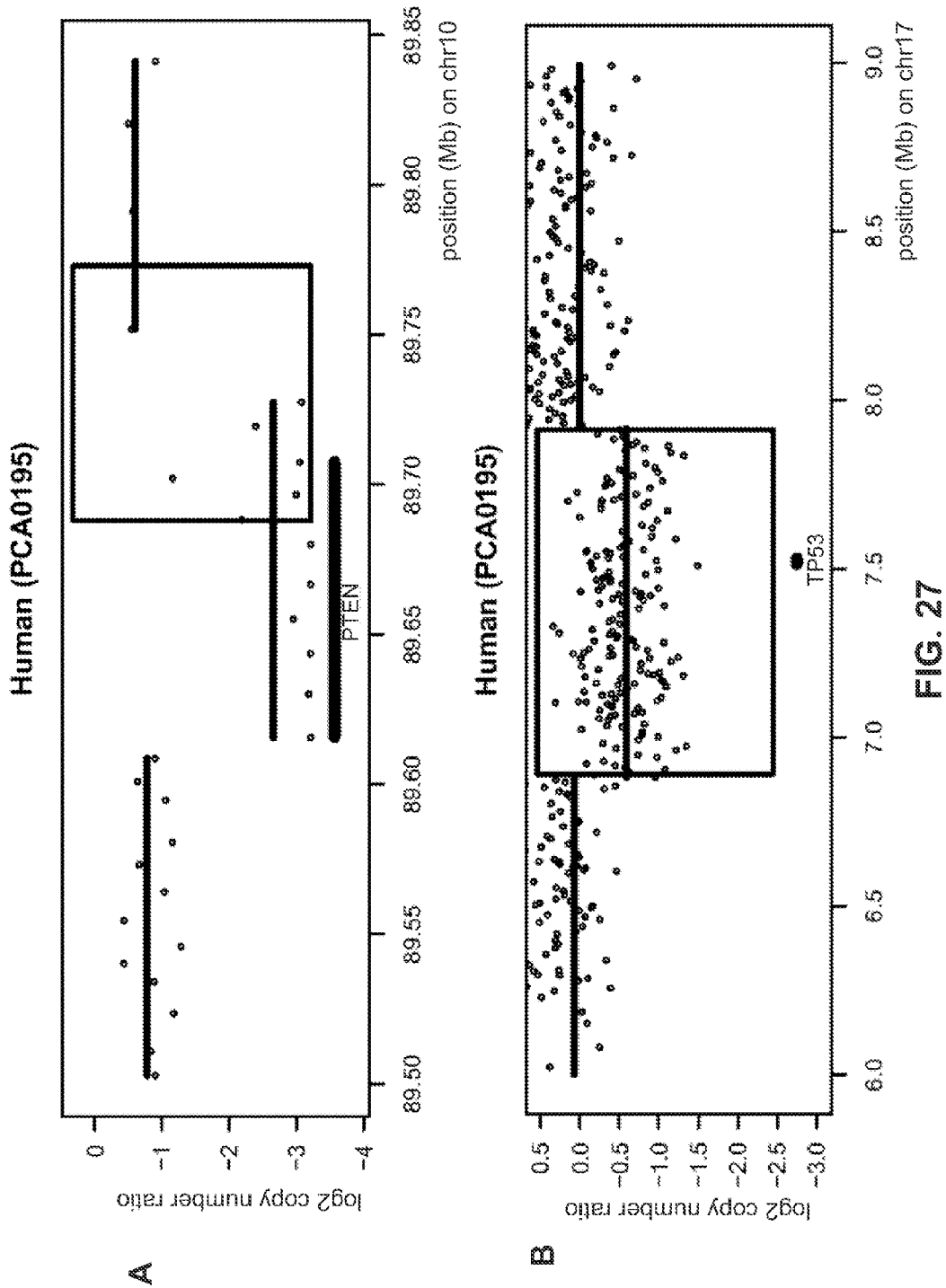
Figure 27:
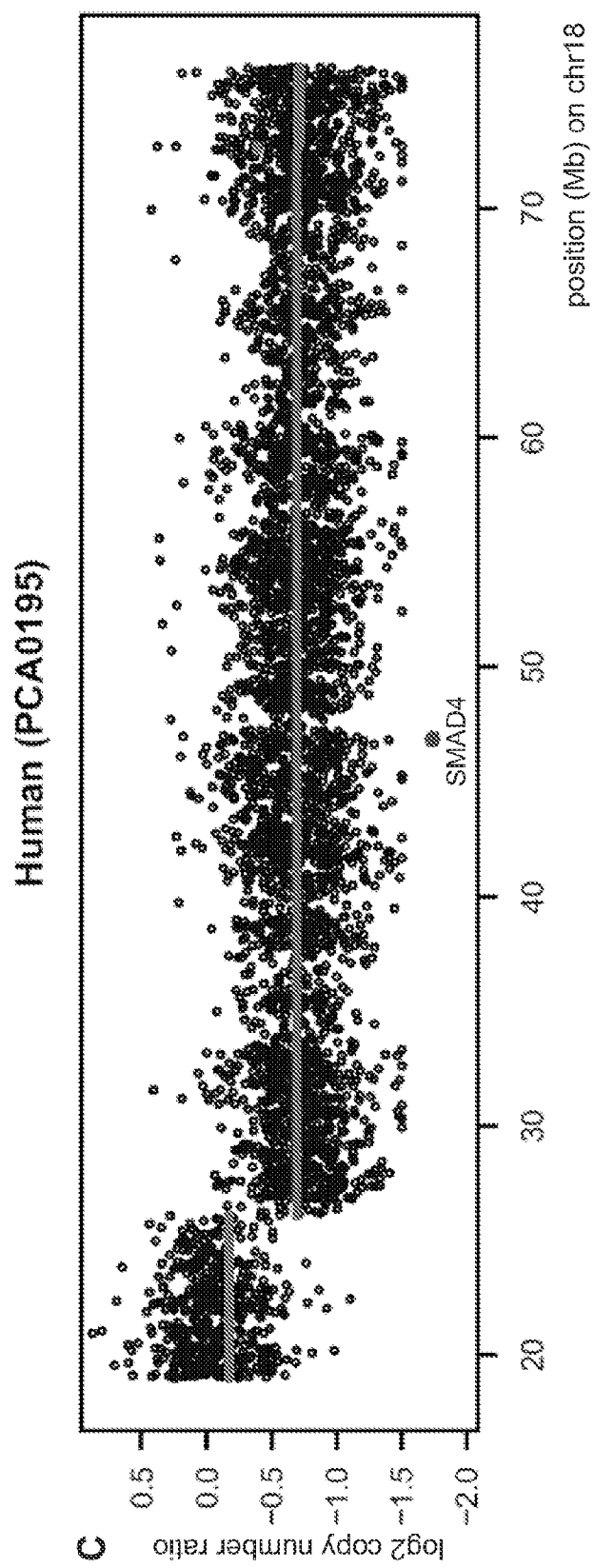

FIG. 27. Co-deletion analysis of PTEN, TP53 and SMAD4 in human prostate cancer sample PCA0195. $\log_2$ ratio of array-CGH plots showing conserved deletion of PTEN (A), TP53 (B), and SMAD4 (C). They axis shows $\log_2$ of copy number ratio (normal, $\log_2=0$); amplifications are above and deletions are below this axis; x axis is chromosome position, in Mbp.

Figure 28:
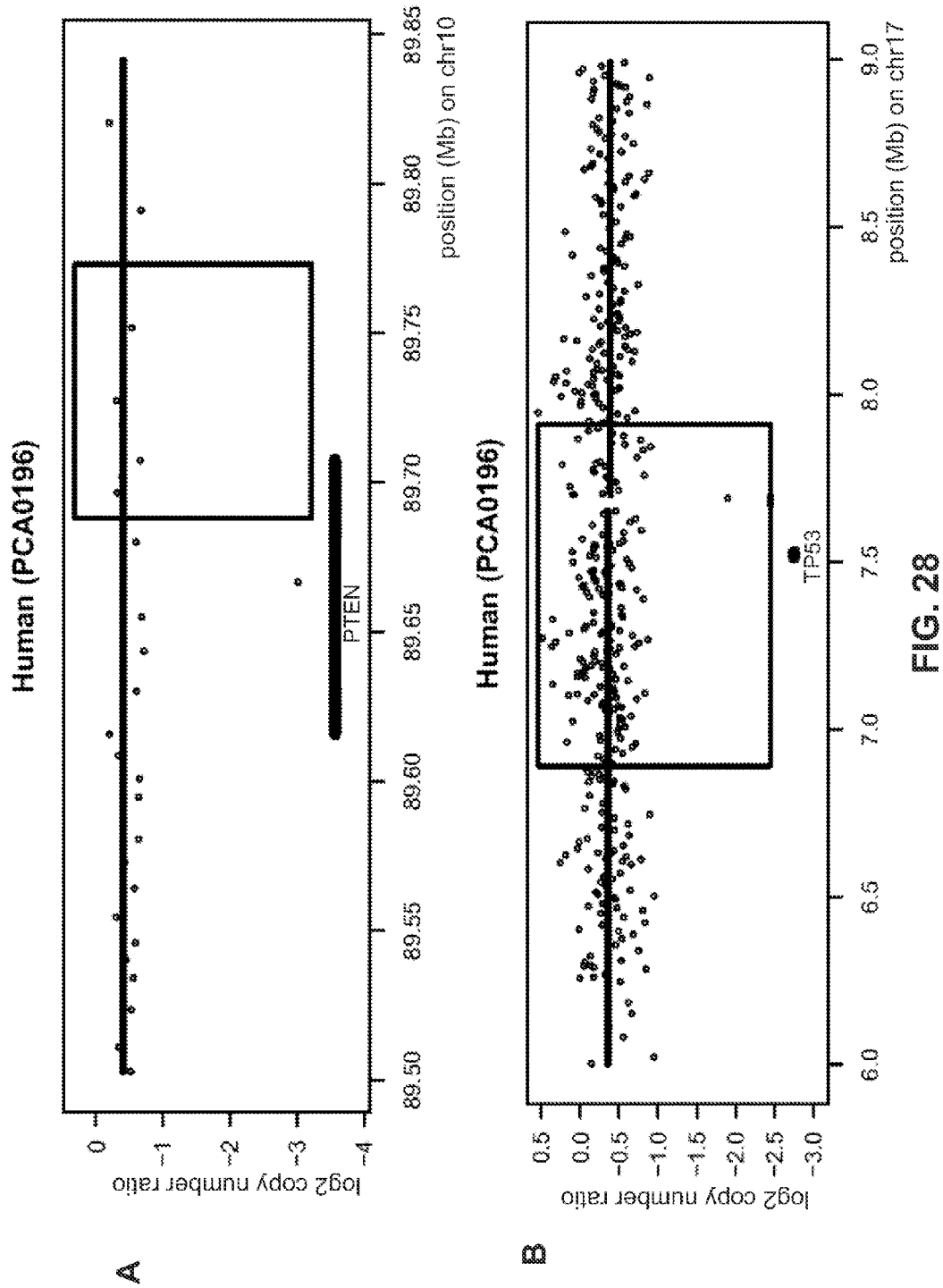
Figure 28:
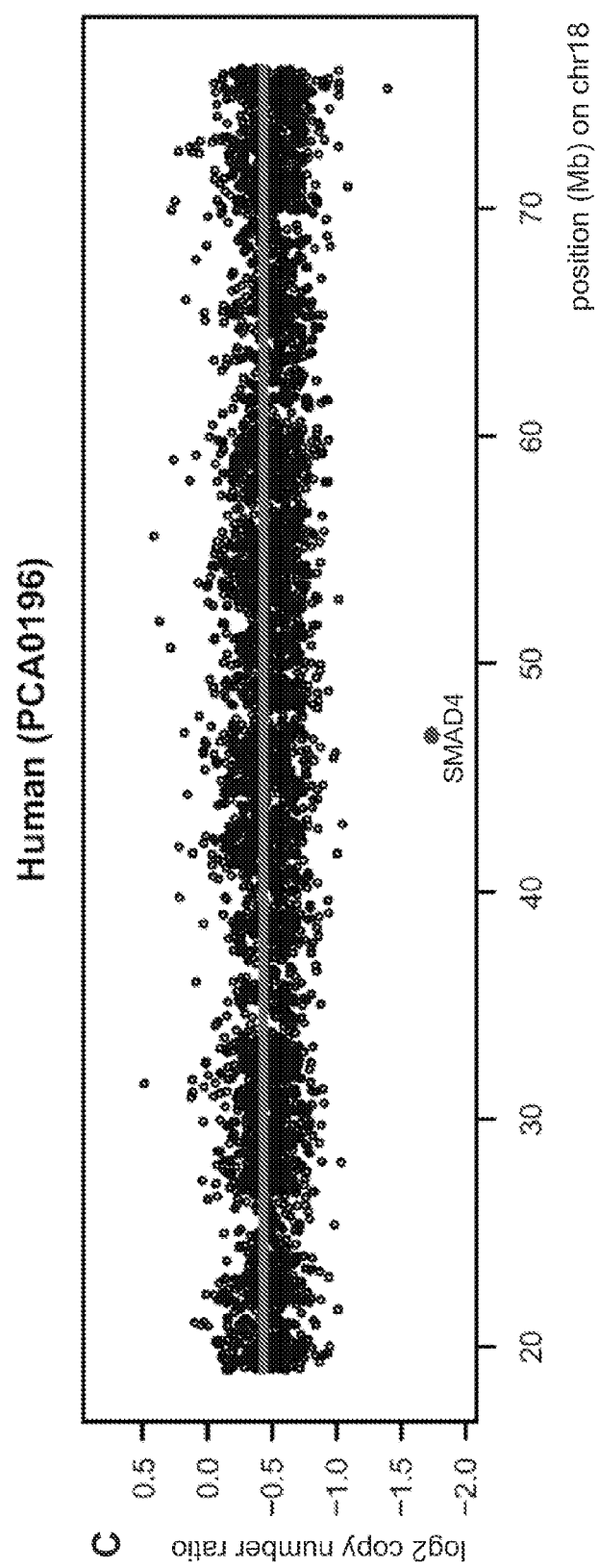

FIG. 28. Co-deletion analysis of PTEN, TP53 and SMAD4 in human prostate cancer sample PCA0196. $\log_2$ ratio of array-CGH plots showing conserved deletion of PTEN (A), TP53 (B), and SMAD4 (C). They axis shows $\log_2$ of copy number ratio (normal, $\log_2=0$); amplifications are above and deletions are below this axis; x axis is chromosome position, in Mbp.

Figure 29:
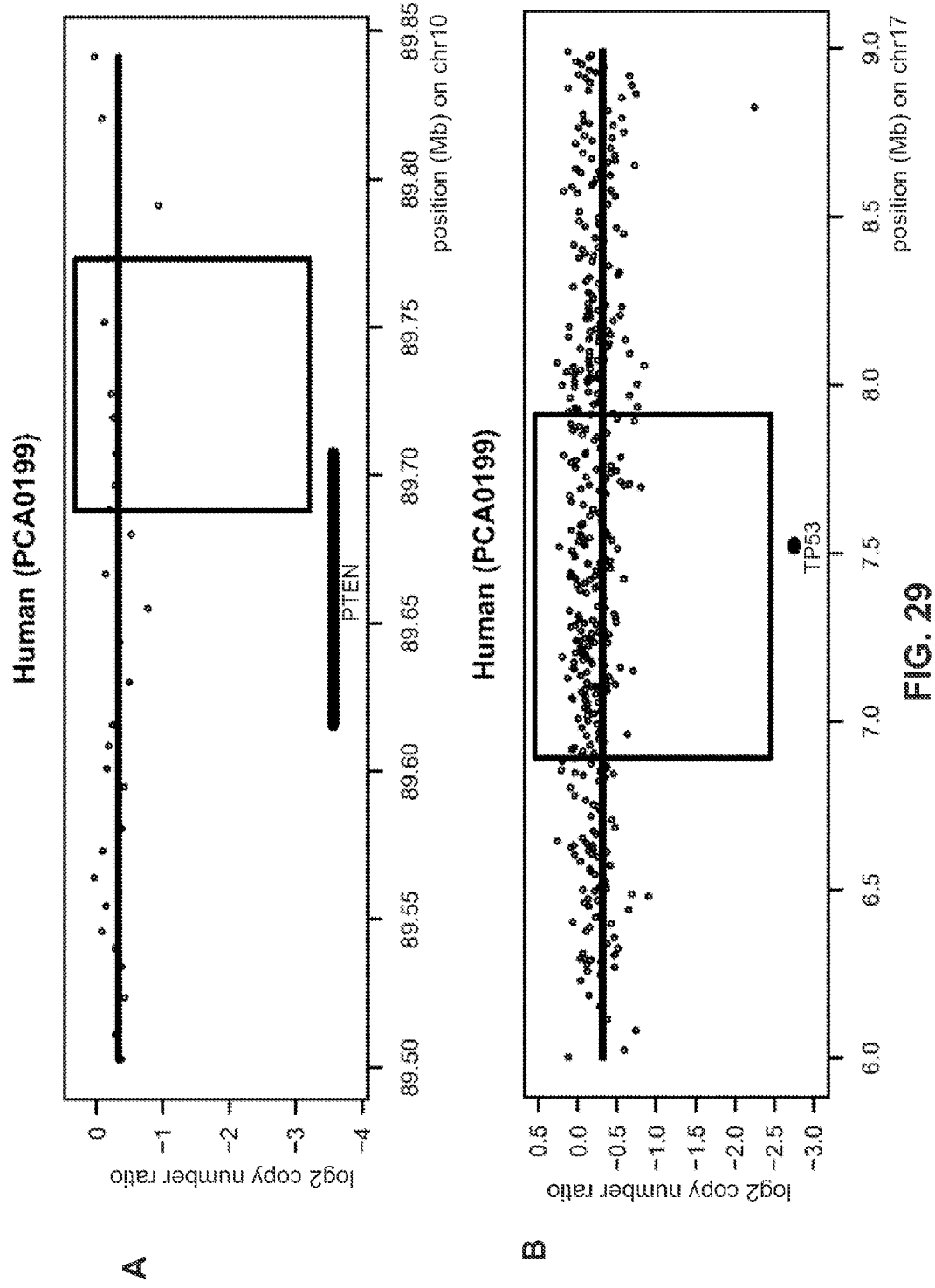
Figure 29:
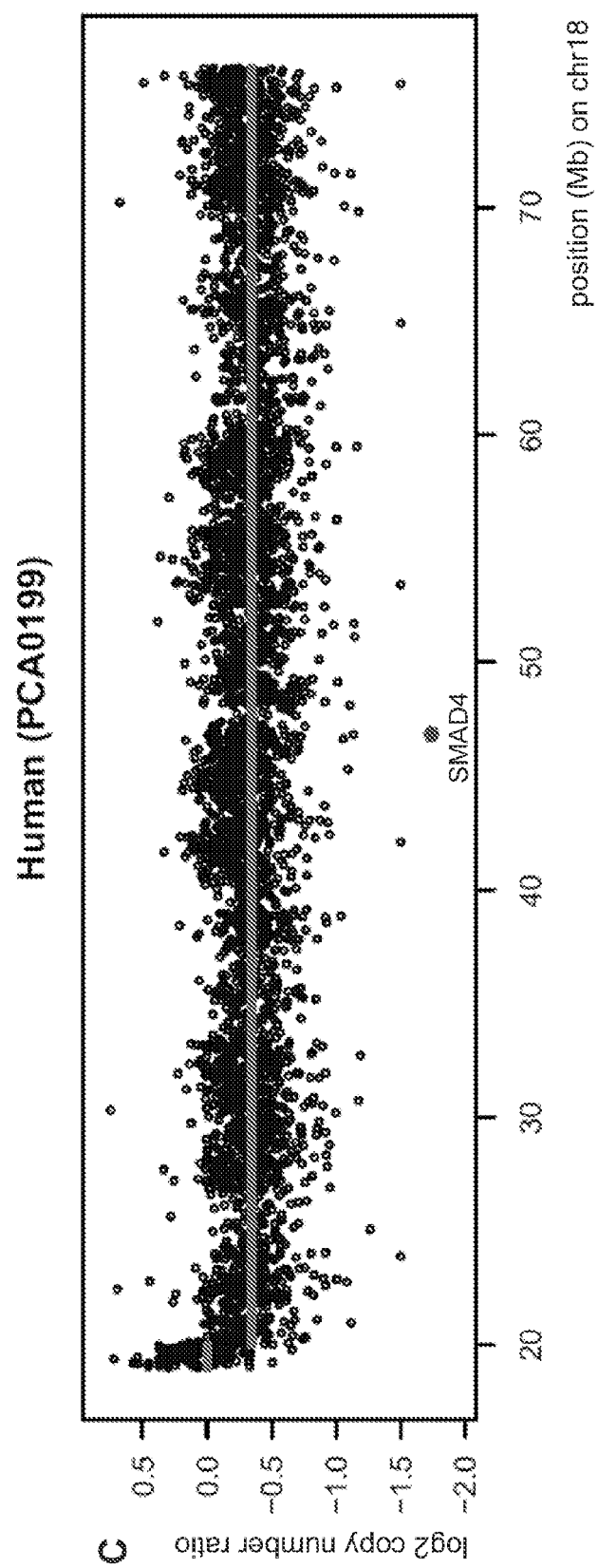

FIG. 29. Co-deletion analysis of PTEN, TP53 and SMAD4 in human prostate cancer sample PCA0199. $\log_2$ ratio of array-CGH plots showing conserved deletion of PTEN (A), TP53 (B), and SMAD4 (C). They axis shows $\log_2$ of copy number ratio (normal, $\log_2=0$); amplifications are above and deletions are below this axis; x axis is chromosome position, in Mbp.

Figure 30:
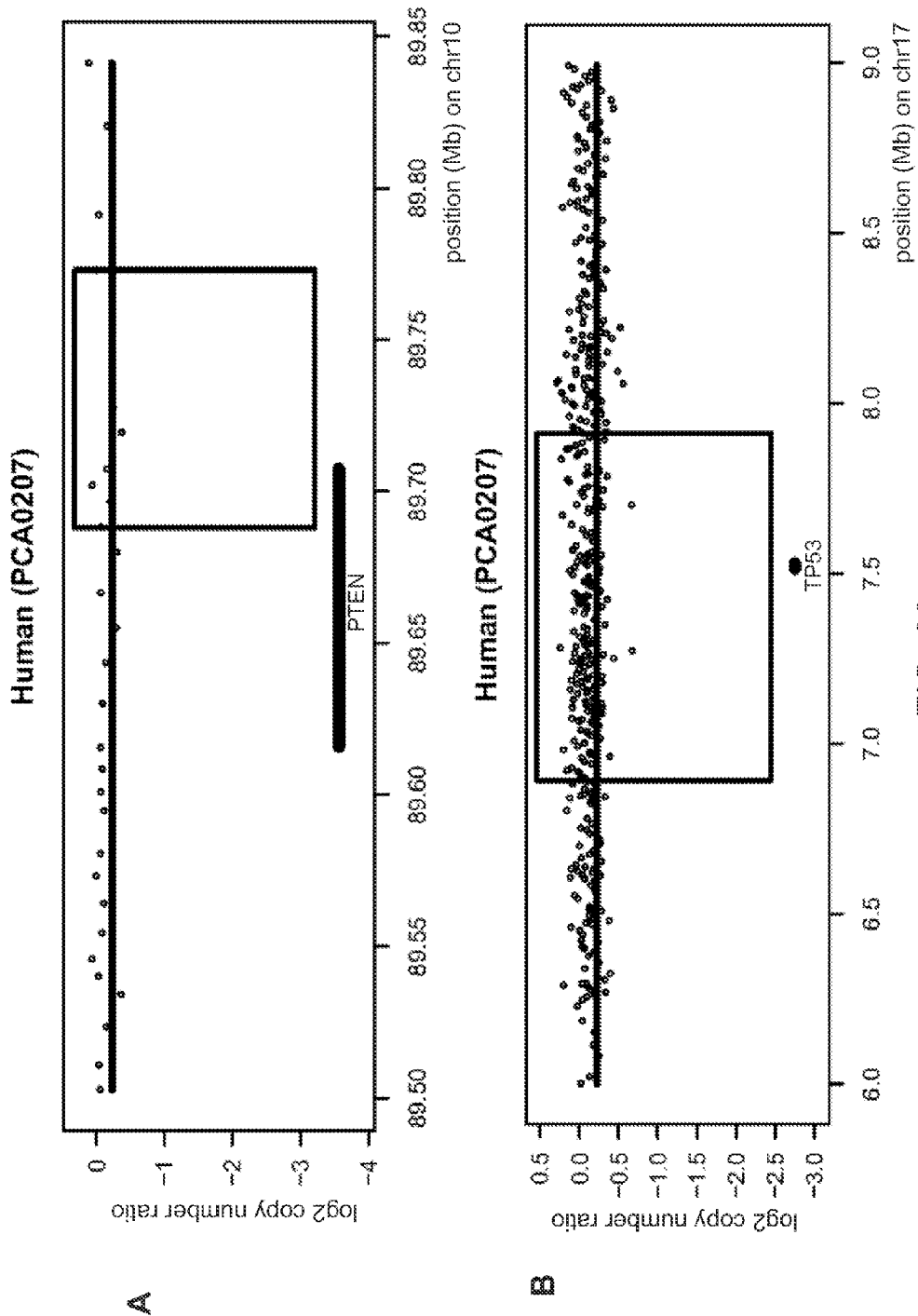
Figure 30:
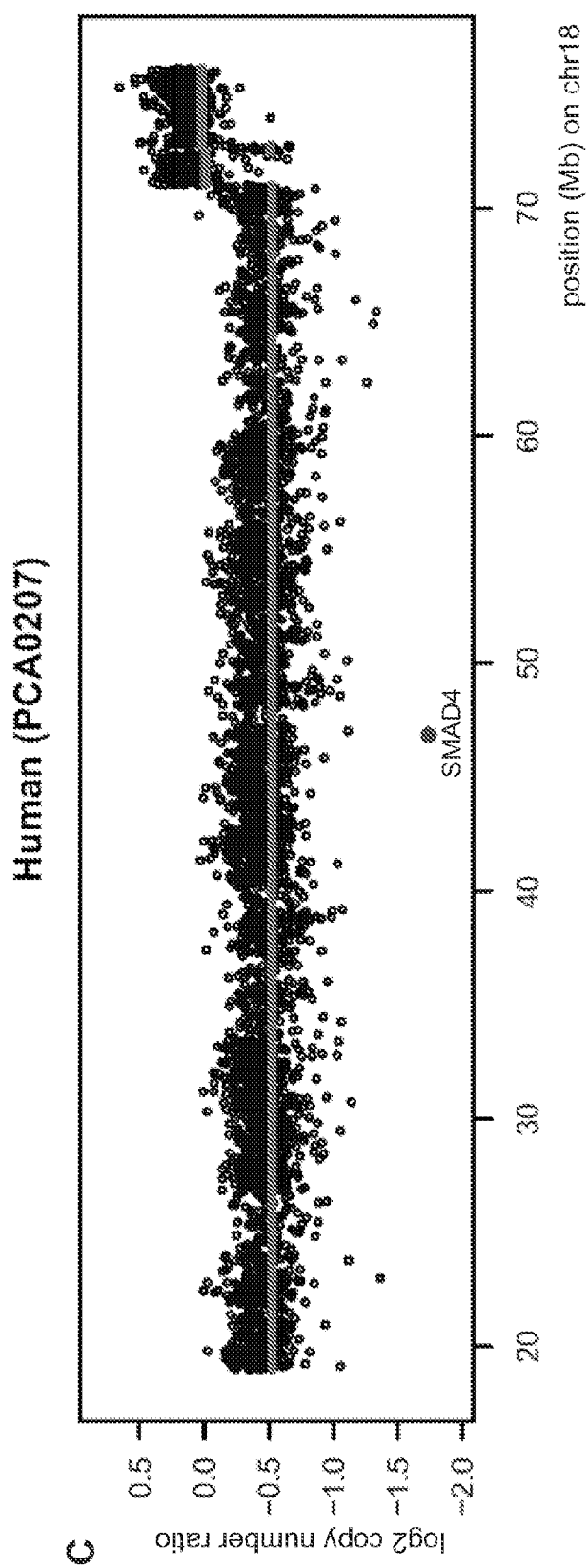

FIG. 30. Co-deletion analysis of PTEN, TP53 and SMAD4 in human prostate cancer sample PCA0207. $\log_2$ ratio of array-CGH plots showing conserved deletion of PTEN (A), TP53 (B), and SMAD4 (C). They axis shows $\log_2$ of copy number ratio (normal, $\log_2=0$); amplifications are above and deletions are below this axis; x axis is chromosome position, in Mbp.

Figure 31C:
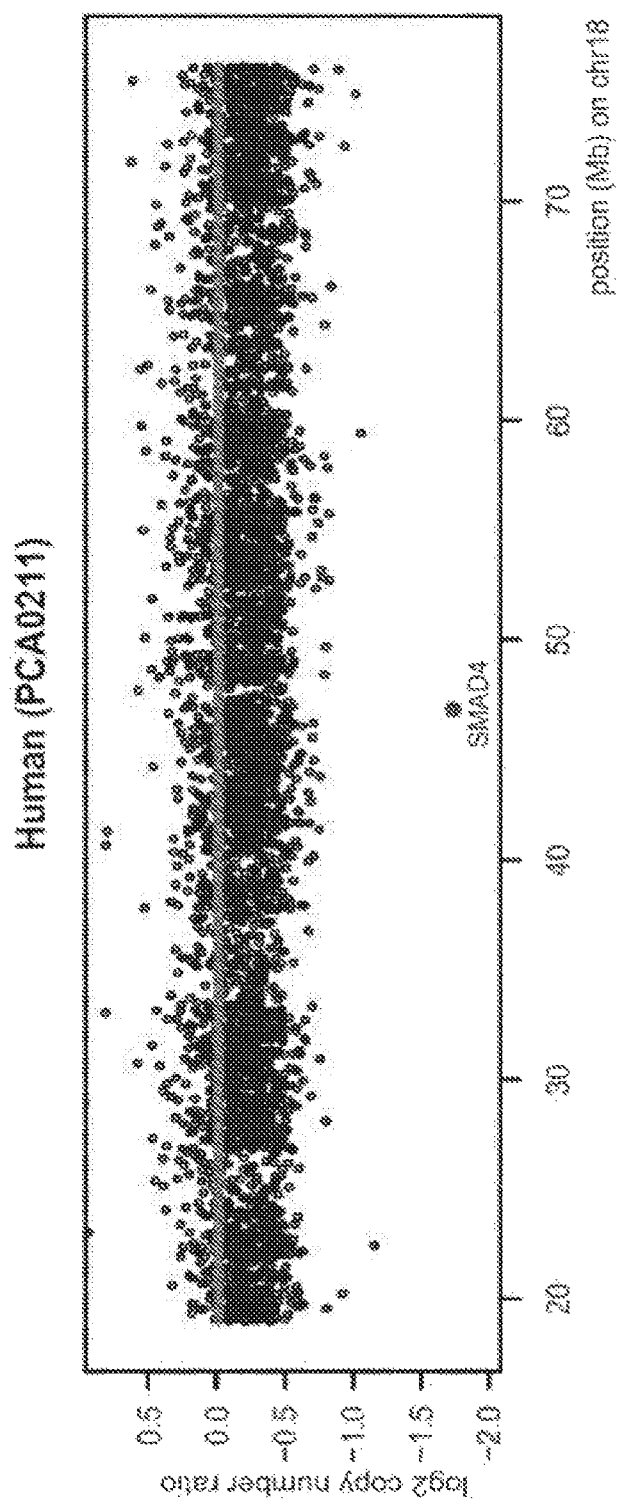

FIGS. 31A, 31B, 31C. Co-deletion analysis of PTEN, TP53 and SMAD4 in human prostate cancer sample PCA0211. $\log_2$ ratio of array-CGH plots showing conserved deletion of PTEN (FIG. 31A), TP53 (FIG. 31B), and SMAD4 (FIG. 31C). They axis shows $\log_2$ of copy number ratio (normal, $\log_2=0$); amplifications are above and deletions are below this axis; x axis is chromosome position, in Mbp.

Figure 32:
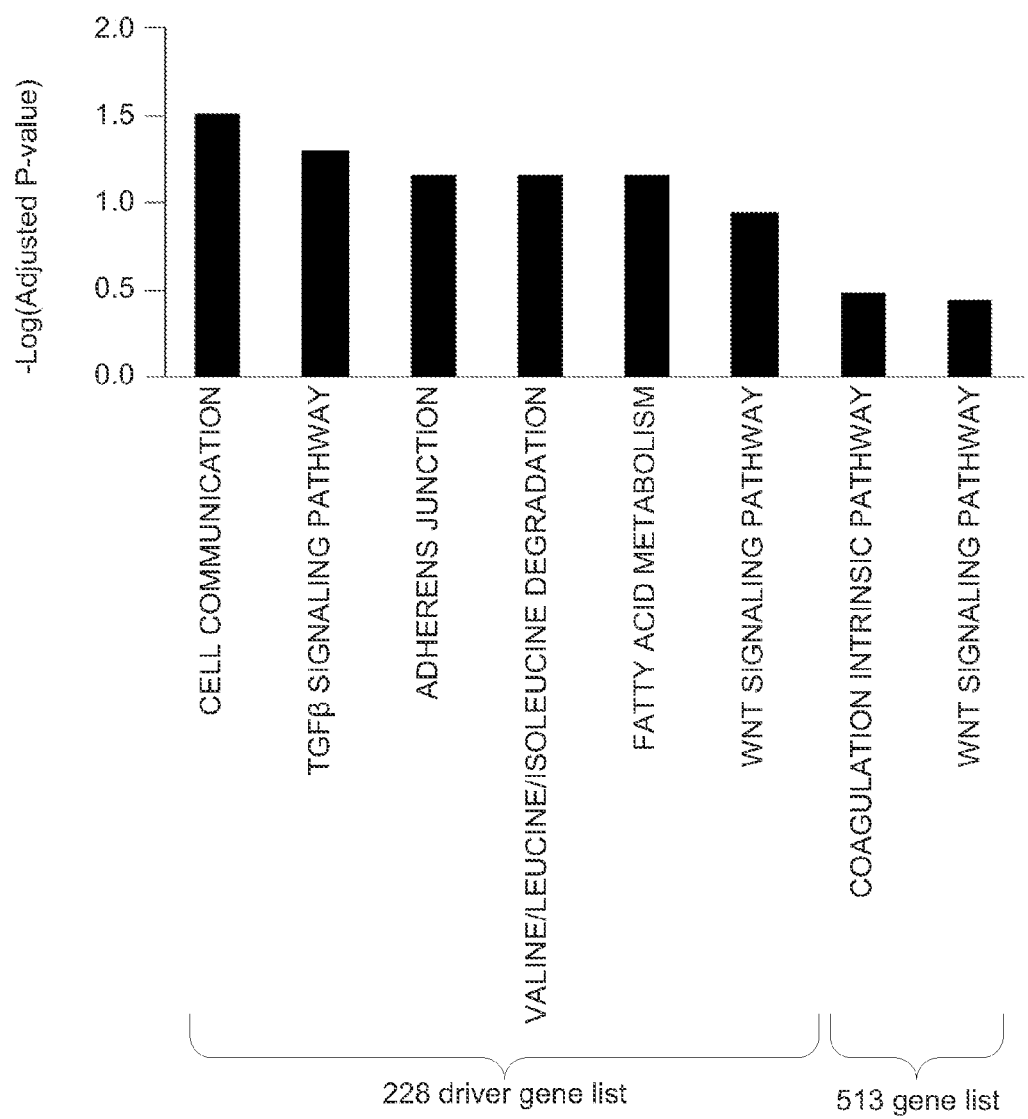

FIG. 32. Pathway enrichment analysis of 228 gene set and 513 gene set. P values were adjusted by false detection rate (FDR).

Figure 33:
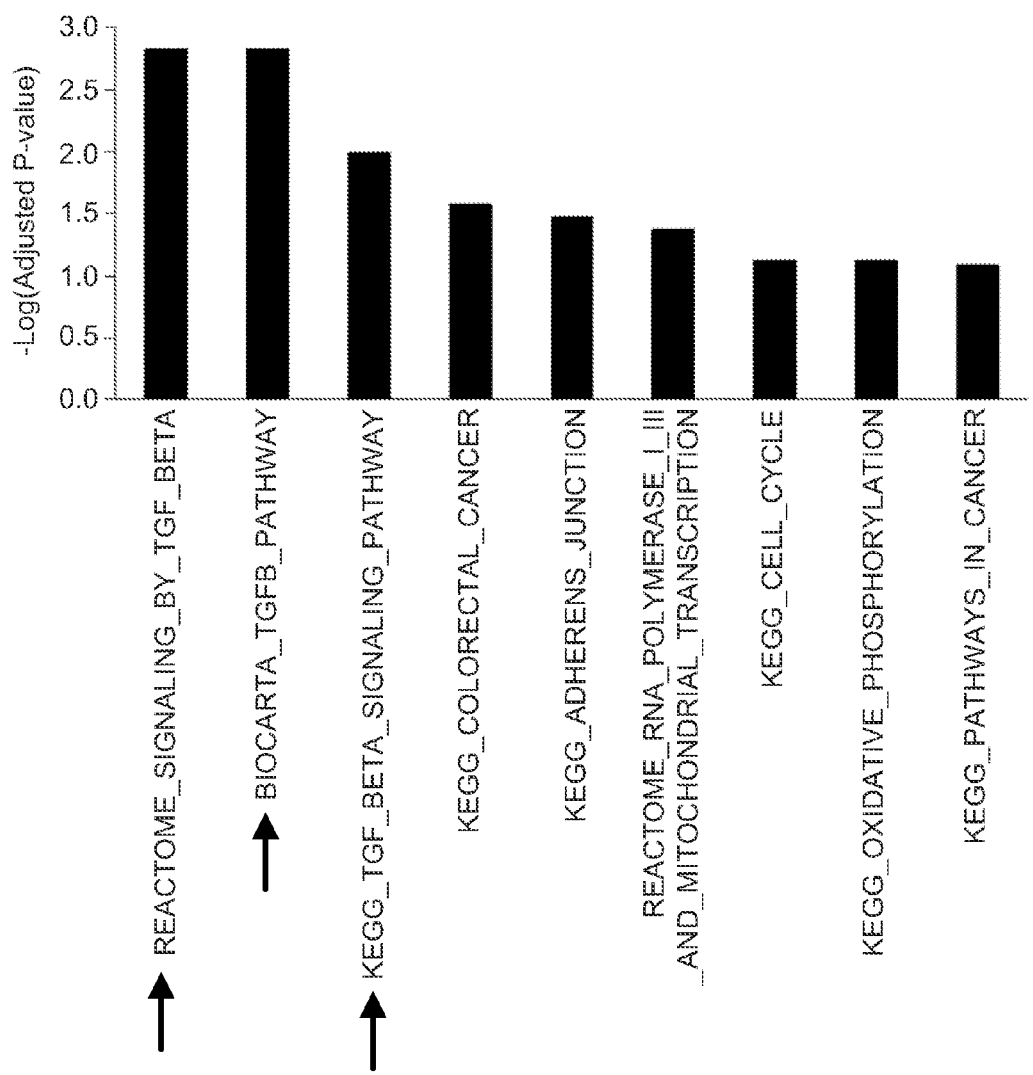

FIG. 33. Pathway enrichment analysis of bone metastasis of 113 gene set. P values were adjusted by false detection rate (FDR). Enrichment of TGF-beta signaling pathway was highlighted by arrows.

Figure 34:
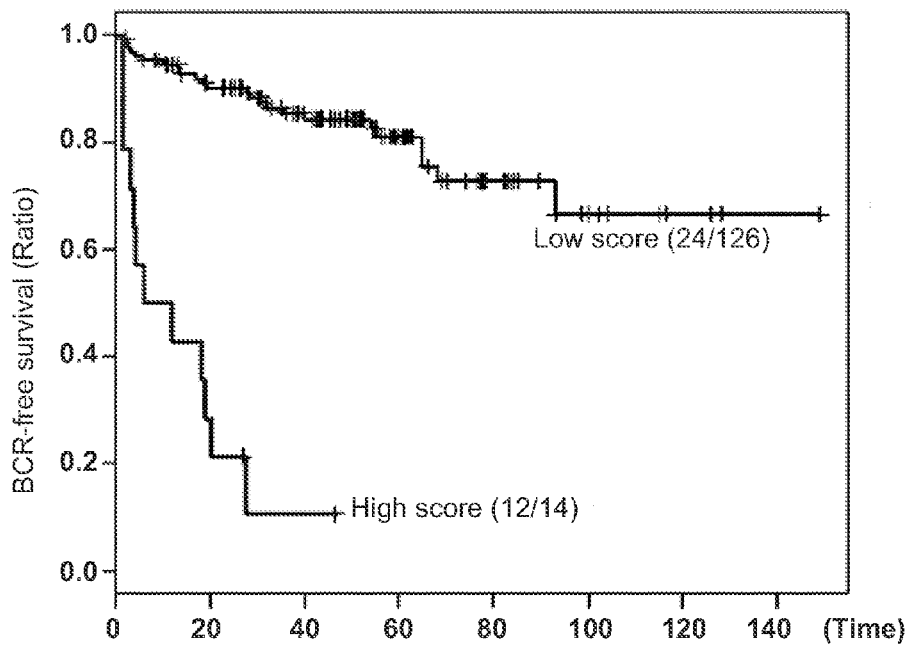
Figure 34:
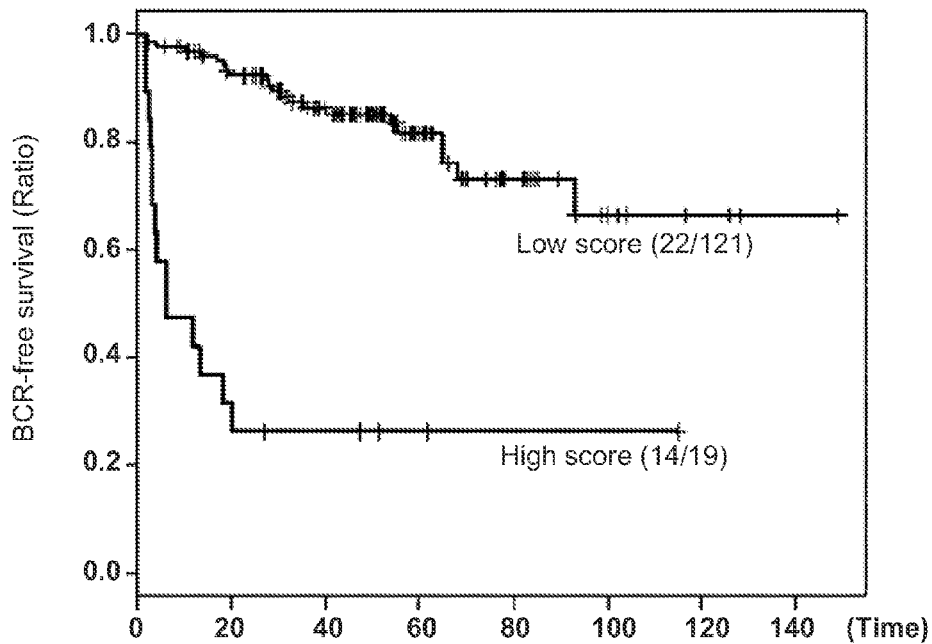
Figure 34:
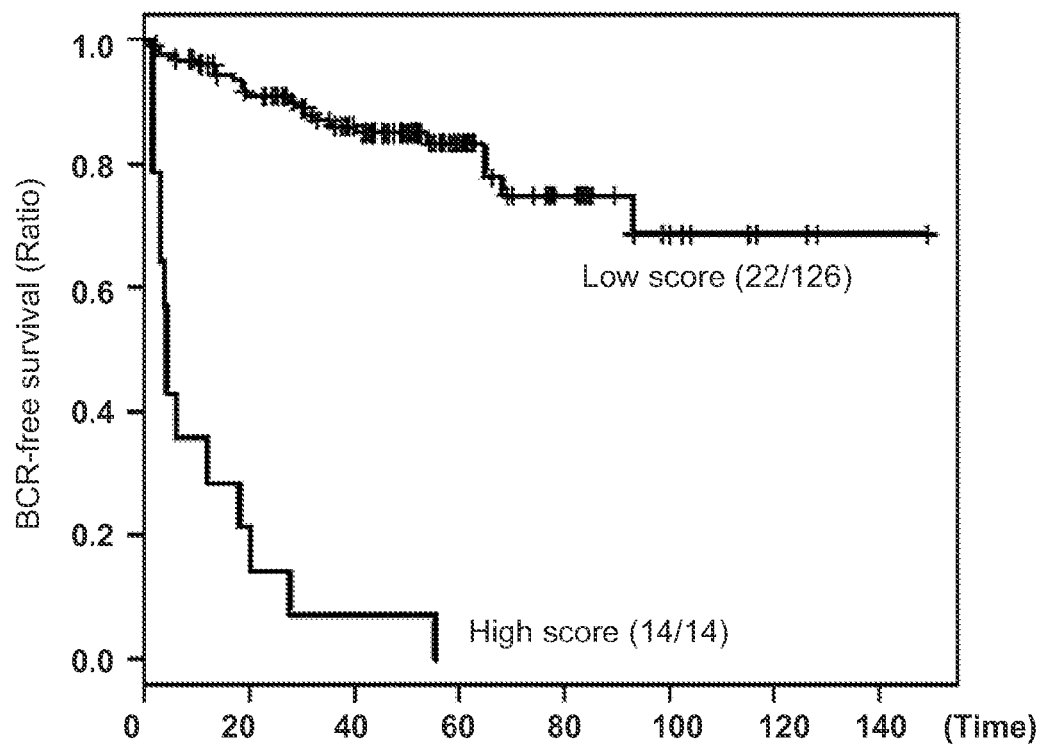

FIG. 34. The new 14 gene set can significantly enhance the previous 4 gene signature of PTEN/SMAD4/SPP1/CCND1 (Ding et al., *Nature* (2011)) to dichotomize prostate cancer cases into low versus high risk groups for BCR in Taylor et al dataset (*Cancer Cell* (2010)). (A) The enriched signaling genes in bone mets formatting a14 gene set (ATP5A1/ATP6V1C1/CUL2/CYC1/DCC/ERCC3/MBD2/MTERF/PARD3/PTK2/RBL2/SM AD2/SMAD4/SMAD7) that can significantly dichotomize prostate cancer cases into low versus high risk groups for BCR in Taylor et al dataset (2010). (B) The previous 4-gene signature (SMAD4/PTEN/CCND1/SPP1) can significantly dichotomize prostate cancer cases into low versus high risk groups for BCR in Taylor et al dataset (2010). (C) The combined gene set can significantly enhance the specificity of SMAD4/PTEN/CCND1/SPP1 dichotomize prostate cancer cases into low versus high risk groups for BCR in Taylor et al dataset (2010).

Figure 35:
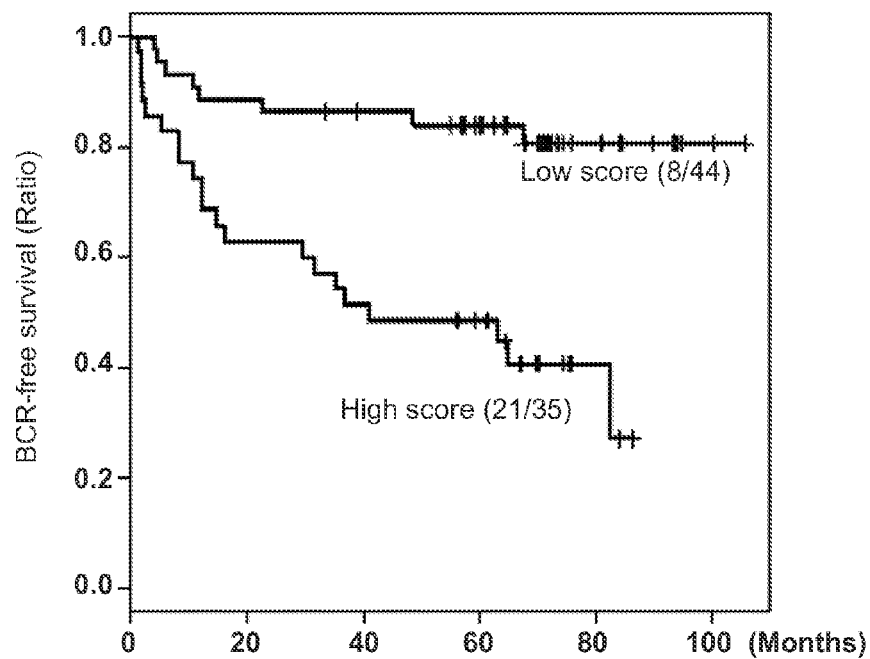
Figure 35:
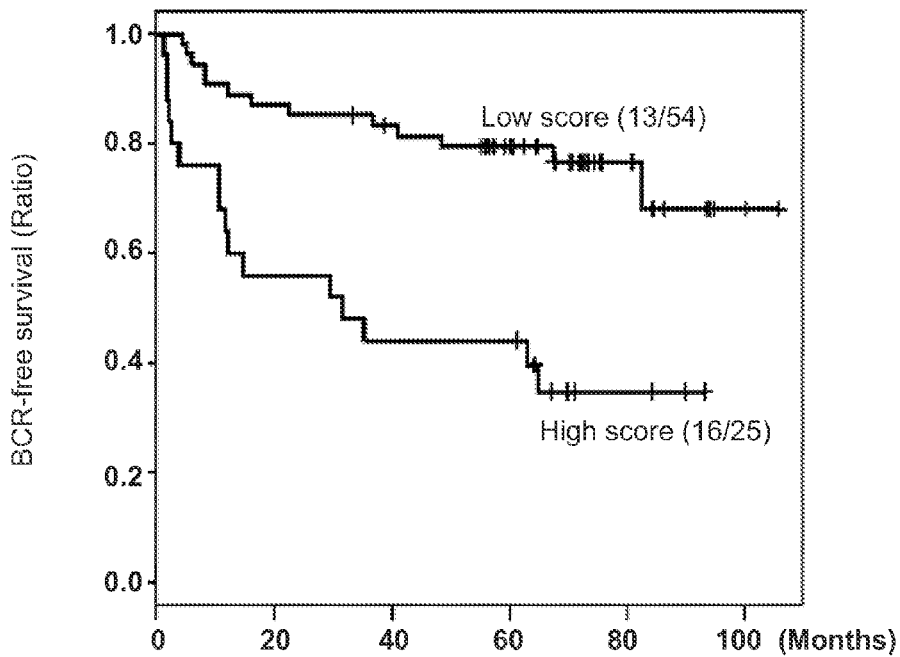
Figure 35:
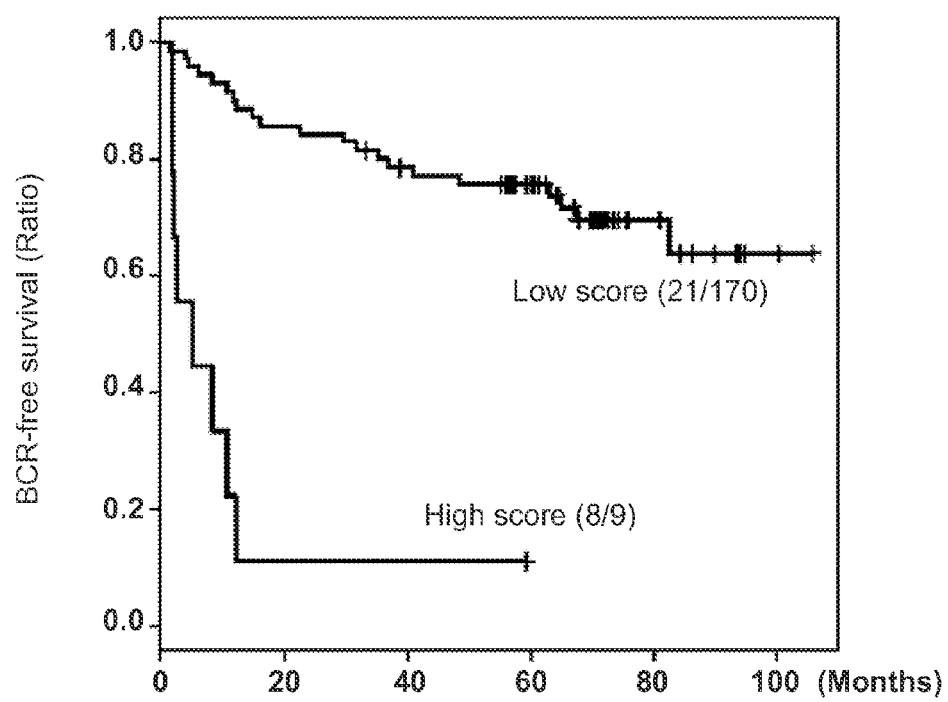

FIG. 35. The new 14 gene set can significantly enhance the previous 4 gene signature of PTEN/SMAD4/SPP1/CCND1 (Ding et al., *Nature* (2011)) to dichotomize prostate cancer cases into low versus high risk groups for BCR in Glinsky et al dataset (2004) (Glinsky et al., *J. Clin. Invest* (2004)). (A) The 14 gene set (ATP5A1/ATP6V1C1/CUL2/CYC1/DCC/ERCC3/MBD2/MTERF/PARD3/PTK2/RBL2/SM AD2/SMAD4/SMAD7) can significantly dichotomize prostate cancer cases into low versus high risk groups for BCR in Glinsky et al dataset (2004). (B) The previous 4-gene signature (SMAD4/PTEN/CCND1/SPP1) can significantly dichotomize prostate cancer cases into low versus high risk groups for BCR in Glinsky et al dataset (2004). (C) The combined gene set can significantly enhance the specificity of SMAD4/PTEN/CCND1/SPP1 dichotomize prostate cancer cases into low versus high risk groups for BCR in Glinsky et al dataset (2004).

DETAILED DESCRIPTION OF THE INVENTION

The present invention relates to the identification of signatures associated with and DETERMINANTS conferring subjects with metastatic prostate cancer or who are at risk for a recurrence of prostate cancer. The invention further provides a murine mouse model for prostate cancer, where the model displays human-like telomere dynamics in a prostate cancer prone mouse model. This mouse model allows the role of telomere dysfunction and telomerase reactivation in shaping both the genomics and biology of prostate to be elucidated. The mouse model can be used to identify prostate cancer genes and prognostic biomarkers.

Human cancers harbor innumerable genetic and epigenetic alterations presenting formidable challenges in deciphering those changes that drive the malignant process and dictate a given tumor's clinical behavior. The need for accurately predictive biomarkers reflective of a tumor's malignant potential is evident across many cancer types, particularly prostate cancer, where current management algorithms result in either under-treatment with consequent risk of death or exposure to unnecessary morbid treatments.

Genetically engineered mouse models have been shown (Sharpless and DePinho, Nat. Rev. Drug Discov. (2006)) to be tremendously powerful as "filters" to mine highly complex genomic datasets in human. In particular, these refined genetically engineered mouse models of human cancers have been documented in high-resolution comparative oncogenomic analyses to harbor substantial overlap in cancer-associated transcriptional and chromosomal DNA aberrations patterns—the latter resulting in the rapid and efficient identification of many novel cancer genes. Similar cross-species comparisons of the serum proteome have also proven effective in the identification of early detection biomarkers for pancreas cancer in humans.

Human prostate cancer genomes are often highly rearranged, displaying numerous chromosomal rearrangements and copy number aberrations of known and potential pathogenetic significance. Telomere dysfunction has been proposed as a mechanism that drives genomic instability in early stage human prostate cancers. In contrast, current mouse models of prostate cancer are notable for minimal cytogenetic aberrations, which may relate to the longer telomeres and more promiscuous expression of telomerase in laboratory mice. Thus, it stands to reason that development of a valid mouse model recapitulating human-like telomere dynamics in a prostate cancer prone mouse model will greatly facilitate our efforts to develop prognostic and early detection biomarkers and possible therapeutic targets.

Both conventional knock-out and inducible Lox-Stop-Lox (LSL) knock-in alleles of the mouse telomerase reverse transcriptase (mTert) gene were utilized in mice engineered to sustain prostate-specific Probasin-Cre deletion of the Pten and p53 tumor suppressor genes (PB-Pten/p53). While telomere dysfunction produced by successive mTert null intercrosses constrained prostate cancer progression in the PB-Pten/p53 model, the inducible telomerase (LSL-mTert) allele which models telomere dysfunction followed by telomerase reactivation showed highly aggressive prostate cancers with spread to lumbar spine. On the tumor biological level, telomerase reactivation was associated with a dramatic alleviation of telomere checkpoint responses including DNA damage foci, cell cycle arrest and apoptosis. Spectral karyotype and array-CGH analyses of these models revealed genomic complexity comparable to that of human prostate cancer with many non-reciprocal translocations and recurrent amplifications and deletions. These copy number aberrations targeted regions syntenic to those in human prostate cancer such a components of the SMAD signaling pathway, suggesting that human and mouse prostate cancers sustain common somatic events in their evolution.

This invention has established a bona fide genetically engineered mouse model of human PCA. This model has not only facilitated the identification of a novel marker set for prostate cancer recurrence in men but also enables mechanistic studies as well as comparative genomic and proteomic analyses in searches for prognostic and early-detection biomarkers.

The data of the invention has demonstrated that the tumor biological impact of SMAD4 inactivation includes increased invasion, increased S phase entry, and decreased senescence.

The data of this invention has also demonstrated that certain SMAD4 direct targets can be useful as biomarkers/DETERMINANTS used in the methods/kits of this invention, including, but not limited to SPP1 and cyclin D1.

The data of this invention also demonstrates that unbiased checkpoint scan identifies TGFβ-Smad4 as a major progression barrier in mouse and human prostate cancer; that genetic inactivation of PTEN and Smad4 generates a metastatic prostate cancer model and that integrative cross-species genomic and functional analysis can identify gene sets of potential clinical utility.

The data of this invention further demonstrates that telomere dysfunction in the Pten/p53 PCAs generates complex chromosomal rearrangements (NRTs) and copy number aberrations; that genomics events in the mouse PCA target regions altered in the human disease; and that genome instability enables acquisition of new biological features including bony metastasis.

Genomic, biological and mouse modeling studies have identified and validated a constellation of genetic and epigenetic events driving disease genesis and progression (Shen et al., Genes Dev. (2010)). Genetic studies of human PCA has identified a number of signature events, principally among which are PTEN and $p27^{Kip1}$ tumor suppressor inactivation (Li et al., Science (1997), Guo et al, Clin. Cancer Res. (1997), Majumder et al., Cancer Cell (2008), ETS family translocation and dysregulation (Tomlins et al., Science (2005), Rubin, Mod. Pathol. (2008)), as well as many other genetic and/or epigenetic alterations including Nkx3.1, c-Myc, SPINK, and FGFRs (Abate-Shen et al., Differentiation (2008), Tomlins et al., Cancer Cell (2008), Jenkins et al., Cancer Res. (1997), Acevedo et al., Cell Cycle (2009)). Global molecular analyses have also identified an array of potential recurrence/metastasis biomarkers such as ECAD (Rubin et al., Hum. Pathol. (2001)), AIPC (Chaib et al., Cancer Res. (2001)), Pim-1 Kinase (Dhanasekaran et al., Nature (2001)), hepsin (Dhanasekaran et al., Nature (2001)), AMACR (Rubin et al, JAMA (2002)), microRNA mir101 (Varambally et al., Science (2008)), the mir101 target EZH2 (Varambally et al., Nature (2002)), EZH2 target DAB21P (Min et al., Nat. Med. (2010)), p53 (Chen et al., Nature (2005)), and SMAD4 (Ding et al., Nature (2011)). Recent copy number profile analysis of a large collection of human prostate cancers has revealed numerous recurrent large and focal amplifications and deletions (Taylor et al., Cancer Cell (2010)), pointing to the existence of many uncharacterized cancer-relevant genes of potential prognostic and therapeutic significance. Identification and ultimate biological and clinical validation of these potential cancer genes are hampered by significant intratumoral cellular and biological heterogeneity of human prostate cancers, paucity of human cell culture model systems, among other challenges. In other solid tumor types, integration of genomic data from genetically engineered mouse models of human cancer has served as a useful filter to facilitate novel cancer gene discovery (Taylor et al., *Cancer Cell* (2010), Kim et al., *Cell* (2006), Zender et al., *Cell* (2006)), particularly in genomically unstable models (Maser et al., *Nature* (2007)).

Many genome instability mechanisms are thought to contribute to the accumulation of myriad somatic genetic events present in human cancers, particularly epithelial cancers (DePinho, *Nature* (2007)). Genetic studies in the mouse revealed a cooperative role for telomere dysfunction and deactivated p53 in driving epithelial carcinogenesis via a DNA double-strand breakage process which produces non-reciprocal translocations, amplifications and deletions (Artandi et al., *Nature* (2000), Chin et al., *Cell* (1999), O'Hagan et al., *Cancer Cell* (2002)). Telomere dysfunction also appears to drive human epithelial cancers and its associated genomic instability on the basis of coincidental telomere erosion, anaphase bridging, and chromosomal instability in early stage human carcinomas of the colon (Rudolph et al., *Nat. Genet.* (2001)), breast (Chin et al., *Nat. Genet.* (2004)), pancreas (Feldmann et al., *J. Hepatobiliary. Pancreat. Surg.* (2007)), and prostate (Meeker et al., *Cancer Res.* (2002). Recent whole genome sequencing data has provided additional evidence that a period of telomere dysfunction serves to shape the genome rearrangement in human carcinomas (Stratton et al., *Nature* (2009). In prostate cancer, telomeres are shorter in cancer cells relative to adjacent normal tissues (Sommerfeld et al., *Cancer Res.* (1996)); and telomere erosion appears to occur early in the evolution of human prostate cancer (Meeker et al., *Cancer Res.* (2002), Vukovic et al., *Oncogene* (2003)).

While telomere dysfunction serves to drive early stages of cancer development, numerous mouse and human studies have shown that subsequent telomerase activation and restoration of telomere function may enable full malignant potential (Stratton et al., *Nature* (2009), Hahn et al., *Nat. Med.* (1999)), including metastatic capability (Chang et al., *Genes Dev.* (2003)). Accordingly, telomerase activity has been documented to be low or undetectable in normal prostate tissues, yet elevated in the majority of prostate tumors (Sommerfeld et al., *Cancer Res.* (1996), Kallakury et al., *Diagn. Mol. Pathol.* (1998), Lin et al., *J. Urol.* (1997), Koeneman et al., *J. Urol.* (1998), Zhang et al., *Cancer Res.* (1998)). In this invention, we exploited the experimental merits of the mouse to substantiate the role of telomeres and telomerase in prostate cancer genesis versus progression and in the generation of translocations, amplifications and deletions. In this mouse model, we further assessed whether cancer-relevant loci were targeted by these chromosomal aberrations and the potential for comparative oncogenomics to identify novel prostate cancer genes and prognostic biomarkers.

Accordingly, the invention provides an animal model for prostate cancer. The animal model of the instant invention thus finds particular utility as a screening tool to elucidate the mechanisms of the various genes involved in both normal and diseased patient populations.

The invention also provides methods for identifying subjects who have metastatic prostate cancer, or who at risk for experiencing a prostate cancer recurrence by the detection of DETERMINANTS associated with the tumor, including those subjects who are asymptomatic for the tumor. These signatures and DETERMINANTS are also useful for monitoring subjects undergoing treatments and therapies for cancer, and for selecting or modifying therapies and treatments that would be efficacious in subjects having cancer, wherein selection and use of such treatments and therapies slow the progression of the tumor, or substantially delay or prevent its onset, or reduce or prevent the incidence of tumor metastasis and recurrence.

DEFINITIONS

"Accuracy" refers to the degree of conformity of a measured or calculated quantity (a test reported value) to its actual (or true) value. Clinical accuracy relates to the proportion of true outcomes (true positives (TP) or true negatives (TN) versus misclassified outcomes (false positives (FP) or false negatives (FN)), and may be stated as a sensitivity, specificity, positive predictive values (PPV) or negative predictive values (NPV), or as a likelihood, odds ratio, among other measures.

"DETERMINANTS" in the context of the present invention encompasses, without limitation, proteins, nucleic acids, and metabolites, together with their polymorphisms, mutations, variants, modifications, subunits, fragments, protein-ligand complexes, and degradation products, protein-ligand complexes, elements, related metabolites, and other analytes or sample-derived measures. DETERMINANTS can also include mutated proteins or mutated nucleic acids. DETERMINANTS also encompass non-blood borne factors or non-analyte physiological markers of health status, such as "clinical parameters" defined herein, as well as "traditional laboratory risk factors", also defined herein. DETERMINANTS also include any calculated indices created mathematically or combinations of any one or more of the foregoing measurements, including temporal trends and differences. Where available, and unless otherwise described herein, DETERMINANTS which are gene products are identified based on the official letter abbreviation or gene symbol assigned by the international Human Genome Organization Naming Committee (HGNC) and listed at the date of this filing at the US National Center for Biotechnology Information (NCBI) web site (http://www.ncbi.nlm.nih gov/sites/entrez?db=gene), also known as Entrez Gene.

"DETERMINANT" OR "DETERMINANTS" encompass one or more of all nucleic acids or polypeptides whose levels are changed in subjects who have prostate cancer or are predisposed to developing metastatic prostate cancer, or at risk of a recurrence of prostate cancer. Individual DETERMINANTS are summarized in Table 2 and are collectively referred to herein as, inter alia, "prostate cancer-associated proteins", "DETERMINANT polypeptides", or "DETERMINANT proteins". The corresponding nucleic acids encoding the polypeptides are referred to as "prostate cancer-associated nucleic acids", "prostate cancer-associated genes", "DETERMINANT nucleic acids", or "DETERMINANT genes". Unless indicated otherwise, "DETERMINANT", "prostate cancer-associated proteins", "prostate cancer-associated nucleic acids" are meant to refer to any of the sequences disclosed herein. The corresponding metabolites of the DETERMINANT proteins or nucleic acids can also be measured, as well as any of the aforementioned traditional risk marker metabolites.

A DETERMINANT may be implicated in cancer progression or have oncogenic activity. For example, MTDH promotes metastasis & chemoresistance (Hu et al., 2009) and activates AKT (Kikuno et al., 2007); PTK2/FAK is known to drive cell motility and proliferation (Chang et al., 2007) and can promote human prostate cancer cell invasiveness (Johnson et al., 2008); EBAG9 promotes metastasis in 4T1 breast cancer model (Hong et al., 2009) and is associated with high Gleason score and recurrence (Takahashi et al., 2003); YWHAZ/14-3-3ζ is amplified in H&N SCC and possesses oncogenic activity (Lin et al., 2009); AKAP9 is oncogenic in thyroid papillary carcinoma via fusion to BRAF (Ciampi et al., 2005) and amplified in metastatic melanoma (Kabbarah et al., 2010); MTUS1 has tumor suppressive activity in breast cancer (Rodrigues-Ferreira et al., 2009); DCC is a potential tumor suppressor gene in colon cancer (Mehlen et al., 1998) and putative metastasis suppressor gene (Rodrigues et al., 2007); APC and Smad2/Smad4 were deleted in up to 20% of human PCA, highlighting the importance of Wnt activation and deactivation of TGFβ pathway (Ding et al., Nature 2011).

Physiological markers of health status (e.g., such as age, family history, and other measurements commonly used as traditional risk factors) are referred to as "DETERMINANT physiology". Calculated indices created from mathematically combining measurements of one or more, preferably two or more of the aforementioned classes of DETERMINANTS are referred to as "DETERMINANT indices".

"Clinical parameters" encompasses all non-sample or non-analyte biomarkers of subject health status or other characteristics, such as, without limitation, age (Age), ethnicity (RACE), gender (Sex), or family history (FamHX).

"Circulating endothelial cell" ("CEC") is an endothelial cell from the inner wall of blood vessels which sheds into the bloodstream under certain circumstances, including inflammation, and contributes to the formation of new vasculature associated with cancer pathogenesis. CECs may be useful as a marker of tumor progression and/or response to antiangiogenic therapy.

"Circulating tumor cell" ("CTC") is a tumor cell of epithelial origin which is shed from the primary tumor upon metastasis, and enters the circulation. The number of circulating tumor cells in peripheral blood is associated with prognosis in patients with metastatic cancer. These cells can be separated and quantified using immunologic methods that detect epithelial cells, and their expression of PCA progression DETERMINANTS can be quantified by qRT-PCR, immunofluorescence, or other approaches.

"FN" is false negative, which for a disease state test means classifying a disease subject incorrectly as non-disease or normal.

"FP" is false positive, which for a disease state test means classifying a normal subject incorrectly as having disease.

A "formula," "algorithm," or "model" is any mathematical equation, algorithmic, analytical or programmed process, or statistical technique that takes one or more continuous or categorical inputs (herein called "parameters") and calculates an output value, sometimes referred to as an "index" or "index value." Non-limiting examples of "formulas" include sums, ratios, and regression operators, such as coefficients or exponents, biomarker value transformations and normalizations (including, without limitation, those normalization schemes based on clinical parameters, such as gender, age, or ethnicity), rules and guidelines, statistical classification models, and neural networks trained on historical populations. Of particular use in combining DETERMINANTS and other DETERMINANTS are linear and non-linear equations and statistical classification analyses to determine the relationship between levels of DETERMINANTS detected in a subject sample and the subject's risk of metastatic disease. In panel and combination construction, of particular interest are structural and synactic statistical classification algorithms, and methods of risk index construction, utilizing pattern recognition features, including established techniques such as cross-correlation, Principal Components Analysis (PCA), factor rotation, Logistic Regression (LogReg), Linear Discriminant Analysis (LDA), Eigengene Linear Discriminant Analysis (ELDA), Support Vector Machines (SVM), Random Forest (RF), Recursive Partitioning Tree (RPART), as well as other related decision tree classification techniques, Shrunken Centroids (SC), StepAIC, Kth-Nearest Neighbor, Boosting, Decision Trees, Neural Networks, Bayesian Networks, Support Vector Machines, and Hidden Markov Models, among others. Other techniques may be used in survival and time to event hazard analysis, including Cox, Weibull, Kaplan-Meier and Greenwood models well known to those of skill in the art. Many of these techniques are useful either combined with a DETERMINANT selection technique, such as forward selection, backwards selection, or stepwise selection, complete enumeration of all potential panels of a given size, genetic algorithms, or they may themselves include biomarker selection methodologies in their own technique. These may be coupled with information criteria, such as Akaike's Information Criterion (AIC) or Bayes Information Criterion (BIC), in order to quantify the tradeoff between additional biomarkers and model improvement, and to aid in minimizing overfit. The resulting predictive models may be validated in other studies, or cross-validated in the study they were originally trained in, using such techniques as Bootstrap, Leave-One-Out (LOO) and 10-Fold cross-validation (10-Fold CV). At various steps, false discovery rates may be estimated by value permutation according to techniques known in the art. A "health economic utility function" is a formula that is derived from a combination of the expected probability of a range of clinical outcomes in an idealized applicable patient population, both before and after the introduction of a diagnostic or therapeutic intervention into the standard of care. It encompasses estimates of the accuracy, effectiveness and performance characteristics of such intervention, and a cost and/or value measurement (a utility) associated with each outcome, which may be derived from actual health system costs of care (services, supplies, devices and drugs, etc.) and/or as an estimated acceptable value per quality adjusted life year (QALY) resulting in each outcome. The sum, across all predicted outcomes, of the product of the predicted population size for an outcome multiplied by the respective outcome's expected utility is the total health economic utility of a given standard of care. The difference between (i) the total health economic utility calculated for the standard of care with the intervention versus (ii) the total health economic utility for the standard of care without the intervention results in an overall measure of the health economic cost or value of the intervention. This may itself be divided amongst the entire patient group being analyzed (or solely amongst the intervention group) to arrive at a cost per unit intervention, and to guide such decisions as market positioning, pricing, and assumptions of health system acceptance. Such health economic utility functions are commonly used to compare the cost-effectiveness of the intervention, but may also be transformed to estimate the acceptable value per QALY the health care system is willing to pay, or the acceptable cost-effective clinical performance characteristics required of a new intervention.

For diagnostic (or prognostic) interventions of the invention, as each outcome (which in a disease classifying diagnostic test may be a TP, FP, TN, or FN) bears a different cost, a health economic utility function may preferentially favor sensitivity over specificity, or PPV over NPV based on the clinical situation and individual outcome costs and value, and thus provides another measure of health economic performance and value which may be different from more direct clinical or analytical performance measures. These different measurements and relative trade-offs generally will converge only in the case of a perfect test, with zero error rate (a.k.a., zero predicted subject outcome misclassifications or FP and FN), which all performance measures will favor over imperfection, but to differing degrees.

"Measuring" or "measurement," or alternatively "detecting" or "detection," means assessing the presence, absence, quantity or amount (which can be an effective amount) of either a given substance within a clinical or subject-derived sample, including the derivation of qualitative or quantitative concentration levels of such substances, or otherwise evaluating the values or categorization of a subject's non-analyte clinical parameters.

"Negative predictive value" or "NPV" is calculated by TN/(TN+FN) or the true negative fraction of all negative test results. It also is inherently impacted by the prevalence of the disease and pre-test probability of the population intended to be tested.

See, e.g., O'Marcaigh et al., Clin. Ped. (1993), which discusses specificity, sensitivity, and positive and negative predictive values of a test, e.g., a clinical diagnostic test. Often, for binary disease state classification approaches using a continuous diagnostic test measurement, the sensitivity and specificity is summarized by Receiver Operating Characteristics (ROC) curves according to Pepe et al, Am. J. Epidemiol (2004), and summarized by the Area Under the Curve (AUC) or c-statistic, an indicator that allows representation of the sensitivity and specificity of a test, assay, or method over the entire range of test (or assay) cut points with just a single value. See also, e.g., Shultz, "Clinical Interpretation Of Laboratory Procedures," chapter 14 in Teitz, Fundamentals of Clinical Chemistry, Burtis and Ashwood (eds.), $4^{th}$ edition 1996, W.B. Saunders Company, pages 192-199; and Zweig et al., Clin. Chem., (1992). An alternative approach using likelihood functions, odds ratios, information theory, predictive values, calibration (including goodness-of-fit), and reclassification measurements is summarized according to Cook, Circulation (2007).

Finally, hazard ratios and absolute and relative risk ratios within subject cohorts defined by a test are a further measurement of clinical accuracy and utility. Multiple methods are frequently used to defining abnormal or disease values, including reference limits, discrimination limits, and risk thresholds.

"Analytical accuracy" refers to the reproducibility and predictability of the measurement process itself, and may be summarized in such measurements as coefficients of variation, and tests of concordance and calibration of the same samples or controls with different times, users, equipment and/or reagents. These and other considerations in evaluating new biomarkers are also summarized in Vasan, 2006.

"Performance" is a term that relates to the overall usefulness and quality of a diagnostic or prognostic test, including, among others, clinical and analytical accuracy, other analytical and process characteristics, such as use characteristics (e.g., stability, ease of use), health economic value, and relative costs of components of the test. Any of these factors may be the source of superior performance and thus usefulness of the test, and may be measured by appropriate "performance metrics," such as AUC, time to result, shelf life, etc. as relevant.

"Positive predictive value" or "PPV" is calculated by TP/(TP+FP) or the true positive fraction of all positive test results. It is inherently impacted by the prevalence of the disease and pre-test probability of the population intended to be tested.

"Risk" in the context of the present invention, relates to the probability that an event will occur over a specific time period, as in the conversion to metastatic events, and can mean a subject's "absolute" risk or "relative" risk. Absolute risk can be measured with reference to either actual observation post-measurement for the relevant time cohort, or with reference to index values developed from statistically valid historical cohorts that have been followed for the relevant time period. Relative risk refers to the ratio of absolute risks of a subject compared either to the absolute risks of low risk cohorts or an average population risk, which can vary by how clinical risk factors are assessed. Odds ratios, the proportion of positive events to negative events for a given test result, are also commonly used (odds are according to the formula p/(1−p) where p is the probability of event and (1−p) is the probability of no event) to no-conversion.

"Risk evaluation," or "evaluation of risk" in the context of the present invention encompasses making a prediction of the probability, odds, or likelihood that an event or disease state may occur, the rate of occurrence of the event or conversion from one disease state to another, i.e., from a primary tumor to metastatic prostate cancer or to one at risk of developing a metastatic, or from at risk of a primary metastatic event to a more secondary metastatic event. Risk evaluation can also comprise prediction of future clinical parameters, traditional laboratory risk factor values, or other indices of cancer, either in absolute or relative terms in reference to a previously measured population. The methods of the present invention may be used to make continuous or categorical measurements of the risk of metastatic prostate cancer thus diagnosing and defining the risk spectrum of a category of subjects defined as being at risk for prostate cancer. In the categorical scenario, the invention can be used to discriminate between normal and other subject cohorts at higher risk for prostate cancers. Such differing use may require different DETERMINANT combinations and individualized panels, mathematical algorithms, and/or cut-off points, but be subject to the same aforementioned measurements of accuracy and performance for the respective intended use.

A "sample" in the context of the present invention is a biological sample isolated from a subject and can include, by way of example and not limitation, tissue biopsies, whole blood, serum, plasma, blood cells, endothelial cells, circulating tumor cells, lymphatic fluid, ascites fluid, interstitial fluid (also known as "extracellular fluid" and encompasses the fluid found in spaces between cells, including, inter alia, gingival cevicular fluid), bone marrow, cerebrospinal fluid (CSF), saliva, mucous, sputum, sweat, urine, or any other secretion, excretion, or other bodily fluids.

Signature is an expression pattern of more than one DETERMINANT.

"Sensitivity" is calculated by TP/(TP+FN) or the true positive fraction of disease subjects.

"Specificity" is calculated by TN/(TN+FP) or the true negative fraction of non-disease or normal subjects.

By "statistically significant", it is meant that the alteration is greater than what might be expected to happen by chance alone (which could be a "false positive"). Statistical significance can be determined by any method known in the art. Commonly used measures of significance include the p-value, which presents the probability of obtaining a result at least as extreme as a given data point, assuming the data point was the result of chance alone. A result is often considered highly significant at a p-value of 0.05 or less.

A "subject" in the context of the present invention is preferably a mammal. The mammal can be a human, non-human primate, mouse, rat, dog, cat, horse, or cow, but are not limited to these examples. Mammals other than humans can be advantageously used as subjects that represent animal models of tumor metastasis. A subject can be male or female. A subject can be one who has been previously diagnosed or identified as having primary tumor or a prostate cancer, and optionally has already undergone, or is undergoing, a therapeutic intervention for the tumor. Alternatively, a subject can also be one who has not been previously diagnosed as having metastatic prostate cancer. For example, a subject can be one who exhibits one or more risk factors for metastatic prostate cancer or prosate cancer recurrence.

"TN" is true negative, which for a disease state test means classifying a non-disease or normal subject correctly.

"TP" is true positive, which for a disease state test means correctly classifying a disease subject.

"Traditional laboratory risk factors" correspond to biomarkers isolated or derived from subject samples and which are currently evaluated in the clinical laboratory and used in traditional global risk assessment algorithms. Traditional laboratory risk factors for tumor metastasis include for example Gleason score, depth of invasion, vessel density, proliferative index, etc. Other traditional laboratory risk factors for tumor metastasis are known to those skilled in the art.

Methods and Uses of the Invention

The invention provides a method for predicting prognosis of a cancer patient. In this method, one obtains a tissue sample from the patient, and measures the levels of two or more DETERMINANTS selected from Table 2, 3 or 5 (see below) in the sample, wherein the measured levels are indicative of the prognosis of the cancer patient. In some embodiments, the levels of two, three, four, five, six, seven, eight, nine, ten, fourteen, fifteen, sixteen, seventeen, eighteen, nineteen, twenty, thirty, forty, fifty, or more DETERMINANTS are measured.

In some embodiments, the prognosis may be that the patient is at a low risk of having metastatic cancer or recurrence of cancer. In other embodiments, the prognosis may be that the patient is at a high risk of having metastatic cancer or recurrence of cancer. In these embodiments, the patient may have melanoma, breast cancer, prostate cancer, or colon cancer.

In some embodiments, an increased risk of cancer recurrence or developing metastatic cancer in the patient is determined by measuring a clinically significant alteration in the levels of the selected DETERMINANTS in the sample. Alternatively, an increased risk of developing metastatic prostate cancer in the patient is determined by comparing the levels of the selected DETERMINANTS to a reference value. In some embodiments, the reference value is an index.

The invention also provides a method for analyzing a tissue sample from a cancer patient. In this method, one obtains the tissue sample from the patient, measures the levels of two or more DETERMINANTS selected from Table 2, 3 or 5 in the sample.

This invention additionally provides a method for identifying a cancer patient in need of adjuvant therapy. In this method, one obtains a tissue sample from the patient, measures the levels of two or more DETERMINANTS selected from Table 2, 3 or 5 in the sample, wherein the measured levels indicate that the patient is in need of adjuvant therapy. For example, the adjuvant therapy may be selected from the group consisting of radiation therapy, chemotherapy, immunotherapy, hormone therapy, and targeted therapy. In some embodiments, the patient has been subjected to a standard of care therapy. In some embodiments, the targeted therapy targets another component of a signaling pathway in which one or more of the selected DETERMINANTS is a component. In alternative embodiments, the targeted therapy targets one or more of the selected DETERMINANTS.

This invention also provides a further method for treating a cancer patient. In this method, one measures the levels of two or more DETERMINANTS selected from Table 2, 3 or 5 in a tissue sample from the patient, and treats the patient with adjuvant therapy if the measured levels indicate that the patient is at a high risk of having metastatic cancer or recurrence of cancer. In some embodiments, the adjuvant therapy is an experimental therapy.

This invention additionally provides a method for monitoring the progression of a tumor in a patient. In this method, one obtains a tumor tissue sample from the patient; and measures the levels of two or more DETERMINANTS selected from Table 2, 3 or 5 in the sample, and wherein the measured levels are indicative of the progression of the tumor in the patient. In some embodiments, a clinically significant alteration in the measured levels between the tumor tissue sample taken form the patient at two different time points is indicative of the progression of the tumor in the patient. In some embodiments, the progression of a tumor in a patient is measured by detecting the levels of the selected DETERMINANTS in a first sample from the patient taken at a first period of time, detecting the levels of the selected DETERMINANTS in a second sample from the patient taken at a second period of time and then comparing the levels of the selected DETERMINANTS to a reference value. In some aspects, the first sample is taken from the patient prior to being treated for the tumor and the second sample is taken from the patient after being treated for the tumor.

The invention also provides a method for monitoring the effectiveness of treatment or selecting a treatment regimen for a recurrent or metastatic cancer in a patient by measuring the levels of two or more DETERMINANTS selected from Table 2, 3, or 5 in a first sample from the patient taken at a first period of time and optionally measuring the level of the selected DETERMINANTS in a second sample from the patient taken at a second period of time. The levels of the selected DETERMINANTS detected at the first period of time are compared to the levels detected at the second period of time or alternatively a reference value. The effectiveness of treatment is monitored by a change in the measured levels of the selected DETERMINANTS from the patient.

The invention also provides a kit for measuring the levels of two or more DETERMINANTS selected from Table 2, 3 or 5. The kit comprises reagents for specifically measuring the levels of the selected DETERMINANTS. In some embodiments, the reagents are nucleic acid molecules. In these embodiments, the nucleic acid molecules are PCR primers or hybridizing probes. In alternative embodiments, the reagents are antibodies or fragments thereof, oligonucleotides, or aptamers.

This invention also provides a method for treating a cancer patient in need thereof. In this method, one measures the level of a DETERMINANT selected from Table 2, 3 or 5, and administers an agent that modulates the level of the selected DETERMINANT. In some embodiments, the administered agent may be a small molecule modulator. In some embodiments, the administered agent may be a small molecule inhibitor. In some embodiments, the administered agent may be, for example, siRNA or an antibody or fragment thereof. In some embodiments, the selected DETERMINANT is AGPAT6, ATAD2, ATP6V1C1, AZIN1, COX6C, CPNE3, DPYS, EBAG9, EFR3A, EXT1, GRINA, HRSP12, KIAA0196, MAL2, MTDH, NSMCE2, NUDCD1, PDE7A, POLR2K, POP1, PTK2, SPAG1, SQLE, SRI, STK3, TAF2, TGS1, TMEM65, TMEM68, TOP1MT, UBR5, WDYHV1, WWP1, or YWHAZ. In some embodiments, the selected DETERMINANT is AGPAT6, AZIN1, CPNE3, DPYS, NSMCE2, NUDCD1, SRI, TGS1, UBR5, or WDYHV1.

This invention also provides a method of identifying a compound capable of reducing the risk of cancer recurrence or development of metastatic cancer. In this method, one provides a cell expressing a DETERMINANT selected from Table 2, 3 or 5, contacts the cell with a candidate compound, and determines whether the candidate compound alters the expression or activity of the selected DETERMINANT, whereby the alteration observed in the presence of the compound indicates that the compound is capable of reducing the risk of cancer recurrence or development of metastatic cancer.

This invention also provides a method of identifying a compound capable of treating cancer. In this method, one provides a cell expressing a DETERMINANT selected from Table 2, 3 or 5, contacts the cell with a candidate compound, and determines whether the candidate compound alters the expression or activity of the selected biomarker, whereby the alteration observed in the presence of the compound indicates that the compound is capable of treating cancer.

This invention also provides a method of identifying a compound capable of reducing the risk of cancer occurrence or development of cancer. In this method, one provides a cell expressing a DETERMINANT selected from Table 2, 3 or 5, contacts the cell with a candidate compound, and determines whether the candidate compound alters the expression or activity of the selected biomarker, whereby the alteration observed in the presence of the compound indicates that the compound is capable of reducing the risk of cancer occurrence or development of cancer.

According to the invention, a DETERMINANT that can be used in the methods or kits provided by the invention may be selected from the DETERMINANTS listed on Table 2, Table 3, or Table 5. In some embodiments, the selected DETERMINANTS may comprise one or more of MAP3K8, RAD21, and TUSC3. In some embodiments, the selected DETERMINANTS may comprise one or more of ATP5A1, ATP6V1C1, CUL2, CYC1, DCC, ERCC3, MBD2, MTERF, PARD3, PTK2, RBL2, SMAD2, SMAD4, SMAD7, DNAJC15, KIF5B, LECT1, DSG2, ACAA2, ASAP1, LMO7, SVIL, DSC2, PCDH9, WDR7, LAMA3, PCDH8, MKX, MSR1, and POLR2K. In some embodiments, the selected DETERMINANTS may comprise one or more of ATP5A1, ATP6V1C1, CUL2, CYC1, DCC, ERCC3, MBD2, MTERF, PARD3, PTK2, RBL2, SMAD2, SMAD4, and SMAD7. In some embodiments, the selected DETERMINANTS may comprise one or more of DNAJC15, KIF5B, LECT1, DSG2, ACAA2, ASAP1, LMO7, SVIL, DSC2, PCDH9, SMAD7, WDR7, LAMA3, PCDH8, MKX, MSR1, and POLR2K. In some embodiments, the selected DETERMINANTS comprise one or more of DNAJC15, KIF5B, LECT1, DSG2, ACAA2, ASAP1, and LMO7. In some embodiments, the selected DETERMINANTS comprise one or more of SVIL, DSC2, PCDH9, SMAD7, WDR7, LAMA3, PCDH8, MKX, MSR1, and POLR2K. In various embodiments, the methods or the kits provided by the invention further comprise measuring the levels of one or more of PTEN, cyclin D1, SMAD4, and SPP1. In some embodiments, the selected DETERMINANTS comprise two or more of ATP5A1, ATP6V1C1, CUL2, CYC1, DCC, ERCC3, MBD2, MTERF, PARD3, PTK2, RBL2, SMAD2, SMAD4, SMAD7, DNAJC15, KIF5B, LECT1, DSG2, ACAA2, ASAP1, LMO7, SVIL, DSC2, PCDH9, WDR7, LAMA3, PCDH8, MKX, MSR1, POLR2K, PTEN, cyclin D1 and SPP1. See, for example, Table 7 for two-DETERMINANT combination.

In another aspect of the invention, the selected DETERMINANTS are associated with DNA gain or the selected DETERMINANTS have a clinically significant increase in the measured levels. For example, the DETERMINANTS are selected from 1) the group consisting of DETERMINANTS 1-300 of Table 2; or 2) the group consisting of DETERMINANTS 8, 9, 12, 13, 18-20, 22, 23, 34, 41, 48-50, 56, 64, 65, 70, 72-79, 81, 84, 87, 88, 102, 104, 114, 124, 134, 139, 154, 169-172, 185, 186, 193, 196, 199, 203, 204, 207, 209, 212, 217, 218, 221, 245, 247, 248, 254, 257, 260, 263, 264, 268, 269, 277, 279-281, 283, 284, 286, 287, 292, 294, and 296-298 of Table 3; or 3) the group consisting of DETERMINANTS 9, 12, 18, 19, 22, 23, 41, 56, 70, 72, 75, 76, 77, 87, 102, 114, 134, 139, 171, 172, 185, 196, 199, 207, 209, 217, 221, 247, 248, 260, 263, 264, 268, 269, 279, 296, and 298 of Table 5.

In another aspect of the invention, the selected DETERMINANTS are associated with DNA loss or the selected DETERMINANTS have a clinically significant decrease in the measured levels. For example, the DETERMINANTS are selected from 1) the group consisting of DETERMINANTS 301-741 of Table 2; 2) DETERMINANTS 303, 308, 310, 312, 313, 316, 319, 322, 324, 326, 328, 329, 343, 353, 360, 368, 371, 376, 378, 384, 386, 389, 391, 392, 398, 400, 403, 404, 405, 406, 407, 412, 416, 421, 422, 424, 430, 432, 435, 437, 440, 445, 446, 451, 459, 466, 468, 469, 470, 471, 473, 477, 481, 482, 484, 485, 486, 487, 490, 492, 493, 494, 496, 498, 502, 503, 505, 506, 509, 514, 515, 520, 521, 522, 525, 526, 527, 530, 533, 534, 536, 542, 547, 552, 553, 554, 555, 563, 570, 580, 582, 584, 585, 586, 587, 589, 592, 594, 595, 599, 600, 603, 604, 612, 614, 616, 617, 622, 625, 628, 629, 632, 637, 642, 648, 651, 652, 654, 655, 656, 658, 659, 660, 661, 662, 666, 669, 670, 671, 675, 676, 680, 681, 682, 685, 687, 689, 690, 691, 692, 695, 711, 718, 719, 722, 723, 724, 725, 730, 735, and 740 of Table 3; or 3) DETERMINANTS 308, 312, 319, 322, 324, 326, 328, 329, 343, 371, 378, 386, 389, 391, 392, 400, 416, 422, 424, 440, 445, 466, 471, 481, 482, 484, 490, 492, 493, 494, 496, 498, 503, 505, 506, 514, 521, 522, 525, 526, 527, 533, 542, 554, 555, 570, 582, 584, 585, 586, 592, 594, 595, 612, 617, 628, 629, 637, 642, 648, 651, 658, 659, 660, 661, 675, 680, 681, 685, 687, 692, 718, 719, 723, 730, and 735 of Table 5.

In some embodiments, at least one of the selected DETERMINANTS is associated with REACTOME TGF-beta signaling pathway. In some embodiments, at least one of the selected DETERMINANTS is associated with BIO-CARTA TGF-beta signaling pathway. In some embodiments, at least one of the selected DETERMINANTS is associated with KEGG TGF-beta signaling pathway. In some embodiments, at least one of the selected DETERMINANTS is associated with KEGG colorectal cancer pathway. In some embodiments, at least one of the selected DETERMINANTS is associated with KEGG Adherens junction pathway. In some embodiments, at least one of the selected DETERMINANTS is associated with REACTOME RNA Polymerase I/III and mitochondrial transcription pathway. In some embodiments, at least one of the selected DETERMINANTS is associated with KEGG cell cycle pathway. In some embodiments, at least one of the selected DETERMINANTS is associated with KEGG oxidative phosphorylation pathway. In some embodiments, at least one of the selected DETERMINANTS is associated with KEGG pathways in cancer.

In another aspect of the invention, at least one of the selected DETERMINANTS is associated with DNA gain and at least one of the selected DETERMINANTS is associated with DNA loss. In some embodiments, at least one of the selected DETERMINANTS has a clinically significant increase in the measured levels and at least one of the selected DETERMINANTS has a clinically significant decrease in the measured levels.

The levels of the selected DETERMINANTS may be measured electrophoretically or immunochemically. For example, the levels of the selected DETERMINANTS are detected by radioimmunoassay, immunofluorescence assay or by an enzyme-linked immunosorbent assay. Optionally, the DETERMINANTS are detected using non-invasive imaging technology.

In some embodiments, the levels of the selected DETERMINANTS are determined based on the DNA copy number alteration. In these embodiments, the DNA copy number alteration of the selected DETERMINANT indicates DNA gain or loss. In some embodiments, the RNA transcript levels of the selected DETERMINANTS are measured. In certain embodiments, the RNA transcript levels may be determined by microarray, quantitative RT-PCR, sequencing, nCounter® multiparameter quantitative detection assay (NanoString), branched DNA assay (e.g., Panomics QuantiGene® Plex technology), or quantitative nuclease protection assay (e.g., Highthroughput Genomics qNPA™). nCounter® system is developed by NanoString Technology. It is based on direct multiplexed measurement of gene expression and capable of providing high levels of precision and sensitivity (<1 copy per cell) (see 72.5.117.165/applications/technology/). In particular, the nCounter® assay uses molecular "barcodes" and single molecule imaging to detect and count hundreds of unique transcripts in a single reaction. Panomics QuantiGene® Plex technology can also be used to assess the RNA expression of DETERMINANTS in this invention. The QuantiGene® platform is based on the branched DNA technology, a sandwich nucleic acid hybridization assay that provides a unique approach for RNA detection and quantification by amplifying the reporter signal rather than the sequence (Flagella et al., *Analytical Biochemistry* (2006)). It can reliably measure quantitatively RNA expression in fresh, frozen or formalin-fixed, paraffin-embedded (FFPE) tissue homogenates (Knudsen et al., *Journal of Molecular Diagnostics* (2008)). In some embodiments, the protein levels of the selected DETERMINANTS are measured. In certain embodiments, the protein levels may be measured, for example, by antibodies, immunohistochemistry or immunofluorescence. In these embodiments, the protein levels may be measured in subcellular compartments, for example, by measuring the protein levels of DETERMINANTS in the nucleus relative to the protein levels of the DETERMINANTS in the cytoplasm. In some embodiments, the protein levels of DETERMINANTS may be measured in the nucleus and/or in the cytoplasm.

In some embodiments, the levels of the DETERMINANTS may be measured separately. Alternatively, the levels of the DETERMINANTS may be measured in a multiplex reaction.

In some embodiments, the noncancerous cells are excluded from the tissue sample. In some embodiments, the tissue sample is a solid tissue sample, a bodily fluid sample, or circulating tumor cells. In some embodiments, the bodily fluid sample may be blood, plasma, urine, saliva, lymph fluid, cerebrospinal fluid (CSF), synovial fluid, cystic fluid, ascites, pleural effusion, interstitial fluid, or ocular fluid. In some embodiments, the solid tissue sample may be a formalin-fixed paraffin embedded tissue sample, a snap-frozen tissue sample, an ethanol-fixed tissue sample, a tissue sample fixed with an organic solvent, a tissue sample fixed with plastic or epoxy, a cross-linked tissue sample, surgically removed tumor tissue, or a biopsy sample (e.g., a core biopsy, an excisional tissue biopsy, or an incisional tissue biopsy). In some embodiments, the tissue sample is a cancerous tissue sample. In some embodiments, the cancerous tissue is melanoma, prostate cancer, breast cancer, or colon cancer tissue.

In some embodiments, at least one standard parameter associated with the cancer is measured in addition to the measured levels of the selected DETERMINANTS. The at least one standard parameter may be, for example, tumor stage, tumor grade, tumor size, tumor visual characteristics, tumor location, tumor growth, lymph node status, tumor thickness (Breslow score), ulceration, age of onset, PSA level, PSA kinetics, or Gleason score.

In some embodiments, the patient may have a primary tumor, a recurrent tumor, or metastatic prostate cancer.

Also included in the invention is metastatic prostate cancer reference expression profile containing a pattern of marker levels of an effective amount of two or more markers selected from Tables 2, 3 or 5. Also included is a machine readable media containing one or more metastatic tumor reference expression profiles and optionally, additional test results and subject information. In a further aspect the invention provides a DETERMINANT panel containing one or more DETERMINANTS that are indicative of a physiological or biochemical pathway associated metastasis or the progression of a tumor.

The invention also provides a mouse wherein the genome of at least one prostate epithelial cell contains a homozygous inactivation of the endogenous PTEN gene, p53 gene, and TERT gene, and the TERT gene can be inducibly re-activated and therefore expressed, and wherein the mouse exhibits an increased susceptibility to development of metastatic prostate cancer upon expression of the TERT gene.

The invention also provides a mouse wherein the genome of at least one prostate epithelial cell contains a homozygous inactivation of the endogenous PTEN gene, p53 gene, and SMAD4 gene, and wherein the mouse exhibits an increased susceptibility to development of metastatic prostate cancer. The invention also provides cells from the mouse models and in some aspects, such cells are epithelial cancer cells.

The methods disclosed herein are used with subjects at risk for developing metastatic prostate cancer, a prostate cancer recurrence or other cancer subjects, such as those with breast cancer who may or may not have already been diagnosed with cancer or other cancer types and subjects undergoing treatment and/or therapies for a primary tumor or metastatic prostate cancer and other cancer types. The methods of the present invention can also be used to monitor or select a treatment regimen for a subject who has a primary tumor or metastatic prostate cancer and other cancer types, and to screen subjects who have not been previously diagnosed as having metastatic prostate cancer and other cancer types, such as subjects who exhibit risk factors for metastasis or recoccurance. Preferably, the methods of the present invention are used to identify and/or diagnose subjects who are asymptomatic for metastatic tumor prostate cancer and other cancer types. "Asymptomatic" means not exhibiting the traditional signs and symptoms.

The methods of the present invention may also used to identify and/or diagnose subjects already at higher risk of developing metastatic prostate cancer or protate cancer recurrence and other metastatic cancer types based on solely on the traditional risk factors.

A subject having metastatic prostate cancer and other metastatic cancer types can be identified by measuring the amounts (including the presence or absence) of an effective number (which can be two or more) of DETERMINANTS in a subject-derived sample and the amounts are then compared to a reference value. Alterations in the amounts and patterns of expression of biomarkers, such as proteins, polypeptides, nucleic acids and polynucleotides, polymorphisms of proteins, polypeptides, nucleic acids, and polynucleotides, mutated proteins, polypeptides, nucleic acids, and polynucleotides, or alterations in the molecular quantities of metabolites or other analytes in the subject sample compared to the reference value are then identified.

A reference value can be relative to a number or value derived from population studies, including without limitation, such subjects having the same cancer, subject having the same or similar age range, subjects in the same or similar ethnic group, subjects having family histories of cancer, or relative to the starting sample of a subject undergoing treatment for a cancer. Such reference values can be derived from statistical analyses and/or risk prediction data of populations obtained from mathematical algorithms and computed indices of cancer metastasis. Reference DETERMINANT indices can also be constructed and used using algorithms and other methods of statistical and structural classification.

In one embodiment of the present invention, the reference value is the amount (of DETERMINANTS in a control sample derived from one or more subjects who are not at risk or at low risk for developing prostate cancer. In another embodiment of the present invention, the reference value is the amount of DETERMINANTS in a control sample derived from one or more subjects who are asymptomatic and/or lack traditional risk factors for metastatic prostate cancer. In a further embodiment, such subjects are monitored and/or periodically retested for a diagnostically relevant period of time ("longitudinal studies") following such test to verify continued absence of metastatic prostate cancer (disease or event free survival). Such period of time may be one year, two years, two to five years, five years, five to ten years, ten years, or ten or more years from the initial testing date for determination of the reference value. Furthermore, retrospective measurement of DETERMINANTS in properly banked historical subject samples may be used in establishing these reference values, thus shortening the study time required.

A reference value can also comprise the amounts of DETERMINANTS derived from subjects who show an improvement in metastatic or recurrence risk factors as a result of treatments and/or therapies for the cancer. A reference value can also comprise the amounts of DETERMINANTS derived from subjects who have confirmed disease by known invasive or non-invasive techniques, or are at high risk for developing prostate cancer, or who have suffered from metastatic or reoccurant prostate cancer.

In another embodiment, the reference value is an index value or a baseline value. An index value or baseline value is a composite sample of an effective amount of DETERMINANTS from one or more subjects who do not have prostate cancer, or subjects who are asymptomatic a metastatic cancer. A baseline value can also comprise the amounts of DETERMINANTS in a sample derived from a subject who has shown an improvement in prostate cancer risk factors as a result of cancer treatments or therapies. In this embodiment, to make comparisons to the subject-derived sample, the amounts of DETERMINANTS are similarly calculated and compared to the index value. Optionally, subjects identified as having prostate cancer, being at increased risk of developing metastatic prostate cancer or prostate cancer reoccurrence are chosen to receive a therapeutic regimen to slow the progression the cancer, or decrease or prevent the risk of developing metastatic or reoccurent prostate cancer.

The progression of metastatic prostate cancer, or effectiveness of a cancer treatment regimen can be monitored by detecting a DETERMINANT in an effective amount (which may be two or more) of samples obtained from a subject over time and comparing the amount of DETERMINANTS detected. For example, a first sample can be obtained prior to the subject receiving treatment and one or more subsequent samples are taken after or during treatment of the subject. The cancer is considered to be progressive (or, alternatively, the treatment does not prevent progression) if the amount of DETERMINANT changes over time relative to the reference value, whereas the cancer is not progressive if the amount of DETERMINANTS remains constant over time (relative to the reference population, or "constant" as used herein). The term "constant" as used in the context of the present invention is construed to include changes over time with respect to the reference value.

For example, the methods of the invention can be used to discriminate the aggressiveness/and or accessing the stage of the tumor (e.g. Stage I, II, II or IV). This will allow patients to be stratified into high or low risk groups and treated accordingly.

Additionally, therapeutic or prophylactic agents suitable for administration to a particular subject can be identified by detecting a DETERMINANT in an effective amount (which may be two or more) in a sample obtained from a subject, exposing the subject-derived sample to a test compound that determines the amount (which may be two or more) of DETERMINANTS in the subject-derived sample. Accordingly, treatments or therapeutic regimens for use in subjects having a cancer, or subjects at risk for developing prostate cancer can be selected based on the amounts of DETERMINANTS in samples obtained from the subjects and compared to a reference value. Two or more treatments or therapeutic regimens can be evaluated in parallel to determine which treatment or therapeutic regimen would be the most efficacious for use in a subject to delay onset, or slow progression of the cancer.

The present invention further provides a method for screening for changes in marker expression associated with metastatic prostate cancer, by determining the amount (which may be two or more) of DETERMINANTS in a subject-derived sample, comparing the amounts of the DETERMINANTS in a reference sample, and identifying alterations in amounts in the subject sample compared to the reference sample.

The present invention further provides a method of treating a patient with a tumor, by identifying a patient with a tumor where an effective amount of DETERMINANTS are altered in a clinically significant manner as measured in a sample from the tumor, an treating the patient with a therapeutic regimen that prevents or reduces tumor metastasis.

Additionally the invention provides a method of selecting a tumor patient in need of adjuvant treatment by assessing the risk of metastasis or recurrence in the patient by measuring an effective amount of DETERMINANTS where a clinically significant alteration two or more DETERMINANTS in a tumor sample from the patient indicates that the patient is in need of adjuvant treatment.

Information regarding a treatment decision for a tumor patient by obtaining information on an effective amount of DETERMINANTS in a tumor sample from the patient, and selecting a treatment regimen that prevents or reduces tumor metastasis or recurrence in the patient if two or more DETERMINANTS are altered in a clinically significant manner.

If the reference sample, e.g., a control sample, is from a subject that does not have a metastatic cancer, or if the reference sample reflects a value that is relative to a person that has a high likelihood of rapid progression to metastatic prostate cancer, a similarity in the amount of the DETERMINANT in the test sample and the reference sample indicates that the treatment is efficacious. However, a difference in the amount of the DETERMINANT in the test sample and the reference sample indicates a less favorable clinical outcome or prognosis.

By "efficacious", it is meant that the treatment leads to a decrease in the amount or activity of a DETERMINANT protein, nucleic acid, polymorphism, metabolite, or other analyte. Assessment of the risk factors disclosed herein can be achieved using standard clinical protocols. Efficacy can be determined in association with any known method for diagnosing, identifying, or treating a disease.

The present invention also provides DETERMINANT panels including one or more DETERMINANTS that are indicative of a general physiological pathway associated with a metastatic lesion. For example, one or more DETERMINANTS that can be used to exclude or distinguish between different disease states that are associated with metastasis. A single DETERMINANT may have several of the aforementioned characteristics according to the present invention, and may alternatively be used in replacement of one or more other DETERMINANTS where appropriate for the given application of the invention.

The present invention also comprises a kit with a detection reagent that binds to two or more DETERMINANT proteins, nucleic acids, polymorphisms, metabolites, or other analytes. Also provided by the invention is an array of detection reagents, e.g., antibodies and/or oligonucleotides that can bind to two or more DETERMINANT proteins or nucleic acids, respectively. In one embodiment, the DETERMINANT are proteins and the array contains antibodies that bind two or more DETERMINANTS listed on Table 2, 3, or 5 sufficient to measure a statistically significant alteration in DETERMINANT expression compared to a reference value. In another embodiment, the DETERMINANTS are nucleic acids and the array contains oligonucleotides or aptamers that bind an effective amount of DETERMINANTS listed on Table 2, 3, or 5 sufficient to measure a statistically significant alteration in DETERMINANT expression compared to a reference value.

In another embodiment, the DETERMINANT are proteins and the array contains antibodies that bind an effective amount of DETERMINANTS listed Tables 2 or 3 sufficient to measure a statistically significant alteration in DETERMINANT expression compared to a reference value. In another embodiment, the DETERMINANTS are nucleic acids and the array contains oligonucleotides or aptamers that bind an effective amount of DETERMINANTS listed on any one of Table 2, 3, or 5 sufficient to measure a statistically significant alteration in DETERMINANT expression compared to a reference value.

Also provided by the present invention is a method for treating one or more subjects at risk for developing a prostate cancer by detecting the presence of altered amounts of an effective amount of DETERMINANTS present in a sample from the one or more subjects; and treating the one or more subjects with one or more cancer-modulating drugs until altered amounts or activity of the DETERMINANTS return to a baseline value measured in one or more subjects at low risk for developing a metastatic disease, or alternatively, in subjects who do not exhibit any of the traditional risk factors for metastatic disease.

Also provided by the present invention is a method for treating one or more subjects having prostate cancer by detecting the presence of altered levels of an effective amount of DETERMINANTS present in a sample from the one or more subjects; and treating the one or more subjects with one or more cancer-modulating drugs until altered amounts or activity of the DETERMINANTS return to a baseline value measured in one or more subjects at low risk for developing prostate cancer.

Also provided by the present invention is a method for evaluating changes in the risk of developing metastatic prostate cancer in a subject diagnosed with cancer, by detecting an effective amount of DETERMINANTS (which may be two or more) in a first sample from the subject at a first period of time, detecting the amounts of the DETERMINANTS in a second sample from the subject at a second period of time, and comparing the amounts of the DETERMINANTS detected at the first and second periods of time.

Diagnostic and Prognostic Indications of the Invention

The invention allows the diagnosis and prognosis of a primary, and/or locally invasive cancer such as prostate, breast, among cancer types. The risk of developing metastatic prostate cancer or prostate cancer recurrence can be detected by measuring an effective amount of DETERMINANT proteins, nucleic acids, polymorphisms, metabolites, and other analytes (which may be two or more) in a test sample (e.g., a subject derived sample), and comparing the effective amounts to reference or index values, often utilizing mathematical algorithms or formula in order to combine information from results of multiple individual DETERMINANTS and from non-analyte clinical parameters into a single measurement or index. Subjects identified as having an increased risk of a metastatic prostate cancer, prostate cancer recurrence, or other metastatic cancer types can optionally be selected to receive treatment regimens, such as administration of prophylactic or therapeutic compounds to prevent or delay the onset of metastatic prostate cancer, prostate cancer recurrence or other metastatic cancer types.

The amount of the DETERMINANT protein, nucleic acid, polymorphism, metabolite, or other analyte can be measured in a test sample and compared to the "normal control level," utilizing techniques such as reference limits, discrimination limits, or risk defining thresholds to define cutoff points and abnormal values. The "normal control level" means the level of one or more DETERMINANTS or combined DETERMINANT indices typically found in a subject not suffering from a prostate cancer. Such normal control level and cutoff points may vary based on whether a DETERMINANT is used alone or in a formula combining with other DETERMINANTS into an index. Alternatively, the normal control level can be a database of DETERMINANT patterns from previously tested subjects who did not develop a prostate cancer over a clinically relevant time horizon.

The present invention may be used to make continuous or categorical measurements of the risk of conversion to metastatic prostate cancer, prostate cancer recurrence or other metastatic cancer types thus diagnosing and defining the risk spectrum of a category of subjects defined as at risk for having a metastatic or recurrent event. In the categorical scenario, the methods of the present invention can be used to discriminate between normal and disease subject cohorts. In other embodiments, the present invention may be used so as to discriminate those at risk for having a metastatic or recurrent event from those having more rapidly progressing (or alternatively those with a shorter probable time horizon to a metastatic or recurrent event) to a metastatic event from those more slowly progressing (or with a longer time horizon to a metastatic event), or those having metastatic cancer from normal. Such differing use may require different DETERMINANT combinations in individual panel, mathematical algorithm, and/or cut-off points, but be subject to the same aforementioned measurements of accuracy and other performance metrics relevant for the intended use.

Identifying the subject at risk of having a metastatic or recurrent event enables the selection and initiation of various therapeutic interventions or treatment regimens in order to delay, reduce or prevent that subject's conversion to a metastatic disease state. Levels of an effective amount of DETERMINANT proteins, nucleic acids, polymorphisms, metabolites, or other analytes also allows for the course of treatment of a metastatic disease or metastatic event to be monitored. In this method, a biological sample can be provided from a subject undergoing treatment regimens, e.g., drug treatments, for cancer. If desired, biological samples are obtained from the subject at various time points before, during, or after treatment.

By virtue of some DETERMINANTS' being functionally active, by elucidating its function, subjects with high DETERMINANTS, for example, can be managed with agents/drugs that preferentially target such function.

The present invention can also be used to screen patient or subject populations in any number of settings. For example, a health maintenance organization, public health entity or school health program can screen a group of subjects to identify those requiring interventions, as described above, or for the collection of epidemiological data. Insurance companies (e.g., health, life or disability) may screen applicants in the process of determining coverage or pricing, or existing clients for possible intervention. Data collected in such population screens, particularly when tied to any clinical progression to conditions like cancer or metastatic events, will be of value in the operations of, for example, health maintenance organizations, public health programs and insurance companies. Such data arrays or collections can be stored in machine-readable media and used in any number of health-related data management systems to provide improved healthcare services, cost effective healthcare, improved insurance operation, etc. See, for example, U.S. Patent Application No. 2002/0038227; U.S. Patent Application No. US 2004/0122296; U.S. Patent Application No. US 2004/0122297; and U.S. Pat. No. 5,018, 067. Such systems can access the data directly from internal data storage or remotely from one or more data storage sites as further detailed herein.

A machine-readable storage medium can comprise a data storage material encoded with machine readable data or data arrays which, when using a machine programmed with instructions for using said data, is capable of use for a variety of purposes, such as, without limitation, subject information relating to metastatic disease risk factors over time or in response drug therapies. Measurements of effective amounts of the biomarkers of the invention and/or the resulting evaluation of risk from those biomarkers can implemented in computer programs executing on programmable computers, comprising, inter alia, a processor, a data storage system (including volatile and non-volatile memory and/or storage elements), at least one input device, and at least one output device. Program code can be applied to input data to perform the functions described above and generate output information. The output information can be applied to one or more output devices, according to methods known in the art. The computer may be, for example, a personal computer, microcomputer, or workstation of conventional design.

Each program can be implemented in a high level procedural or object oriented programming language to communicate with a computer system. However, the programs can be implemented in assembly or machine language, if desired. The language can be a compiled or interpreted language. Each such computer program can be stored on a storage media or device (e.g., ROM or magnetic diskette or others as defined elsewhere in this disclosure) readable by a general or special purpose programmable computer, for configuring and operating the computer when the storage media or device is read by the computer to perform the procedures described herein. The health-related data management system of the invention may also be considered to be implemented as a computer-readable storage medium, configured with a computer program, where the storage medium so configured causes a computer to operate in a specific and predefined manner to perform various functions described herein.

Levels of an effective amount of DETERMINANT proteins, nucleic acids, polymorphisms, metabolites, or other analytes can then be determined and compared to a reference value, e.g. a control subject or population whose metastatic state is known or an index value or baseline value. The reference sample or index value or baseline value may be taken or derived from one or more subjects who have been exposed to the treatment, or may be taken or derived from one or more subjects who are at low risk of developing cancer or a metastatic event, or may be taken or derived from subjects who have shown improvements in as a result of exposure to treatment. Alternatively, the reference sample or index value or baseline value may be taken or derived from one or more subjects who have not been exposed to the treatment. For example, samples may be collected from subjects who have received initial treatment for cancer or a metastatic event and subsequent treatment for cancer or a metastatic event to monitor the progress of the treatment. A reference value can also comprise a value derived from risk prediction algorithms or computed indices from population studies such as those disclosed herein.

The DETERMINANTS of the present invention can thus be used to generate a "reference DETERMINANT profile" of those subjects who do not have cancer or are not at risk of having a metastatic event, and would not be expected to develop cancer or a metastatic event. The DETERMINANTS disclosed herein can also be used to generate a "subject DETERMINANT profile" taken from subjects who have cancer or are at risk for having a metastatic event. The subject DETERMINANT profiles can be compared to a reference DETERMINANT profile to diagnose or identify subjects at risk for developing cancer or a metastatic event, to monitor the progression of disease, as well as the rate of progression of disease, and to monitor the effectiveness of treatment modalities. The reference and subject DETERMINANT profiles of the present invention can be contained in a machine-readable medium, such as but not limited to, analog tapes like those readable by a VCR, CD-ROM, DVD-ROM, USB flash media, among others. Such machine-readable media can also contain additional test results, such as, without limitation, measurements of clinical parameters and traditional laboratory risk factors. Alternatively or additionally, the machine-readable media can also comprise subject information such as medical history and any relevant family history. The machine-readable media can also contain information relating to other disease-risk algorithms and computed indices such as those described herein.

Differences in the genetic makeup of subjects can result in differences in their relative abilities to metabolize various drugs, which may modulate the symptoms or risk factors of cancer or metastatic events. Subjects that have cancer, or at risk for developing cancer, a recurrent cancer or a metastatic cancer can vary in age, ethnicity, and other parameters. Accordingly, use of the DETERMINANTS disclosed herein, both alone and together in combination with known genetic factors for drug metabolism, allow for a pre-determined level of predictability that a putative therapeutic or prophylactic to be tested in a selected subject will be suitable for treating or preventing cancer or a metastatic event in the subject.

To identify therapeutics or drugs that are appropriate for a specific subject, a test sample from the subject can also be exposed to a therapeutic agent or a drug, and the level of one or more of DETERMINANT proteins, nucleic acids, polymorphisms, metabolites or other analytes can be determined. The amount of one or more DETERMINANTS can be compared to sample derived from the subject before and after treatment or exposure to a therapeutic agent or a drug, or can be compared to samples derived from one or more subjects who have shown improvements in risk factors (e.g., clinical parameters or traditional laboratory risk factors) as a result of such treatment or exposure.

A subject cell (i.e., a cell isolated from a subject) can be incubated in the presence of a candidate agent and the pattern of DETERMINANT expression in the test sample is measured and compared to a reference profile, e.g., a metastatic disease reference expression profile or a non-disease reference expression profile or an index value or baseline value. The test agent can be any compound or composition or combination thereof, including, dietary supplements. For example, the test agents are agents frequently used in cancer treatment regimens and are described herein.

The aforementioned methods of the invention can be used to evaluate or monitor the progression and/or improvement of subjects who have been diagnosed with a cancer, and who have undergone surgical interventions.

Performance and Accuracy Measures of the Invention

The performance and thus absolute and relative clinical usefulness of the invention may be assessed in multiple ways as noted above. Amongst the various assessments of performance, the invention is intended to provide accuracy in clinical diagnosis and prognosis. The accuracy of a diagnostic or prognostic test, assay, or method concerns the ability of the test, assay, or method to distinguish between subjects having cancer, or at risk for cancer or a metastatic event, is based on whether the subjects have, a "significant alteration" (e.g., clinically significant "diagnostically significant) in the levels of a DETERMINANT. By "effective amount" it is meant that the measurement of an appropriate number of DETERMINANTS (which may be one or more) to produce a "significant alteration," (e.g. level of expression or activity of a DETERMINANT) that is different than the predetermined cut-off point (or threshold value) for that DETERMINANT(S) and therefore indicates that the subject has cancer or is at risk for having a metastatic event for which the DETERMINANT(S) is a determinant. The difference in the level of DETERMINANT between normal and abnormal is preferably statistically significant. As noted below, and without any limitation of the invention, achieving statistical significance, and thus the preferred analytical, diagnostic, and clinical accuracy, generally but not always requires that combinations of several DETERMINANTS be used together in panels and combined with mathematical algorithms in order to achieve a statistically significant DETERMINANT index.

In the categorical diagnosis of a disease state, changing the cut point or threshold value of a test (or assay) usually changes the sensitivity and specificity, but in a qualitatively inverse relationship. Therefore, in assessing the accuracy and usefulness of a proposed medical test, assay, or method for assessing a subject's condition, one should always take both sensitivity and specificity into account and be mindful of what the cut point is at which the sensitivity and specificity are being reported because sensitivity and specificity may vary significantly over the range of cut points. Use of statistics such as AUC, encompassing all potential cut point values, is preferred for most categorical risk measures using the invention, while for continuous risk measures, statistics of goodness-of-fit and calibration to observed results or other gold standards, are preferred.

By predetermined level of predictability it is meant that the method provides an acceptable level of clinical or diagnostic accuracy. Using such statistics, an "acceptable degree of diagnostic accuracy", is herein defined as a test or assay (such as the test of the invention for determining the clinically significant presence of DETERMINANTS, which thereby indicates the presence of cancer and/or a risk of having a metastatic event) in which the AUC (area under the ROC curve for the test or assay) is at least 0.60, desirably at least 0.65, more desirably at least 0.70, preferably at least 0.75, more preferably at least 0.80, and most preferably at least 0.85.

By a "very high degree of diagnostic accuracy", it is meant a test or assay in which the AUC (area under the ROC curve for the test or assay) is at least 0.75, 0.80, desirably at least 0.85, more desirably at least 0.875, preferably at least 0.90, more preferably at least 0.925, and most preferably at least 0.95.

Alternatively, the methods predict the presence or absence of a cancer, metastatic cancer or response to therapy with at least 75% accuracy, more preferably 80%, 85%, 90%, 95%, 97%, 98%, 99% or greater accuracy.

The predictive value of any test depends on the sensitivity and specificity of the test, and on the prevalence of the condition in the population being tested. This notion, based on Bayes' theorem, provides that the greater the likelihood that the condition being screened for is present in an individual or in the population (pre-test probability), the greater the validity of a positive test and the greater the likelihood that the result is a true positive. Thus, the problem with using a test in any population where there is a low likelihood of the condition being present is that a positive result has limited value (i.e., more likely to be a false positive). Similarly, in populations at very high risk, a negative test result is more likely to be a false negative.

As a result, ROC and AUC can be misleading as to the clinical utility of a test in low disease prevalence tested populations (defined as those with less than 1% rate of occurrences (incidence) per annum, or less than 10% cumulative prevalence over a specified time horizon). Alternatively, absolute risk and relative risk ratios as defined elsewhere in this disclosure can be employed to determine the degree of clinical utility. Populations of subjects to be tested can also be categorized into quartiles by the test's measurement values, where the top quartile (25% of the population) comprises the group of subjects with the highest relative risk for developing cancer or metastatic event, and the bottom quartile comprising the group of subjects having the lowest relative risk for developing cancer or a metastatic event. Generally, values derived from tests or assays having over 2.5 times the relative risk from top to bottom quartile in a low prevalence population are considered to have a "high degree of diagnostic accuracy," and those with five to seven times the relative risk for each quartile are considered to have a "very high degree of diagnostic accuracy." Nonetheless, values derived from tests or assays having only 1.2 to 2.5 times the relative risk for each quartile remain clinically useful are widely used as risk factors for a disease; such is the case with total cholesterol and for many inflammatory biomarkers with respect to their prediction of future metastatic events. Often such lower diagnostic accuracy tests must be combined with additional parameters in order to derive meaningful clinical thresholds for therapeutic intervention, as is done with the aforementioned global risk assessment indices.

A health economic utility function is an yet another means of measuring the performance and clinical value of a given test, consisting of weighting the potential categorical test outcomes based on actual measures of clinical and economic value for each. Health economic performance is closely related to accuracy, as a health economic utility function specifically assigns an economic value for the benefits of correct classification and the costs of misclassification of tested subjects. As a performance measure, it is not unusual to require a test to achieve a level of performance which results in an increase in health economic value per test (prior to testing costs) in excess of the target price of the test.

In general, alternative methods of determining diagnostic accuracy are commonly used for continuous measures, when a disease category or risk category (such as those at risk for having a metastatic event) has not yet been clearly defined by the relevant medical societies and practice of medicine, where thresholds for therapeutic use are not yet established, or where there is no existing gold standard for diagnosis of the pre-disease. For continuous measures of risk, measures of diagnostic accuracy for a calculated index are typically based on curve fit and calibration between the predicted continuous value and the actual observed values (or a historical index calculated value) and utilize measures such as R squared, Hosmer-Lemeshow P-value statistics and confidence intervals. It is not unusual for predicted values using such algorithms to be reported including a confidence interval (usually 90% or 95% CI) based on a historical observed cohort's predictions, as in the test for risk of future breast cancer recurrence commercialized by Genomic Health, Inc. (Redwood City, Calif.).

In general, by defining the degree of diagnostic accuracy, i.e., cut points on a ROC curve, defining an acceptable AUC value, and determining the acceptable ranges in relative concentration of what constitutes an effective amount of the DETERMINANTS of the invention allows for one of skill in the art to use the DETERMINANTS to identify, diagnose, or prognose subjects with a pre-determined level of predictability and performance.

Risk Markers of the Invention (DETERMINANTS)

The biomarkers and methods of the present invention allow one of skill in the art to identify, diagnose, or otherwise assess those subjects who do not exhibit any symptoms of cancer or a metastatic event, but who nonetheless may be at risk for developing cancer or a metastatic event.

One skilled in the art will recognize that the DETERMINANTS presented herein encompasses all forms and variants, including but not limited to, polymorphisms, isoforms, mutants, derivatives, precursors including nucleic acids and pro-proteins, cleavage products, receptors (including soluble and transmembrane receptors), ligands, protein-ligand complexes, and post-translationally modified variants (such as cross-linking or glycosylation), fragments, and degradation products, as well as any multi-unit nucleic acid, protein, and glycoprotein structures comprised of any of the DETERMINANTS as constituent sub-units of the fully assembled structure.

One skilled in the art will note that the above listed DETERMINANTS come from a diverse set of physiological and biological pathways, including many which are not commonly accepted to be related to metastatic disease. These groupings of different DETERMINANTS, even within those high significance segments, may presage differing signals of the stage or rate of the progression of the disease. Such distinct groupings of DETERMINANTS may allow a more biologically detailed and clinically useful signal from the DETERMINANTS as well as opportunities for pattern recognition within the DETERMINANT algorithms combining the multiple DETERMINANT signals.

The present invention concerns, in one aspect, a subset of DETERMINANTS; other DETERMINANTS and even biomarkers which are not listed in Table 2, 3, or 5, but related to these physiological and biological pathways, may prove to be useful given the signal and information provided from these studies. To the extent that other biomarker pathway participants (i.e., other biomarker participants in common pathways with those biomarkers contained within the list of DETERMINANTS in Table 2, 3, or 5) are also relevant pathway participants in cancer or a metastatic event, they may be functional equivalents to the biomarkers thus far disclosed in Table 2, 3, or 5. These other pathway participants are also considered DETERMINANTS in the context of the present invention, provided they additionally share certain defined characteristics of a good biomarker, which would include both involvement in the herein disclosed biological processes and also analytically important characteristics such as the bioavailability of said biomarkers at a useful signal to noise ratio, and in a useful and accessible sample matrix such as blood serum or a tumor biopsy. Such requirements typically limit the diagnostic usefulness of many members of a biological pathway, and frequently occurs only in pathway members that constitute secretory substances, those accessible on the plasma membranes of cells, as well as those that are released into the serum upon cell death, due to apoptosis or for other reasons such as endothelial remodeling or other cell turnover or cell necrotic processes, whether or not they are related to the disease progression of cancer or metastatic event. However, the remaining and future biomarkers that meet this high standard for DETERMINANTS are likely to be quite valuable.

Furthermore, other unlisted biomarkers will be very highly correlated with the biomarkers listed as DETERMINANTS in Table 2, 3, or 5 (for the purpose of this application, any two variables will be considered to be "very highly correlated" when they have a Coefficient of Determination ($R^2$) of 0.5 or greater). The present invention encompasses such functional and statistical equivalents to the aforementioned DETERMINANTS. Furthermore, the statistical utility of such additional DETERMINANTS is substantially dependent on the cross-correlation between multiple biomarkers and any new biomarkers will often be required to operate within a panel in order to elaborate the meaning of the underlying biology.

One or more, preferably two or more of the listed DETERMINANTS can be detected in the practice of the present invention. For example, two (2), three (3), four (4), five (5), ten (10), fifteen (15), twenty (20), forty (40), fifty (50), seventy-five (75), one hundred (100), one hundred and twenty five (125), one hundred and fifty (150), one hundred and seventy-five (175), two hundred (200), two hundred and ten (210), two hundred and twenty (220) or more DETERMINANTS can be detected.

In some aspects, all DETERMINANTS listed herein can be detected. Preferred ranges from which the number of DETERMINANTS can be detected include ranges bounded by any minimum selected from between one and 741, particularly two, three, four, five, six, seven, eight, nine, ten, eleven, twelve, thirteen, fourteen, fifteen, sixteen, seventeen, eighteen, nineteen, twenty, twenty-one, twenty-five, thirty, fifty, seventy-five, one hundred, one hundred and twenty five, one hundred and fifty, one hundred and seventy-five, two hundred, two hundred and ten, two hundred and twenty, paired with any maximum up to the total known DETERMINANTS, particularly four, five, ten, twenty, fifty, and seventy-five. Particularly preferred ranges include two to five (2-5), two to ten (2-10), two to fifty (2-50), two to seventy-five (2-75), two to one hundred (2-100), five to ten (5-10), five to twenty (5-20), five to fifty (5-50), five to seventy-five (5-75), five to one hundred (5-100), ten to twenty (10-20), ten to fifty (10-50), ten to seventy-five (10-75), ten to one hundred (10-100), twenty to fifty (20-50), twenty to seventy-five (20-75), twenty to one hundred (20-100), fifty to seventy-five (50-75), fifty to one hundred (50-100), one hundred to one hundred and twenty-five (100-125), one hundred and twenty-five to one hundred and fifty (125-150), one hundred and fifty to one hundred and seventy five (150-175), one hundred and seventy-five to two hundred (175-200), two hundred to two hundred and ten (200-210), two hundred and ten to two hundred and twenty (210-220).

Construction of DETERMINANT Panels

Groupings of DETERMINANTS can be included in "panels." A "panel" within the context of the present invention means a group of biomarkers (whether they are DETERMINANTS, clinical parameters, or traditional laboratory risk factors) that includes more than one DETERMINANT. A panel can also comprise additional biomarkers, e.g., clinical parameters, traditional laboratory risk factors, known to be present or associated with cancer or cancer metastasis, in combination with a selected group of the DETERMINANTS listed in Table 2.

As noted above, many of the individual DETERMINANTS, clinical parameters, and traditional laboratory risk factors listed, when used alone and not as a member of a multi-biomarker panel of DETERMINANTS, have little or no clinical use in reliably distinguishing individual normal subjects, subjects at risk for having a metastatic event, and subjects having cancer from each other in a selected general population, and thus cannot reliably be used alone in classifying any subject between those three states. Even where there are statistically significant differences in their mean measurements in each of these populations, as commonly occurs in studies which are sufficiently powered, such biomarkers may remain limited in their applicability to an individual subject, and contribute little to diagnostic or prognostic predictions for that subject. A common measure of statistical significance is the p-value, which indicates the probability that an observation has arisen by chance alone; preferably, such p-values are 0.05 or less, representing a 5% or less chance that the observation of interest arose by chance. Such p-values depend significantly on the power of the study performed.

Despite this individual DETERMINANT performance, and the general performance of formulas combining only the traditional clinical parameters and few traditional laboratory risk factors, the present inventors have noted that certain specific combinations of two or more DETERMINANTS can also be used as multi-biomarker panels comprising combinations of DETERMINANTS that are known to be involved in one or more physiological or biological pathways, and that such information can be combined and made clinically useful through the use of various formulae, including statistical classification algorithms and others, combining and in many cases extending the performance characteristics of the combination beyond that of the individual DETERMINANTS. These specific combinations show an acceptable level of diagnostic accuracy, and, when sufficient information from multiple DETERMINANTS is combined in a trained formula, often reliably achieve a high level of diagnostic accuracy transportable from one population to another.

The general concept of how two less specific or lower performing DETERMINANTS are combined into novel and more useful combinations for the intended indications, is a key aspect of the invention. Multiple biomarkers can often yield better performance than the individual components when proper mathematical and clinical algorithms are used; this is often evident in both sensitivity and specificity, and results in a greater AUC. Secondly, there is often novel unperceived information in the existing biomarkers, as such was necessary in order to achieve through the new formula an improved level of sensitivity or specificity. This hidden information may hold true even for biomarkers which are generally regarded to have suboptimal clinical performance on their own. In fact, the suboptimal performance in terms of high false positive rates on a single biomarker measured alone may very well be an indicator that some important additional information is contained within the biomarker results—information which would not be elucidated absent the combination with a second biomarker and a mathematical formula.

Several statistical and modeling algorithms known in the art can be used to both assist in DETERMINANT selection choices and optimize the algorithms combining these choices. Statistical tools such as factor and cross-biomarker correlation/covariance analyses allow more rationale approaches to panel construction. Mathematical clustering and classification tree showing the Euclidean standardized distance between the DETERMINANTS can be advantageously used. Pathway informed seeding of such statistical classification techniques also may be employed, as may rational approaches based on the selection of individual DETERMINANTS based on their participation across in particular pathways or physiological functions.

Ultimately, formula such as statistical classification algorithms can be directly used to both select DETERMINANTS and to generate and train the optimal formula necessary to combine the results from multiple DETERMINANTS into a single index. Often, techniques such as forward (from zero potential explanatory parameters) and backwards selection (from all available potential explanatory parameters) are used, and information criteria, such as AIC or BIC, are used to quantify the tradeoff between the performance and diagnostic accuracy of the panel and the number of DETERMI- NANTS used. The position of the individual DETERMINANT on a forward or backwards selected panel can be closely related to its provision of incremental information content for the algorithm, so the order of contribution is highly dependent on the other constituent DETERMINANTS in the panel.

Construction of Clinical Algorithms

Any formula may be used to combine DETERMINANT results into indices useful in the practice of the invention. As indicated above, and without limitation, such indices may indicate, among the various other indications, the probability, likelihood, absolute or relative risk, time to or rate of conversion from one to another disease states, or make predictions of future biomarker measurements of metastatic disease. This may be for a specific time period or horizon, or for remaining lifetime risk, or simply be provided as an index relative to another reference subject population.

Although various preferred formula are described here, several other model and formula types beyond those mentioned herein and in the definitions above are well known to one skilled in the art. The actual model type or formula used may itself be selected from the field of potential models based on the performance and diagnostic accuracy characteristics of its results in a training population. The specifics of the formula itself may commonly be derived from DETERMINANT results in the relevant training population. Amongst other uses, such formula may be intended to map the feature space derived from one or more DETERMINANT inputs to a set of subject classes (e.g. useful in predicting class membership of subjects as normal, at risk for having a metastatic event, having cancer), to derive an estimation of a probability function of risk using a Bayesian approach (e.g. the risk of cancer or a metastatic event), or to estimate the class-conditional probabilities, then use Bayes' rule to produce the class probability function as in the previous case.

Preferred formulas include the broad class of statistical classification algorithms, and in particular the use of discriminant analysis. The goal of discriminant analysis is to predict class membership from a previously identified set of features. In the case of linear discriminant analysis (LDA), the linear combination of features is identified that maximizes the separation among groups by some criteria. Features can be identified for LDA using an eigengene based approach with different thresholds (ELDA) or a stepping algorithm based on a multivariate analysis of variance (MANOVA). Forward, backward, and stepwise algorithms can be performed that minimize the probability of no separation based on the Hotelling-Lawley statistic.

Eigengene-based Linear Discriminant Analysis (ELDA) is a feature selection technique developed by Shen et al. (2006). The formula selects features (e.g. biomarkers) in a multivariate framework using a modified eigen analysis to identify features associated with the most important eigenvectors. "Important" is defined as those eigenvectors that explain the most variance in the differences among samples that are trying to be classified relative to some threshold.

A support vector machine (SVM) is a classification formula that attempts to find a hyperplane that separates two classes. This hyperplane contains support vectors, data points that are exactly the margin distance away from the hyperplane. In the likely event that no separating hyperplane exists in the current dimensions of the data, the dimensionality is expanded greatly by projecting the data into larger dimensions by taking non-linear functions of the original variables (Venables and Ripley, 2002). Although not required, filtering of features for SVM often improves prediction. Features (e.g., biomarkers) can be identified for a support vector machine using a non-parametric Kruskal-Wallis (KW) test to select the best univariate features. A random forest (RF, Breiman, 2001) or recursive partitioning (RPART, Breiman et al., 1984) can also be used separately or in combination to identify biomarker combinations that are most important. Both KW and RF require that a number of features be selected from the total. RPART creates a single classification tree using a subset of available biomarkers.

Other formula may be used in order to pre-process the results of individual DETERMINANT measurement into more valuable forms of information, prior to their presentation to the predictive formula. Most notably, normalization of biomarker results, using either common mathematical transformations such as logarithmic or logistic functions, as normal or other distribution positions, in reference to a population's mean values, etc. are all well known to those skilled in the art. Of particular interest are a set of normalizations based on Clinical Parameters such as age, gender, race, or sex, where specific formula are used solely on subjects within a class or continuously combining a Clinical Parameter as an input. In other cases, analyte-based biomarkers can be combined into calculated variables which are subsequently presented to a formula.

In addition to the individual parameter values of one subject potentially being normalized, an overall predictive formula for all subjects, or any known class of subjects, may itself be recalibrated or otherwise adjusted based on adjustment for a population's expected prevalence and mean biomarker parameter values, according to the technique outlined in D'Agostino et al, *JAMA* (2001), or other similar normalization and recalibration techniques. Such epidemiological adjustment statistics may be captured, confirmed, improved and updated continuously through a registry of past data presented to the model, which may be machine readable or otherwise, or occasionally through the retrospective query of stored samples or reference to historical studies of such parameters and statistics. Additional examples that may be the subject of formula recalibration or other adjustments include statistics used in studies by Pepe, M. S. et al, 2004 on the limitations of odds ratios; Cook, N. R., 2007 relating to ROC curves. Finally, the numeric result of a classifier formula itself may be transformed post-processing by its reference to an actual clinical population and study results and observed endpoints, in order to calibrate to absolute risk and provide confidence intervals for varying numeric results of the classifier or risk formula. An example of this is the presentation of absolute risk, and confidence intervals for that risk, derived using an actual clinical study, chosen with reference to the output of the recurrence score formula in the Oncotype Dx product of Genomic Health, Inc. (Redwood City, Calif.). A further modification is to adjust for smaller sub-populations of the study based on the output of the classifier or risk formula and defined and selected by their Clinical Parameters, such as age or sex.

Combination with Clinical Parameters and Traditional Laboratory Risk Factors

Any of the aforementioned Clinical Parameters may be used in the practice of the invention as a DETERMINANT input to a formula or as a pre-selection criteria defining a relevant population to be measured using a particular DETERMINANT panel and formula. As noted above, Clinical Parameters may also be useful in the biomarker normalization and pre-processing, or in DETERMINANT selection, panel construction, formula type selection and derivation, and formula result post-processing. A similar approach can be taken with the Traditional Laboratory Risk Factors, as either an input to a formula or as a pre-selection criterium.

Measurement of DETERMINANTS

The actual measurement of levels or amounts of the DETERMINANTS can be determined at the protein or nucleic acid level using any method known in the art. For example, at the nucleic acid level, Northern and Southern hybridization analysis, as well as ribonuclease protection assays using probes which specifically recognize one or more of these sequences can be used to determine gene expression. Alternatively, amounts of DETERMINANTS can be measured using reverse-transcription-based PCR assays (RT-PCR), e.g., using primers specific for the differentially expressed sequence of genes or by branch-chain RNA amplification and detection methods by Panomics, Inc. Amounts of DETERMINANTS can also be determined at the protein level, e.g., by measuring the levels of peptides encoded by the gene products described herein, or subcellular localization or activities thereof using technological platform such as for example AQUA® (HistoRx, New Haven, Conn.) or U.S. Pat. No. 7,219,016. Such methods are well known in the art and include, e.g., immunoassays based on antibodies to proteins encoded by the genes, aptamers or molecular imprints. Any biological material can be used for the detection/quantification of the protein or its activity. Alternatively, a suitable method can be selected to determine the activity of proteins encoded by the marker genes according to the activity of each protein analyzed.

The DETERMINANT proteins, polypeptides, mutations, and polymorphisms thereof can be detected in any suitable manner, but is typically detected by contacting a sample from the subject with an antibody which binds the DETERMINANT protein, polypeptide, mutation, or polymorphism and then detecting the presence or absence of a reaction product. The antibody may be monoclonal, polyclonal, chimeric, or a fragment of the foregoing, as discussed in detail above, and the step of detecting the reaction product may be carried out with any suitable immunoassay. The sample from the subject is typically a biological fluid as described above, and may be the same sample of biological fluid used to conduct the method described above.

Immunoassays carried out in accordance with the present invention may be homogeneous assays or heterogeneous assays. In a homogeneous assay the immunological reaction usually involves the specific antibody (e.g., anti-DETERMINANT protein antibody), a labeled analyte, and the sample of interest. The signal arising from the label is modified, directly or indirectly, upon the binding of the antibody to the labeled analyte. Both the immunological reaction and detection of the extent thereof can be carried out in a homogeneous solution. Immunochemical labels which may be employed include free radicals, radioisotopes, fluorescent dyes, enzymes, bacteriophages, or coenzymes.

In a heterogeneous assay approach, the reagents are usually the sample, the antibody, and means for producing a detectable signal. Samples as described above may be used. The antibody can be immobilized on a support, such as a bead (such as protein A and protein G agarose beads), plate or slide, and contacted with the specimen suspected of containing the antigen in a liquid phase. The support is then separated from the liquid phase and either the support phase or the liquid phase is examined for a detectable signal employing means for producing such signal. The signal is related to the presence of the analyte in the sample. Means for producing a detectable signal include the use of radioactive labels, fluorescent labels, or enzyme labels. For example, if the antigen to be detected contains a second binding site, an antibody which binds to that site can be conjugated to a detectable group and added to the liquid phase reaction solution before the separation step. The presence of the detectable group on the solid support indicates the presence of the antigen in the test sample. Examples of suitable immunoassays are oligonucleotides, immunoblotting, immunofluorescence methods, immunoprecipitation, chemiluminescence methods, electrochemiluminescence (ECL) or enzyme-linked immunoassays.

Those skilled in the art will be familiar with numerous specific immunoassay formats and variations thereof which may be useful for carrying out the method disclosed herein. See generally E. Maggio, Enzyme-Immunoassay, (1980) (CRC Press, Inc., Boca Raton, Fla.); see also U.S. Pat. No. 4,727,022 to Skold et al. titled "Methods for Modulating Ligand-Receptor Interactions and their Application," U.S. Pat. No. 4,659,678 to Forrest et al. titled "Immunoassay of Antigens," U.S. Pat. No. 4,376,110 to David et al., titled "Immunometric Assays Using Monoclonal Antibodies," U.S. Pat. No. 4,275,149 to Litman et al., titled "Macromolecular Environment Control in Specific Receptor Assays," U.S. Pat. No. 4,233,402 to Maggio et al., titled "Reagents and Method Employing Channeling," and U.S. Pat. No. 4,230,767 to Boguslaski et al., titled "Heterogenous Specific Binding Assay Employing a Coenzyme as Label."

Antibodies can be conjugated to a solid support suitable for a diagnostic assay (e.g., beads such as protein A or protein G agarose, microspheres, plates, slides or wells formed from materials such as latex or polystyrene) in accordance with known techniques, such as passive binding. Antibodies as described herein may likewise be conjugated to detectable labels or groups such as radiolabels (e.g., $^{35}S$, $^{125}I$, $^{131}I$), enzyme labels (e.g., horseradish peroxidase, alkaline phosphatase), and fluorescent labels (e.g., fluorescein, Alexa, green fluorescent protein, rhodamine) in accordance with known techniques.

Antibodies can also be useful for detecting post-translational modifications of DETERMINANT proteins, polypeptides, mutations, and polymorphisms, such as tyrosine phosphorylation, threonine phosphorylation, serine phosphorylation, glycosylation (e.g., O-GlcNAc). Such antibodies specifically detect the phosphorylated amino acids in a protein or proteins of interest, and can be used in immunoblotting, immunofluorescence, and ELISA assays described herein. These antibodies are well-known to those skilled in the art, and commercially available. Post-translational modifications can also be determined using metastable ions in reflector matrix-assisted laser desorption ionization-time of flight mass spectrometry (MALDI-TOF) (Wirth et al. Proteomics (2002)).

For DETERMINANT proteins, polypeptides, mutations, and polymorphisms known to have enzymatic activity, the activities can be determined in vitro using enzyme assays known in the art. Such assays include, without limitation, kinase assays, phosphatase assays, reductase assays, among many others. Modulation of the kinetics of enzyme activities can be determined by measuring the rate constant $K_M$ using known algorithms, such as the Hill plot, Michaelis-Menten equation, linear regression plots such as Lineweaver-Burk analysis, and Scatchard plot.

Using sequence information provided by the database entries for the DETERMINANT sequences, expression of the DETERMINANT sequences can be detected (if present) and measured using techniques well known to one of ordinary skill in the art. For example, sequences within the sequence database entries corresponding to DETERMI- NANT sequences, or within the sequences disclosed herein, can be used to construct probes for detecting DETERMINANT RNA sequences in, e.g., Northern blot hybridization analyses or methods which specifically, and, preferably, quantitatively amplify specific nucleic acid sequences. As another example, the sequences can be used to construct primers for specifically amplifying the DETERMINANT sequences in, e.g., amplification-based detection methods such as reverse-transcription based polymerase chain reaction (RT-PCR). When alterations in gene expression are associated with gene amplification, deletion, polymorphisms, and mutations, sequence comparisons in test and reference populations can be made by comparing relative amounts of the examined DNA sequences in the test and reference cell populations.

Expression of the genes disclosed herein can be measured at the RNA level using any method known in the art. For example, Northern hybridization analysis using probes which specifically recognize one or more of these sequences can be used to determine gene expression. Alternatively, expression can be measured using reverse-transcription-based PCR assays (RT-PCR), e.g., using primers specific for the differentially expressed sequences. RNA can also be quantified using, for example, other target amplification methods (e.g., TMA, SDA, NASBA), or signal amplification methods (e.g., bDNA), and the like.

Alternatively, DETERMINANT protein and nucleic acid metabolites can be measured. The term "metabolite" includes any chemical or biochemical product of a metabolic process, such as any compound produced by the processing, cleavage or consumption of a biological molecule (e.g., a protein, nucleic acid, carbohydrate, or lipid). Metabolites can be detected in a variety of ways known to one of skill in the art, including the refractive index spectroscopy (RI), ultra-violet spectroscopy (UV), fluorescence analysis, radiochemical analysis, near-infrared spectroscopy (near-IR), nuclear magnetic resonance spectroscopy (NMR), light scattering analysis (LS), mass spectrometry, pyrolysis mass spectrometry, nephelometry, dispersive Raman spectroscopy, gas chromatography combined with mass spectrometry, liquid chromatography combined with mass spectrometry, matrix-assisted laser desorption ionization-time of flight (MALDI-TOF) combined with mass spectrometry, ion spray spectroscopy combined with mass spectrometry, capillary electrophoresis, NMR and IR detection. (See, WO 04/056456 and WO 04/088309, each of which are hereby incorporated by reference in their entireties) In this regard, other DETERMINANT analytes can be measured using the above-mentioned detection methods, or other methods known to the skilled artisan. For example, circulating calcium ions ($Ca^{2+}$) can be detected in a sample using fluorescent dyes such as the Fluo series, Fura-2A, Rhod-2, among others. Other DETERMINANT metabolites can be similarly detected using reagents that are specifically designed or tailored to detect such metabolites.

Kits

The invention also includes a DETERMINANT-detection reagent, e.g., nucleic acids that specifically identify one or more DETERMINANT nucleic acids by having homologous nucleic acid sequences, such as oligonucleotide sequences, complementary to a portion of the DETERMINANT nucleic acids or antibodies to proteins encoded by the DETERMINANT nucleic acids packaged together in the form of a kit. The oligonucleotides can be fragments of the DETERMINANT genes. For example the oligonucleotides can be 200, 150, 100, 50, 25, 10 or less nucleotides in length. The kit may contain in separate containers a nucleic acid or antibody (either already bound to a solid matrix or packaged separately with reagents for binding them to the matrix), control formulations (positive and/or negative), and/or a detectable label such as fluorescein, green fluorescent protein, rhodamine, cyanine dyes, Alexa dyes, luciferase, radio labels, among others. Instructions (e.g., written, tape, VCR, CD-ROM, etc.) for carrying out the assay may be included in the kit. The assay may for example be in the form of a Northern hybridization or a sandwich ELISA as known in the art.

For example, DETERMINANT detection reagents can be immobilized on a solid matrix such as a porous strip to form at least one DETERMINANT detection site. The measurement or detection region of the porous strip may include a plurality of sites containing a nucleic acid. A test strip may also contain sites for negative and/or positive controls. Alternatively, control sites can be located on a separate strip from the test strip. Optionally, the different detection sites may contain different amounts of immobilized nucleic acids, e.g., a higher amount in the first detection site and lesser amounts in subsequent sites. Upon the addition of test sample, the number of sites displaying a detectable signal provides a quantitative indication of the amount of DETERMINANTS present in the sample. The detection sites may be configured in any suitably detectable shape and are typically in the shape of a bar or dot spanning the width of a test strip.

Alternatively, the kit contains a nucleic acid substrate array comprising one or more nucleic acid sequences. The nucleic acids on the array specifically identify one or more nucleic acid sequences represented by DETERMINANTS listed on Table 2, 3, or 5. In various embodiments, the expression of 2, 3, 4, 5, 6, 7, 8, 9, 10, 15, 20, 25, 40, 50, 100, 125, 150, 175, 200, 220 or more of the sequences represented by DETERMINANTS listed on Table 2, 3, or 5 can be identified by virtue of binding to the array. The substrate array can be on, e.g., a solid substrate, e.g., a "chip" as described in U.S. Pat. No. 5,744,305. Alternatively, the substrate array can be a solution array, e.g., xMAP (Luminex, Austin, Tex.), Cyvera (Illumina, San Diego, Calif.), CellCard (Vitra Bioscience, Mountain View, Calif.) and Quantum Dots' Mosaic (Invitrogen, Carlsbad, Calif.).

Suitable sources for antibodies for the detection of DETERMINANTS include commercially available sources such as, for example, Abazyme, Abnova, Affinity Biologicals, AntibodyShop, Biogenesis, Biosense Laboratories, Calbiochem, Cell Sciences, Chemicon International, Chemokine, Clontech, Cytolab, DAKO, Diagnostic BioSystems, eBioscience, Endocrine Technologies, Enzo Biochem, Eurogentec, Fusion Antibodies, Genesis Biotech, GloboZymes, Haematologic Technologies, Immunodetect, Immunodiagnostik, Immunometrics, Immunostar, Immunovision, Biogenex, Invitrogen, Jackson ImmunoResearch Laboratory, KMI Diagnostics, Koma Biotech, LabFrontier Life Science Institute, Lee Laboratories, Lifescreen, Maine Biotechnology Services, Mediclone, MicroPharm Ltd., ModiQuest, Molecular Innovations, Molecular Probes, Neoclone, Neuromics, New England Biolabs, Novocastra, Novus Biologicals, Oncogene Research Products, Orbigen, Oxford Biotechnology, Panvera, PerkinElmer Life Sciences, Pharmingen, Phoenix Pharmaceuticals, Pierce Chemical Company, Polymun Scientific, Polysiences, Inc., Promega Corporation, Proteogenix, Protos Immunoresearch, QED Biosciences, Inc., R&D Systems, Repligen, Research Diagnostics, Roboscreen, Santa Cruz Biotechnology, Seikagaku America, Serological Corporation, Serotec, SigmaAldrich, StemCell Technologies, Synaptic Systems GmbH, Technopharm, Terra Nova Biotechnology, TiterMax, Trillium Diagnostics, Upstate Biotechnology, US Biological, Vector Laboratories, Wako Pure Chemical Industries, and Zeptometrix. However, the skilled artisan can routinely make antibodies, nucleic acid probes, e.g., oligonucleotides, aptamers, siRNAs, antisense oligonucleotides, against any of the DETERMINANTS in Table 2 or Table 3.

Methods of Treating or Preventing Cancer

The invention provides a method for treating, preventing or alleviating a symptom of cancer in a subject by decreasing expression or activity of DETERMINANTS 1-300 or increasing expression or activity of DETERMINANTS 301-741 Therapeutic compounds are administered prophylactically or therapeutically to subject suffering from at risk of (or susceptible to) developing cancer. Such subjects are identified using standard clinical methods or by detecting an aberrant level of expression or activity of (e.g., DETERMINANTS 1-741). Therapeutic agents include inhibitors of cell cycle regulation, cell proliferation, and protein kinase activity.

The therapeutic method includes increasing the expression, or function, or both of one or more gene products of genes whose expression is decreased ("underexpressed genes") in a cancer cell relative to normal cells of the same tissue type from which the cancer cells are derived. In these methods, the subject is treated with an effective amount of a compound, which increases the amount of one of more of the underexpressed genes in the subject. Administration can be systemic or local. Therapeutic compounds include a polypeptide product of an underexpressed gene, or a biologically active fragment thereof a nucleic acid encoding an underexpressed gene and having expression control elements permitting expression in the cancer cells; for example an agent which increases the level of expression of such gene endogenous to the cancer cells (i.e., which up-regulates expression of the underexpressed gene or genes). Administration of such compounds counter the effects of aberrantly-under expressed of the gene or genes in the subject's cells and improves the clinical condition of the subject The method also includes decreasing the expression, or function, or both, of one or more gene products of genes whose expression is aberrantly increased ("overexpressed gene") in cancer cells relative to normal cells. Expression is inhibited in any of several ways known in the art. For example, expression is inhibited by administering to the subject a nucleic acid that inhibits, or antagonizes, the expression of the overexpressed gene or genes, e.g., an antisense oligonucleotide which disrupts expression of the overexpressed gene or genes.

Alternatively, function of one or more gene products of the overexpressed genes is inhibited by administering a compound that binds to or otherwise inhibits the function of the gene products. For example, the compound is an antibody which binds to the overexpressed gene product or gene products.

These modulatory methods are performed ex vivo or in vitro (e.g., by culturing the cell with the agent) or, alternatively, in vivo (e.g., by administering the agent to a subject). The method involves administering a protein or combination of proteins or a nucleic acid molecule or combination of nucleic acid, molecules as therapy to counteract aberrant expression or activity of the differentially expressed genes.

Diseases and disorders that are characterized by increased (relative to a subject not suffering from the disease or disorder) levels or biological activity of the genes may be treated with therapeutics that antagonize (i.e., reduce or inhibit) activity of the overexpressed gene or genes. Therapeutics that antagonize activity are administered therapeutically or prophylactically. (e.g. vaccines)

Therapeutics that may be utilized include, e.g., (i) a polypeptide, or analogs, derivatives, fragments or homologs thereof of the overexpressed or underexpressed sequence or sequences; (ii) antibodies to the overexpressed or underexpressed sequence or sequences; (iii) nucleic acids encoding the over or underexpressed sequence or sequences; (iv) antisense nucleic acids or nucleic acids that are "dysfunctional" (i.e., due to a heterologous insertion within the coding sequences of coding sequences of one or more overexpressed or underexpressed sequences); (v) small molecules; (vi) siRNA, (vii) aptamers or (viii) modulators (i.e., inhibitors, agonists and antagonists that alter the interaction between an over/underexpressed polypeptide and its binding partner. The dysfunctional antisense molecule are utilized to "knockout" endogenous function of a polypeptide by homologous recombination (see, e.g., Capecchi, *Science* (1989))

Diseases and disorders that are characterized by decreased (relative to a subject not suffering from the disease or disorder) levels or biological activity may be treated with therapeutics that increase (i.e., are agonists to) activity. Therapeutics that upregulate activity may be administered in a therapeutic or prophylactic manner. Therapeutics that may be utilized include, but are not limited to, a polypeptide (or analogs, derivatives, fragments or homologs thereof) or an agonist that increases bioavailability.

Generation of Transgenic Animals

Transgenic animals of the invention have one or two null mTet alleles, harboring a Lox-Stop-Lox (LSL) cassette in the first intron of the mTet gene. Upon Cre-mediated excision of the LSL cassette, mTert expression is restored. Transgenic animals of the invention have one or null endogenous alleles of the Pten and p53 genes. Transgenic animals of the invention have one or two null mTet alleles and one or null endogenous alleles of the Pten and p53 genes. Inactivation can be achieved by modification of the endogenous gene, usually, a deletion, substitution or addition to a coding or noncoding region of the gene. The modification can prevent synthesis of a gene product or can result in a gene product lacking functional activity. Typical modifications are the introduction of an exogenous segment, such as a selection marker, within an exon thereby disrupting the exon or the deletion of an exon.

Inactivation of endogenous genes in mice can be achieved by homologous recombination between an endogenous gene in a mouse embryonic stem (ES) cell and a targeting construct. Typically, the targeting construct contains a positive selection marker flanked by segments of the gene to be targeted. Usually the segments are from the same species as the gene to be targeted (e.g., mouse). However, the segments can be obtained from another species, such as human, provided they have sufficient sequence identity with the gene to be targeted to undergo homologous recombination with it. Typically, the construct also contains a negative selection marker positioned outside one or both of the segments designed to undergo homologous recombination with the endogenous gene (see U.S. Pat. No. 6,204,061). Optionally, the construct also contains a pair of site-specific recombination sites, such as frt, position within or at the ends of the segments designed to undergo homologous recombination with the endogenous gene. The construct is introduced into ES cells, usually by electroporation, and undergoes homologous recombination with the endogenous gene introducing the positive selection marker and parts of the flanking segments (and frt sites, if present) into the endogenous gene. ES cells having undergone the desired recombination can be selected by positive and negative selection. Positive selection selects for cells that have undergone the desired homologous recombination, and negative selection selects against cells that have undergone negative recombination. These cells are obtained from preimplantation embryos cultured in vitro. Bradley et al., *Nature* (1984)) (incorporated by reference in its entirety for all purposes). Transformed ES cells are combined with blastocysts from a non-human animal. The ES cells colonize the embryo and in some embryos form or contribute to the germline of the resulting chimeric animal. See Jaenisch, *Science*, (1988) (incorporated by reference in its entirety for all purposes). Chimeric animals can be bred with nontransgenic animals to generate heterozygous transgenic animals. Heterozygous animals can be bred with each other to generate homozygous animals. Either heterozygous or homozygous animals can be bred with a transgenic animal expressing the flp recombinase. Expression of the recombinase results in excision of the portion of DNA between introduced frt sites, if present.

Functional inactivation can also be achieved for other species, such as rats, rabbits and other rodents, ovines such as sheep, caprines such as goats, porcines such as pigs, and bovines such as cattle and buffalo, are suitable. For animals other than mice, nuclear transfer technology is preferred for generating functionally inactivated genes. See Lai et al., *Sciences* (2002). Various types of cells can be employed as donors for nuclei to be transferred into oocytes, including ES cells and fetal fibrocytes. Donor nuclei are obtained from cells cultured in vitro into which a construct has been introduced and undergone homologous recombination with an endogenous gene, as described above (see WO 98/37183 and WO 98/39416, each incorporated by reference in their entirety for all purposes). Donor nuclei are introduced into oocytes by means of fusion, induced electrically or chemically (see any one of WO 97/07669, WO 98/30683 and WO 98/39416), or by microinjection (see WO 99/37143, incorporated by reference in its entirety for all purposes). Transplanted oocytes are subsequently cultured to develop into embryos which are subsequently implanted in the oviducts of pseudopregnant female animals, resulting in birth of transgenic offspring (see any one of WO 97/07669, WO 98/30683 and WO 98/39416). Transgenic animals bearing heterozygous transgenes can be bred with each other to generate transgenic animals bearing homozygous transgenes The Cre/loxP system (conditional gene inactivation system) is a tool for tissue-specific (and in connection with the tet system also time-specific) inactivation of genes, for example, but not limited to genes that cannot be investigated in differentiated tissues because of their early embryonic lethality in mice with conventional knockouts. It can also be used for the removal of a transgene (which was overexpressed in a specific tissue) at a certain time point to study the invert effect of a downregulation of the transgene in a time course experiment. In general, two mouse lines are required for conditional gene inactivation. First, a conventional transgenic mouse line with Cre targeted to a specific tissue or cell type, and secondly a mouse strain that embodies a target gene (endogenous gene or transgene) flanked by two loxP sites in a direct orientation ("floxed gene"). Recombination (excision and consequently inactivation of the target gene) occurs only in those cells expressing Cre recombinase. Hence, the target gene remains active in all cells and tissues which do not express Cre.

Some transgenic animals of the invention have both an inactivation of one or both alleles of Pten and p53 genes and/or one or two null mTet alleles that confer an additional phenotype related to prostate cancer, its pathology or underlying biochemical processes. This disruption can be achievement by recombinase-mediated excision of Pten, p53 or mTet genes with embedded LoxP site or by for example LSL cassette knock-in, and RNAi-mediated extinction of these genes either in a germline configuration or in somatic transduction of prostate epithelium in situ or in cell culture followed by reintroduction of these primary cells into the renal capsule or orthotopically. Other engineering strategies are also obvious including chimera formation using targeted ES clones that avoid germline transmission.

EXAMPLES

Example 1

General Methods mTert Knockout Allele, Pten and Trp53 Conditional Alleles.

mTert knockout allele and the Pten$^{loxP}$ conditional knockout alleles have been described elsewhere (Zheng et al., *Nature* (2008), Farazi et al., *Cancer Res*. (2006)). p53$^{loxP}$ strain was generously provided by A. Berns (Marino et al., *Genes Dev*. (2000)). Prostate epithelium-specific deletion was effected by the PB-Cre4 (Wu et al., *Mech. Dev*. (2001) and was obtained from MMHCC (http://mouse.ncifcrf.gov/search_results.asp).

Generation of the LSL-mTERT$^{loxP}$ Allele.

We knock-in the LSL cassette into the first intron (FIG. 1A). The presence of the LSL cassette produces a null mTert allele and its removal by PB-Cre expression restores activity under the control of the native mTert promoter. This mouse model scheme allows for excellent specific control telomerase reconstitution in prostate epithelia cells. Following introduction the construct into ES cells and screening of ES cells and germline transmission and NeoR cassette deletion via EIIa-Cre, the LSL-mTert allele has been backcrossed 4 generations onto the C57Bl/6 background.

Mating Scheme.

Figure 6:
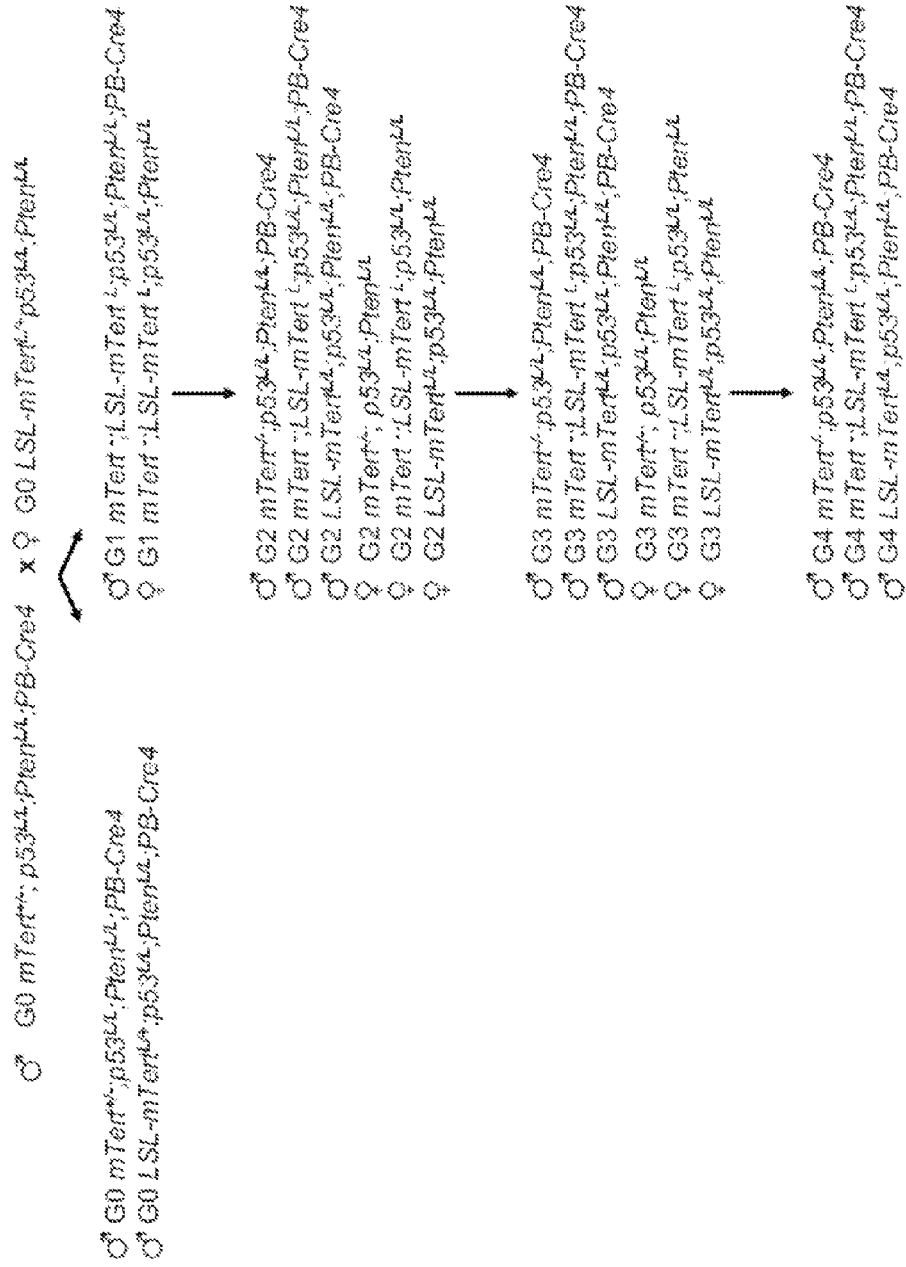
FIG. 6. Breeding scheme used to produce the experimental cohorts. 5 alleles of mTert, LSL-mTert$^{L/L}$, Pten$^{L/L}$, p53$^{L/L}$, PB-Cre4 were used to generate the telomere intact mTert$^{+/+}$ PB-Pten/p53 mice, G3/4 telomere dysfunctional mTert$^{-/-}$ mice, G3/4 telomerase reactivation on the backdrop of telomere dysfunctional LSL-Tert mice.
Figure 7:
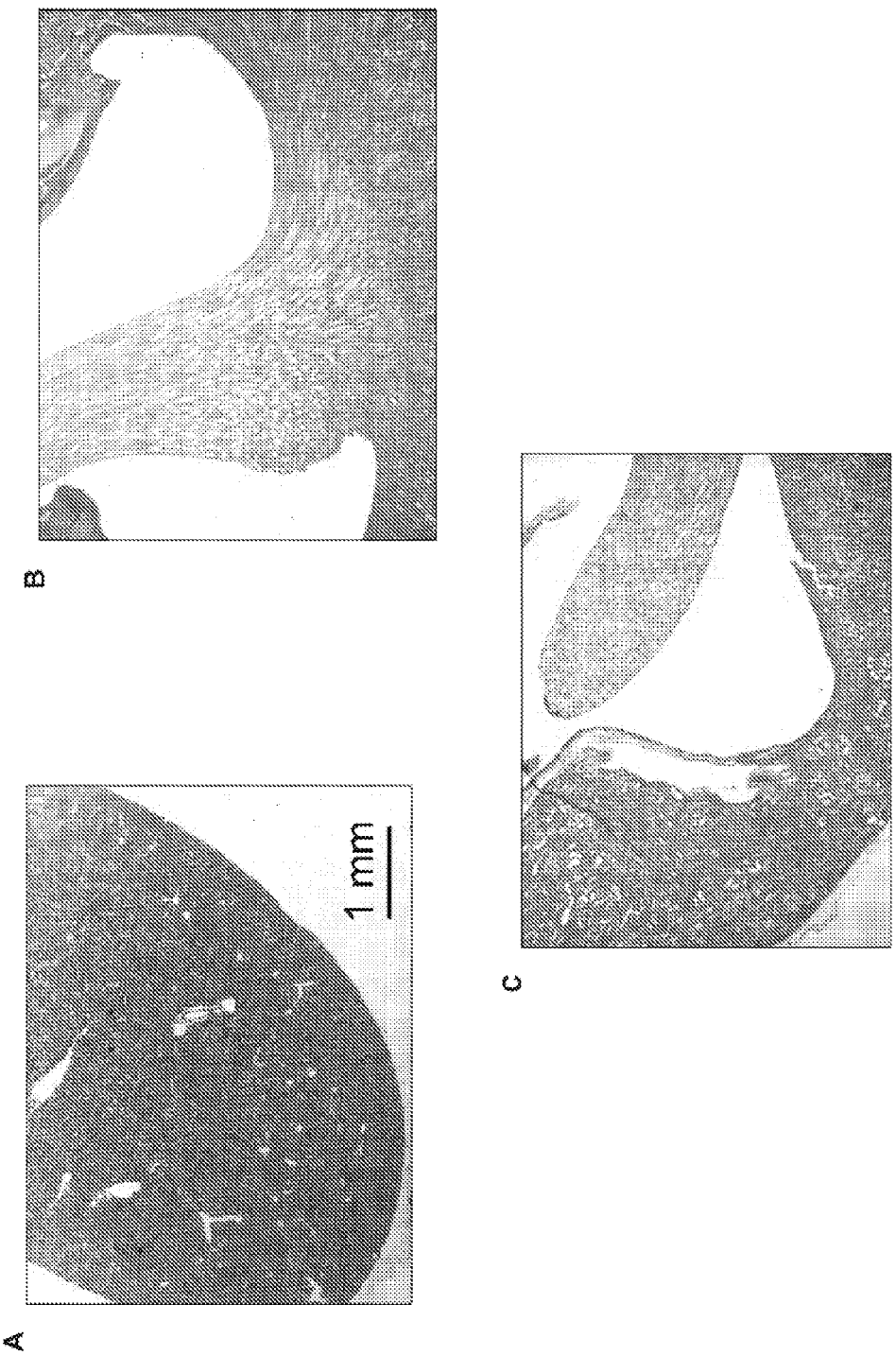
FIG. 7. Histological analyses revealed presence of high-grade prostate intraepithelial neoplasia (HPIN) by age 9 weeks in all three cohorts. (A-C) H&E sections of the HPIN in the anterior prostate (AP) tumors at age of 9 weeks from G0 mTert+/+ PB-Pten/p53 (A), G4 mTert-/- PB-Pten/p53 (B), and G4 LSL-mTert PB-Pten/p53 (C).

As depicted in FIG. 6, the LSL-mTERT$^{loxP}$ mice were crossed with G0 mTert$^{+/-}$ p53$^{L/L}$ Pten$^{L/L}$ PB-Cre4 mice to generate G0 mTert$^{+/+}$ LSL-mTert$^{+/+}$ p53$^{L/L}$ Pten$^{L/L}$ PB-Cre4, G0 mTert$^{+/+}$ LSL-mTert$^{L/+}$ p53$^{L/L}$ Pten$^{L/L}$ PB-Cre4, and G0 mTert$^{+/-}$ LSL-mTert$^{+/+}$ p53$^{L/L}$ Pten$^{L/L}$ PB-Cre4 mice. These mice were then intercross to generate G0 mTert$^{+/+}$ LSL-mTert$^{+/+}$ p53$^{L/L}$ Pten$^{L/L}$ PB-Cre4 and G1 mTert$^{-/-}$ LSL-mTert$^{+/+}$ p53$^{L/L}$ Pten$^{L/L}$ PB-Cre4; G1 mTert$^{+/-}$ LSL-mTert$^{L/+}$ p53$^{L/L}$ Pten$^{L/L}$ PB-Cre4, and G1 mTert$^{+/+}$ LSL-mTert$^{L/L}$ p53$^{L/L}$ Pten$^{L/L}$ PB-Cre4. G1 mice were then intercrossed to generate G2, G3, and G4 mice.

Tissue Analysis.

Normal and tumor tissues were fixed in 10% neutral-buffered formalin overnight then processed, paraffin-embedded, sectioned and stained with hematoxylin and eosin according to standard protocol. For immunohistochemistry, 5 micron sections were incubated with primary antibodies overnight at 4° C. in a humidified chamber. For rabbit antibodies, sections were subsequently developed using Dako Envision. Mouse monoclonal staining was developed using MOM kit (Vector). Representative sections from at least three mice were counted for each genotype.

For Western blot analysis, tissues and cells were lysed in RIPA buffer (20 mM Tris pH 7.5, 150 mM NaCl, 1% Nonidet P-40, 0.5% Sodium Deoxycholate, 1 mM EDTA, 0.1% SDS) containing complete mini protease inhibitors (Roche) and phosphatase inhibitors. Western blots were obtained utilizing 20-50 μg of lysate protein, and were incubated with antibodies against HSP70 (610607, BD Transduction Laboratories).

Laser Capture Microdissection and DNA Extraction.

Laser capture microdissection was done as previously described (Emmert-Buck et al., 1996). Genomic DNA of microdissected prostate tumor cells was extracted with phenol-chloroform prior to PCR analysis.

TUNEL Assay.

To determine apoptosis in prostate tumor cells, TUNEL staining was performed using the ApopTag Plus peroxidase kit (Chemicon) according to according to the manufacture's protocol. To quantify the apoptosis in tumor cells, we selected 3 to 5 high-power fields per mouse apoptotic cells were counted by two independent investigators. The percentage of apoptotic cells from each group of mice was compared.

Cytogenetics, Quantitative Telomere FISH and Spectral Karyotyping Analysis.

We prepared metaphase chromosomes from prostate tumor cells or early passage. We subjected metaphases to Giemsa staining or quantitative FISH analysis of telomeric sequences with Cy-3-labeled T2AG3 peptide-nucleic acid (PNA) probe. We carried out spectral karyotyping analysis according to the manufacturer's recommendations, using mouse chromosome paint probes (Applied Spectral Imaging) on a Nikon Eclipse 800 microscope equipped with an ASI interferometer and workstation. Depending on the quality of metaphase spreads, 10-20 metaphases from each sample were analyzed in detail.

Establishment of Mouse Prostate Tumor Cell Lines.

Tumors were dissected from prostates of G0 Pten$^{loxp/loxp}$ Trp53$^{loxp/loxp}$ PB-Cre4$^+$, G3 and G4 mice, G3 and G4 mice, minced, and digested with 0.5% type I collagenase (Invitrogen) as described previously. After filtering through a 40-μm mesh, the trapped fragments were plated in tissue culture dishes coated with type I collagen (BD Pharmingen). Cell lines were established and maintained in DMEM plus 10% fetal bovine serum (FBS, Omega Scientific), 25 μg/mL bovine pituitary extract, 5 μg/mL bovine insulin, and 6 ng/mL recombinant human epidermal growth factor (Sigma-Aldrich).

RNA Isolation and Real-Time PCR.

Total RNA was extracted using the RNeasy Mini kit (Qiagen) and treated with RQ1 RNase-free DNase Set (Promega). Firststrand cDNA was synthesized using 1 μg of total RNA and SuperscriptII (Invitrogen). Real-time qPCR was performed in triplicates with a MxPro3000 and SYBR GreenER qPCR mix (Invitrogen). The relative amount of specific mRNA was normalized to GAPDH. Primer sequences are available upon request.

Array-CGH Analysis for Minimal Common Regions (MCRs) of Chromosomal Amplifications or Deletions of Prostate Tumors in (LSL-TERT Mice).

The array-CGH data of 18 later generations (G3 or G4) mTert$^{+/-}$ LSL-mTert$^{L/+}$ p53$^{L/L}$ Pten$^{L/L}$ PB-Cre4, and mTert$^{+/+}$ LSL-mTert$^{L/L}$ p53$^{L/L}$ Pten$^{L/L}$ PB-Cre4 mice were analyzed with the MCR algorithm[25] to detect focal genomic regions with copy number alteration (CNA) events in at least two mice. Mouse genome data build mm9 was used in the analysis. A total of 2183 genes from 57 amplified regions (Table 2) and 3531 genes from 38 deletion regions were detected by the MCR algorithm.

Array-CGH Analysis for Recurrent Focal and Arm-Level Chromosomal Copy Number Alterations in Human Prostate Tumors with the GISTIC2 Algorithm.

The array-CGH data of 194 human prostate tumors[2] were analyzed with the GISTIC2 algorithm[47] to detect focal genomic regions with copy number alteration (CNA) events. Focal regions with q-values smaller than 0.25 are considered significant, which resulted in 16 amplified and 39 deleted regions. Arm-level changes with q-values smaller than 0.005 are considered significant, which suggested chromosome 7p, 7q, and 8q amplification and 6q, 8p, 12p, 13q, 16q, 17p, and 18q deletion.

Homolog Mapping for CNA Synteny Regions Cross Human and Mouse Tumors.

We used NCBI homologene database (version 39.2) to map human and mouse homolog genes and detect synteny CNA regions. The homologene analysis characterized 300 amplified genes and 441 deleted genes that commonly recurred in human and mouse prostate tumors.

Clinical Outcome Analysis.

The raw Affymetrix HG-U133A expression profiles and clinical information of 79 prostate cancer patients from Glinsky et al. cohort (Table 2)[3] were generously provided by Dr. William Gerald. The raw dataset was analyzed by MASS algorithm. Low-expression probesets with less than 20% present calls across the 79 samples were excluded from the data. The remaining 13,027 probesets map to 8,763 genes with unique symbols, and the mean log-transformed probeset levels were used as the gene expression profiles.

A univariate Cox proportional hazard analysis was conducted using the R survival package for invasion assay positive genes to identify those expression in PCA tumors was positively associated with biochemical recurrence (BCR, defined by post-op PSA>0.2 ng/ml) in the Glinsky et al. dataset[3].

Kaplan-Meier analysis for the survival difference of the two cancer patient clusters was conducted using the R survival package. C-statistics analysis was conducted using the R survcomp package. The statistical procedures used in the analyses include a bootstrapping step that estimates the distribution of C-statistics of all models across 10,000 random bootstrapping instances, and a comparative step that uses the t-test to compare the C-statistics of models and evaluate the statistical significance. Multivariate Cox proportional hazards model analysis with the 4-gene signature was used to estimate the coefficients of individual genes, which combined the 4-gene expression levels into an integrated risk score model defined.

Co-Deletion Analysis in Human Clinical Samples.

Figure 5:
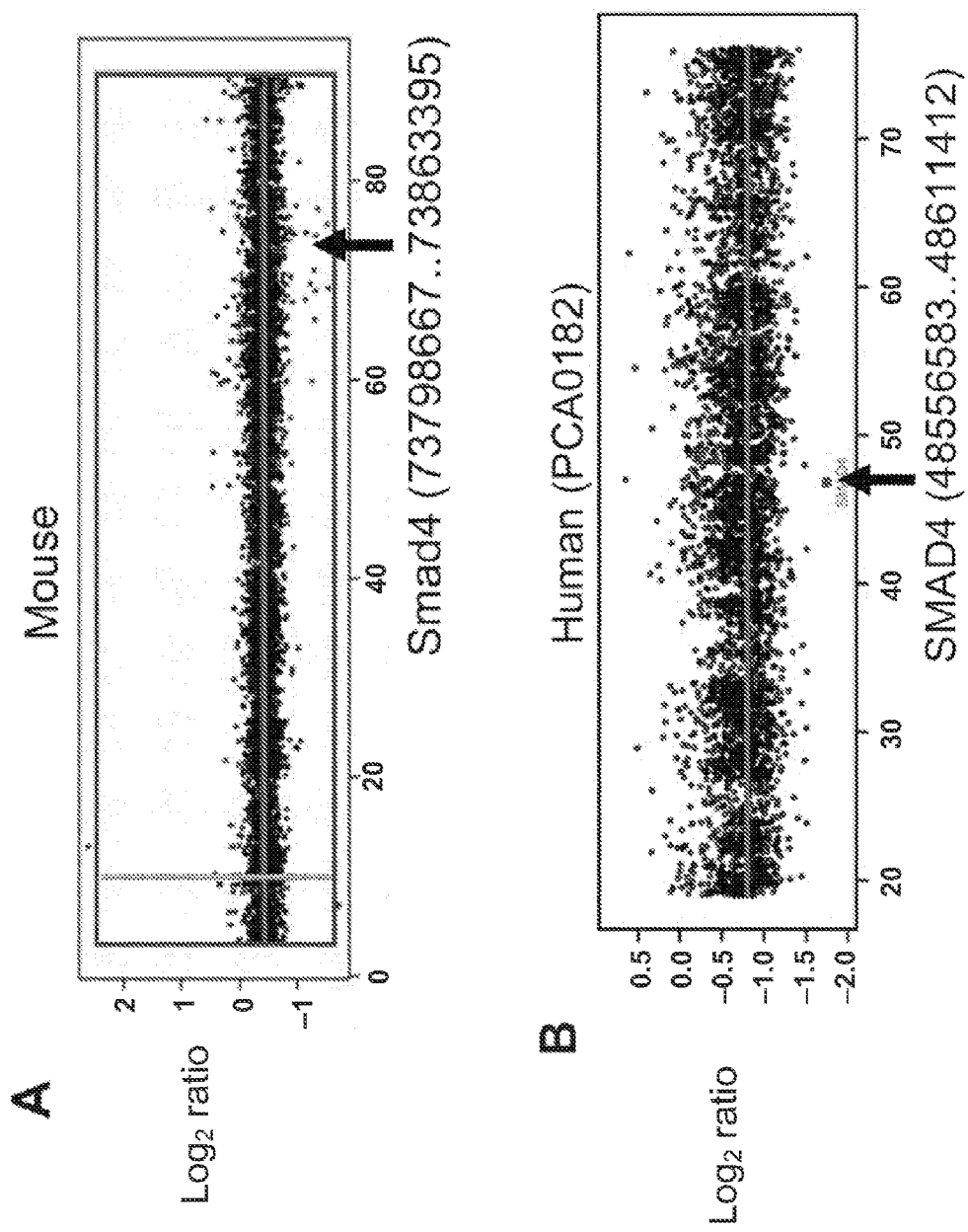
FIG. 5. Co-deletion of SMAD4 together with PTEN and TP53 lead to aggressive prostate cancer progression. (A-B) Log$_2$ ratio of array-CGH plots showing conserved deletion of SMAD4 in both mouse G3,G4 LSL-mTert-PB-Pten/p53 (A) and human prostate sample (B). They axis shows log$_2$ of copy number ratio (normal, log$_2$=0); amplifications are above and deletions are below this axis; x axis is chromosome position, in Mbp. (C-D) Log$_2$ ratio of array-CGH plots showing co-deletion of PTEN (C) and TP53 (D) in that same human prostate sample that with SMAD4 deletion. (E) Co-deletion analysis of PTEN, TP53 and SMAD4 in human prostate cancer samples (n=194). The P-value (Fisher's exact test)=2.9e-6 (asterisk-). (F) Survival curves showing significant decrease in lifespan in the PB-Pten/p53/Smad4 (n=24) (asterisk) compared with the PB-Pten/p53 cohort (n=25) or PB-Pten/Smad4 (n=44) by Kaplan-Meier overall cumulative survival analysis (P<0.0001). (G) H&E sections of the prostate tumors of PB-Pten/p53/Smad4 in spinal bone at 19 weeks of age.
Figure 5:
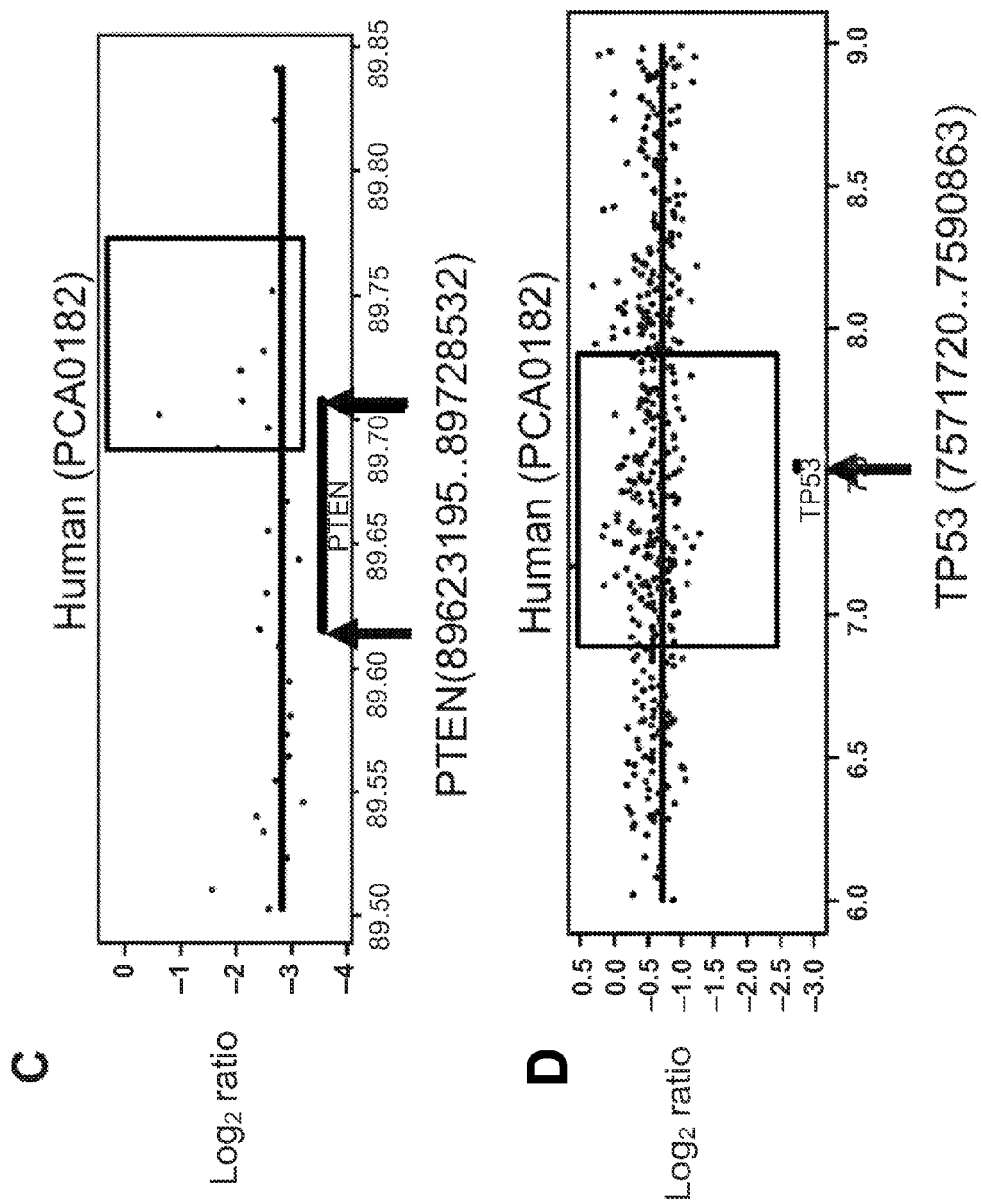
Figure 5:
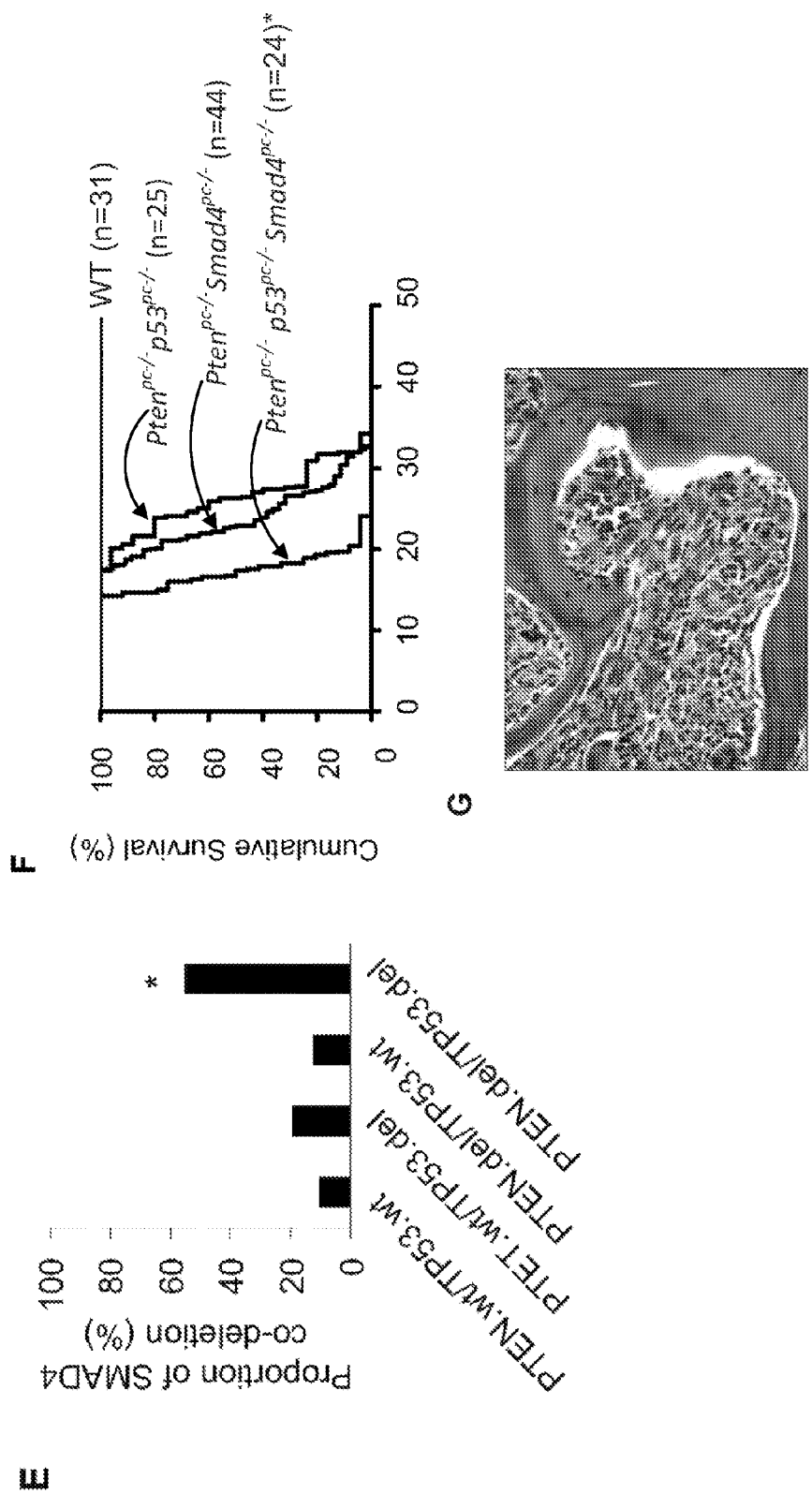

Based on the results of GISTIC2 analysis, 194 human prostate tumors (Taylor et al., 2010) were classified into 4 groups according to PTEN and p53 focal deletion status (FIG. 5E). The numbers of SMAD4 deletion events (chr18q copy number <−0.1 in log-2 scale) in each group were used to estimate the significance P value of co-deletion enrichment by Fisher's exact test in R environment.

Correlation Analysis Between Gene Copy Numbers and Gene Expression Changes.

The Spearman correlation coefficients between individual gene copy numbers and expression levels (both in log-2 scale) in matching samples were calculated in R environment to estimate the significance P values.

Oncomine Consensus Analysis.

Six prostate cancer cohorts[48-53] in the Oncomine database (www.oncomine.com) were used to filter our candidate marker gene lists. We tested the following hypotheses: if genes in the amplified regions are related to invasive phenotypes in any of the 6 cohorts, or if genes in the deleted regions are related to indolent phenotypes in any of the 6 cohorts.

Bone Metastasis Related Copy Number Changes.

We tested if genes recurrently amplified or deleted in the whole prostate cancer cohort of Taylor et al. showed consistent copy number alteration patterns in tumors with documented bone metastasis (Taylor et al., 2010). For each candidate gene, we counted the number of gene gain (copy number >0.3 in log-2 scale) and loss (copy number <−0.3 in log-2 scale) in 14 bone metastasis tumors. Consistent changes are defined if an amplified CNA gene is more likely to have gain than loss or a deleted CNA gene more likely to be lost than gained in bone metastatic tumors.

Survival Analysis.

We applied Cox proportional hazard regression on biomarkers of interest to get a multivariate linear regression model that best predict the biochemical recurrence of prostate cancer. Tumors were subsequently divided into high-risk and lowrisk groups according to the scores. Kaplan-Meier curves were plotted by R software, and the statistical significance was estimated by log-rank test.

Prognostic Model Construction.

To identify the markers that enhance the existing 4-gene model in predicting prostate cancer recurrence, we adopted a stepwise forward selection approach. Using the 4-gene model as the core model, we test each gene separately to check if adding the marker into the model will enhance the fitness of the multivariate model while keeping the individual adjusted P values below a threshold.

To construct high-sensitivity and high-specificity recurrence models for low risk and high risk tumor detection respectively, we adopted a stepwise selection algorithm. Briefly speaking, we started from selecting the best one marker and the optimal expression cutoff that maximize sensitivity or specificity, followed by iterating the selection step while in each step adding one more PD that best enhanced the current best model until any addition of one can no longer increase the prediction performance.

Example 2

Figure 1:
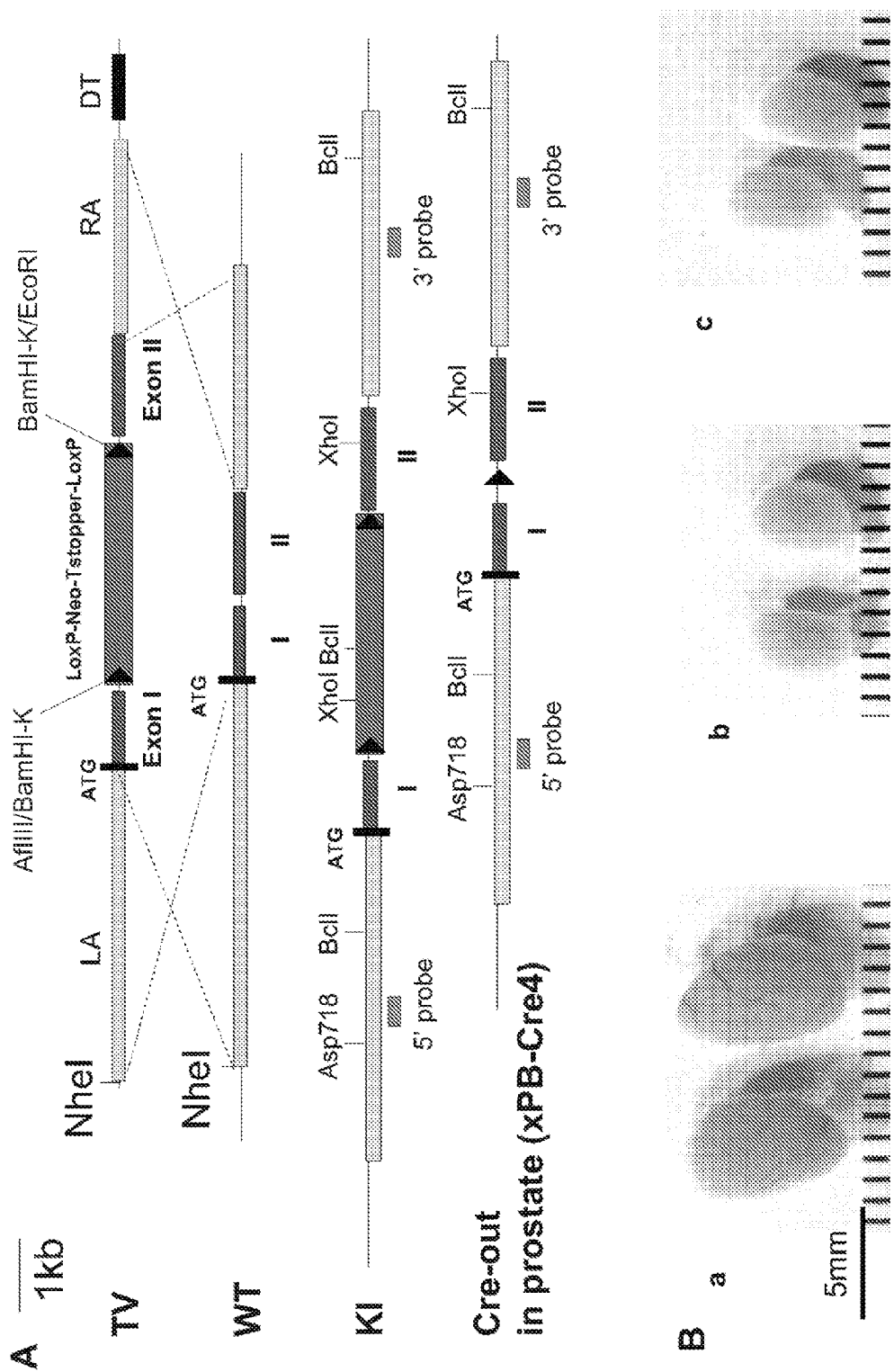
FIG. 1. Telomere dysfunction inhibited prostate tumor growth, while telomerase reactivation on the background of telomere dysfunction rescue prostate tumor growth. (A) Knock-in strategy for LSL-mTert construct. Cre-mediated recombination can remove the LSL cassette only in the prostate by PB-Cre4 to restore endogenous mTert expression in epithelial cells. (B,C) Later generations (G3, G4) of mTert$^{-/-}$ or LSL-mTert PB-Pten/p53 allele mouse generates telomere dysfunction were shown by decreased weight of the testis (B), and an increase of the apoptotic bodies in intestinal crypts (C). (D-F) Quantification of body weight (D), the weight of testis (E), and apoptotic bodies per 100 intestinal crypts of G0 mTert$^{+/+}$ PB-Pten/p53 (denoted as G0 mTert$^{+/+}$, n=20), G4 mTert$^{-/-}$ PB-Pten/p53 (denoted as G4 mTert$^{-/-}$, n=31), and G4 LSL-mTert PB-Pten/p53 (denoted as G4 LSL-mTert, n=20) mice (F). Error bars represent s.d.*, $p<0.05$.
Figure 1:
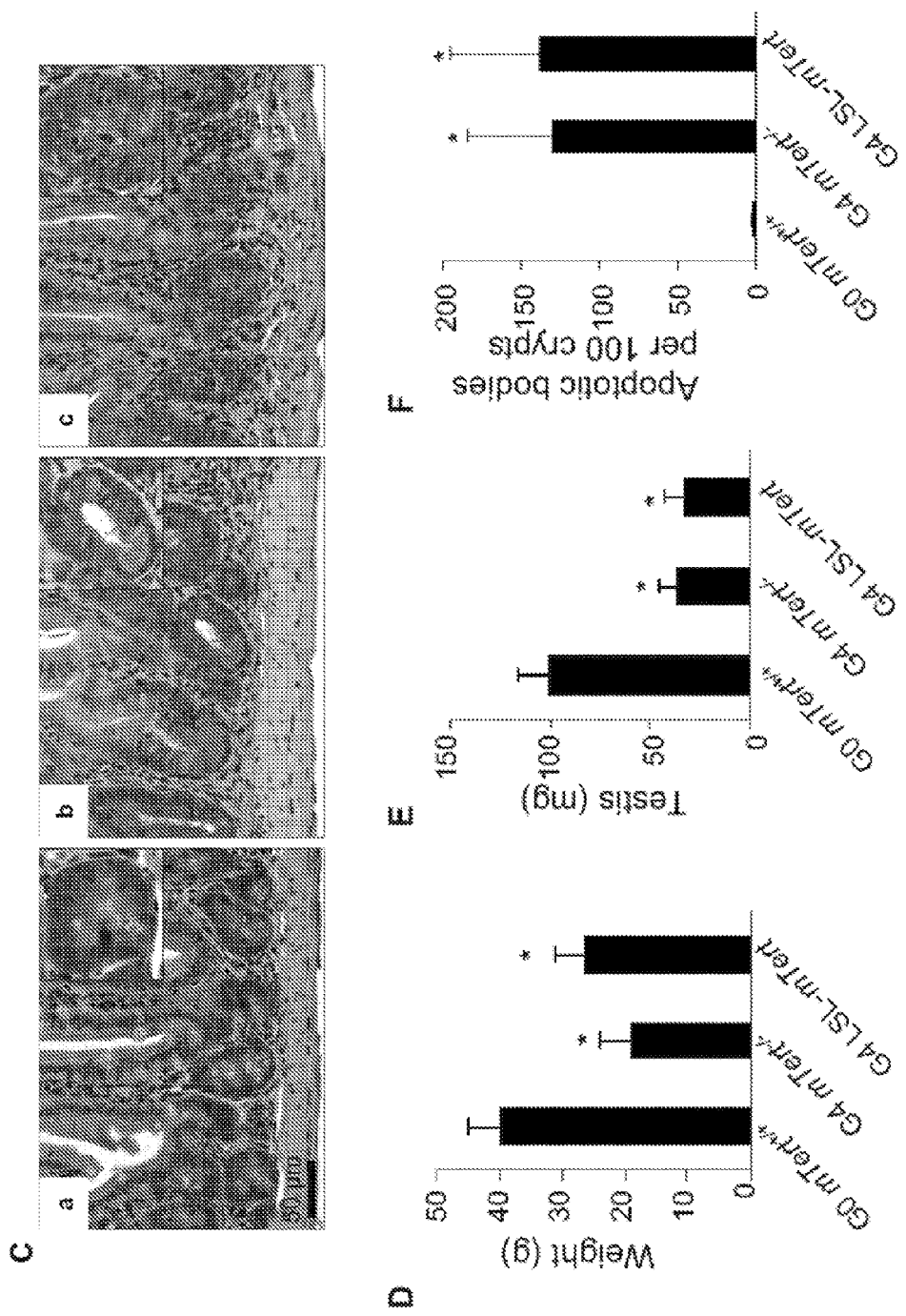

Telomerase Reactivation Enables Emergence of Aggressive Prostate Cancers with Skeletal Metastases A novel inducible telomerase reverse transcriptase (mTert) allele was generated by embedding a Lox-Stop-Lox (LSL) cassette in the first intron (FIG. 1A). Upon successive generational intercrosses of LSL-mTert homozygous mice, late generations show classical constitutional signs of telomere dysfunction including reduced body weight, widespread organ atrophy, diminished proliferation and increased apoptosis in highly proliferative tissues, among other phenotypes as reported previously (Lee et al., Nature (1998)) (FIG. 6, FIG. 1B-F) (FIG. 1). The LSL-mTert mice were intercrossed with those possessing the prostate-specific Cre deletor transgene, PB-Cre4 (Wu et al., Mech. Dev. (2001)), and conditional knockout alleles of Pten (Zheng et al., Nature (2008)) and p53 (Jonkers et al., Nat. Genet. (2001)), hereafter PB-Pten/p53. All alleles were backcrossed a minimum of 4 times onto the C57Bl/6 strain.

The PB-Pten/p53 alleles were carried through successive generational mating of LSL-mTert homozygous mice (FIG. 6), generating 'telomere-intact' controls (wildtype and LSL-mTert heterozygous mice, designated 'G0 PB-Pten/p53') and 'telomere dysfunctional' experimental mice (third and fourth generation LSL-mTert homozygotes, designated G3/G4 LSL-mTert PB-Pten/p53). In parallel, we generated control and experimental cohorts of PB-Pten/p53 mice harboring the conventional mTert null allele (mTert-) (Farazi et al., Cancer Res. (2006)), producing analogous G0 and G3/4 groups for study of telomere dysfunction only.

Figure 2:
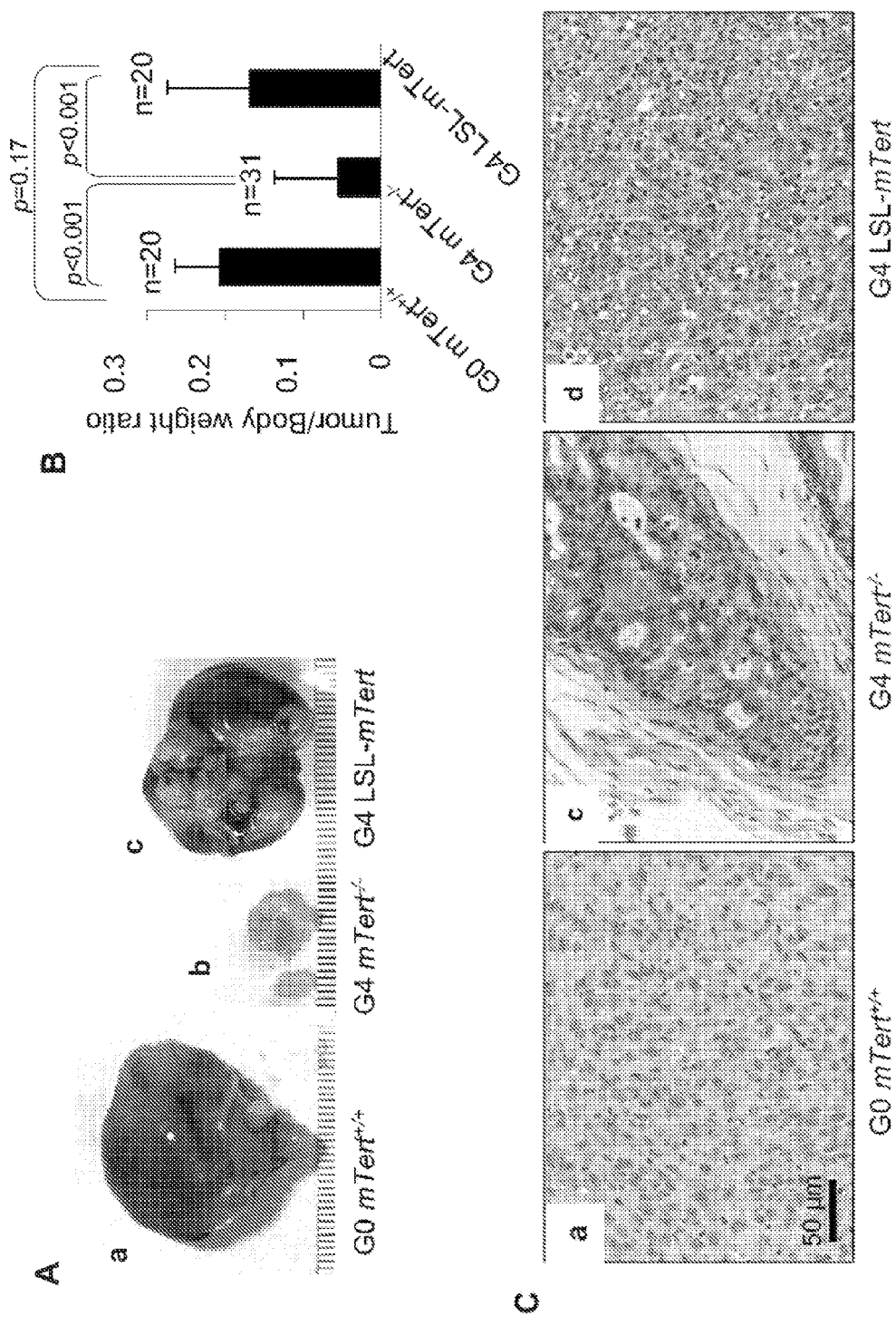
FIG. 2. Telomere dysfunction inhibited prostate tumor progression from HPIN to invasive tumor, while telomerase reactivation on background of telomere dysfunction promotes aggressive spread of G3/4 LSL-mTert PB-Pten/p53 prostate tumors to spinal bones. (A) Gross anatomy of representative prostates at 24 weeks of age. (B) Quantification of the prostate tumor to body weight ratio of G0 mTert$^{+/+}$ (n=20), G4 mTert$^{-/-}$ (n=31), and G4 LSL-Tert (n=20) mice. Error bars represent s.d. (C) H&E sections of the prostate tumors from G0 mTert$^{+/+}$, G4 mTert$^{-/-}$, and LSL-G4 Tert at 24 weeks of age. (D) Quantification of the invasive prostate tumors of G0 mTert$^{+/+}$ (n=20), G4 mTert$^{-/-}$ (n=31), and G4 LSL-Tert (n=20) mice. (E) H&E sections of the prostate tumors of G4 LSL-Tert in spinal bone at 24 weeks of age. (F) Quantification of the mice with prostate tumors spotted in the spinal bones of G0 mTert$^{+/+}$ (n=20), G4 mTert$^{-/-}$ (n=31), and G4 LSL-Tert (n=20) mice.
Figure 2:
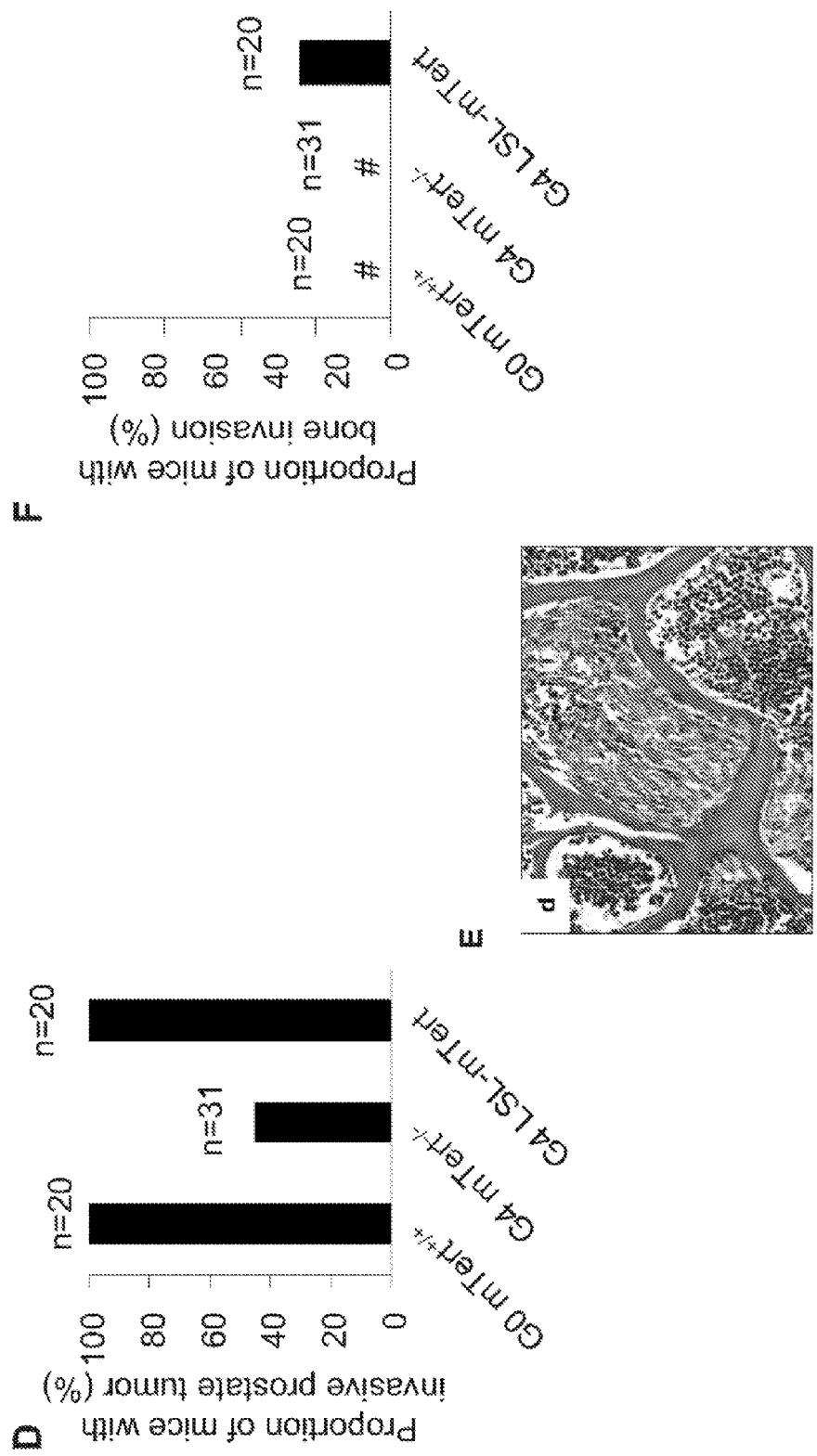

Consistent with previous reports (Chen et al, Nature (2005)), all G0 PB-Pten/p53 mice developed rapidly progressive locally invasive prostate adenocarcinomas, resulting in lethal urinary obstruction and renal failure by 34 weeks of age (FIG. 2A-D); whereas, G3/4 mTert$^{-/-}$ PB-Pten/p53 mice tumors had significantly smaller poorly progressive tumors over the same period (FIG. 2A-B). Notably, G3/4 LSL-mTert PB-Pten/p53 mice developed bulky lethal tumors by 24 weeks of age (FIG. 2A-B). Correspondingly, serial histological analyses revealed presence of high-grade prostate intraepithelial neoplasia (HPIN) by age 9 weeks in all three cohorts. However, G4 mTert$^{-/-}$ PB-Pten/p53 failed to progress beyond HPIN through 24 weeks of age (Table 1, FIG. 2C-D), a pattern consistent with the established role of telomere dysfunction in facilitating cancer initiation yet constraining full malignant progression (Rudolph et al., Nat. Genet. (2001)), Chang et al., Genes Dev. (2003), Gonzalez-Suarez et al., Nat. Genet. (2000), Jaskelioff et al., Oncogene (2009)). In sharp contrast, G0 mTert+/+ PB-Pten/p53 and G3/4 LSL-mTert PB-Pten/p53 tumors evolved rapidly to invasive adenocarcinoma by 24 weeks of age (FIG. 2C-D). A distinctive feature of the G3/4 LSL-mTert PB-Pten/p53 was the presence of metastatic lesions in the lumbar spine (5/20, 25%) (FIG. 2E-F). Thus, telomerase reactivation in the setting of telomere dysfunction and dual deficiencies of Pten and p53 enables full malignant progression including acquisition of unprecedented tumor biological properties such as bony tumor growth.

Figure 3:
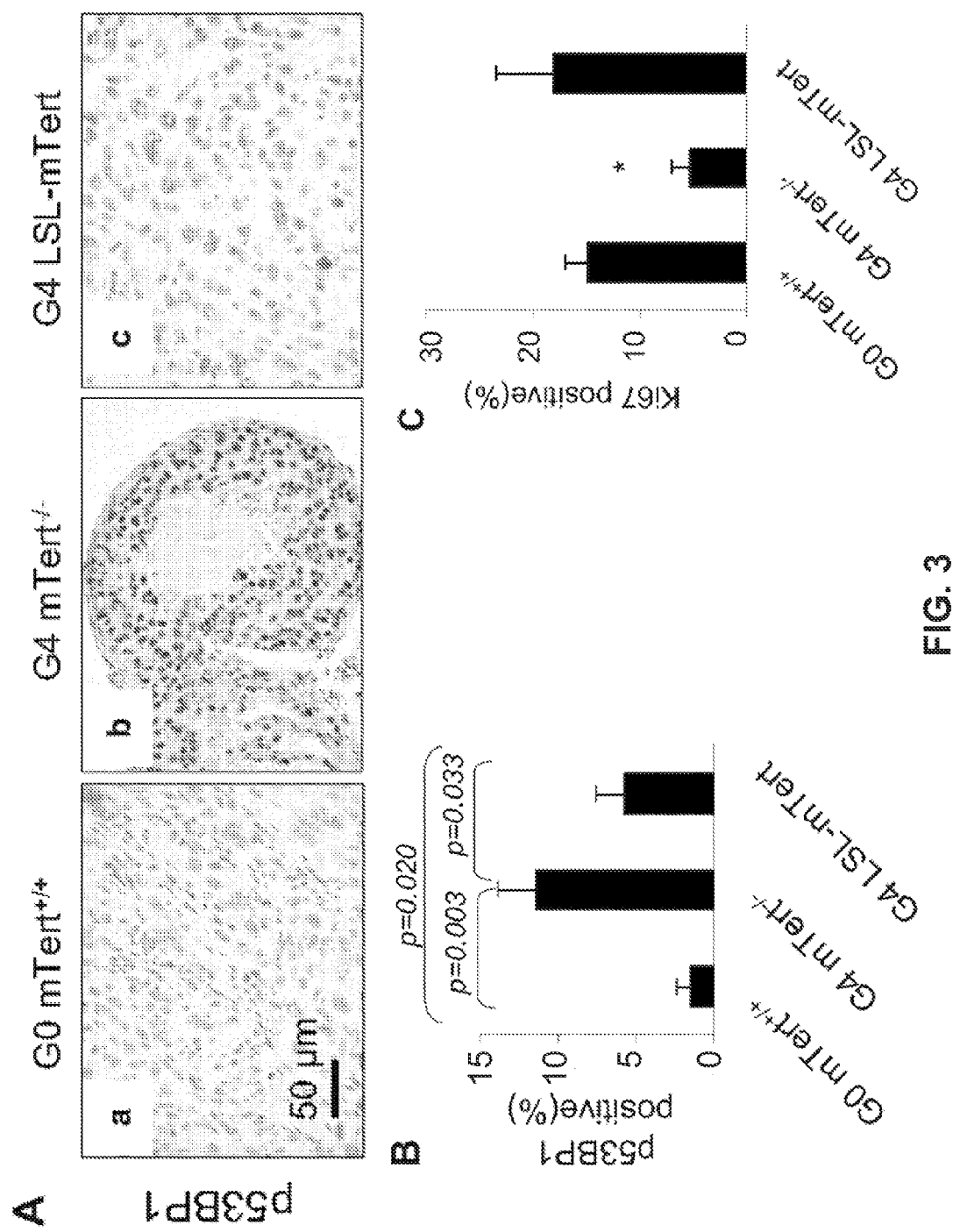
FIG. 3 Telomerase reactivation maintains telomere length and allows tumor cells to proliferate. (A) Telomere dysfunction induced a strong p53BP1 signal in G4 mTert$^{-/-}$ cells (panel b), but the G4 LSL-Tert cells were significantly rescued (panel c). (B) Quantification of p53BP1 positive prostate tumor. Error bars represent s.d. for a representative experiment performed in triplicate. (C-E) Telomere dysfunction induced apoptosis and blockage of proliferation. Quantification of TUNEL positive (C), Caspase-3 activation positive (D), and Ki67 positive prostate tumor cells (E). Error bars represent s.d. for a representative experiment performed in triplicate.
Figure 3:
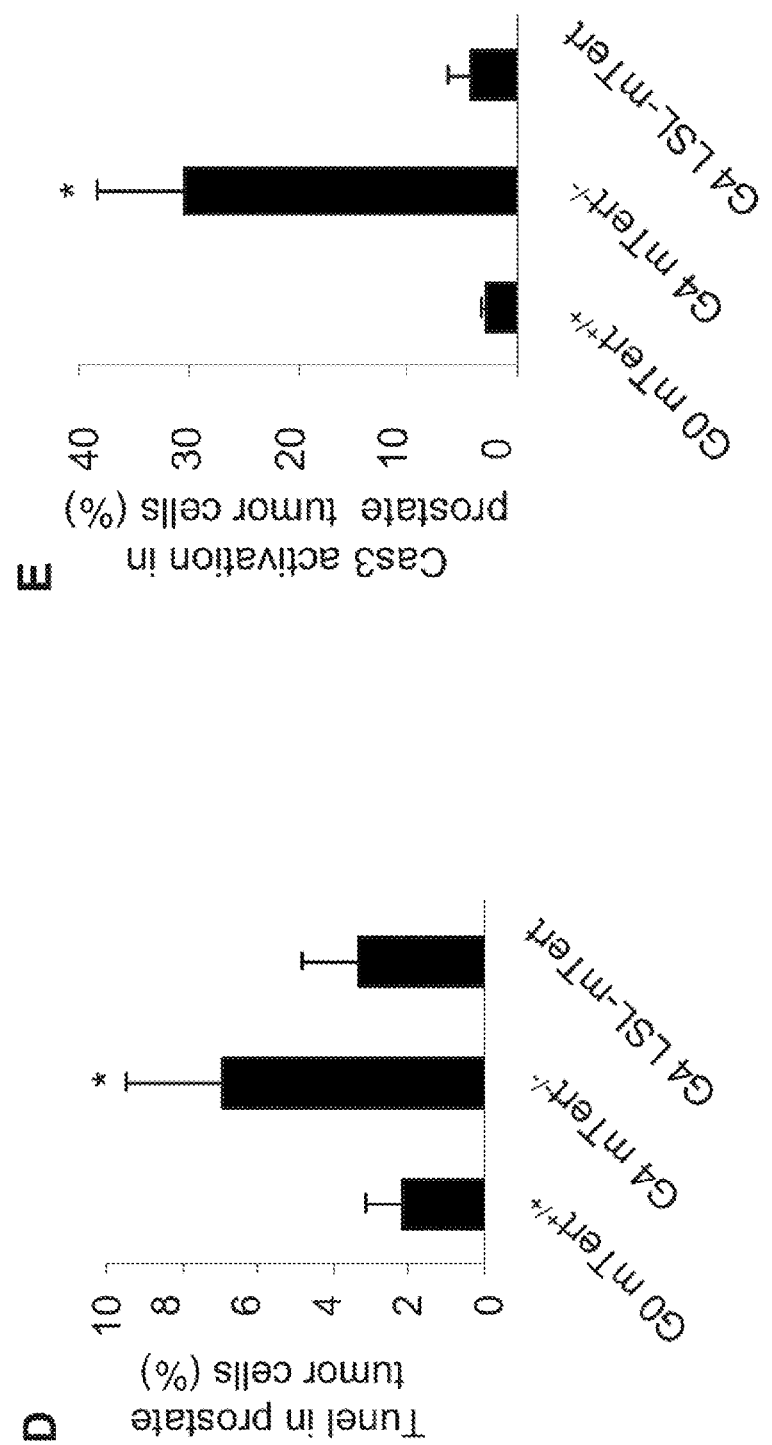
Figure 8:
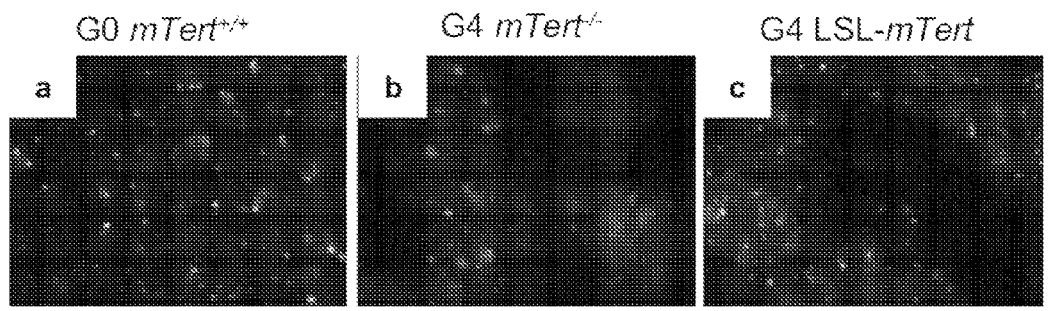
FIG. 8. Relative to G0 mTert+/+ PB-Pten/p53 samples, telomere reserves were significantly decreased in G4 mTert-/- PB-Pten/p53 samples and were intermediate in the G4 LSL-mTert PB-Pten/p53 sample. (A) Telomere in situ FISH (spell out) of prostate tumors shows severe telomere erosion in G4 mTer$^{t-/-}$ cells (panel b), compared to G0 mTer$^{t+/+}$ cells (panel a). Telomeres of G4 LSL-Tert cells were significantly maintained (panel c), compared to G4 mTer$^{t-/-}$ cells. (B) Relative telomere length in prostate tumors. Error bars represent s.d. for at least 4 to 6 independent measurements for each genotype.
Figure 8:
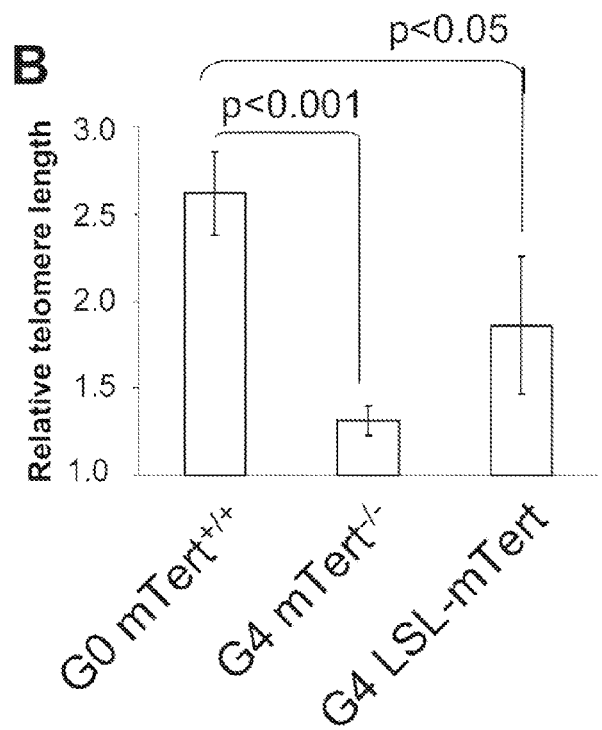

Next, we monitored the impact of telomere dysfunction and telomerase reactivation on the molecular and cell biological levels in prostate tumors of each of the models at the same age. Quantitative Telomere-FISH analysis revealed that telomere reserves were significantly decreased in G4 mTert−/− PB-Pten/p53 samples relative to G0 mTert+/+ PB-Pten/p53 samples (FIG. 8). G4 LSL-mTert PB-Pten/p53 sample showed significant longer telomere, compared to the G4 mTert−/− PB-Pten/p53 (FIG. 8). Eroded dysfunctional telomeres generate a DNA damage response (Takai et al., Curr. Biol. (2003), IJpma et al., Mol. Biol. Cell (2003). To further assess the functional status of telomeres, we audited the level of DNA damage signaling via analysis of p53BP1 foci in prostate tumor cells at the same age. Strong anti-p53BP1 signal was detected in G4 mTert$^{-/-}$ PB-Pten/p53 prostate tumor cells and this signal was greatly reduced in G0 mTert+/+ PB-Pten/p53 and LSL-mTert PB-Pten/p53 prostate tumor cells (FIG. 3C-D; n=3 each). Correspondingly, TUNEL, activated Caspase-3, and Ki67 assays showed markedly increased apoptosis and decreased proliferation in the G4 mTert−/− PB-Pten/p53 prostate tumor samples compared with G0 mTert+/+ PB-Pten/p53 and G4 LSL-mTert PB-Pten/p53 prostate tumor samples (FIG. 3C-E). These findings are consistent with telomerase-mediated alleviation of telomere checkpoints in the prostate cancers of the G4 LSL-mTert PB-Pten/p53 model.

Taken together, the molecular and phenotypic characterization of these three models demonstrated that telomerase reactivation not only enables the bypass of the progression block conferred by telomere dysfunction by quelling the DNA damage signals, but also engenders the acquisition of new tumor biological properties (bony tumor growth) not observed in tumors which did not experience a period of telomere dysfunction with subsequent telomerase reactivation in their evolution. This thus provides the first genetic proof in support of the thesis that telomerase reactivation and genome stabilization is necessary to drive full malignant progression in epithelial cancers.

Example 3

Figure 4:
FIG. 4. Oncogenomic alterations that occur in G3/4 LSL-mTert prostate tumors. (A) Representative SKY images from metaphase spreads from G0 (panel a) and G3 and G4 (panel b) prostate tumors. (B) Quantification of cytogenetic aberrations (recurrences) detected by SKY in G0 mTert+/+ PB-Pten/p53 and G3/4 G4 LSL-mTert PB-Pten/p53. (C) Quantification of cytogenetic aberrations (recurrences) detected by SKY in G0 mTert+/+ PB-Pten/p53 (green) and G3/4 G4 LSL-mTert PB-Pten/p53 (red) prostate tumors. (D) Recurrence plot of CNAs defined by array-CGH for 18 mouse prostate tumors. The x axis shows the physical location of each chromosome. The percentage of prostate tumors harboring gains (bright red, log 2>0.6, losses (green, log 2<−0.3), and deletions (dark green, log 2<−0.6) for each locus is depicted.
Figure 4:
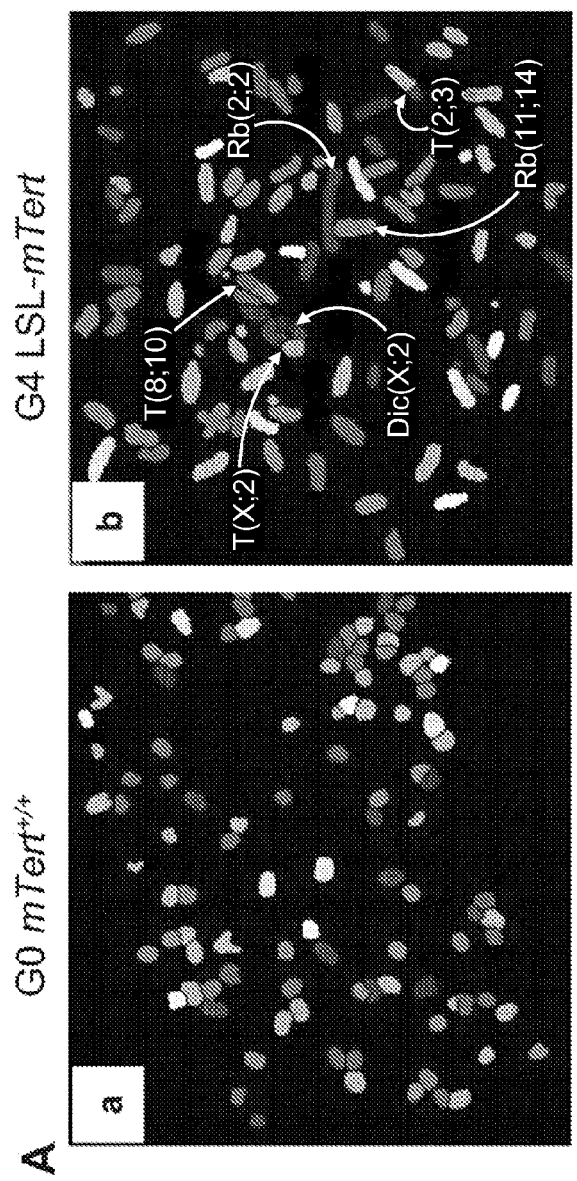
Figure 4:
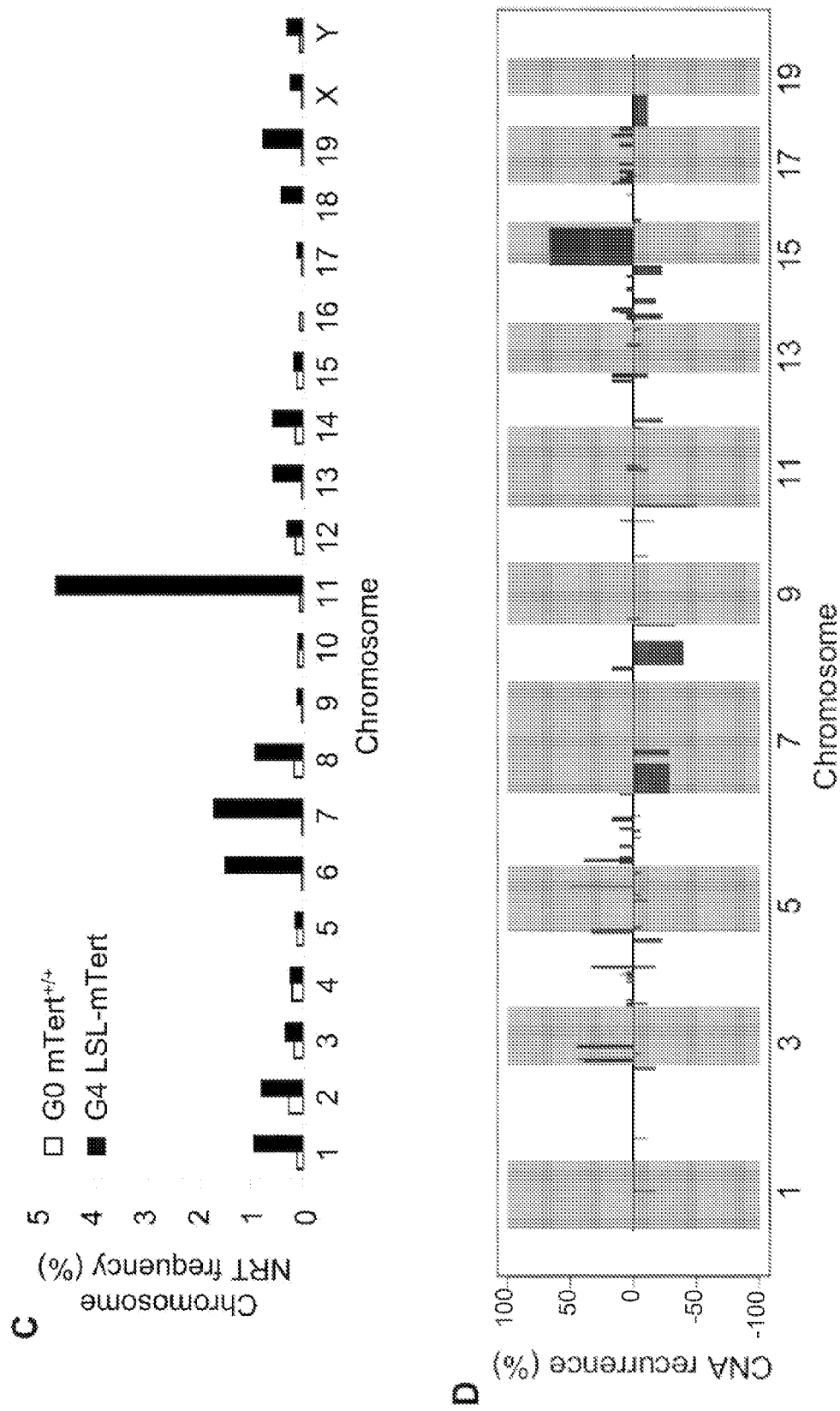
Figure 9:
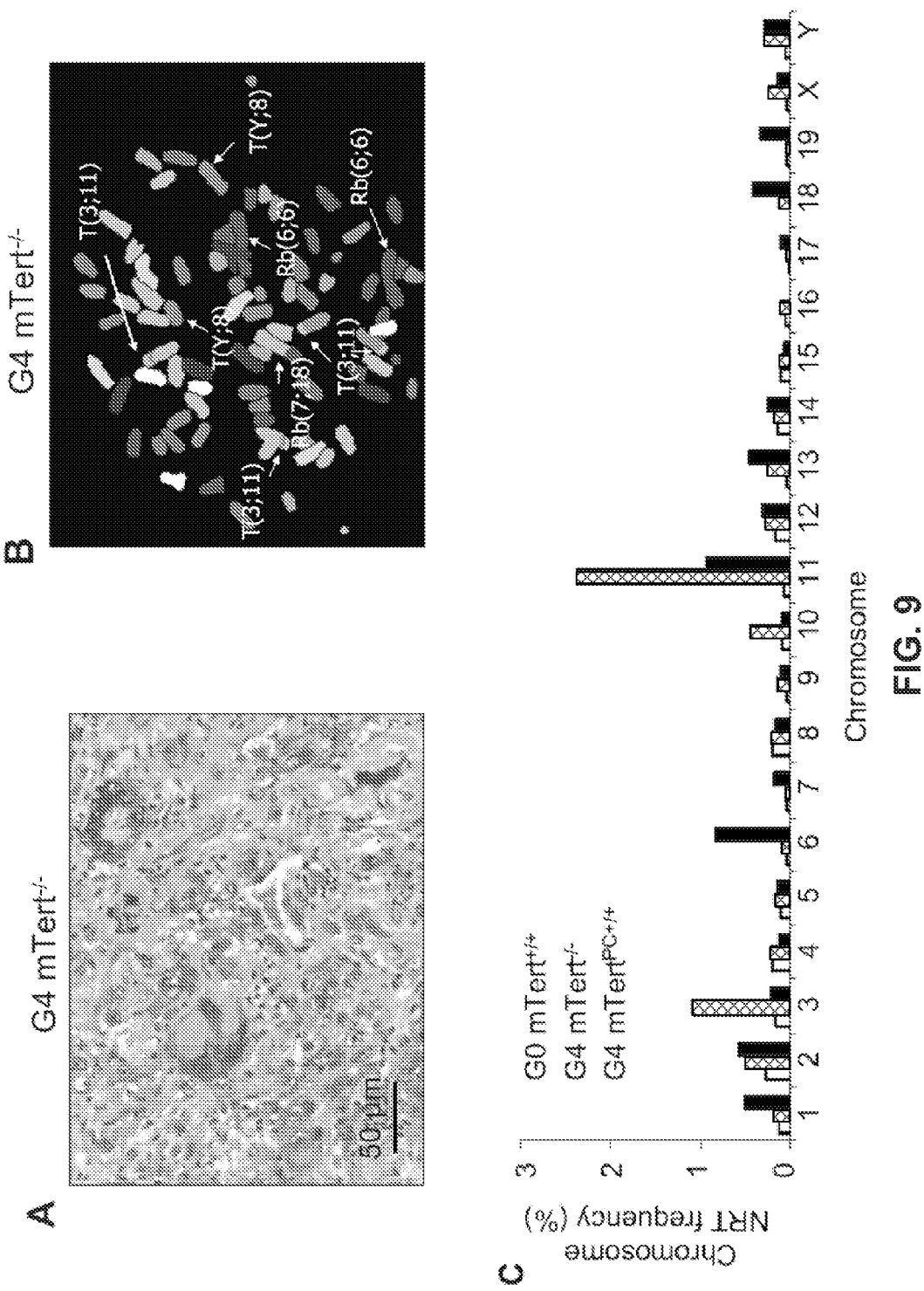
FIG. 9. Oncogenomic alterations that occur in G3/4 G4 mTert-/- PB-Pten/p53 prostate tumors. (A) H&E sections of the prostate tumors from the invasion escape of G4 mTert-/- PB-Pten/p53 at 24 weeks of age. (B) Representative SKY images from metaphase spreads from mTert-/- PB-Pten/p53 prostate tumors. (C) Quantification of cytogenetic aberrations (recurrences) detected by SKY in mTert-/- PB-Pten/p53 prostate tumors. (D) Quantification of cytogenetic aberrations (recurrences) detected by SKY in G0 mTert+/+ PB-Pten/p53, G3/4 G4 mTert-/- PB-Pten/p53, and G3/4 G4 LSL-mTert PB-Pten/p53 prostate tumors.
Figure 9:
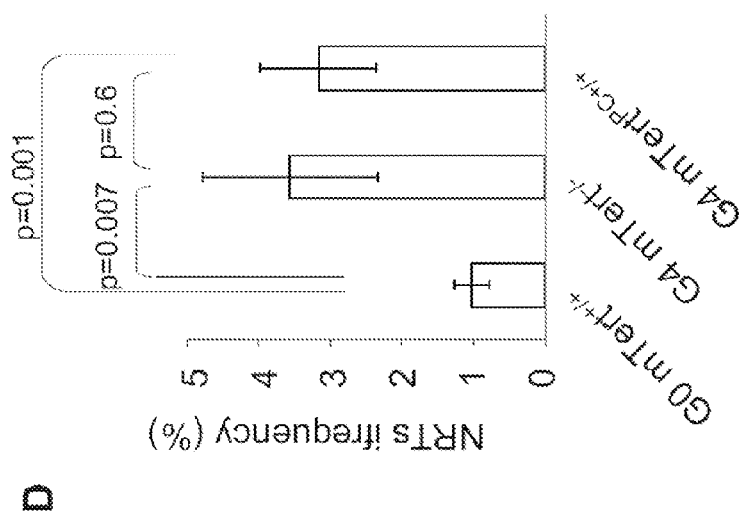

Telomere Dysfunction in Murine Prostate Cancers Generates Recurrent Copy Number Aberrations with Relevance to Human Prostate Cancer The extensive level of telomere dysfunction in the G4 LSL-mTert PB-Pten/p53 mouse, combined with the onset telomerase activation in the prostate only upon sexual maturity at 5-7 weeks of age (i.e., PB-Cre4 is androgen-responsive) (Chen et al., Nature (2005), Wu et al., Mech. Dev. (2001)), presumably allowed for the accumulation of baseline instability prior to telomerase reactivation. To assess this supposition, we conducted spectral karyotype (SKY) and array-comparative genome hybridization (array-CGH) analyses of G0 mTert+/+ PB-Pten/p53 and G4 LSL-mTert PB-Pten/p53 prostate cancers. SKY analysis revealed a higher frequency of chromosomal structural aberrations in the G4 mTert LSL-mTert PB-Pten/p53 tumor samples (n=5) relative to G0 mTert+/+ PB-Pten/p53 controls (n=4) (FIG. 4A-B; 3.2 versus 1.0 per 100 chromosomes, respectively, P<0.05, t-test). These aberrations included multicentric chromosomes, non-reciprocal translocations, and p-p, p-q and q-q chromosome arm fusions involving homologous and/or non-homologous chromosomes (FIG. 4C). In addition, 14/31 G3/4 mTert−/− PB-Pten/p53 mice eventually developed small modestly advanced invasive prostate cancers which exhibited highly anaplastic features such as nuclear pleomorphism (Table 1, FIG. 2D, FIG. 9A). SKY analysis of these G4 mTert−/− PB-Pten/p53 tumors revealed cytogenetic complexity comparable that of the G4 LSL-mTert PB-Pten/p53 tumors (FIG. 9B-D).

Figure 10:
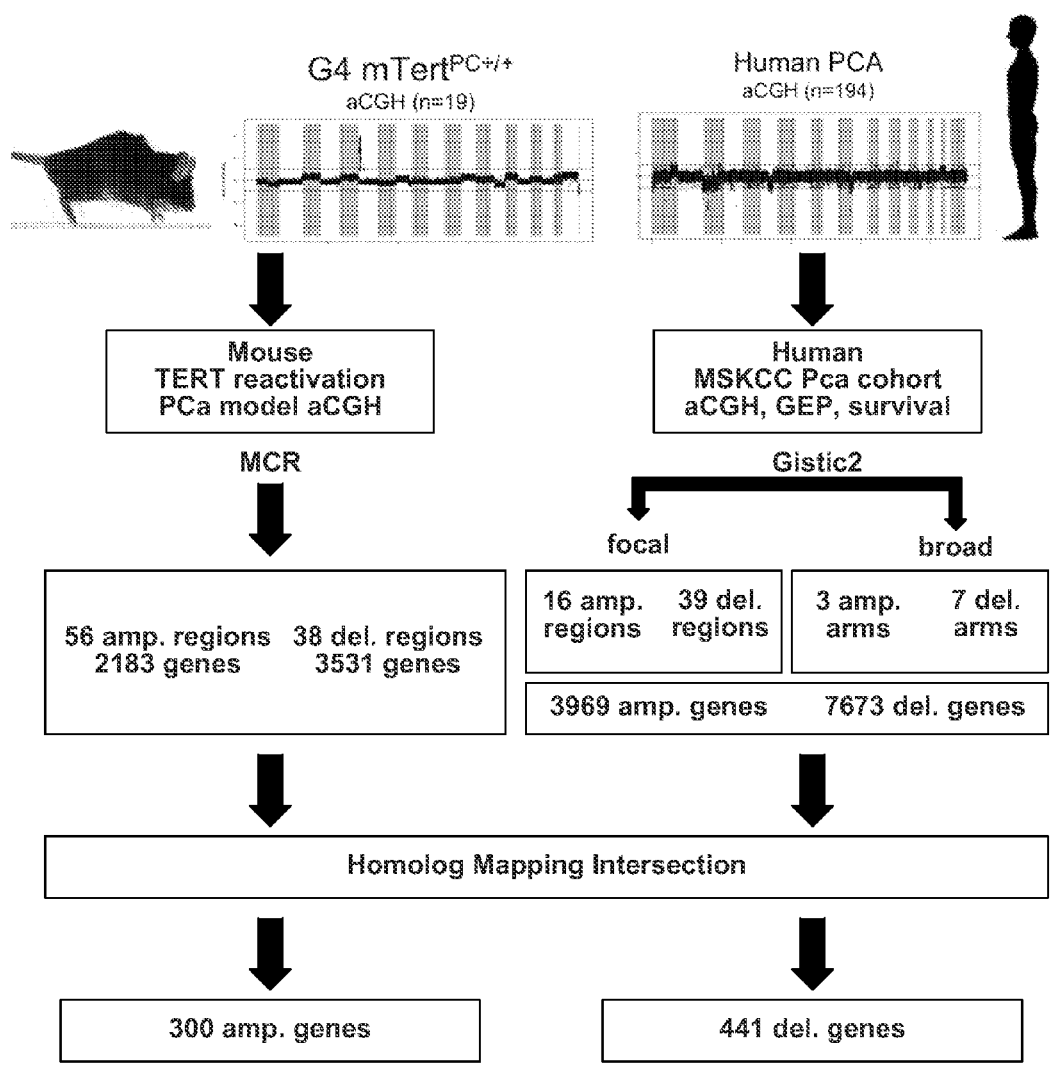
FIG. 10 and FIG. 11. Genomic alterations in both mouse and human prostate tumor cells and derivation of 113 (37 amp and 76 del) genes correlated with bone metastasis. There are a total of 94 MCRs in the aCGH dataset of G3/G4 LSL-Tert prostate tumors (n=18). There are 741 genes (300 amp and 441 del) having the same genomic alteration pattern of amplification or deletion between the mouse prostate tumor dataset and Taylor et al (2010) human prostate cancer dataset (n=194). Among these 741 genes, there are a total of 228 genes (77 amp and 151 del) shown to be correlated with prostate cancer progression. Among these 228 genes, there are a total of 113 (37 amp and 76 del) genes shown to be correlated with bone metastasis.
Figure 11:
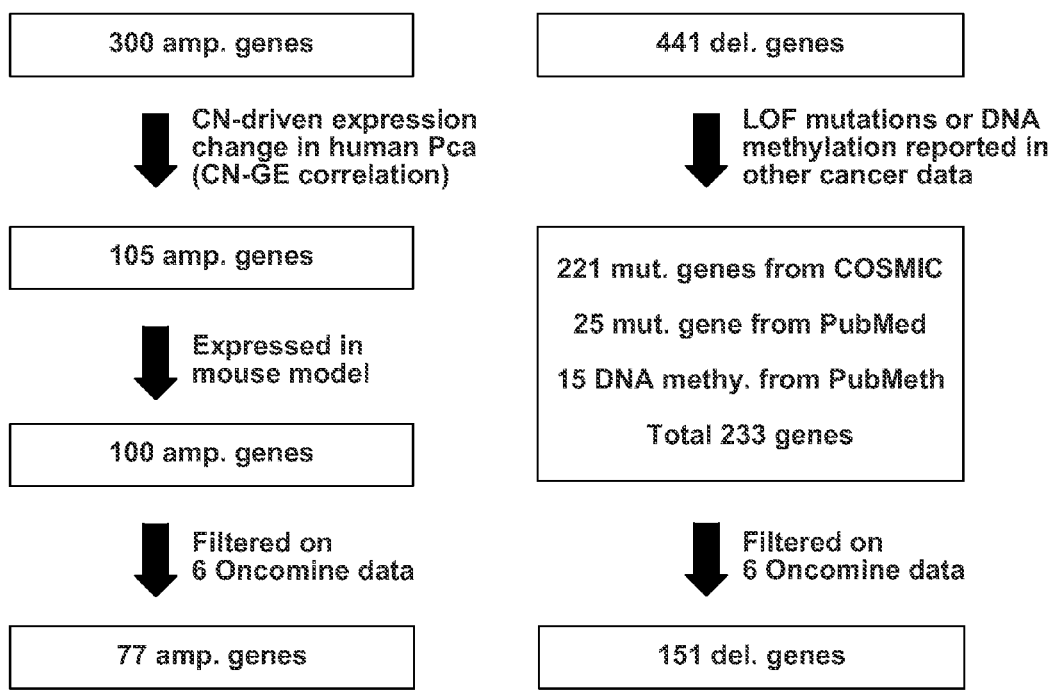

Telomere dysfunction and the ensuing bridge-fusion-breakage process generate DNA double-strand breaks that enable regional amplifications and deletions often at the sites of breakage (O'Hagan et al., 2002). Under biological selection, this process results in enrichment for aberrations at cancer-relevant loci (Maser et al., Nature (2007), Artandi et al., Nature (2000)), prompting us to conduct array-CGH and transcriptional profile analyses of 18 G3/G4 LSL-mTert PB-Pten/p53 tumors (Table 1). Array-CGH revealed 94 copy number alterations (CNAs) encompassing 2183 amplified and 3531 deleted genes (FIG. 10, Table 2 showing gene lists). We next asked whether these CNAs were syntenic to those observed in 194 human prostate cancer profiles possessing 55 recurrent focal CNAs and 10 recurrent large chromosomal arm gains or losses as defined by GISTIC2 algorithm (Beroukhim et al, Proc. Natl. Acad. Sci. U.S.A. (2007)) (FIG. 10). Twenty-two of the 94 murine CNAs corresponded to regions subject to copy number changes in the human prostate cancer profiles. (P=0.189, permutation test) These cross-species comparisons resulted in a significant reduction in the total number of genes resident in these conserved CNAs—300 amplified genes and 441 deleted genes (FIG. 10, Table 2). One cross-species conserved CNA involving mouse chromosome 15 and human chromosome 8 was notable for high recurrence in both species (mouse: 12/18, 67%; human: 43/194, 22%)[2] (Table 2, FIG. 4D). This region contains the prostate cancer-relevant Myc oncogene as well as other known cancer genes such as FDZ6 (Table 2).

To further refine the candidate gene list, each amplified gene was examined for gene copy-driven expression in mouse and human samples, while each deleted gene was looked up in COSMIC database (Forbes et al., Nucleic Acids Res. (2010), Forbes et al., Nucleic Acids Res. (2011)) for non-synonymous mutation, in PubMeth database (Ongenaert et al., Nucleic Acids Res. (2008)) for promoter hyper-methylation, and in NCBI Pubmed for cancer mutations in any cancer types. An additional clinical relevance filter checked whether an amplified or deleted gene is over- or under-expressed in metastatic tumors versus primary in 6 prostate cancer cohorts from Oncomine compendium (Lapointe et al., Proc. Natl. Acad. Sci. U.S.A. (2004), LaTulippe et al., Cancer Res. (2002), Vanaja et al., Cancer Res. (2003), Varambally et al., Cancer Cell (2005), Yu et al., J. Clin. Oncol. (2004), Holzbeierlein et al., Am. J. Pathol. (2004)). This exercise further culled the list to 77 amplified and 151 deleted genes (FIG. 10, Table 3). Pathway enrichment analysis revealed that these 77/151 genes showed significant enrichment for cancer-relevant pathways such as cell communication (P=0.002, FDR=0.03), TGF beta signaling (P=0.006, FDR=0.05), fatty acid metabolism (P=0.021, FDR=0.07), and WNT signaling (P=0.042, FDR=0.11) (Table 4). In contrast, the remaining CNA genes (223 amplified and 290 deleted) only weakly enriched with WNT signaling (P=0.046, FDR=0.37).

With regard to TFG beta signaling genes, the deletion of the Smad2/Smad4 region in 2/18 (11%) G3/G4 LSL-mTert PB-Pten/p53 tumors was particularly noteworthy in light of recent work validating the role of Smad4 as a bona fide tumor suppressor in prostate cancer in the mouse—specifically that dual deficiencies of Pten and Smad4 drives prostate cancer progression (Ding et al., Nature (2011)). In human prostate cancer, there is frequent epigenetic silencing of the SMAD4 promoter in advanced disease (Aitchison et al., Prostate (2008)) and the SMAD4 region is subject to deletion in approximately 35/194 (18%) human prostate tumors, although the region of deletion is large (Taylor et al., Cancer Cell (2010)).

The occurrence of spontaneous Smad4 deletion in the background of Pten and p53 deficiency (FIG. 5A) raised the possibility that these three genetic events may cooperate to drive prostate cancer progression. To determine the potential cooperative actions of these genetic events, we examined co-occurrence in human prostate cancers of the Taylor dataset. The loss of SMAD4 was a significant event together with TP53 and PTEN loss in human prostate cancer (FIG. 5B-D, FIG. 17-31) enriched in the prostate metastasis samples (FIG. 5E, p=2.9e-6 by Fisher's exact test). These statistical findings prompted us to secure in vivo genetic evidence of cooperativity via prostate-specific deletion of Smad4, Pten and/or p53 on a telomere-intact background. These genetic studies demonstrated that prostate-specific deletion of all three tumor suppressors generates a more aggressive prostate cancer phenotype relative to prostates sustaining single or double deficiencies for Pten and p53 or Smad4. The life span of the triple deletion of Pten/p53/Smad4 is significantly shorter (P<0.0001, logrank test) with median survival time 17.05 weeks, while median survival time is 26.3 weeks for double deletion of Pten and p53 and 22.8 weeks for double deletion of Pten and Smad4. Most notably, 3/24 of these mice displayed bone metastasis (FIG. 5G). Therefore, this in vivo genetic study validated the cooperative roles of Pten, p53 and Smad4 deficiencies in the progression of prostate cancer.

Kaplan-Meier analysis for biochemical recurrence (BCR, defined by post-op PSA>0.2 ng/ml) of the two cancer patient clusters in the Taylor et al dataset (2010) was conducted using the R survival package. The combined new 17 gene set can significantly enhance the sensitivity and specificity of SMAD4/PTEN/CCND1/SPP1 dichotomize prostate cancer cases into low versus high risk groups for BCR in Tayor et al dataset (FIG. 15C).

Kaplan-Meier analysis for biochemical recurrence (BCR, defined by post-op PSA>0.2 ng/ml) of the two cancer patient clusters in the Glinsky et al. dataset (Glinsky et al., *J. Clin. Invest* (2004)) was conducted using the R survival package. The combined new 17 gene set (DNAJC15, KIF5B, LECT1, DSG2, ACAA2, ASAP1, LMO7, SVIL, DSC2, PCDH9, SMAD7, WDR7, LAMA3, PCDH8, MKX, MSR1, POLR2K) can significantly enhance the sensitivity and specificity of SMAD4/PTEN/CCND1/SPP1 dichotomize prostate cancer cases into low versus high risk groups for BCR in Glinsky et al dataset (FIG. 16C).

Example 4

TGFβ/Smad4 Pathway in Prostate Tumors with Bone Metastasis

As a first step to identify molecular events capable of driving metastasis to the bone, we asked whether a subset of the 228 candidate genes of Table 3 are subjected to consistent amplification/deletion in the 14 bone metastasis in the cohort reported by Taylor et al (Taylor et al., *Cancer Cell* (2010)). Specifically, we interrogated each of the 77 amplified or 151 deleted candidates for evidence that it is more likely to be amplified or deleted in bone metastasis, respectively. The resultant 113 gene list (comprising of 37 amplified and 76 deleted genes associated with bone-metastasis) was then enlisted into knowledge-based pathway analysis. Interestingly, TGFβ signaling genes represented the most significantly enriched network among the 9 significant pathways with FDR<0.1 (Table 6; FIG. 33). Corroborating with this pathway analysis result is the observation that Smad4 is encompassed by genomic loss in 2 of the 18 (11%) G3/G4 LSL-mTert PBPten/p53 tumor genomes, suggesting that TGFβ signaling and SMAD4 specifically may be targeted during prostate cancer skeletal metastasis. This is consistent with recent reports on the pathogenetic and prognostic roles of SMAD4 in human prostate cancer (Ding et al., *Nature* (2011)) and its frequent epigenetic silencing in advanced disease (Aitchison et al., *Prostate* (2008)).

In summary, pathway analysis of the cross-species conserved gene list triangulated with the biological phenotype in human prostate cancers led to the hypothesis that TGFβ/SMAD4 signaling is an important driver of bone metastasis in the context of Pten and p53 deficiencies. Utilizing the combined Pten/p53/Smad4 GEM model, we demonstrate the new tumor biological properties (skeletal metastases) of this GEM model is not present in Pten/p53 or Pten/Smad4 telomere-intact GEM models. This invention establishes, in a genetic manner, that telomerase reactivation in tumor cells experiencing telomere dysfunction provides a mechanism for selection of cooperative events required to progress fully and manifest the tumor biological properties governed by such genomic events.

Example 5

Evolutionarily Conserved Genomically Altered Genes Correlating with Bone Metastasis are Prognostic in Human The in vivo genetic experiment above proving a driver role for Smad4 in bone metastasis suggests that additional genes on our bone metastasis-associated gene list may have functional importance as well. Since SMAD4 has also been shown to carry prognostic significance (Ding et al., *Nature* (2011)), we reasoned that prognostic relevance may serve as a surrogate for biological importance. As a proof of concept, we focused on the 14 genes (ATP5A1/ATP6V1C1/CUL2/CYC1/DCC/ERCC3/MBD2/MTERF/PARD3/PTK2/RBL2/SM AD2/SMAD4/SMAD7) that are represented in the 9 pathways found to be significantly enriched in the bone-metastasis associated gene list (Table 6). Specifically, we assessed how robustly these 14 genes can stratify risk for biochemical recurrence (BCR>0.2 ng/ml) among the 140 patients with outcome annotation (Taylor et al., *Cancer Cell* (2010)). The overall risk score based on the 14-gene signature was significantly prognostic of BCR with hazard ratio of 13 (P-value<$10^{-14}$, overall C-index=0.93, see FIG. 34) by multivariate Cox regression. Further support for these 14 genes as likely drivers of bone metastasis phenotype derived from the observation that they provided independent prognostic value to the previously reported 4-gene signature (comprising of PTEN/SMAD4/CCND1/SPP1) derived from the Pten/Smad4 model (Ding et al., *Nature* (2011)), consistent with the fact that bone metastasis was not observed in the Pten/Smad4 GEM model (hazard ratio=8.7, P=2.16×$10^{-13}$, and overall C-index=0.93, see FIG. 34). In particular, combination of 14-gene with the 4-gene signature increases the predictive power of either gene set alone (hazard ratio=20, P<$10^{-14}$, and overall C-index=0.96, see FIG. 34).

Taken together, the prognostic correlation of these 14 genes represented in the 9 functional pathways enriched in the bone-metastasis associated gene set provides the correlative evidence for biological relevance of these genes to human prostate cancers. Additionally, these results serve as validation of the integrative approaches adopted by this invention which leverages the clear genotype-phenotype correlation in model systems with the power of genomic and bioinformatic analyses to elucidate molecular mechanisms driving bone metastasis in human prostate cancers.

The above-described genetic studies in vivo, together with human and mouse prostate cancer genomic data, provide evidence that telomere dysfunction plays a critical role in prostate cancer initiation and progression, permitting acquisition of and selection for cancer-relevant genomic events upon telomerase reactivation. In addition, our studies establish first formal proof that telomere dysfunction and subsequent telomerase activation enables evolving cancers to progress fully and acquire new tumor biological properties including cardinal features of advanced human prostate cancer. Finally, comparative oncogenomic analysis of gene copy number and expression profiles with genotype-phenotype correlation resulted in identification of genes associated with progression to bone metastasis, highlighting the utility of this integrative approach for cancer gene discovery in prostate cancer.

Our inducible telomerase model system enabled genetic analysis of the impact of physiological endogenous telomerase reactivation in a naturally arising solid tumor with short dysfunctional telomeres. These studies established that telomerase reactivation enabled rapidly progressive disease in all cases. At the same time, we established that antecedent telomere dysfunction enabled the acquisition of genomic events including those capable of endowing tumors with new biological properties such as bone metastases, a phenotype not observed in G0 PB-Pten/p53 tumors (telomere intact). Thus, we conclude that a period of telomere dysfunction is a mechanism for the development of chromosomal aberrations targeting genes involved in prostate cancer development including bone metastasis.

We suggest that reactivation of telomerase in setting of pre-existing genome instability can be a genomic mechanism for selection of cooperative events required for ultimate progression—in other words, it is not merely a permissive step by removing DNA damage, but telomerase reactivation is instead an active driver of progression. The above-described experimental data provides formal genetic proof for this thesis. By triangulating the list of genes resident in syntenic sCNAs in mouse and human prostate cancers with biological phenotype in human (e.g. documented bone metastasis), we have defined a prioritized list of bone-metastasis associated genes. Pathway analysis with this list revealed dominance of TGFβ/SMAD4 network, coupled with the observation of spontaneously acquired Smad4 genomic loss in two of the mouse tumors, led to the hypothesis that TGFβ signaling and SMAD4 inactivation is a driver for bone metastasis in prostate cancers. Again, leveraging the power of genetic engineering in the mouse, we went on to perform the definitive genetic validation experiment proving the cooperativity of p53/Pten/Smad4 co-deletion in driving prostate tumorigenesis and progression to bone metastasis in vivo.

This invention provides in vivo genetic evidence that telomerase reactivation quells DNA damage signaling and stabilizes the genome of an initiated cancer to permit cancer progression. This invention also provides the first genetic proof in naturally occurring and initiated cancer in vivo that telomere dysfunction followed by telomerase re-activation serves as a mechanism for the generation of and selection for cancer-relevant genomic alterations to drive progression and new tumor biological hallmarks such as metastasis to bone. Thus, telomerase serves as an active driver of cancer progression in the setting of telomere-based crisis. Furthermore, the validation of telomere dysfunction as a relevant genome instability mechanism in prostate cancer, the generation of highly rearranged genomes with syntenic events, and the in silico documentation that altered genes are enriched for cancer relevance collectively provide a system to enhance the mining of complex human prostate cancer genomes to identify genetic events governing prostate cancer progression.

TABLE 1

Murine prostate cancer model used in this invention.

| Group | Mouse # | mTert | H&E | PCA in bone | Sky |
|---|---|---|---|---|---|
| A | 4005 | mTert$^{+/+}$ | giant invasive | | |
| A | 4145 | mTert$^{+/+}$ | giant invasive | | |
| A | 4361 | mTert$^{+/+}$ | giant invasive | | |
| A | 4485 | mTert$^{+/+}$ | giant invasive | | |
| A | 4610 | mTert$^{+/+}$ | giant invasive | | |
| A | 5187 | mTert$^{+/+}$ | giant invasive | | |
| A | 5466 | mTert$^{+/+}$ | giant invasive | | |
| A | 5468 | mTert$^{+/+}$ | giant invasive | | |
| A | 5810 | mTert$^{+/+}$ | giant invasive | | |
| A | 6040 | mTert$^{+/+}$ | giant invasive | | yes |
| A | 6337 | mTert$^{+/+}$ | giant invasive | | |
| A | 6679 | mTert$^{+/+}$ | giant invasive | | |
| A | 6681 | mTert$^{+/+}$ | giant invasive | | yes |
| A | 6729 | mTert$^{+/+}$ | giant invasive | yes | yes |
| A | 7250 | mTert$^{+/+}$ | giant invasive | | |
| A | 7257 | mTert$^{+/+}$ | giant invasive | | |
| A | 7534 | mTert$^{+/+}$ | giant invasive | | |
| A | 8432 | mTert$^{+/+}$ | giant invasive | | |
| A | 4998 | mTert$^{+/+}$ | giant invasive | | yes |
| A | 11232 | mTert$^{+/+}$ | giant invasive | | |
| B | 2669 | mTert$^{-/-}$ | HPIN | | |

TABLE 1-continued

Murine prostate cancer model used in this invention.

| Group | Mouse # | mTert | H&E | PCA in bone | Sky |
|---|---|---|---|---|---|
| B | 12030 | mTert$^{-/-}$ | HPIN | | |
| B | 11713 | mTert$^{-/-}$ | HPIN | | |
| B | 11635 | mTert$^{-/-}$ | HPIN | | |
| B | 11566 | mTert$^{-/-}$ | HPIN | | |
| B | 11024 | mTert$^{-/-}$ | HPIN | | |
| B | 10934 | mTert$^{-/-}$ | HPIN | | |
| B | 10538 | mTert$^{-/-}$ | HPIN | | |
| B | 10026 | mTert$^{-/-}$ | HPIN | | |
| B | 8738 | mTert$^{-/-}$ | HPIN | | |
| B | 7111 | mTert$^{-/-}$ | HPIN | | yes |
| B | 7110 | mTert$^{-/-}$ | HPIN | | yes |
| B | 6834 | mTert$^{-/-}$ | HPIN | | |
| B | 4128 | mTert$^{-/-}$ | HPIN | | |
| B | 2670 | mTert$^{-/-}$ | HPIN | | |
| B | 12319 | mTert$^{-/-}$ | HPIN | | |
| B | 12073 | mTert$^{-/-}$ | HPIN | | |
| B | 11769 | mTert$^{-/-}$ | small but invasive | | |
| B | 11714 | mTert$^{-/-}$ | one lobe HPIN, one lobe invasive tumor | | |
| B | 8671 | mTert$^{-/-}$ | HPIN and invasive | | |
| B | 7825 | mTert$^{-/-}$ | small but invasive tumor | | |
| B | 7132 | mTert$^{-/-}$ | one lobe HPIN, one invasive | | |
| B | 7742 | mTert$^{-/-}$ | invasive | | |
| B | 5817 | mTert$^{-/-}$ | giant invasive | | yes |
| B | 5382 | mTert$^{-/-}$ | invasive | | yes |
| B | 4569 | mTert$^{-/-}$ | HPIN and invasive | | |
| B | 4375 | mTert$^{-/-}$ | giant invasive | | |
| B | 4370 | mTert$^{-/-}$ | giant invasive | | |
| B | 4232 | mTert$^{-/-}$ | one lobe HPIN, one invasive | | |
| B | 4122 | mTert$^{-/-}$ | big and invasive | | |
| B | 4072 | mTert$^{-/-}$ | big and invasive | | |
| C | 4174 | mTertpc$^{+/-}$ | giant invasive | | yes |
| C | 7106 | mTertpc$^{+/-}$ | giant invasive | | yes |
| C | 7523 | mTertpc$^{+/-}$ | giant invasive | | |
| C | 7525 | mTert$^{pc-/-}$ | giant invasive | | |
| C | 7526 | mTert$^{pc-/-}$ | giant invasive | | |
| C | 8584 | mTert$^{pc-/-}$ | giant invasive | | |
| C | 8589 | mTertpc$^{+/-}$ | giant invasive | | yes |
| C | 8591 | mTertpc$^{+/-}$ | giant invasive | | yes |
| C | 8781 | mTert$^{pc-/-}$ | giant invasive | yes | yes |
| C | 9492 | mTert$^{pc-/-}$ | giant invasive | yes | |
| C | 9493 | mTert$^{pc-/-}$ | giant invasive | | |
| C | 10025 | mTertpc$^{+/-}$ | giant invasive | yes | |
| C | 10118 | mTert$^{pc-/-}$ | giant invasive | | |
| C | 11563 | mTertpc$^{+/-}$ | giant invasive | | |
| C | 11649 | mTertpc$^{+/-}$ | giant invasive | | |
| C | 11756 | mTert$^{pc-/-}$ | giant invasive | yes | |
| C | 11819 | mTertpc$^{+/-}$ | giant invasive | | |
| C | 11923 | mTertpc$^{+/-}$ | giant invasive | | |
| C | 11959 | mTertpc$^{+/-}$ | giant invasive | | |
| C | 11960 | mTert$^{pc-/-}$ | giant invasive | yes | |

TABLE 2

Copy number driven gene expression gene list.

| Determinant No. | Gene Symbol | Amplification (300 genes) | Deletion (441 genes) |
|---|---|---|---|
| 1 | ABCB1 | amplification | |
| 2 | ABCB4 | amplification | |
| 3 | ABRA | amplification | |
| 4 | ACN9 | amplification | |
| 5 | ADAM22 | amplification | |
| 6 | ADCK5 | amplification | |

TABLE 2-continued

Copy number driven gene expression gene list.

| Determinant No. | Gene Symbol | Amplification (300 genes) | Deletion (441 genes) |
|---|---|---|---|
| 7 | ADCY8 | amplification | |
| 8 | AGPAT6 | amplification | |
| 9 | AKAP9 | amplification | |
| 10 | ANGPT1 | amplification | |
| 11 | ANK1 | amplification | |
| 12 | ANKIB1 | amplification | |
| 13 | ANKRD46 | amplification | |
| 14 | ANXA13 | amplification | |
| 15 | ARC | amplification | |
| 16 | ARF5 | amplification | |
| 17 | ARHGAP39 | amplification | |
| 18 | ARMC1 | amplification | |
| 19 | ASAP1 | amplification | |
| 20 | ATAD2 | amplification | |
| 21 | ATP6V0D2 | amplification | |
| 22 | ATP6V1C1 | amplification | |
| 23 | AZIN1 | amplification | |
| 24 | BAALC | amplification | |
| 25 | BAI1 | amplification | |
| 26 | BOP1 | amplification | |
| 27 | C7ORF23 | amplification | |
| 28 | C7ORF62 | amplification | |
| 29 | C7ORF63 | amplification | |
| 30 | C7ORF64 | amplification | |
| 31 | C8ORF30A | amplification | |
| 32 | C8ORF47 | amplification | |
| 33 | C8ORF55 | amplification | |
| 34 | C8ORF76 | amplification | |
| 35 | C8ORF82 | amplification | |
| 36 | C8ORF85 | amplification | |
| 37 | CAPZA2 | amplification | |
| 38 | CAV1 | amplification | |
| 39 | CDK14 | amplification | |
| 40 | CDK6 | amplification | |
| 41 | CHCHD7 | amplification | |
| 42 | CHRAC1 | amplification | |
| 43 | CLDN12 | amplification | |
| 44 | CNGB3 | amplification | |
| 45 | COL14A1 | amplification | |
| 46 | COL22A1 | amplification | |
| 47 | COLEC10 | amplification | |
| 48 | COMMD5 | amplification | |
| 49 | COX6C | amplification | |
| 50 | CPNE3 | amplification | |
| 51 | CPSF1 | amplification | |
| 52 | CRH | amplification | |
| 53 | CROT | amplification | |
| 54 | CSMD3 | amplification | |
| 55 | CTHRC1 | amplification | |
| 56 | CYC1 | amplification | |
| 57 | CYHR1 | amplification | |
| 58 | CYP11B1 | amplification | |
| 59 | CYP11B2 | amplification | |
| 60 | CYP51A1 | amplification | |
| 61 | DBF4 | amplification | |
| 62 | DCAF13 | amplification | |
| 63 | DENND3 | amplification | |
| 64 | DEPDC6 | amplification | |
| 65 | DERL1 | amplification | |
| 66 | DGAT1 | amplification | |
| 67 | DLX5 | amplification | |
| 68 | DLX6 | amplification | |
| 69 | DLX6-AS | amplification | |
| 70 | DMTF1 | amplification | |
| 71 | DNAJC5B | amplification | |
| 72 | DPYS | amplification | |
| 73 | DSCC1 | amplification | |
| 74 | EBAG9 | amplification | |
| 75 | EEF1D | amplification | |
| 76 | EFR3A | amplification | |
| 77 | EIF2C2 | amplification | |
| 78 | EIF3E | amplification | |
| 79 | EIF3H | amplification | |
| 80 | ENPP2 | amplification | |
| 81 | ENY2 | amplification | |
| 82 | EPPK1 | amplification | |
| 83 | EXOSC4 | amplification | |
| 84 | EXT1 | amplification | |
| 85 | FAM133B | amplification | |
| 86 | FAM135B | amplification | |
| 87 | FAM49B | amplification | |
| 88 | FAM82B | amplification | |
| 89 | FAM83A | amplification | |
| 90 | FAM83H | amplification | |
| 91 | FAM84B | amplification | |
| 92 | FAM91A1 | amplification | |
| 93 | FBXL6 | amplification | |
| 94 | FBXO32 | amplification | |
| 95 | FBXO43 | amplification | |
| 96 | FER1L6 | amplification | |
| 97 | FLJ43860 | amplification | |
| 98 | FOXH1 | amplification | |
| 99 | FSCN3 | amplification | |
| 100 | FZD1 | amplification | |
| 101 | FZD6 | amplification | |
| 102 | GATAD1 | amplification | |
| 103 | GCC1 | amplification | |
| 104 | GINS4 | amplification | |
| 105 | GLCCI1 | amplification | |
| 106 | GML | amplification | |
| 107 | GOLGA7 | amplification | |
| 108 | GPAA1 | amplification | |
| 109 | GPIHBP1 | amplification | |
| 110 | GPNMB | amplification | |
| 111 | GPR20 | amplification | |
| 112 | GPT | amplification | |
| 113 | GRHL2 | amplification | |
| 114 | GRINA | amplification | |
| 115 | GRM3 | amplification | |
| 116 | GRM8 | amplification | |
| 117 | GSDMC | amplification | |
| 118 | GSDMD | amplification | |
| 119 | GTPBP10 | amplification | |
| 120 | HAS2 | amplification | |
| 121 | HAS2-AS | amplification | |
| 122 | HEATR7A | amplification | |
| 123 | HHLA1 | amplification | |
| 124 | HRSP12 | amplification | |
| 125 | HSF1 | amplification | |
| 126 | ICA1 | amplification | |
| 127 | IGF2BP3 | amplification | |
| 128 | JRK | amplification | |
| 129 | KCNK9 | amplification | |
| 130 | KCNQ3 | amplification | |
| 131 | KCNS2 | amplification | |
| 132 | KCNV1 | amplification | |
| 133 | KHDRBS3 | amplification | |
| 134 | KIAA0196 | amplification | |
| 135 | KIAA1324L | amplification | |
| 136 | KIFC2 | amplification | |
| 137 | KLF10 | amplification | |
| 138 | KLHL38 | amplification | |
| 139 | KRIT1 | amplification | |
| 140 | LAPTM4B | amplification | |
| 141 | LRP12 | amplification | |
| 142 | LRRC14 | amplification | |
| 143 | LRRC24 | amplification | |
| 144 | LRRC6 | amplification | |
| 145 | LY6D | amplification | |
| 146 | LY6E | amplification | |
| 147 | LY6H | amplification | |
| 148 | LY6K | amplification | |
| 149 | LYN | amplification | |
| 150 | LYNX1 | amplification | |
| 151 | LYPD2 | amplification | |
| 152 | MAF1 | amplification | |
| 153 | MAFA | amplification | |
| 154 | MAL2 | amplification | |
| 155 | MAPK15 | amplification | |
| 156 | MATN2 | amplification | |

TABLE 2-continued

Copy number driven gene expression gene list.

| Determinant No. | Gene Symbol | Amplification (300 genes) | Deletion (441 genes) |
|---|---|---|---|
| 157 | MED30 | amplification | |
| 158 | MET | amplification | |
| 159 | MFSD3 | amplification | |
| 160 | MIR148A | amplification | |
| 161 | MIR151 | amplification | |
| 162 | MIR30B | amplification | |
| 163 | MIR30D | amplification | |
| 164 | MIR486 | amplification | |
| 165 | MIR592 | amplification | |
| 166 | MIR875 | amplification | |
| 167 | MOS | amplification | |
| 168 | MRPL13 | amplification | |
| 169 | MTBP | amplification | |
| 170 | MTDH | amplification | |
| 171 | MTERF | amplification | |
| 172 | MTFR1 | amplification | |
| 173 | MTSS1 | amplification | |
| 174 | MYC | amplification | |
| 175 | NAPRT1 | amplification | |
| 176 | NCALD | amplification | |
| 177 | NDRG1 | amplification | |
| 178 | NDUFB9 | amplification | |
| 179 | NFKBIL2 | amplification | |
| 180 | NIPAL2 | amplification | |
| 181 | NKX6-3 | amplification | |
| 182 | NOV | amplification | |
| 183 | NPVF | amplification | |
| 184 | NRBP2 | amplification | |
| 185 | NSMCE2 | amplification | |
| 186 | NUDCD1 | amplification | |
| 187 | NXPH1 | amplification | |
| 188 | OC90 | amplification | |
| 189 | ODF1 | amplification | |
| 190 | OPLAH | amplification | |
| 191 | OSR2 | amplification | |
| 192 | OXR1 | amplification | |
| 193 | PABPC1 | amplification | |
| 194 | PARP10 | amplification | |
| 195 | PAX4 | amplification | |
| 196 | PDE7A | amplification | |
| 197 | PEX1 | amplification | |
| 198 | PGCP | amplification | |
| 199 | PHF20L1 | amplification | |
| 200 | PKHD1L1 | amplification | |
| 201 | PLAG1 | amplification | |
| 202 | PLEC | amplification | |
| 203 | POLR2K | amplification | |
| 204 | POP1 | amplification | |
| 205 | PPP1R16A | amplification | |
| 206 | PSCA | amplification | |
| 207 | PTK2 | amplification | |
| 208 | PTP4A3 | amplification | |
| 209 | PUF60 | amplification | |
| 210 | PVT1 | amplification | |
| 211 | PYCRL | amplification | |
| 212 | RAD21 | amplification | |
| 213 | RECQL4 | amplification | |
| 214 | RGS22 | amplification | |
| 215 | RHPN1 | amplification | |
| 216 | RIMS2 | amplification | |
| 217 | RNF139 | amplification | |
| 218 | RNF19A | amplification | |
| 219 | RPL30 | amplification | |
| 220 | RPL8 | amplification | |
| 221 | RPS20 | amplification | |
| 222 | RRM2B | amplification | |
| 223 | RSPO2 | amplification | |
| 224 | RUNDC3B | amplification | |
| 225 | SAMD12 | amplification | |
| 226 | SCRIB | amplification | |
| 227 | SCRT1 | amplification | |
| 228 | SCXA | amplification | |
| 229 | SDC2 | amplification | |
| 230 | SDR16C5 | amplification | |
| 231 | SDR16C6 | amplification | |
| 232 | SFRP1 | amplification | |
| 233 | SHARPIN | amplification | |
| 234 | SLA | amplification | |
| 235 | SLC25A32 | amplification | |
| 236 | SLC25A40 | amplification | |
| 237 | SLC30A8 | amplification | |
| 238 | SLC39A4 | amplification | |
| 239 | SLC45A4 | amplification | |
| 240 | SLC7A13 | amplification | |
| 241 | SLURP1 | amplification | |
| 242 | SND1 | amplification | |
| 243 | SNTB1 | amplification | |
| 244 | SNX31 | amplification | |
| 245 | SPAG1 | amplification | |
| 246 | SPATC1 | amplification | |
| 247 | SQLE | amplification | |
| 248 | SRI | amplification | |
| 249 | ST3GAL1 | amplification | |
| 250 | ST7 | amplification | |
| 251 | STEAP1 | amplification | |
| 252 | STEAP2 | amplification | |
| 253 | STEAP4 | amplification | |
| 254 | STK3 | amplification | |
| 255 | SYBU | amplification | |
| 256 | TAC1 | amplification | |
| 257 | TAF2 | amplification | |
| 258 | TATDN1 | amplification | |
| 259 | TG | amplification | |
| 260 | TGS1 | amplification | |
| 261 | TIGD5 | amplification | |
| 262 | TM7SF4 | amplification | |
| 263 | TMEM65 | amplification | |
| 264 | TMEM68 | amplification | |
| 265 | TMEM71 | amplification | |
| 266 | TMEM74 | amplification | |
| 267 | TNFRSF11B | amplification | |
| 268 | TOP1MT | amplification | |
| 269 | TRAPPC9 | amplification | |
| 270 | TRHR | amplification | |
| 271 | TRIB1 | amplification | |
| 272 | TRIM55 | amplification | |
| 273 | TRMT12 | amplification | |
| 274 | TRPS1 | amplification | |
| 275 | TSPYL5 | amplification | |
| 276 | TSTA3 | amplification | |
| 277 | TTC35 | amplification | |
| 278 | UBA52 | amplification | |
| 279 | UBR5 | amplification | |
| 280 | UTP23 | amplification | |
| 281 | VPS13B | amplification | |
| 282 | VPS28 | amplification | |
| 283 | WDR67 | amplification | |
| 284 | WDYHV1 | amplification | |
| 285 | WISP1 | amplification | |
| 286 | WWP1 | amplification | |
| 287 | YWHAZ | amplification | |
| 288 | ZC3H3 | amplification | |
| 289 | ZFAT | amplification | |
| 290 | ZFP41 | amplification | |
| 291 | ZFPM2 | amplification | |
| 292 | ZHX1 | amplification | |
| 293 | ZHX2 | amplification | |
| 294 | ZNF250 | amplification | |
| 295 | ZNF251 | amplification | |
| 296 | ZNF623 | amplification | |
| 297 | ZNF7 | amplification | |
| 298 | ZNF706 | amplification | |
| 299 | ZNF707 | amplification | |
| 300 | ZNF800 | amplification | |
| 301 | ABCC12 | | deletion |
| 302 | ABHD3 | | deletion |
| 303 | ACAA2 | | deletion |
| 304 | ACSL1 | | deletion |
| 305 | ADAM29 | | deletion |
| 306 | ADCY7 | | deletion |

TABLE 2-continued

Copy number driven gene expression gene list.

| Determinant No. | Gene Symbol | Amplification (300 genes) | Deletion (441 genes) |
|---|---|---|---|
| 307 | AGA | | deletion |
| 308 | AKAP11 | | deletion |
| 309 | AKTIP | | deletion |
| 310 | ALDH7A1 | | deletion |
| 311 | ALPK2 | | deletion |
| 312 | AMMECR1L | | deletion |
| 313 | ANKRD29 | | deletion |
| 314 | ANKRD37 | | deletion |
| 315 | AP3S1 | | deletion |
| 316 | APC | | deletion |
| 317 | AQP4 | | deletion |
| 318 | ARHGAP12 | | deletion |
| 319 | ARMC4 | | deletion |
| 320 | ASAH1 | | deletion |
| 321 | ASB5 | | deletion |
| 322 | ASXL3 | | deletion |
| 323 | ATG12 | | deletion |
| 324 | ATP5A1 | | deletion |
| 325 | ATP6V1B2 | | deletion |
| 326 | ATP8B1 | | deletion |
| 327 | B4GALT6 | | deletion |
| 328 | BAMBI | | deletion |
| 329 | BIN1 | | deletion |
| 330 | BNIP3L | | deletion |
| 331 | BRD7 | | deletion |
| 332 | C13ORF15 | | deletion |
| 333 | C13ORF18 | | deletion |
| 334 | C13ORF30 | | deletion |
| 335 | C13ORF31 | | deletion |
| 336 | C13ORF34 | | deletion |
| 337 | C16ORF78 | | deletion |
| 338 | C16ORF87 | | deletion |
| 339 | C18ORF10 | | deletion |
| 340 | C18ORF21 | | deletion |
| 341 | C18ORF25 | | deletion |
| 342 | C18ORF32 | | deletion |
| 343 | C18ORF34 | | deletion |
| 344 | C18ORF45 | | deletion |
| 345 | C18ORF55 | | deletion |
| 346 | C18ORF8 | | deletion |
| 347 | C1ORF31 | | deletion |
| 348 | C4ORF41 | | deletion |
| 349 | C4ORF47 | | deletion |
| 350 | C5ORF13 | | deletion |
| 351 | CABLES1 | | deletion |
| 352 | CABYR | | deletion |
| 353 | CAMK4 | | deletion |
| 354 | CASP3 | | deletion |
| 355 | CBLN1 | | deletion |
| 356 | CBLN2 | | deletion |
| 357 | CCBE1 | | deletion |
| 358 | CCDC11 | | deletion |
| 359 | CCDC110 | | deletion |
| 360 | CCDC111 | | deletion |
| 361 | CCDC112 | | deletion |
| 362 | CCDC122 | | deletion |
| 363 | CCDC68 | | deletion |
| 364 | CCNY | | deletion |
| 365 | CD226 | | deletion |
| 366 | CDH2 | | deletion |
| 367 | CDKN2AIP | | deletion |
| 368 | CDO1 | | deletion |
| 369 | CELF4 | | deletion |
| 370 | CEP120 | | deletion |
| 371 | CHD9 | | deletion |
| 372 | CHST9 | | deletion |
| 373 | CLDN22 | | deletion |
| 374 | CLN5 | | deletion |
| 375 | CNDP1 | | deletion |
| 376 | CNDP2 | | deletion |
| 377 | CNOT7 | | deletion |
| 378 | COG3 | | deletion |
| 379 | COMMD10 | | deletion |
| 380 | COMMD6 | | deletion |
| 381 | CPB2 | | deletion |
| 382 | CPLX4 | | deletion |
| 383 | CREM | | deletion |
| 384 | CSGALNACT1 | | deletion |
| 385 | CSNK1G3 | | deletion |
| 386 | CUL2 | | deletion |
| 387 | CXXC1 | | deletion |
| 388 | CYB5A | | deletion |
| 389 | CYLD | | deletion |
| 390 | CYP4V2 | | deletion |
| 391 | DACH1 | | deletion |
| 392 | DCC | | deletion |
| 393 | DCP2 | | deletion |
| 394 | DCTD | | deletion |
| 395 | DGKH | | deletion |
| 396 | DIAPH3 | | deletion |
| 397 | DIS3 | | deletion |
| 398 | DMXL1 | | deletion |
| 399 | DNAJA2 | | deletion |
| 400 | DNAJC15 | | deletion |
| 401 | DOK6 | | deletion |
| 402 | DSC1 | | deletion |
| 403 | DSC2 | | deletion |
| 404 | DSC3 | | deletion |
| 405 | DSG1 | | deletion |
| 406 | DSG2 | | deletion |
| 407 | DSG3 | | deletion |
| 408 | DSG4 | | deletion |
| 409 | DTNA | | deletion |
| 410 | DTWD2 | | deletion |
| 411 | DYM | | deletion |
| 412 | EDNRB | | deletion |
| 413 | EFHA2 | | deletion |
| 414 | EIF3J | | deletion |
| 415 | ELAC1 | | deletion |
| 416 | ELF1 | | deletion |
| 417 | ELP2 | | deletion |
| 418 | ENO1 | | deletion |
| 419 | ENOX1 | | deletion |
| 420 | ENPP6 | | deletion |
| 421 | EPB41L4A | | deletion |
| 422 | EPC1 | | deletion |
| 423 | EPSTI1 | | deletion |
| 424 | ERCC3 | | deletion |
| 425 | ESCO1 | | deletion |
| 426 | ESD | | deletion |
| 427 | F11 | | deletion |
| 428 | FAM149A | | deletion |
| 429 | FAM170A | | deletion |
| 430 | FAM59A | | deletion |
| 431 | FAM69C | | deletion |
| 432 | FAT1 | | deletion |
| 433 | FBXL3 | | deletion |
| 434 | FBXO15 | | deletion |
| 435 | FBXO8 | | deletion |
| 436 | FECH | | deletion |
| 437 | FEM1C | | deletion |
| 438 | FGF20 | | deletion |
| 439 | FGL1 | | deletion |
| 440 | FHOD3 | | deletion |
| 441 | FRG2B | | deletion |
| 442 | FTMT | | deletion |
| 443 | FTO | | deletion |
| 444 | FZD8 | | deletion |
| 445 | GALNT1 | | deletion |
| 446 | GALNT7 | | deletion |
| 447 | GALNTL6 | | deletion |
| 448 | GALR1 | | deletion |
| 449 | GATA6 | | deletion |
| 450 | GJD4 | | deletion |
| 451 | GLRA3 | | deletion |
| 452 | GPM6A | | deletion |
| 453 | GPR17 | | deletion |
| 454 | GPT2 | | deletion |
| 455 | GRAMD3 | | deletion |
| 456 | GREB1L | | deletion |

TABLE 2-continued

Copy number driven gene expression gene list.

| Determinant No. | Gene Symbol | Amplification (300 genes) | Deletion (441 genes) |
|---|---|---|---|
| 457 | GRP | | deletion |
| 458 | GTF2F2 | | deletion |
| 459 | GYPC | | deletion |
| 460 | HAND2 | | deletion |
| 461 | HAUS1 | | deletion |
| 462 | HDHD2 | | deletion |
| 463 | HEATR3 | | deletion |
| 464 | HELT | | deletion |
| 465 | HMGB2 | | deletion |
| 466 | HMGXB4 | | deletion |
| 467 | HMOX1 | | deletion |
| 468 | HPGD | | deletion |
| 469 | HRH4 | | deletion |
| 470 | HSD17B4 | | deletion |
| 471 | HTR2A | | deletion |
| 472 | IER3IP1 | | deletion |
| 473 | IMPACT | | deletion |
| 474 | ING2 | | deletion |
| 475 | INO80C | | deletion |
| 476 | INTS10 | | deletion |
| 477 | IRF2 | | deletion |
| 478 | IRF2BP2 | | deletion |
| 479 | IRG1 | | deletion |
| 480 | ISX | | deletion |
| 481 | ITFG1 | | deletion |
| 482 | IWS1 | | deletion |
| 483 | KATNAL2 | | deletion |
| 484 | KBTBD7 | | deletion |
| 485 | KCNN2 | | deletion |
| 486 | KCTD1 | | deletion |
| 487 | KCTD12 | | deletion |
| 488 | KCTD4 | | deletion |
| 489 | KIAA0427 | | deletion |
| 490 | KIAA0564 | | deletion |
| 491 | KIAA1430 | | deletion |
| 492 | KIAA1462 | | deletion |
| 493 | KIAA1632 | | deletion |
| 494 | KIAA1704 | | deletion |
| 495 | KIAA1712 | | deletion |
| 496 | KIF5B | | deletion |
| 497 | KLF12 | | deletion |
| 498 | KLF5 | | deletion |
| 499 | KLHL1 | | deletion |
| 500 | KLHL14 | | deletion |
| 501 | KLKB1 | | deletion |
| 502 | LAMA3 | | deletion |
| 503 | LARGE | | deletion |
| 504 | LCP1 | | deletion |
| 505 | LECT1 | | deletion |
| 506 | LIMS2 | | deletion |
| 507 | LIPG | | deletion |
| 508 | LMAN1 | | deletion |
| 509 | LMO7 | | deletion |
| 510 | LONP2 | | deletion |
| 511 | LOX | | deletion |
| 512 | LOXHD1 | | deletion |
| 513 | LPL | | deletion |
| 514 | LRCH1 | | deletion |
| 515 | LRP1B | | deletion |
| 516 | LRP2BP | | deletion |
| 517 | LRRC63 | | deletion |
| 518 | LYZL1 | | deletion |
| 519 | LZTS1 | | deletion |
| 520 | MALT1 | | deletion |
| 521 | MAP3K2 | | deletion |
| 522 | MAP3K8 | | deletion |
| 523 | MAP7 | | deletion |
| 524 | MAPK4 | | deletion |
| 525 | MAPRE2 | | deletion |
| 526 | MBD1 | | deletion |
| 527 | MBD2 | | deletion |
| 528 | MBP | | deletion |
| 529 | MC4R | | deletion |
| 530 | MCC | | deletion |
| 531 | MCM5 | | deletion |
| 532 | ME2 | | deletion |
| 533 | MED4 | | deletion |
| 534 | MEP1B | | deletion |
| 535 | MEX3C | | deletion |
| 536 | MIB1 | | deletion |
| 537 | MICB | | deletion |
| 538 | MIR1-2 | | deletion |
| 539 | MIR187 | | deletion |
| 540 | MIR383 | | deletion |
| 541 | MIR759 | | deletion |
| 542 | MKX | | deletion |
| 543 | MLF1IP | | deletion |
| 544 | MOCOS | | deletion |
| 545 | MPP7 | | deletion |
| 546 | MRO | | deletion |
| 547 | MSR1 | | deletion |
| 548 | MTMR7 | | deletion |
| 549 | MTNR1A | | deletion |
| 550 | MTPAP | | deletion |
| 551 | MTRF1 | | deletion |
| 552 | MTUS1 | | deletion |
| 553 | MYCBP2 | | deletion |
| 554 | MYLK3 | | deletion |
| 555 | MYO5B | | deletion |
| 556 | MYO7B | | deletion |
| 557 | MZT1 | | deletion |
| 558 | N4BP1 | | deletion |
| 559 | NAA16 | | deletion |
| 560 | NARS | | deletion |
| 561 | NAT1 | | deletion |
| 562 | NAT2 | | deletion |
| 563 | NDFIP2 | | deletion |
| 564 | NEDD4L | | deletion |
| 565 | NEIL3 | | deletion |
| 566 | NETO1 | | deletion |
| 567 | NETO2 | | deletion |
| 568 | NKD1 | | deletion |
| 569 | NOD2 | | deletion |
| 570 | NOL4 | | deletion |
| 571 | NPC1 | | deletion |
| 572 | NUDT15 | | deletion |
| 573 | NUFIP1 | | deletion |
| 574 | NUTF2 | | deletion |
| 575 | ODZ3 | | deletion |
| 576 | OLFM4 | | deletion |
| 577 | ONECUT2 | | deletion |
| 578 | OR1D2 | | deletion |
| 579 | ORC6 | | deletion |
| 580 | OSBPL1A | | deletion |
| 581 | PAPD5 | | deletion |
| 582 | PARD3 | | deletion |
| 583 | PCDH17 | | deletion |
| 584 | PCDH20 | | deletion |
| 585 | PCDH8 | | deletion |
| 586 | PCDH9 | | deletion |
| 587 | PCM1 | | deletion |
| 588 | PDGFRL | | deletion |
| 589 | PDLIM3 | | deletion |
| 590 | PGGT1B | | deletion |
| 591 | PHAX | | deletion |
| 592 | PHKB | | deletion |
| 593 | PIAS2 | | deletion |
| 594 | PIBF1 | | deletion |
| 595 | PIK3C3 | | deletion |
| 596 | PMAIP1 | | deletion |
| 597 | POLI | | deletion |
| 598 | POLR2D | | deletion |
| 599 | POU4F1 | | deletion |
| 600 | PPIC | | deletion |
| 601 | PRDM6 | | deletion |
| 602 | PROC | | deletion |
| 603 | PRR16 | | deletion |
| 604 | PSD3 | | deletion |
| 605 | PSMA8 | | deletion |
| 606 | PSTPIP2 | | deletion |

TABLE 2-continued

Copy number driven gene expression gene list.

| Determinant No. | Gene Symbol | Amplification (300 genes) | Deletion (441 genes) |
|---|---|---|---|
| 607 | RAB18 | | deletion |
| 608 | RAB27B | | deletion |
| 609 | RAP1GAP2 | | deletion |
| 610 | RAX | | deletion |
| 611 | RBBP8 | | deletion |
| 612 | RBL2 | | deletion |
| 613 | RBM26 | | deletion |
| 614 | RBM34 | | deletion |
| 615 | REEP5 | | deletion |
| 616 | RIOK3 | | deletion |
| 617 | RIT2 | | deletion |
| 618 | RNF125 | | deletion |
| 619 | RNF138 | | deletion |
| 620 | RNF165 | | deletion |
| 621 | RNF219 | | deletion |
| 622 | ROCK1 | | deletion |
| 623 | RPGRIP1L | | deletion |
| 624 | RPL17 | | deletion |
| 625 | RPRD1A | | deletion |
| 626 | RSL24D1 | | deletion |
| 627 | RTTN | | deletion |
| 628 | SALL1 | | deletion |
| 629 | SAP130 | | deletion |
| 630 | SAP30 | | deletion |
| 631 | SCARNA17 | | deletion |
| 632 | SCEL | | deletion |
| 633 | SCRG1 | | deletion |
| 634 | SEC11C | | deletion |
| 635 | SEMA6A | | deletion |
| 636 | SERP2 | | deletion |
| 637 | SETBP1 | | deletion |
| 638 | SFI1 | | deletion |
| 639 | SFT2D3 | | deletion |
| 640 | SGCZ | | deletion |
| 641 | SH2D4A | | deletion |
| 642 | SIAH1 | | deletion |
| 643 | SIAH3 | | deletion |
| 644 | SIGLEC15 | | deletion |
| 645 | SKA1 | | deletion |
| 646 | SKOR2 | | deletion |
| 647 | SLAIN1 | | deletion |
| 648 | SLC14A1 | | deletion |
| 649 | SLC14A2 | | deletion |
| 650 | SLC18A1 | | deletion |
| 651 | SLC25A30 | | deletion |
| 652 | SLC25A4 | | deletion |
| 653 | SLC25A46 | | deletion |
| 654 | SLC35F3 | | deletion |
| 655 | SLC39A6 | | deletion |
| 656 | SLC7A2 | | deletion |
| 657 | SLITRK1 | | deletion |
| 658 | SLITRK6 | | deletion |
| 659 | SMAD2 | | deletion |
| 660 | SMAD4 | | deletion |
| 661 | SMAD7 | | deletion |
| 662 | SNCAIP | | deletion |
| 663 | SNORA31 | | deletion |
| 664 | SNORD58B | | deletion |
| 665 | SNRPD1 | | deletion |
| 666 | SNX2 | | deletion |
| 667 | SNX20 | | deletion |
| 668 | SNX24 | | deletion |
| 669 | SNX25 | | deletion |
| 670 | SOCS6 | | deletion |
| 671 | SORBS2 | | deletion |
| 672 | SPATA4 | | deletion |
| 673 | SPCS3 | | deletion |
| 674 | SPERT | | deletion |
| 675 | SPG11 | | deletion |
| 676 | SPRY2 | | deletion |
| 677 | SRFBP1 | | deletion |
| 678 | SRP19 | | deletion |
| 679 | SS18 | | deletion |
| 680 | ST8SIA3 | | deletion |
| 681 | ST8SIA5 | | deletion |
| 682 | STARD4 | | deletion |
| 683 | STARD6 | | deletion |
| 684 | STOX2 | | deletion |
| 685 | SUCLA2 | | deletion |
| 686 | SUGT1 | | deletion |
| 687 | SVIL | | deletion |
| 688 | SYT4 | | deletion |
| 689 | TAF4B | | deletion |
| 690 | TARBP1 | | deletion |
| 691 | TBC1D4 | | deletion |
| 692 | TCF4 | | deletion |
| 693 | TDRD3 | | deletion |
| 694 | TICAM2 | | deletion |
| 695 | TLR3 | | deletion |
| 696 | TMED7 | | deletion |
| 697 | TMEM188 | | deletion |
| 698 | TMX3 | | deletion |
| 699 | TNFAIP8 | | deletion |
| 700 | TNFSF11 | | deletion |
| 701 | TOM1 | | deletion |
| 702 | TOMM20 | | deletion |
| 703 | TOX3 | | deletion |
| 704 | TPT1 | | deletion |
| 705 | TRIM36 | | deletion |
| 706 | TSC22D1 | | deletion |
| 707 | TSHZ1 | | deletion |
| 708 | TSLP | | deletion |
| 709 | TTC39C | | deletion |
| 710 | TTR | | deletion |
| 711 | TUSC3 | | deletion |
| 712 | TXNL1 | | deletion |
| 713 | UCHL3 | | deletion |
| 714 | UFSP2 | | deletion |
| 715 | VEGFC | | deletion |
| 716 | VPS35 | | deletion |
| 717 | VPS37A | | deletion |
| 718 | WAC | | deletion |
| 719 | WBP4 | | deletion |
| 720 | WDR17 | | deletion |
| 721 | WDR33 | | deletion |
| 722 | WDR36 | | deletion |
| 723 | WDR7 | | deletion |
| 724 | WWC2 | | deletion |
| 725 | YTHDC2 | | deletion |
| 726 | ZADH2 | | deletion |
| 727 | ZBTB7C | | deletion |
| 728 | ZC3H13 | | deletion |
| 729 | ZDHHC2 | | deletion |
| 730 | ZEB1 | | deletion |
| 731 | ZNF236 | | deletion |
| 732 | ZNF24 | | deletion |
| 733 | ZNF397 | | deletion |
| 734 | ZNF407 | | deletion |
| 735 | ZNF423 | | deletion |
| 736 | ZNF438 | | deletion |
| 737 | ZNF474 | | deletion |
| 738 | ZNF516 | | deletion |
| 739 | ZNF521 | | deletion |
| 740 | ZNF608 | | deletion |
| 741 | ZSCAN30 | | deletion |

TABLE 3

Integrative approach further combined the cross-species amplifications and deletions with publicly retrieved cancer mutation, methylation, and transcriptome data, generating a list of 77 amplified and 151 deleted PCA prognostic determinants (PDs).

| Determinant No. | PDs | GeneName | AMP DEL | upP.Ho | upP.Lap | upP.LaT | upP.van | upP.Var | upP.Yu | Count |
|---|---|---|---|---|---|---|---|---|---|---|
| 8 | PD1 | AGPAT6 | AMP | NA | NA | NA | 0.217946 | 0.0264 | NA | 1 |
| 9 | PD2 | AKAP9 | AMP | 0.05471 | 5.51E−04 | 0.23576 | 0.703938 | 0.22508 | 0.45363 | 1 |
| 12 | PD3 | ANKIB1 | AMP | NA | 0.003032 | NA | 0.521475 | 3.63E−04 | NA | 2 |
| 13 | PD4 | ANKRD46 | AMP | 0.88957 | 0.029742 | 0.89119 | 0.090499 | 0.03486 | 0.83392 | 2 |
| 18 | PD5 | ARMC1 | AMP | NA | 0.021098 | NA | 0.601844 | 6.46E−04 | NA | 2 |
| 19 | PD6 | ASAP1 | AMP | NA | 0.036458 | NA | 0.067086 | 1.63E−04 | NA | 2 |
| 20 | PD7 | ATAD2 | AMP | NA | 0.055993 | NA | 0.056803 | 1.05E−04 | NA | 1 |
| 22 | PD8 | ATP6V1C1 | AMP | 0.12421 | 0.085423 | 0.01446 | 0.054752 | 3.77E−04 | 1.30E−07 | 3 |
| 23 | PD9 | AZIN1 | AMP | 0.03956 | 0.915142 | 0.04987 | 0.33621 | 0.02103 | 0.016 | 4 |
| 34 | PD10 | C8ORF76 | AMP | NA | 0.007872 | NA | 0.442677 | 6.17E−04 | NA | 2 |
| 41 | PD11 | CHCHD7 | AMP | NA | 0.79397 | NA | 0.836287 | 0.00229 | NA | 1 |
| 48 | PD12 | COMMD5 | AMP | NA | 7.77E−04 | NA | 0.197694 | 0.01312 | NA | 2 |
| 49 | PD13 | COX6C | AMP | 0.03296 | 0.009102 | 0.14233 | 0.348064 | 3.86E−04 | 0.00991 | 4 |
| 50 | PD14 | CPNE3 | AMP | 0.04525 | 0.361751 | 0.04914 | 0.808221 | 0.41518 | 9.09E−04 | 3 |
| 56 | PD15 | CYC1 | AMP | 0.00814 | 0.002747 | 0.01422 | 0.321037 | 0.14611 | 1.49E−05 | 4 |
| 64 | PD16 | DEPDC6 | AMP | NA | 0.001757 | NA | 0.276384 | 0.98597 | NA | 1 |
| 65 | PD17 | DERL1 | AMP | NA | 0.089832 | NA | 0.12877 | 7.00E−04 | NA | 1 |
| 70 | PD18 | DMTF1 | AMP | 0.52708 | NA | 0.0662 | 0.627951 | 0.1129 | 1.04E−04 | 1 |
| 72 | PD19 | DPYS | AMP | NA | 0.012606 | 0.75857 | 0.210724 | 0.99865 | 0.94823 | 1 |
| 73 | PD20 | DSCC1 | AMP | NA | 5.83E−04 | NA | 0.417512 | 7.42E−05 | NA | 2 |
| 74 | PD21 | EBAG9 | AMP | 0.64939 | NA | 0.2489 | 0.820623 | 0.72444 | 1.87E−06 | 1 |
| 75 | PD22 | EEF1D | AMP | 0.27258 | 0.004546 | 0.15316 | 0.857826 | 0.07527 | 0.1703 | 1 |
| 76 | PD23 | EFR3A | AMP | 0.73414 | 0.007994 | 0.66914 | 0.387171 | 0.91297 | 0.99997 | 1 |
| 77 | PD24 | EIF2C2 | AMP | NA | 0.00389 | 0.00155 | 0.044785 | 7.16E−04 | 1.14E−07 | 5 |
| 78 | PD25 | EIF3E | AMP | 0.46338 | 0.119577 | 0.45561 | 0.354651 | 0.99588 | 0.00228 | 1 |
| 79 | PD26 | EIF3H | AMP | 0.12312 | 0.48177 | 0.34815 | 0.038412 | 0.03399 | 0.03522 | 3 |
| 81 | PD27 | ENY2 | AMP | NA | 0.117552 | NA | 0.247419 | 0.04459 | NA | 1 |
| 84 | PD28 | EXT1 | AMP | 0.61787 | 0.989534 | 0.37532 | 0.35169 | 8.86E−04 | 3.23E−06 | 2 |
| 87 | PD29 | FAM49B | AMP | NA | 0.327191 | NA | 0.016178 | 0.02423 | NA | 2 |
| 88 | PD30 | FAM82B | AMP | NA | 0.001928 | NA | 0.496775 | 0.24049 | NA | 1 |
| 102 | PD31 | GATAD1 | AMP | 0.2912 | 0.789965 | 0.08302 | 0.591964 | 0.01181 | 0.23735 | 1 |
| 104 | PD32 | GINS4 | AMP | NA | NA | NA | 0.048529 | 0.02057 | NA | 1 |
| 114 | PD33 | GRINA | AMP | 0.00986 | 1.05E−04 | 0.02378 | 0.604278 | 0.03164 | 0.11769 | 4 |
| 124 | PD34 | HRSP12 | AMP | 0.02142 | 0.007667 | 0.07278 | 0.163316 | 0.6865 | 0.00552 | 3 |
| 134 | PD35 | KIAA0196 | AMP | 0.09645 | NA | 0.72763 | 0.539342 | 0.43622 | 0.04678 | 1 |
| 139 | PD36 | KRIT1 | AMP | 0.15087 | 0.020978 | 0.004 | 0.013417 | 0.0041 | 2.70E−06 | 5 |
| 154 | PD37 | MAL2 | AMP | NA | 0.062341 | NA | 0.882402 | 0.00326 | NA | 1 |
| 169 | PD38 | MTBP | AMP | NA | NA | NA | 0.56228 | 0.02574 | NA | 1 |
| 170 | PD39 | MTDH | AMP | NA | 0.001712 | 0.01448 | 0.274721 | 0.00839 | 0.58569 | 3 |
| 171 | PD40 | MTERF | AMP | NA | 9.82E−04 | 7.97E−06 | 0.080102 | 0.17924 | 0.88131 | 2 |
| 172 | PD41 | MTFR1 | AMP | 0.02683 | 0.022331 | 0.04408 | 0.302828 | 0.01749 | 1.99E−07 | 5 |
| 185 | PD42 | NSMCE2 | AMP | NA | 0.007916 | NA | 0.098115 | 0.00553 | NA | 2 |
| 186 | PD43 | NUDCD1 | AMP | NA | 0.04879 | NA | 0.481766 | 0.00157 | NA | 2 |
| 193 | PD44 | PABPC1 | AMP | 0.03294 | 0.148872 | 0.07105 | 0.414925 | 0.01604 | 3.11E−06 | 3 |
| 196 | PD45 | PDE7A | AMP | NA | 0.132618 | NA | 0.263113 | 0.00769 | NA | 1 |
| 199 | PD46 | PHF20L1 | AMP | NA | 0.001288 | NA | 0.221656 | 3.82E−04 | NA | 2 |
| 203 | PD47 | POLR2K | AMP | 0.34593 | 0.083489 | 0.00814 | 0.087445 | 0.01102 | 0.00538 | 3 |
| 204 | PD48 | POP1 | AMP | NA | 2.68E−05 | 0.53352 | 0.017861 | 0.00149 | 0.93518 | 3 |
| 207 | PD49 | PTK2 | AMP | 0.01782 | 0.586117 | 0.00311 | 0.494837 | 3.32E−04 | 0.17466 | 3 |
| 209 | PD50 | PUF60 | AMP | 0.02648 | 2.41E−04 | 0.0223 | 0.415597 | 0.03684 | 0.3536 | 4 |
| 212 | PD51 | RAD21 | AMP | 0.000309 | 0.016963 | 3.91E−06 | 0.054738 | 0.00979 | 0.00209 | 5 |
| 217 | PD52 | RNF139 | AMP | 0.67852 | 0.026808 | 0.2851 | 0.647388 | 0.97281 | 0.13614 | 1 |
| 218 | PD53 | RNF19A | AMP | NA | 0.001562 | NA | 0.033254 | 0.00144 | NA | 3 |
| 221 | PD54 | RPS20 | AMP | 0.50492 | 0.171712 | 0.93214 | 0.89304 | 0.02302 | 0.8905 | 1 |
| 245 | PD55 | SPAG1 | AMP | NA | 0.032037 | NA | 0.141283 | 0.0026 | NA | 2 |
| 247 | PD56 | SQLE | AMP | 0.07232 | 0.012876 | 0.02986 | 0.055675 | 5.94E−06 | 4.05E−05 | 4 |
| 248 | PD57 | SRI | AMP | 0.76963 | 0.045625 | 0.84685 | 0.749964 | 0.99808 | 0.99972 | 1 |
| 254 | PD58 | STK3 | AMP | 0.22197 | 0.645308 | 0.08308 | 0.833353 | 0.19697 | 0.00612 | 1 |
| 257 | PD59 | TAF2 | AMP | 0.02777 | 3.40E−05 | 0.00317 | 0.153746 | 0.00342 | 0.08931 | 4 |
| 260 | PD60 | TGS1 | AMP | NA | 0.015925 | NA | 0.117524 | 0.02268 | NA | 2 |
| 263 | PD61 | TMEM65 | AMP | NA | 0.016029 | NA | 0.140141 | 7.65E−04 | NA | 2 |
| 264 | PD62 | TMEM68 | AMP | NA | 0.027752 | NA | 0.503164 | 0.91584 | NA | 1 |
| 268 | PD63 | TOP1MT | AMP | NA | NA | NA | 0.61768 | 0.01247 | NA | 1 |
| 269 | PD64 | TRAPPC9 | AMP | NA | NA | NA | 0.704428 | 0.01772 | NA | 1 |
| 277 | PD65 | TTC35 | AMP | 0.09176 | 0.642902 | 0.24713 | 0.649507 | 0.78633 | 0.01509 | 1 |
| 279 | PD66 | UBR5 | AMP | 0.05752 | 0.002116 | 0.01938 | 0.097385 | 0.11532 | 0.00156 | 3 |
| 280 | PD67 | UTP23 | AMP | NA | NA | NA | 0.222203 | 0.00257 | NA | 1 |
| 281 | PD68 | VPS13B | AMP | 0.1728 | 0.750331 | 0.16772 | 0.2504 | 0.00562 | 1 | 1 |
| 283 | PD69 | WDR67 | AMP | NA | 0.003203 | 0.00791 | 0.002834 | 2.68E−04 | 0.06765 | 4 |
| 284 | PD70 | WDYHV1 | AMP | NA | 0.022828 | NA | 0.585875 | 0.00276 | NA | 2 |
| 286 | PD71 | WWP1 | AMP | 0.06192 | 0.179087 | 0.00851 | 0.982408 | 0.47898 | 0.00766 | 2 |
| 287 | PD72 | YWHAZ | AMP | 0.00301 | 0.021078 | 0.00106 | 0.209565 | 0.00211 | 0.16303 | 4 |
| 292 | PD73 | ZHX1 | AMP | NA | 0.007453 | NA | 0.347984 | 0.48004 | NA | 1 |
| 294 | PD74 | ZNF250 | AMP | NA | 0.046638 | 0.35616 | 0.207615 | 0.02819 | 1 | 2 |

TABLE 3-continued

Integrative approach further combined the cross-species amplifications and deletions with publicly retrieved cancer mutation, methylation, and transcriptome data, generating a list of 77 amplified and 151 deleted PCA prognostic determinants (PDs).

| Determinant No. | PDs | GeneName | AMP DEL | upP.Ho | upP.Lap | upP.LaT | upP.van | upP.Var | upP.Yu | Count |
|---|---|---|---|---|---|---|---|---|---|---|
| 296 | PD75 | ZNF623 | AMP | 0.02117 | NA | 0.0263 | 0.528602 | 0.00404 | 0.04365 | 4 |
| 297 | PD76 | ZNF7 | AMP | 0.09469 | 0.097333 | 0.17841 | 0.304134 | 0.04002 | 0.0552 | 1 |
| 298 | PD77 | ZNF706 | AMP | NA | 0.002898 | NA | 0.001659 | 6.31E−05 | NA | 3 |
| 303 | PD78 | ACAA2 | DEL | 0.6979 | 0.713777 | 0.21716 | 0.528437 | 0.60627 | 0.00291 | 1 |
| 308 | PD79 | AKAP11 | DEL | 0.07568 | 0.06287 | 0.51308 | 0.261338 | 9.05E−04 | 8.08E−14 | 2 |
| 310 | PD80 | ALDH7A1 | DEL | 0.00103 | 0.012384 | 0.18802 | 0.005912 | 8.50E−05 | 0.79381 | 4 |
| 312 | PD81 | AMMECR1L | DEL | NA | 0.971619 | NA | 0.729332 | 2.68E−04 | NA | 1 |
| 313 | PD82 | ANKRD29 | DEL | NA | NA | NA | 0.764164 | 0.01788 | NA | 1 |
| 316 | PD83 | APC | DEL | NA | 0.413391 | 0.10162 | 0.055214 | 5.19E−04 | 0.92753 | 1 |
| 319 | PD84 | ARMC4 | DEL | NA | NA | NA | 0.381929 | 0.00212 | NA | 1 |
| 322 | PD85 | ASXL3 | DEL | NA | NA | NA | 0.036787 | 0.57869 | NA | 1 |
| 324 | PD86 | ATP5A1 | DEL | 0.12771 | NA | 0.23898 | 0.544066 | 0.01035 | 4.19E−10 | 2 |
| 326 | PD87 | ATP8B1 | DEL | 0.92236 | 0.241627 | 0.84238 | 0.098611 | 0.02747 | 8.00E−08 | 2 |
| 328 | PD88 | BAMBI | DEL | 0.8714 | 0.87102 | 0.92974 | 0.593013 | 0.91453 | 0.02099 | 1 |
| 329 | PD89 | BIN1 | DEL | 0.30556 | 0.783858 | 0.04217 | 0.445522 | 2.18E−05 | 1.23E−07 | 3 |
| 343 | PD90 | C18ORF34 | DEL | NA | NA | NA | NA | 0.00849 | NA | 1 |
| 353 | PD91 | CAMK4 | DEL | NA | NA | 0.05123 | 0.558773 | 3.73E−04 | 0.01588 | 2 |
| 360 | PD92 | CCDC111 | DEL | NA | 0.992872 | NA | 0.617153 | 0.01235 | NA | 1 |
| 368 | PD93 | CDO1 | DEL | NA | NA | 0.00112 | 0.33874 | 1.58E−05 | 0.32779 | 2 |
| 371 | PD94 | CHD9 | DEL | 0.0000783 | 0.505319 | 0.16024 | 0.005594 | 0.00581 | 0.0888 | 3 |
| 376 | PD95 | CNDP2 | DEL | NA | 0.100467 | NA | 0.018005 | 0.00106 | NA | 2 |
| 378 | PD96 | COG3 | DEL | NA | 0.048584 | NA | 0.120685 | 7.08E−05 | NA | 2 |
| 384 | PD97 | CSGALNACT1 | DEL | NA | 0.022367 | NA | 0.221202 | 0.03097 | NA | 2 |
| 386 | PD98 | CUL2 | DEL | 0.08496 | 0.154956 | 0.60765 | 0.297283 | 0.5558 | 0.00108 | 1 |
| 389 | PD99 | CYLD | DEL | 0.12284 | 5.60E−04 | 0.08827 | 0.098299 | 0.04277 | 4.24E−05 | 3 |
| 391 | PD100 | DACH1 | DEL | 0.04717 | 2.78E−04 | 0.75243 | 1.04E−05 | 5.61E−04 | 0.01364 | 5 |
| 392 | PD101 | DCC | DEL | NA | NA | 0.76934 | 0.010995 | 0.12412 | 0.30337 | 1 |
| 398 | PD102 | DMXL1 | DEL | 0.03873 | 0.021287 | 0.2 | 0.045559 | 0.00148 | 1.73E−04 | 5 |
| 400 | PD103 | DNAJC15 | DEL | NA | 0.083352 | NA | 0.326864 | 0.03102 | NA | 1 |
| 403 | PD104 | DSC2 | DEL | 0.64528 | 0.173192 | 0.14328 | 0.184634 | 0.0088 | 0.07863 | 1 |
| 404 | PD105 | DSC3 | DEL | NA | 0.300896 | 0.33796 | 0.367441 | 4.03E−04 | 0.27093 | 1 |
| 405 | PD106 | DSG1 | DEL | NA | NA | 0.39228 | 0.766262 | 0.88679 | 5.27E−05 | 1 |
| 406 | PD107 | DSG2 | DEL | 0.5299 | 0.011301 | 0.99471 | 0.180832 | 0.02411 | 1.29E−09 | 3 |
| 407 | PD108 | DSG3 | DEL | NA | 0.930595 | 0.75291 | 0.264154 | 0.01178 | 0.0134 | 2 |
| 412 | PD109 | EDNRB | DEL | NA | 6.41E−04 | 0.11328 | 0.837327 | 0.49336 | 0.29616 | 1 |
| 416 | PD110 | ELF1 | DEL | 0.01746 | 3.61E−04 | 0.67021 | 0.573557 | 0.00157 | 5.13E−07 | 4 |
| 421 | PD111 | EPB41L4A | DEL | NA | 0.002507 | NA | 2.38E−04 | 0.00389 | NA | 3 |
| 422 | PD112 | EPC1 | DEL | NA | 0.358127 | NA | 0.221798 | 6.70E−05 | NA | 1 |
| 424 | PD113 | ERCC3 | DEL | 0.90023 | 0.116141 | 0.99225 | 0.754262 | 0.00243 | 3.25E−11 | 2 |
| 430 | PD114 | FAM59A | DEL | NA | 0.032444 | NA | 0.568481 | 0.86792 | NA | 1 |
| 432 | PD115 | FAT1 | DEL | 0.50121 | 0.126415 | 0.66327 | 0.352319 | 9.01E−04 | 5.57E−04 | 2 |
| 435 | PD116 | FBXO8 | DEL | NA | 0.008653 | NA | 0.525566 | 6.52E−04 | NA | 2 |
| 437 | PD117 | FEM1C | DEL | 0.01312 | 0.001389 | 0.02931 | 0.506632 | 0.00908 | 0.84918 | 4 |
| 440 | PD118 | FHOD3 | DEL | NA | 0.936624 | NA | 0.017802 | 1.23E−04 | NA | 2 |
| 445 | PD119 | GALNT1 | DEL | 0.73362 | 0.012908 | 0.50227 | 0.815828 | 0.16483 | 0.00579 | 2 |
| 446 | PD120 | GALNT7 | DEL | NA | NA | NA | 0.199106 | 0.0129 | NA | 1 |
| 451 | PD121 | GLRA3 | DEL | NA | NA | 0.01679 | 0.079112 | 0.18684 | 0.01318 | 2 |
| 459 | PD122 | GYPC | DEL | 0.01527 | 0.312389 | 0.03987 | 0.754247 | 0.05458 | 0.02278 | 3 |
| 466 | PD123 | HMGXB4 | DEL | 0.55213 | 0.010162 | 0.87968 | 0.401971 | 0.03682 | 0.14951 | 2 |
| 468 | PD124 | HPGD | DEL | 0.94438 | 0.311853 | 0.63603 | 0.263057 | 1.60E−04 | 0.99523 | 1 |
| 469 | PD125 | HRH4 | DEL | NA | NA | NA | 2.75E−04 | 0.28199 | NA | 1 |
| 470 | PD126 | HSD17B4 | DEL | 0.35847 | 0.012563 | 0.18397 | 0.106383 | 0.26316 | 0.98271 | 1 |
| 471 | PD127 | HTR2A | DEL | NA | 0.61408 | 0.32928 | 0.034459 | 0.26977 | 0.98817 | 1 |
| 473 | PD128 | IMPACT | DEL | NA | 0.03976 | NA | 0.24518 | 2.28E−04 | NA | 2 |
| 477 | PD129 | IRF2 | DEL | 0.40337 | 3.01E−05 | 0.05021 | 0.589592 | 0.64778 | 2.74E−10 | 2 |
| 481 | PD130 | ITFG1 | DEL | NA | 0.001175 | NA | 0.301084 | 0.00633 | NA | 2 |
| 482 | PD131 | IWS1 | DEL | NA | 0.87708 | NA | 0.409111 | 1.95E−05 | NA | 1 |
| 484 | PD132 | KBTBD7 | DEL | NA | 0.002473 | NA | 0.454506 | 4.06E−04 | NA | 2 |
| 485 | PD133 | KCNN2 | DEL | NA | 0.648566 | NA | 0.309786 | 0.04231 | NA | 1 |
| 486 | PD134 | KCTD1 | DEL | NA | 0.359142 | NA | 0.17875 | 0.02743 | NA | 1 |
| 487 | PD135 | KCTD12 | DEL | 0.68739 | NA | 0.73943 | 0.791982 | 0.03583 | 0.00117 | 2 |
| 490 | PD136 | KIAA0564 | DEL | 0.01864 | 0.208034 | 0.10815 | 0.019385 | 0.12997 | 0.02986 | 3 |
| 492 | PD137 | KIAA1462 | DEL | NA | 0.00392 | 0.99365 | 0.4981 | 5.94E−04 | 0.00402 | 3 |
| 493 | PD138 | KIAA1632 | DEL | NA | 0.016507 | NA | 0.298085 | 0.59906 | NA | 1 |
| 494 | PD139 | KIAA1704 | DEL | NA | 0.374666 | NA | 0.297732 | 0.00521 | NA | 1 |
| 496 | PD140 | KIF5B | DEL | 0.62434 | 0.005821 | 0.75259 | 0.139132 | 0.01765 | 1.01E−10 | 3 |
| 498 | PD141 | KLF5 | DEL | NA | 0.550446 | 0.17449 | 0.004124 | 0.70257 | 4.86E−06 | 2 |
| 502 | PD142 | LAMA3 | DEL | 0.99605 | 0.895323 | 0.5649 | 0.333792 | 0.04813 | 0.48107 | 1 |
| 503 | PD143 | LARGE | DEL | 0.000108 | NA | 0.06287 | 0.012723 | 0.21091 | 0.10481 | 2 |
| 505 | PD144 | LECT1 | DEL | NA | NA | 0.44164 | 0.857727 | 0.17327 | 0.0063 | 1 |
| 506 | PD145 | LIMS2 | DEL | NA | NA | NA | 0.016367 | 1.20E−05 | NA | 2 |
| 509 | PD146 | LMO7 | DEL | NA | 3.51E−05 | 0.31931 | 0.044279 | 0.1613 | 0.51242 | 2 |
| 514 | PD147 | LRCH1 | DEL | NA | 9.07E−05 | 0.06598 | 0.508112 | 4.13E−05 | 0.65919 | 2 |
| 515 | PD148 | LRP1B | DEL | NA | NA | NA | 0.042386 | 0.03827 | NA | 2 |

TABLE 3-continued

Integrative approach further combined the cross-species amplifications and deletions with publicly retrieved cancer mutation, methylation, and transcriptome data, generating a list of 77 amplified and 151 deleted PCA prognostic determinants (PDs).

| Determinant No. | PDs | GeneName | AMP DEL | upP.Ho | upP.Lap | upP.LaT | upP.van | upP.Var | upP.Yu | Count |
|---|---|---|---|---|---|---|---|---|---|---|
| 520 | PD149 | MALT1 | DEL | 0.7125 | 0.375954 | 0.21517 | 0.222936 | 1.80E-04 | 0.0033 | 2 |
| 521 | PD150 | MAP3K2 | DEL | NA | 0.200777 | NA | 0.458006 | 0.00415 | NA | 1 |
| 522 | PD151 | MAP3K8 | DEL | NA | 0.391258 | 0.09963 | 0.575423 | 3.48E-04 | 0.71054 | 1 |
| 525 | PD152 | MAPRE2 | DEL | 0.11916 | 0.115541 | 0.35263 | 0.570368 | 0.00673 | 0.01713 | 2 |
| 526 | PD153 | MBD1 | DEL | 0.20051 | 0.854254 | 0.19116 | 0.539335 | 0.03601 | 2.20E-06 | 2 |
| 527 | PD154 | MBD2 | DEL | 0.41398 | 0.943347 | 0.58623 | 0.491569 | 0.01613 | 0.99383 | 1 |
| 530 | PD155 | MCC | DEL | 0.04802 | 0.02228 | 0.01823 | 0.465124 | 0.00118 | 2.39E-06 | 5 |
| 533 | PD156 | MED4 | DEL | NA | 0.04561 | NA | 0.175621 | 0.00275 | NA | 2 |
| 534 | PD157 | MEP1B | DEL | NA | NA | 0.06071 | 0.13458 | 0.24143 | 0.0013 | 1 |
| 536 | PD158 | MIB1 | DEL | NA | 0.031467 | NA | 0.212107 | 0.00245 | NA | 2 |
| 542 | PD159 | MKX | DEL | NA | 3.00E-05 | NA | 2.23E-07 | 0.00325 | NA | 3 |
| 547 | PD160 | MSR1 | DEL | NA | NA | 0.39676 | 0.608892 | 0.03636 | 0.76899 | 1 |
| 552 | PD161 | MTUS1 | DEL | 0.0118 | 0.001754 | 0.13901 | 0.373327 | 0.00867 | 1.93E-04 | 4 |
| 553 | PD162 | MYCBP2 | DEL | 0.03559 | 0.826307 | 0.08272 | 0.264376 | 0.02378 | 0.95813 | 2 |
| 554 | PD163 | MYLK3 | DEL | NA | NA | NA | 0.001233 | 0.05612 | NA | 1 |
| 555 | PD164 | MYO5B | DEL | NA | 0.001229 | NA | 0.019524 | 0.39535 | NA | 2 |
| 563 | PD165 | NDFIP2 | DEL | NA | 0.010929 | NA | 0.366434 | 0.01484 | NA | 2 |
| 570 | PD166 | NOL4 | DEL | NA | NA | 5.27E-04 | 0.00356 | 0.99815 | 0.92422 | 2 |
| 580 | PD167 | OSBPL1A | DEL | NA | 0.115354 | 0.3728 | 0.598388 | 0.54976 | 1.08E-05 | 1 |
| 582 | PD168 | PARD3 | DEL | 0.13101 | 0.036693 | 0.46334 | 0.034202 | 0.09206 | 0.05407 | 2 |
| 584 | PD169 | PCDH20 | DEL | NA | NA | NA | 0.011108 | 0.3747 | NA | 1 |
| 585 | PD170 | PCDH8 | DEL | 0.00374 | NA | 0.06886 | 0.006767 | 0.18985 | 1.86E-06 | 3 |
| 586 | PD171 | PCDH9 | DEL | NA | NA | 0.1196 | 0.009807 | 0.00246 | 0.84164 | 2 |
| 587 | PD172 | PCM1 | DEL | 0.12657 | 0.088236 | 0.42525 | 0.305345 | 0.02894 | 0.09336 | 1 |
| 589 | PD173 | PDLIM3 | DEL | 0.00000035 | 0.011612 | 1.14E-04 | 0.005655 | 1.30E-07 | 6.04E-08 | 6 |
| 592 | PD174 | PHKB | DEL | 0.60874 | 0.005086 | 0.61018 | 0.110771 | 0.00421 | 0.01393 | 3 |
| 594 | PD175 | PIBF1 | DEL | 0.02274 | 0.021214 | 0.00177 | 0.643912 | 0.00194 | 1.40E-08 | 5 |
| 595 | PD176 | PIK3C3 | DEL | NA | 4.14E-06 | 0.01703 | 0.015241 | 0.00755 | 5.04E-08 | 5 |
| 599 | PD177 | POU4F1 | DEL | 0.02705 | NA | 0.02277 | 0.015565 | 0.70829 | 7.97E-13 | 4 |
| 600 | PD178 | PPIC | DEL | 0.55976 | 0.436404 | 0.4587 | 0.546142 | 0.01208 | 0.52358 | 1 |
| 603 | PD179 | PRR16 | DEL | NA | NA | NA | 0.014057 | 0.20716 | NA | 1 |
| 604 | PD180 | PSD3 | DEL | 0.75813 | 0.043168 | 0.71882 | 0.037462 | 0.53236 | 0.03524 | 3 |
| 612 | PD181 | RBL2 | DEL | 0.01891 | NA | 0.00677 | 0.577087 | 7.34E-04 | 1.22E-07 | 4 |
| 614 | PD182 | RBM34 | DEL | 0.95278 | 0.803386 | 0.71189 | 0.340654 | 0.00673 | 0.00464 | 2 |
| 616 | PD183 | RIOK3 | DEL | 0.38886 | 0.003189 | 0.38143 | 0.047268 | 7.85E-04 | 0.1299 | 3 |
| 617 | PD184 | RIT2 | DEL | NA | NA | 0.8599 | 0.723954 | 0.62373 | 0.00516 | 1 |
| 622 | PD185 | ROCK1 | DEL | 0.11675 | 0.096195 | 0.4045 | 0.613222 | 0.53805 | 1.61E-08 | 1 |
| 625 | PD186 | RPRDIA | DEL | NA | 0.043234 | NA | 0.160293 | 0.33259 | NA | 1 |
| 628 | PD187 | SALL1 | DEL | NA | NA | 0.24073 | 0.783036 | 0.99063 | 0.01242 | 1 |
| 629 | PD188 | SAP130 | DEL | NA | 0.799904 | NA | 0.639156 | 0.01606 | NA | 1 |
| 632 | PD189 | SCEL | DEL | NA | 0.667132 | 0.28102 | 0.370258 | 0.30819 | 7.65E-05 | 1 |
| 637 | PD190 | SETBP1 | DEL | 0.00384 | NA | 0.00239 | 0.06506 | 0.11477 | 0.00103 | 3 |
| 642 | PD191 | SIAH1 | DEL | 0.00407 | 7.00E-04 | 0.72178 | 0.253773 | 0.2575 | 7.26E-07 | 3 |
| 648 | PD192 | SLC14A1 | DEL | NA | 0.074271 | 0.01664 | 6.22E-04 | 3.63E-04 | 2.67E-04 | 4 |
| 651 | PD193 | SLC25A30 | DEL | NA | NA | NA | 0.458145 | 0.01013 | NA | 1 |
| 652 | PD194 | SLC25A4 | DEL | 0.13327 | 0.005203 | 0.28397 | 0.215689 | 0.00734 | 0.00323 | 3 |
| 654 | PD195 | SLC35F3 | DEL | NA | NA | NA | 0.37405 | 0.01648 | NA | 1 |
| 655 | PD196 | SLC39A6 | DEL | 0.23761 | 0.015113 | 0.06698 | 0.152996 | 0.05085 | 0.01062 | 2 |
| 656 | PD197 | SLC7A2 | DEL | NA | 0.072873 | 0.07386 | 0.031598 | 0.0335 | 0.99975 | 2 |
| 658 | PD198 | SLITRK6 | DEL | NA | NA | NA | 1.95E-04 | 0.92441 | NA | 1 |
| 659 | PD199 | SMAD2 | DEL | 0.00000231 | 0.014063 | 0.0605 | 0.14373 | 0.09569 | 5.85E-04 | 3 |
| 660 | PD200 | SMAD4 | DEL | 0.00293 | 0.00911 | 0.16543 | 0.145061 | 0.00271 | 1.17E-11 | 4 |
| 661 | PD201 | SMAD7 | DEL | 0.00216 | 0.762807 | 0.19313 | 0.173849 | 0.19091 | 9.94E-06 | 2 |
| 662 | PD202 | SNCAIP | DEL | NA | 0.460247 | NA | 0.027934 | 0.73285 | NA | 1 |
| 666 | PD203 | SNX2 | DEL | 0.17666 | 0.001511 | 0.89104 | 0.351631 | 0.00555 | 0.1049 | 2 |
| 669 | PD204 | SNX25 | DEL | NA | 0.136012 | NA | 0.177924 | 0.00347 | NA | 1 |
| 670 | PD205 | SOCS6 | DEL | NA | 0.034125 | 0.8803 | 0.645836 | 0.03332 | 0.61859 | 2 |
| 671 | PD206 | SORBS2 | DEL | 0.00028 | 0.006641 | 0.00708 | 0.044607 | 3.61E-04 | 1.96E-08 | 6 |
| 675 | PD207 | SPG11 | DEL | 0.45483 | NA | 0.22203 | 0.289656 | 0.05715 | 1.44E-06 | 1 |
| 676 | PD208 | SPRY2 | DEL | 0.1516 | 0.001152 | 0.09289 | 0.082545 | 0.00122 | 0.09065 | 2 |
| 680 | PD209 | ST8SIA3 | DEL | NA | NA | 0.09362 | 0.312924 | 0.41551 | 0.0082 | 1 |
| 681 | PD210 | ST8SIA5 | DEL | NA | NA | 0.33435 | 0.653832 | 0.97966 | 3.72E-04 | 1 |
| 682 | PD211 | STARD4 | DEL | NA | 0.016624 | NA | 0.666443 | 0.06161 | NA | 1 |
| 685 | PD212 | SUCLA2 | DEL | 0.2074 | 1.24E-04 | 0.92863 | 0.033839 | 2.87E-04 | 0.98193 | 3 |
| 687 | PD213 | SVIL | DEL | 0.0000503 | 5.84E-04 | 0.0016 | 0.0735 | 9.62E-06 | 1.04E-10 | 5 |
| 689 | PD214 | TAF4B | DEL | NA | 0.671957 | 0.65177 | 0.680769 | 0.0941 | 0.00914 | 1 |
| 690 | PD215 | TARBP1 | DEL | 0.51313 | 0.728908 | 0.43663 | 0.305718 | 4.24E-04 | 2.69E-16 | 2 |
| 691 | PD216 | TBC1D4 | DEL | 0.66718 | 0.069162 | 0.29313 | 0.398181 | 0.28044 | 2.02E-05 | 1 |
| 692 | PD217 | TCF4 | DEL | 0.10138 | 0.008672 | 0.30894 | 0.458196 | 0.01253 | 0.25621 | 2 |
| 695 | PD218 | TLR3 | DEL | 0.80762 | NA | 0.56764 | 0.036034 | 0.00128 | 1.99E-04 | 3 |
| 711 | PD219 | TUSC3 | DEL | 0.33271 | 5.51E-04 | 0.15414 | 0.092742 | 0.10787 | 3.83E-08 | 2 |
| 718 | PD220 | WAC | DEL | NA | 0.22034 | NA | 0.565345 | 0.01428 | NA | 1 |
| 719 | PD221 | WBP4 | DEL | 0.0000018 | 5.94E-05 | 0.01444 | 0.130772 | 3.02E-05 | 3.58E-04 | 5 |
| 722 | PD222 | WDR36 | DEL | NA | 0.179801 | NA | 0.45116 | 0.00871 | NA | 1 |

TABLE 3-continued

Integrative approach further combined the cross-species amplifications and deletions with publicly retrieved cancer mutation, methylation, and transcriptome data, generating a list of 77 amplified and 151 deleted PCA prognostic determinants (PDs).

| Determinant No. | PDs | GeneName | AMP DEL | upP.Ho | upP.Lap | upP.LaT | upP.van | upP.Var | upP.Yu | Count |
|---|---|---|---|---|---|---|---|---|---|---|
| 723 | PD223 | WDR7 | DEL | 0.10795 | 0.019351 | 0.02239 | 0.659934 | 0.9946 | 3.94E−10 | 3 |
| 724 | PD224 | WWC2 | DEL | NA | 0.19701 | NA | 0.016602 | 0.00216 | NA | 2 |
| 725 | PD225 | YTHDC2 | DEL | 0.0525 | 0.101509 | 0.51029 | 0.306786 | 8.38E−04 | 0.01205 | 2 |
| 730 | PD226 | ZEB1 | DEL | NA | 0.18408 | NA | 0.165995 | 0.00284 | NA | 1 |
| 735 | PD227 | ZNF423 | DEL | NA | 5.20E−04 | 0.05894 | 0.067857 | 0.03463 | 4.62E−07 | 3 |
| 740 | PD228 | ZNF608 | DEL | NA | 0.007611 | NA | 0.163085 | 0.00153 | NA | 2 |

TABLE 4

Pathway enrichment analysis of 228 genes (77 amplified and 151 deleted) PCA progression determinants.

| Name | Description | P | FDR | nSet_Gene | nHit_Gene | Hit_Genes |
|---|---|---|---|---|---|---|
| HSA01430_CELL_COMMUNICATION | Genes involved in cell communication | 0.00183 | 0.0311 | 97 | 6 | DSC2/DSC3/DSG1/DSG2/DSG3/LAMA3 |
| HSA04350_TGF_BETA_SIGNALING_PATHWAY | Genes involved in TGF-beta signaling pathway | 0.00599 | 0.0509 | 87 | 5 | RBL2/ROCK1/SMAD2/SMAD4/SMAD7 |
| HSA04520_ADHERENS_JUNCTION | Genes involved in adherens junction | 0.0168 | 0.0696 | 74 | 4 | LMO7/PARD3/SMAD2/SMAD4 |
| HSA00280_VALINE_LEUCINE_AND_ISO-LEUCINE_DEGRADATION | Genes involved in valine, leucine and isoleucine degradation | 0.017 | 0.0696 | 41 | 3 | ACAA2/ALDH7A1/HSD17B4 |
| HSA00071_FATTY_ACID_METABOLISM | Genes involved in fatty acid metabolism | 0.0205 | 0.0696 | 44 | 3 | ACAA2/ALDH7A1/HSD17B4 |
| HSA04310_WNT_SIGNALING_PATHWAY | Genes involved in Wnt signaling pathway | 0.0419 | 0.115 | 143 | 5 | APC/ROCK1/SIAH1/SMAD2/SMAD4 |

TABLE 5

37 amplified and 76 deleted genes that were specifically altered in 14 human bone metastatic tumors in Taylor et al data set (2010). AMP, gene amplification; DEL, gene deletion; BM, bone metastasis.

| Determinant No. | Name | AMP or DEL | Enriched in BM |
|---|---|---|---|
| 308 | AKAP11 | DEL | BM |
| 9 | AKAP9 | AMP | BM |
| 312 | AMMECR1L | DEL | BM |
| 12 | ANKIB1 | AMP | BM |
| 18 | ARMC1 | AMP | BM |
| 319 | ARMC4 | DEL | BM |
| 19 | ASAP1 | AMP | BM |
| 322 | ASXL3 | DEL | BM |
| 324 | ATP5A1 | DEL | BM |
| 22 | ATP6V1C1 | AMP | BM |
| 326 | ATP8B1 | DEL | BM |
| 23 | AZIN1 | AMP | BM |
| 328 | BAMBI | DEL | BM |
| 329 | BIN1 | DEL | BM |
| 343 | C18ORF34 | DEL | BM |
| 41 | CHCHD7 | AMP | BM |
| 371 | CHD9 | DEL | BM |
| 378 | COG3 | DEL | BM |
| 386 | CUL2 | DEL | BM |
| 56 | CYC1 | AMP | BM |
| 389 | CYLD | DEL | BM |
| 391 | DACH1 | DEL | BM |
| 392 | DCC | DEL | BM |
| 70 | DMTF1 | AMP | BM |
| 400 | DNAJC15 | DEL | BM |
| 72 | DPYS | AMP | BM |
| 75 | EEF1D | AMP | BM |
| 76 | EFR3A | AMP | BM |
| 77 | EIF2C2 | AMP | BM |
| 416 | ELF1 | DEL | BM |
| 422 | EPC1 | DEL | BM |
| 424 | ERCC3 | DEL | BM |
| 87 | FAM49B | AMP | BM |
| 440 | FHOD3 | DEL | BM |
| 445 | GALNT1 | DEL | BM |
| 102 | GATAD1 | AMP | BM |
| 114 | GRINA | AMP | BM |
| 466 | HMGXB4 | DEL | BM |
| 471 | HTR2A | DEL | BM |
| 481 | ITFG1 | DEL | BM |
| 482 | IWS1 | DEL | BM |
| 484 | KBTBD7 | DEL | BM |

TABLE 5-continued 37 amplified and 76 deleted genes that were specifically altered in 14 human bone metastatic tumors in Taylor et al data set (2010). AMP, gene amplification; DEL, gene deletion; BM, bone metastasis.

| Determinant No. | Name | AMP or DEL | Enriched in BM |
|---|---|---|---|
| 134 | KIAA0196 | AMP | BM |
| 490 | KIAA0564 | DEL | BM |
| 492 | KIAA1462 | DEL | BM |
| 493 | KIAA1632 | DEL | BM |
| 494 | KIAA1704 | DEL | BM |
| 496 | KIF5B | DEL | BM |
| 498 | KLF5 | DEL | BM |
| 139 | KRIT1 | AMP | BM |
| 503 | LARGE | DEL | BM |
| 505 | LECT1 | DEL | BM |
| 506 | LIMS2 | DEL | BM |
| 514 | LRCH1 | DEL | BM |
| 521 | MAP3K2 | DEL | BM |
| 522 | MAP3K8 | DEL | BM |
| 525 | MAPRE2 | DEL | BM |
| 526 | MBD1 | DEL | BM |
| 527 | MBD2 | DEL | BM |
| 533 | MED4 | DEL | BM |
| 542 | MKX | DEL | BM |
| 171 | MTERF | AMP | BM |
| 172 | MTFR1 | AMP | BM |
| 554 | MYLK3 | DEL | BM |
| 555 | MYO5B | DEL | BM |
| 570 | NOL4 | DEL | BM |
| 185 | NSMCE2 | AMP | BM |
| 582 | PARD3 | DEL | BM |
| 584 | PCDH20 | DEL | BM |
| 585 | PCDH8 | DEL | BM |
| 586 | PCDH9 | DEL | BM |
| 196 | PDE7A | AMP | BM |
| 199 | PHF20L1 | AMP | BM |
| 592 | PHKB | DEL | BM |
| 594 | PIBF1 | DEL | BM |
| 595 | PIK3C3 | DEL | BM |
| 207 | PTK2 | AMP | BM |
| 209 | PUF60 | AMP | BM |
| 612 | RBL2 | DEL | BM |
| 617 | RIT2 | DEL | BM |
| 217 | RNF139 | AMP | BM |
| 221 | RPS20 | AMP | BM |
| 628 | SALL1 | DEL | BM |
| 629 | SAP130 | DEL | BM |
| 637 | SETBP1 | DEL | BM |
| 642 | SIAH1 | DEL | BM |
| 648 | SLC14A1 | DEL | BM |
| 651 | SLC25A30 | DEL | BM |
| 658 | SLITRK6 | DEL | BM |
| 659 | SMAD2 | DEL | BM |
| 660 | SMAD4 | DEL | BM |
| 661 | SMAD7 | DEL | BM |
| 675 | SPG11 | DEL | BM |
| 247 | SQLE | AMP | BM |
| 248 | SRI | AMP | BM |
| 680 | ST8SIA3 | DEL | BM |
| 681 | ST8SIA5 | DEL | BM |
| 685 | SUCLA2 | DEL | BM |
| 687 | SVIL | DEL | BM |
| 692 | TCF4 | DEL | BM |
| 260 | TGS1 | AMP | BM |
| 263 | TMEM65 | AMP | BM |
| 264 | TMEM68 | AMP | BM |
| 268 | TOP1MT | AMP | BM |
| 269 | TRAPPC9 | AMP | BM |
| 279 | UBR5 | AMP | BM |
| 718 | WAC | DEL | BM |
| 719 | WBP4 | DEL | BM |
| 723 | WDR7 | DEL | BM |
| 730 | ZEB1 | DEL | BM |
| 735 | ZNF423 | DEL | BM |
| 296 | ZNF623 | AMP | BM |
| 298 | ZNF706 | AMP | BM |

TABLE 6

Pathway enrichment analysis of bone metastasis of 113 gene set. P values were adjusted by false detection rate (FDR).

| Name | Description | P | FDR | nSet_Gene | nHit_Gene | Hit_Genes |
|---|---|---|---|---|---|---|
| REACTOME_SIGNALING_BY_TGF_BETA | http://www.broadinstitute.org/gsea/msigdb/cards/REACTOME_SIGNALING_BY_TGF_BETA.html | 0.000106 | 0.0015 | 15 | 3 | SMAD2/SMAD4/SMAD7 |
| BIOCARTA_TGFB_PATHWAY | http://www.broadinstitute.org/gsea/msigdb/cards/BIOCARTA_TGFB_PATHWAY.html | 0.000187 | 0.0015 | 18 | 3 | SMAD2/SMAD4/SMAD7 |
| KEGG_TGF_BETA_SIGNALING_PATHWAY | http://www.broadinstitute.org/gsea/msigdb/cards/KEGG_TGF_BETA_SIGNALING_PATHWAY.html | 0.00188 | 0.0101 | 83 | 4 | RBL2/SMAD2/SMAD4/SMAD7 |
| KEGG_COLORECTAL_CANCER | http://www.broadinstitute.org/gsea/msigdb/cards/KEGG_COLORECTAL_CANCER.html | 0.00679 | 0.0272 | 61 | 3 | DCC/SMAD2/SMAD4 |
| KEGG_ADHERENS_JUNCTION | http://www.broadinstitute.org/gsea/msigdb/cards/KEGG_ADHERENS_JUNCTION.html | 0.0107 | 0.0343 | 72 | 3 | PARD3/SMAD2/SMAD4 |
| REACTOME_RNA_POLYMERASE_I_III_AND_MITOCHONDRIAL_TRANSCRIPTION | http://www.broadinstitute.org/gsea/msigdb/cards/REACTOME_RNA_POLYMERASE_I_III_AND_MITOCHONDRIAL_TRANSCRIPTION.html | 0.0162 | 0.0432 | 84 | 3 | ERCC3/MBD2/MTERF |
| KEGG_CELL_CYCLE | http://www.broadinstitute.org/gsea/msigdb/cards/KEGG_CELL_CYCLE.html | 0.035 | 0.0748 | 113 | 3 | RBL2/SMAD2/SMAD4 |
| KEGG_OXIDATIVE_PHOSPHORYLATION | http://www.broadinstitute.org/gsea/msigdb/cards/KEGG_OXIDATIVE_PHOSPHORYLATION.html | 0.0374 | 0.0748 | 116 | 3 | ATP5A1/ATP6V1C1/CYC1 |

TABLE 6-continued

Pathway enrichment analysis of bone metastasis of 113 gene set. P values were adjusted by false detection rate (FDR).

| Name | Description | P | FDR | nSet_Gene | nHit_Gene | Hit_Genes |
|---|---|---|---|---|---|---|
| KEGG_PATHWAYS_IN_CANCER | http://www.broadinstitute.org/gsea/msigdb/cards/KEGG_PATHWAYS_IN_CANCER.html | 0.0469 | 0.0834 | 310 | 5 | CUL2/DCC/PTK2/SMAD2/SMAD4 |

TABLE 7

Two-Determinant Combinations

| | ATP5A1 | ATP6V1C1 | CUL2 | CYC1 | DCC | ERCC3 | MBD2 | MTERF | PARD3 | PTK2 | RBL2 | SMAD2 |
|---|---|---|---|---|---|---|---|---|---|---|---|---|
| ATP5A1 | | + | + | + | + | + | + | + | + | + | + | + |
| ATP6V1C1 | | | + | + | + | + | + | + | + | + | + | + |
| CUL2 | | | | + | + | + | + | + | + | + | + | + |
| CYC1 | | | | | + | + | + | + | + | + | + | + |
| DCC | | | | | | + | + | + | + | + | + | + |
| ERCC3 | | | | | | | + | + | + | + | + | + |
| MBD2 | | | | | | | | + | + | + | + | + |
| MTERF | | | | | | | | | + | + | + | + |
| PARD3 | | | | | | | | | | + | + | + |
| PTK2 | | | | | | | | | | | + | + |
| RBL2 | | | | | | | | | | | | + |
| SMAD2 | | | | | | | | | | | | |
| SMAD4 | | | | | | | | | | | | |
| SMAD7 | | | | | | | | | | | | |
| DNAJC15 | | | | | | | | | | | | |
| KIF5B | | | | | | | | | | | | |
| LECT1 | | | | | | | | | | | | |
| DSG2 | | | | | | | | | | | | |
| ACAA2 | | | | | | | | | | | | |
| ASAP1 | | | | | | | | | | | | |
| LMO7 | | | | | | | | | | | | |
| SVIL | | | | | | | | | | | | |
| DSC2 | | | | | | | | | | | | |
| PCDH9 | | | | | | | | | | | | |
| WDR7 | | | | | | | | | | | | |
| LAMA3 | | | | | | | | | | | | |
| PCDH8 | | | | | | | | | | | | |
| MKX | | | | | | | | | | | | |
| MSR1 | | | | | | | | | | | | |
| POLR2K | | | | | | | | | | | | |
| PTEN | | | | | | | | | | | | |
| Cyclin D1 | | | | | | | | | | | | |

| | SMAD4 | SMAD7 | DNAJC15 | KIF5B | LECT1 | DSG2 | ACAA2 | ASAP1 | LMO7 | SVIL | DSC2 |
|---|---|---|---|---|---|---|---|---|---|---|---|
| ATP5A1 | + | + | + | + | + | + | + | + | + | + | + |
| ATP6V1C1 | + | + | + | + | + | + | + | + | + | + | + |
| CUL2 | + | + | + | + | + | + | + | + | + | + | + |
| CYC1 | + | + | + | + | + | + | + | + | + | + | + |
| DCC | + | + | + | + | + | + | + | + | + | + | + |
| ERCC3 | + | + | + | + | + | + | + | + | + | + | + |
| MBD2 | + | + | + | + | + | + | + | + | + | + | + |
| MTERF | + | + | + | + | + | + | + | + | + | + | + |
| PARD3 | + | + | + | + | + | + | + | + | + | + | + |
| PTK2 | + | + | + | + | + | + | + | + | + | + | + |
| RBL2 | + | + | + | + | + | + | + | + | + | + | + |
| SMAD2 | + | + | + | + | + | + | + | + | + | + | + |
| SMAD4 | | + | + | + | + | + | + | + | + | + | + |
| SMAD7 | | | + | + | + | + | + | + | + | + | + |
| DNAJC15 | | | | + | + | + | + | + | + | + | + |
| KIF5B | | | | | + | + | + | + | + | + | + |
| LECT1 | | | | | | + | + | + | + | + | + |
| DSG2 | | | | | | | + | + | + | + | + |
| ACAA2 | | | | | | | | + | + | + | + |
| ASAP1 | | | | | | | | | + | + | + |
| LMO7 | | | | | | | | | | + | + |
| SVIL | | | | | | | | | | | + |
| DSC2 | | | | | | | | | | | |
| PCDH9 | | | | | | | | | | | |
| WDR7 | | | | | | | | | | | |
| LAMA3 | | | | | | | | | | | |
| PCDH8 | | | | | | | | | | | |

TABLE 7-continued

Two-Determinant Combinations

MKX
MSR1
POLR2K
PTEN
Cyclin D1

|  | PCDH9 | WDR7 | LAMA3 | PCDH8 | MKX | MSR1 | POLR2K | PTEN | Cyclin D1 | SPP1 |
|---|---|---|---|---|---|---|---|---|---|---|
| ATP5A1 | + | + | + | + | + | + | + | + | + | + |
| ATP6V1C1 | + | + | + | + | + | + | + | + | + | + |
| CUL2 | + | + | + | + | + | + | + | + | + | + |
| CYC1 | + | + | + | + | + | + | + | + | + | + |
| DCC | + | + | + | + | + | + | + | + | + | + |
| ERCC3 | + | + | + | + | + | + | + | + | + | + |
| MBD2 | + | + | + | + | + | + | + | + | + | + |
| MTERF | + | + | + | + | + | + | + | + | + | + |
| PARD3 | + | + | + | + | + | + | + | + | + | + |
| PTK2 | + | + | + | + | + | + | + | + | + | + |
| RBL2 | + | + | + | + | + | + | + | + | + | + |
| SMAD2 | + | + | + | + | + | + | + | + | + | + |
| SMAD4 | + | + | + | + | + | + | + | + | + | + |
| SMAD7 | + | + | + | + | + | + | + | + | + | + |
| DNAJC15 | + | + | + | + | + | + | + | + | + | + |
| KIF5B | + | + | + | + | + | + | + | + | + | + |
| LECT1 | + | + | + | + | + | + | + | + | + | + |
| DSG2 | + | + | + | + | + | + | + | + | + | + |
| ACAA2 | + | + | + | + | + | + | + | + | + | + |
| ASAP1 | + | + | + | + | + | + | + | + | + | + |
| LMO7 | + | + | + | + | + | + | + | + | + | + |
| SVIL | + | + | + | + | + | + | + | + | + | + |
| DSC2 | + | + | + | + | + | + | + | + | + | + |
| PCDH9 |  | + | + | + | + | + | + | + | + | + |
| WDR7 |  |  | + | + | + | + | + | + | + | + |
| LAMA3 |  |  |  | + | + | + | + | + | + | + |
| PCDH8 |  |  |  |  | + | + | + | + | + | + |
| MKX |  |  |  |  |  | + | + | + | + | + |
| MSR1 |  |  |  |  |  |  | + | + | + | + |
| POLR2K |  |  |  |  |  |  |  | + | + | + |
| PTEN |  |  |  |  |  |  |  |  | + | + |
| Cyclin D1 |  |  |  |  |  |  |  |  |  | + |

REFERENCE LIST

1. Ding, Z. et al. SMAD4-dependent barrier constrains prostate cancer growth and metastatic progression. *Nature* 470, 269-273 (2011).
2. Taylor, B. S. et al. Integrative genomic profiling of human prostate cancer. *Cancer Cell* 18, 11-22 (2010).
3. Glinsky, G. V., Glinskii, A. B., Stephenson, A. J., Hoffman, R. M. & Gerald, W. L. Gene expression profiling predicts clinical outcome of prostate cancer. *J. Clin. Invest* 113, 913-923 (2004).
4. Sharpless, N. E. & DePinho, R. A. The mighty mouse: genetically engineered mouse models in cancer drug development. *Nat. Rev. Drug Discov.* 5, 741-754 (2006).
5. Shen, M. M. & Abate-Shen, C. Molecular genetics of prostate cancer: new prospects for old challenges. *Genes Dev.* 24, 1967-2000 (2010).
6. Li, J. et al. PTEN, a putative protein tyrosine phosphatase gene mutated in human brain, breast, and prostate cancer. *Science* 275, 1943-1947 (1997).
7. Guo, Y., Sklar, G. N., Borkowski, A. & Kyprianou, N. Loss of the cyclin-dependent kinase inhibitor p27(Kip1) protein in human prostate cancer correlates with tumor grade. *Clin. Cancer Res.* 3, 2269-2274 (1997).
8. Majumder, P. K. et al. A prostatic intraepithelial neoplasia-dependent p27 Kip1 checkpoint induces senescence and inhibits cell proliferation and cancer progression. *Cancer Cell* 14, 146-155 (2008).
9. Tomlins, S. A. et al. Recurrent fusion of TMPRSS2 and ETS transcription factor genes in prostate cancer. *Science* 310, 644-648 (2005).
10. Rubin, M. A. Targeted therapy of cancer: new roles for pathologists—prostate cancer. *Mod. Pathol.* 21 Suppl 2, S44-S55 (2008).
11. Abate-Shen, C., Shen, M. M. & Gelmann, E. Integrating differentiation and cancer: The Nkx3.1 homeobox gene in prostate organogenesis and carcinogenesis. *Differentiation* (2008).
12. Tomlins, S. A. et al. The role of SPINK1 in ETS rearrangement-negative prostate cancers. *Cancer Cell* 13, 519-528 (2008).
13. Jenkins, R. B., Qian, J., Lieber, M. M. & Bostwick, D. G. Detection of c-myc oncogene amplification and chromosomal anomalies in metastatic prostatic carcinoma by fluorescence in situ hybridization. *Cancer Res.* 57, 524-531 (1997).
14. Acevedo, V. D., Ittmann, M. & Spencer, D. M. Paths of FGFR-driven tumorigenesis. *Cell Cycle* 8, 580-588 (2009).
15. Rubin, M. A. et al. E-cadherin expression in prostate cancer: a broad survey using high-density tissue microarray technology. *Hum. Pathol.* 32, 690-697 (2001).
16. Chaib, H. et al. Activated in prostate cancer: a PDZ domain-containing protein highly expressed in human primary prostate tumors. *Cancer Res.* 61, 2390-2394 (2001).

17. Dhanasekaran, S. M. et al. Delineation of prognostic biomarkers in prostate cancer. *Nature* 412, 822-826 (2001).
18. Rubin, M. A. et al. alpha-Methylacyl coenzyme A racemase as a tissue biomarker for prostate cancer. *JAMA* 287, 1662-1670 (2002).
19. Varambally, S. et al. Genomic Loss of microRNA-101 Leads to Overexpression of Histone Methyltransferase EZH2 in Cancer. *Science* (2008).
20. Varambally, S. et al. The polycomb group protein EZH2 is involved in progression of prostate cancer. *Nature* 419, 624-629 (2002).
21. Min, J. et al. An oncogene-tumor suppressor cascade drives metastatic prostate cancer by coordinately activating Ras and nuclear factor-kappaB. *Nat. Med.* 16, 286-294 (2010).
22. Chen, Z. et al. Crucial role of p53-dependent cellular senescence in suppression of Pten-deficient tumorigenesis. *Nature* 436, 725-730 (2005).
23. Kim, M. et al. Comparative oncogenomics identifies NEDD9 as a melanoma metastasis gene. *Cell* 125, 1269-1281 (2006).
24. Zender, L. et al. Identification and validation of oncogenes in liver cancer using an integrative oncogenomic approach. *Cell* 125, 1253-1267 (2006).
25. Maser, R. S. et al. Chromosomally unstable mouse tumours have genomic alterations similar to diverse human cancers. *Nature* 447, 966-971 (2007).
26. DePinho, R. A. The age of cancer. *Nature* 408, 248-254 (2000).
27. Artandi, S. E. et al. Telomere dysfunction promotes non-reciprocal translocations and epithelial cancers in mice. *Nature* 406, 641-645 (2000).
28. Chin, L. et al. p53 deficiency rescues the adverse effects of telomere loss and cooperates with telomere dysfunction to accelerate carcinogenesis. *Cell* 97, 527-538 (1999).
29. O'Hagan, R. C. et al. Telomere dysfunction provokes regional amplification and deletion in cancer genomes. *Cancer Cell* 2, 149-155 (2002).
30. Rudolph, K. L., Millard, M., Bosenberg, M. W. & DePinho, R. A. Telomere dysfunction and evolution of intestinal carcinoma in mice and humans. *Nat. Genet.* 28, 155-159 (2001).
31. Chin, K. et al. In situ analyses of genome instability in breast cancer. *Nat. Genet.* 36, 984-988 (2004).
32. Feldmann, G., Beaty, R., Hruban, R. H. & Maitra, A. Molecular genetics of pancreatic intraepithelial neoplasia. *J Hepatobiliary. Pancreat. Surg.* 14, 224-232 (2007).
33. Meeker, A. K. et al. Telomere shortening is an early somatic DNA alteration in human prostate tumorigenesis. *Cancer Res.* 62, 6405-6409 (2002).
34. Stratton, M. R., Campbell, P. J. & Futreal, P. A. The cancer genome. *Nature* 458, 719-724 (2009).
35. Sommerfeld, H. J. et al. Telomerase activity: a prevalent marker of malignant human prostate tissue. *Cancer Res.* 56, 218-222 (1996).
36. Vukovic, B. et al. Evidence of multifocality of telomere erosion in high-grade prostatic intraepithelial neoplasia (HPIN) and concurrent carcinoma. *Oncogene* 22, 1978-1987 (2003).
37. Hahn, W. C. et al. Inhibition of telomerase limits the growth of human cancer cells. *Nat. Med.* 5, 1164-1170 (1999).
38. Chang, S., Khoo, C. M., Naylor, M. L., Maser, R. S. & DePinho, R. A. Telomere-based crisis: functional differences between telomerase activation and ALT in tumor progression. *Genes Dev.* 17, 88-100 (2003).
39. Kallakury, B. V. et al. Telomerase activity in human benign prostate tissue and prostatic adenocarcinomas. *Diagn. Mol. Pathol.* 6, 192-198 (1997).
40. Lin, Y. et al. Telomerase activity in primary prostate cancer. *J. Urol.* 157, 1161-1165 (1997).
41. Koeneman, K. S. et al. Telomerase activity, telomere length, and DNA ploidy in prostatic intraepithelial neoplasia (PIN). *J. Urol.* 160, 1533-1539 (1998).
42. Zhang, W., Kapusta, L. R., Slingerland, J. M. & Klotz, L. H. Telomerase activity in prostate cancer, prostatic intraepithelial neoplasia, and benign prostatic epithelium. *Cancer Res.* 58, 619-621 (1998).
43. Zheng, H. et al. p53 and Pten control neural and glioma stem/progenitor cell renewal and differentiation. *Nature* 455, 1129-1133 (2008).
44. Farazi, P. A., Glickman, J., Horner, J. & DePinho, R. A. Cooperative interactions of p53 mutation, telomere dysfunction, and chronic liver damage in hepatocellular carcinoma progression. *Cancer Res.* 66, 4766-4773 (2006).
45. Marino, S., Vooijs, M., van der, G. H., Jonkers, J. & Berns, A. Induction of medulloblastomas in p53-null mutant mice by somatic inactivation of Rb in the external granular layer cells of the cerebellum. *Genes Dev.* 14, 994-1004 (2000).
46. Wu, X. et al. Generation of a prostate epithelial cell-specific Cre transgenic mouse model for tissue-specific gene ablation. *Mech. Dev.* 101, 61-69 (2001).
47. Beroukhim, R. et al. Assessing the significance of chromosomal aberrations in cancer: methodology and application to glioma. *Proc. Natl. Acad. Sci. U.S.A* 104, 20007-20012 (2007).
48. Holzbeierlein, J. et al. Gene expression analysis of human prostate carcinoma during hormonal therapy identifies androgen-responsive genes and mechanisms of therapy resistance. *Am. J. Pathol.* 164, 217-227 (2004).
49. Lapointe, J. et al. Gene expression profiling identifies clinically relevant subtypes of prostate cancer. *Proc. Natl. Acad. Sci. U.S.A* 101, 811-816 (2004).
50. LaTulippe, E. et al. Comprehensive gene expression analysis of prostate cancer reveals distinct transcriptional programs associated with metastatic disease. *Cancer Res.* 62, 4499-4506 (2002).
51. Vanaja, D. K., Cheville, J. C., Iturria, S. J. & Young, C. Y. Transcriptional silencing of zinc finger protein 185 identified by expression profiling is associated with prostate cancer progression. *Cancer Res.* 63, 3877-3882 (2003).
52. Varambally, S. et al. Integrative genomic and proteomic analysis of prostate cancer reveals signatures of metastatic progression. *Cancer Cell* 8, 393-406 (2005).
53. Yu, Y. P. et al. Gene expression alterations in prostate cancer predicting tumor aggression and preceding development of malignancy. *J. Clin. Oncol.* 22, 2790-2799 (2004).
54. Lee, H. W. et al. Essential role of mouse telomerase in highly proliferative organs. *Nature* 392, 569-574 (1998).
55. Jonkers, J. et al. Synergistic tumor suppressor activity of BRCA2 and p53 in a conditional mouse model for breast cancer. *Nat. Genet.* 29, 418-425 (2001).
56. Gonzalez-Suarez, E., Samper, E., Flores, J. M. & Blasco, M. A. Telomerase-deficient mice with short telomeres are resistant to skin tumorigenesis. *Nat. Genet.* 26, 114-117 (2000).
57. Jaskelioff, M. et al. Telomerase deficiency and telomere dysfunction inhibit mammary tumors induced by polyomavirus middle T oncogene. *Oncogene* 28, 4225-4236 (2009).

58. Takai, H., Smogorzewska, A. & de Lange, T. DNA damage foci at dysfunctional telomeres. *Curr. Biol.* 13, 1549-1556 (2003).
59. IJpma, A. S. & Greider, C. W. Short telomeres induce a DNA damage response in Saccharomyces cerevisiae. *Mol. Biol. Cell* 14, 987-1001 (2003).
60. Forbes, S. A. et al. COSMIC (the Catalogue of Somatic Mutations in Cancer): a resource to investigate acquired mutations in human cancer. *Nucleic Acids Res.* 38, D652-D657 (2010).
61. Forbes, S. A. et al. COSMIC: mining complete cancer genomes in the Catalogue of Somatic Mutations in Cancer. *Nucleic Acids Res.* 39, D945-D950 (2011).
62. Ongenaert, M. et al. PubMeth: a cancer methylation database combining text-mining and expert annotation. *Nucleic Acids Res.* 36, D842-D846 (2008).
63. Holzbeierlein, J. et al. Gene expression analysis of human prostate carcinoma during hormonal therapy identifies androgen-responsive genes and mechanisms of therapy resistance. *Am. J Pathol.* 164, 217-227 (2004).
64. Aitchison, A. A. et al. Promoter methylation correlates with reduced Smad4 expression in advanced prostate cancer. *Prostate* 68, 661-674 (2008).

What is claimed is:

1. A method for treating a cancer patient, comprising:
   immunohistochemically measuring the levels of DERL1 and CUL2 in a tissue sample from the patient, detecting a decrease in the CUL2 level and an increase in the DERL1 level relative to a reference value, and
   treating the patient with adjuvant therapy.
2. The method of claim 1, wherein the tissue sample is a solid tissue sample, a bodily fluid sample, or circulating tumor cells.
3. The method of claim 1, wherein the solid tissue sample is a formalin-fixed paraffin embedded tissue sample, a snap-frozen tissue sample, an ethanol-fixed tissue sample, a tissue sample fixed with an organic solvent, a tissue sample fixed with plastic or epoxy, a cross-linked tissue sample, a surgically removed tumor tissue, or a biopsy sample.
4. The method of claim 1, wherein the tissue sample comprises prostate cancer tissue.
5. The method of claim 1, wherein the levels of DERL1 and CUL2 are detected by immunofluorescence assay.
6. The method of claim 3, wherein the biopsy sample is a core biopsy, an excisional tissue biopsy, or an incisional tissue biopsy.
7. The method of claim 1, which comprises measuring the levels of two to five DETERMINANTS 1-741 of Table 2.
8. The method of claim 1, which further comprises measuring a level of SMAD4 in a sample from the patient, wherein a decrease in a SMAD4 level relative to a reference value is indicative of a prognosis that the patient is at high risk of having metastatic cancer or recurrence of cancer.
9. A reaction mixture comprising a prostate tissue sample, a DERL1 antibody or fragment thereof, and a CUL2 antibody or fragment thereof.
10. The reaction mixture of claim 9, further comprising a first label that indicates presence of the DERL1 antibody or fragment thereof and a second label that indicates presence of the CUL2 antibody or fragment thereof.
11. The reaction mixture of claim 9, further comprising a SMAD4 antibody or fragment thereof.
12. The reaction mixture of claim 11, further comprising a third label that indicates presence of the SMAD4 antibody or fragment thereof.

* * * * *

UNITED STATES PATENT AND TRADEMARK OFFICE
CERTIFICATE OF CORRECTION

PATENT NO.         : 9,458,510 B2
APPLICATION NO.    : 14/127413
DATED              : October 4, 2016
INVENTOR(S)        : Ronald A. Depinho et al.

It is certified that error appears in the above-identified patent and that said Letters Patent is hereby corrected as shown below:

On the Title Page

(73) Assignee: delete "MIETAMARK GENETICS, INC., CAMBRIDGE, MA (US)" and insert -- DANA-FARBER CANCER INSTITUTE, INC., BOSTON, MA (US) --.

In the Specification

At Column 8, Line number 64, delete "They" and insert -- The y --.

At Column 10, Line number 57, delete "They" and insert -- The y --.

At Column 10, Line number 64, delete "They" and insert -- The y --.

At Column 11, Line number 4, delete "They" and insert -- The y --.

At Column 11, Line number 11, delete "They" and insert -- The y --.

At Column 11, Line number 18, delete "They" and insert -- The y --.

At Column 11, Line number 25, delete "They" and insert -- The y --.

At Column 11, Line number 32, delete "They" and insert -- The y --.

At Column 11, Line number 39, delete "They" and insert -- The y --.

At Column 11, Line number 46, delete "They" and insert -- The y --.

At Column 11, Line number 53, delete "They" and insert -- The y --.

Signed and Sealed this
Eighteenth Day of July, 2017

Joseph Matal
*Performing the Functions and Duties of the
Under Secretary of Commerce for Intellectual Property and
Director of the United States Patent and Trademark Office*

CERTIFICATE OF CORRECTION (continued)
U.S. Pat. No. 9,458,510 B2

At Column 11, Line number 60, delete "They" and insert -- The y --.

At Column 11, Line number 67, delete "They" and insert -- The y --.

At Column 12, Line number 7, delete "They" and insert -- The y --.

At Column 12, Line number 14, delete "They" and insert -- The y --.

At Column 12, Line number 22, delete "They" and insert -- The y --.